United States Patent
Ghiron et al.

(10) Patent No.: US 8,163,729 B2
(45) Date of Patent: Apr. 24, 2012

(54) MODULATORS OF α7 NICOTINIC ACETYLCHOLINE RECEPTORS AND THERAPEUTIC USES THEREOF

(75) Inventors: Chiara Ghiron, Asciano (IT); Arianna Nencini, Siena (IT); Iolanda Micco, Colle val D'Elsa (IT); Riccardo Zanaletti, Colle val D'Elsa (IT); Laura Maccari, Arbia (IT); Hendrick Bothmann, Monteriggioni (IT); Simon N. Haydar, Newtown, PA (US); Maurizio Varrone, Colle val D'Elsa (IT); Carmela Pratelli, Siena (IT); Boyd L. Harrison, Princeton Junction, NJ (US)

(73) Assignees: Wyeth, Madison, NJ (US); Siena Biotech S.p.A., Siena (IT)

( * ) Notice: Subject to any disclaimer, the term of this patent is extended or adjusted under 35 U.S.C. 154(b) by 0 days.

(21) Appl. No.: 12/523,189

(22) PCT Filed: Jan. 16, 2008

(86) PCT No.: PCT/IB2008/000090
§ 371 (c)(1),
(2), (4) Date: Aug. 13, 2009

(87) PCT Pub. No.: WO2008/087529
PCT Pub. Date: Jul. 24, 2008

(65) Prior Publication Data
US 2010/0029606 A1 Feb. 4, 2010

Related U.S. Application Data

(60) Provisional application No. 60/880,629, filed on Jan. 16, 2007.

(51) Int. Cl.
*A61K 31/4439* (2006.01)
*A61K 31/553* (2006.01)
*A61K 31/5513* (2006.01)
*A61K 31/5377* (2006.01)
*A61K 31/4709* (2006.01)
*C07D 401/12* (2006.01)
*C07D 413/12* (2006.01)
*C07D 401/14* (2006.01)
*A61P 25/00* (2006.01)

(52) U.S. Cl. ............... 514/210.2; 514/211.15; 514/218; 514/236.5; 514/314; 540/544; 540/575; 544/140; 546/165; 546/275.4

(58) Field of Classification Search .................. None
See application file for complete search history.

(56) References Cited

U.S. PATENT DOCUMENTS

| | | | |
|---|---|---|---|
| 3,946,018 A | 3/1976 | Deak et al. | |
| 4,053,598 A | 10/1977 | Daum et al. | |
| 4,624,954 A | 11/1986 | Jirkovsky et al. | |
| 4,665,183 A | 5/1987 | Jirkovsky et al. | |
| 4,904,658 A | 2/1990 | Tseng et al. | |
| 5,143,916 A | 9/1992 | Lavielle et al. | |
| 5,219,857 A | 6/1993 | Tseng et al. | |
| 5,260,331 A | 11/1993 | White et al. | |
| 5,422,355 A | 6/1995 | White et al. | |
| 5,538,956 A | 7/1996 | Minchin et al. | |
| 5,563,020 A | 10/1996 | Totsuka et al. | |
| 6,127,357 A | 10/2000 | Cliffe et al. | |
| 6,288,091 B1 | 9/2001 | Crute et al. | |
| 6,448,276 B1 | 9/2002 | Yerxa | |
| 6,465,482 B2 | 10/2002 | Mewshaw et al. | |
| 6,469,007 B2 | 10/2002 | Childers et al. | |
| 6,586,436 B2 | 7/2003 | Childers et al. | |
| 6,605,623 B1 | 8/2003 | Ko et al. | |
| 6,620,808 B2 | 9/2003 | Van Der Klish et al. | |
| 6,635,270 B2 | 10/2003 | Hong et al. | |
| 6,677,333 B1 | 1/2004 | Seko et al. | |
| 6,727,263 B2 | 4/2004 | Moltzen et al. | |
| 6,821,985 B2 | 11/2004 | Chenard et al. | |
| 6,825,212 B2 | 11/2004 | Bernotas et al. | |
| 6,878,742 B2 | 4/2005 | Kreft et al. | |
| 6,995,176 B2 | 2/2006 | Bernotas et al. | |
| 7,041,695 B2 | 5/2006 | Cole | |
| 7,091,227 B2 | 8/2006 | Scott et al. | |
| 7,183,411 B2 | 2/2007 | Codd et al. | |

(Continued)

FOREIGN PATENT DOCUMENTS

| | | |
|---|---|---|
| DE | 2406490 A1 | 8/1974 |
| EP | 0434561 A2 | 6/1991 |
| EP | 0462638 A1 | 12/1991 |
| EP | 0690051 B1 | 1/1996 |
| JP | 06016638 A | 1/1994 |
| JP | 2002030073 A | 1/2002 |
| WO | WO-9313083 A1 | 7/1993 |
| WO | WO-9402475 A1 | 2/1994 |
| WO | WO-9413643 A1 | 6/1994 |
| WO | WO-9413644 A1 | 6/1994 |

(Continued)

OTHER PUBLICATIONS

Bothmann et al., caplus an 2007:998814 (2007).*

(Continued)

*Primary Examiner* — Sun Jae Loewe
(74) *Attorney, Agent, or Firm* — Choate, Hall & Stewart, LLP; John P. Rearick; Xiaodong Li

(57) ABSTRACT

The present invention provides compounds of formula (I) and compositions thereof, methods of making them, and methods of using them to modulate alpha7 nicotinic acetylcholine receptors and/or to treat any of a variety of disorders, diseases, and conditions. Provided compounds can affect, among other things, neurological, psychiatric and/or inflammatory system.

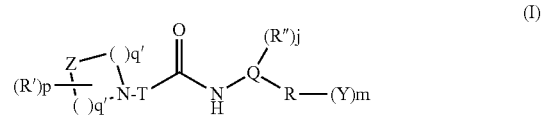

(I)

19 Claims, 21 Drawing Sheets

U.S. PATENT DOCUMENTS

| | | | |
|---|---|---|---|
| 2001/0044445 | A1 | 11/2001 | Bamaung et al. |
| 2004/0127536 | A1 | 7/2004 | Bhagwat et al. |
| 2004/0220189 | A1 | 11/2004 | Sun et al. |
| 2005/0009832 | A1 | 1/2005 | Sun et al. |
| 2005/0085476 | A1 | 4/2005 | Seko et al. |
| 2005/0154045 | A1 | 7/2005 | Luithle et al. |
| 2005/0197356 | A1 | 9/2005 | Graziani et al. |
| 2005/0197379 | A1 | 9/2005 | Summers et al. |
| 2005/0282825 | A1 | 12/2005 | Malamas et al. |
| 2005/0282826 | A1 | 12/2005 | Malamas et al. |
| 2007/0010515 | A1 | 1/2007 | Masuda et al. |
| 2008/0275028 | A1 | 11/2008 | Gaviraghi et al. |
| 2009/0181952 | A1 | 7/2009 | Haydar et al. |
| 2009/0181953 | A1 | 7/2009 | Mirmehrabi et al. |
| 2009/0264648 | A1 | 10/2009 | Chew et al. |
| 2010/0016343 | A1 | 1/2010 | Ghiron et al. |
| 2010/0016360 | A1 | 1/2010 | Haydar et al. |
| 2010/0016598 | A1 | 1/2010 | Valacchi et al. |
| 2010/0130474 | A1 | 5/2010 | Bothmann et al. |

FOREIGN PATENT DOCUMENTS

| | | |
|---|---|---|
| WO | WO-9413661 A1 | 6/1994 |
| WO | WO-9413676 A1 | 6/1994 |
| WO | WO-9413677 A1 | 6/1994 |
| WO | WO-9418196 | 8/1994 |
| WO | WO-9638414 A1 | 12/1996 |
| WO | WO-9703982 A1 | 2/1997 |
| WO | WO-9730998 A1 | 8/1997 |
| WO | WO-9736907 A1 | 10/1997 |
| WO | WO97/43262 | 11/1997 |
| WO | WO98/49145 | 11/1998 |
| WO | WO98/50363 | 11/1998 |
| WO | WO-9903850 A1 | 1/1999 |
| WO | WO99/32117 | 7/1999 |
| WO | WO-9942456 A2 | 8/1999 |
| WO | WO-9950247 A1 | 10/1999 |
| WO | WO-9951240 A1 | 10/1999 |
| WO | WO-9962505 A2 | 12/1999 |
| WO | WO-0042044 A1 | 7/2000 |
| WO | WO-0044726 A1 | 8/2000 |
| WO | WO-0112188 A1 | 2/2001 |
| WO | WO-0132604 A1 | 5/2001 |
| WO | WO-0136417 A1 | 5/2001 |
| WO | WO-0174773 A2 | 10/2001 |
| WO | WO-0174815 A2 | 10/2001 |
| WO | WO-0177100 A2 | 10/2001 |
| WO | WO-0198268 A2 | 12/2001 |
| WO | WO02/14311 | 2/2002 |
| WO | WO02/24694 | 3/2002 |
| WO | WO02/066446 A1 | 8/2002 |
| WO | WO-0266468 A2 | 8/2002 |
| WO | WO03/028725 A1 | 4/2003 |
| WO | WO03/028728 A1 | 4/2003 |
| WO | WO03/033489 A1 | 4/2003 |
| WO | WO-03070707 A1 | 8/2003 |
| WO | WO-03078431 A1 | 9/2003 |
| WO | WO-2004004714 A1 | 1/2004 |
| WO | WO-2004006924 A1 | 1/2004 |
| WO | WO-2004013137 A1 | 2/2004 |
| WO | WO-2004039366 A1 | 5/2004 |
| WO | WO-2005061519 A1 | 7/2005 |
| WO | WO-2005075479 A1 | 8/2005 |
| WO | WO-2006008133 A2 | 1/2006 |
| WO | WO-2006023844 A2 | 3/2006 |
| WO | WO-2006077428 A1 | 7/2006 |
| WO | WO-2006091858 A1 | 8/2006 |
| WO | WO-2007098826 A2 | 9/2007 |
| WO | WO-2008087529 A1 | 7/2008 |
| WO | WO-2009071577 A1 | 6/2009 |
| WO | WO-2009091813 A1 | 7/2009 |
| WO | WO-2009091831 A1 | 7/2009 |
| WO | WO-2009091832 A1 | 7/2009 |
| WO | WO-2010009290 A1 | 1/2010 |

OTHER PUBLICATIONS

U.S. Appl. No. 60/880,629, Ghiron et al.
U.S. Appl. No. 61/021,015, Chew et al.
U.S. Appl. No. 61/021,017, Haydar et al.
U.S. Appl. No. 61/081,211, Bothmann et al.
U.S. Appl. No. 61/081,198, Ghiron.
U.S. Appl. No. 61/081,221, Haydar.
U.S. Appl. No. 61/081,206, Ghiron.
U.S. Appl. No. 61/021,006, Mirmenhrabi et al.
U.S. Appl. No. 12/161,177, Bothmann et al.
U.S. Appl. No. 12/503,997, filed May 27, 2010, Bothmann et al.
Agarwal, et al., J. Ind. Chem. Soc., 58(8), 787-8 (1981).
Akaike, A. et al. (1994) Nicotine-induced protection of cultured cortical neurons against N-methyl-D-aspartate receptor-mediated glutamate cytotoxicity. Brain Res. 644, 181-187.
Andre, V. et al. (2010) Dopamine and Glutamate in Huntington's Disease: A Balancing Act, CNS Neuroscience & Therapeutics, 1-16.
Anderson et al. "1,3-Dipolar Addition of Pyridine N-Imine to Acetylenes and the Use of C-13 NMR in Several Structural Assignments," *Journal of Heterocyclic Chemistry* 1981, 18, 1149-1152.
Bencherif, M. et al. (2000) TC-2559: a novel orally active ligand selective at neuronal acetylcholine receptors. Eur. J. Pharmacol. 409, 45-55.
Boreskov, Yu G. et al. Russ. J. Bioorg. Chem. vol. 21, No. 10, 1995, p. 689-695 (English Translation).
Brumwell, et al., J. Neurosci., 22(18), 8101-09 (2002).
Brzezinski, et al., "Synthesis of Compounds with Heteroconjugated Intramolecular Hydrogen Bonds with Strong Proton Polarizability", Polish Journal of Chemistry, 57(1-3), 249-52 (1983).
Buchwald et al., "Long-term, continuous intravenous heparin administration by an implantable infusion pump in ambulatory patients with recurrent venous thrombosis," *Surgery* 1980, 88:507.
Bundgaard et al., "Glycolamide Esters as Biolabile Prodrugs of Carboxylic Acid Agents: Synthesis, Stability, Bioconversion, and Physicochemical Properties," *J. Pharmaceutical Sciences*, 77:285 et seq. (1988).
Bundgaard et al., "Means to enhance penetration: Prodrugs as a means to improve the delivery of peptide drugs," *Adv. Drug Delivery Reviews*, 8:1-38 (1992).
Casamenti, "Long-term ethanol consumption by rats: effect on acetylcholine release in vivo, choline acetyltransferase activity, and behavior," *Neuroscience* 1993, 56,(2), 465-71.
Cochrane, "Acetylcholinesterase Inhibitors for the Treatment of Wernicke-Korsakoff Syndrome—Three Further Cases Show Response to Donepezil," *Alcohol & Alcoholism*. 2005, 40(2), 151-4.
Crochemore, et al., "Disease-related regressive alterations of forebrain cholinergic system in SOD1 mutant transgenic mice," *Neurochem. Int.* 2005, 46(5):357-68.
Cubo, et al., "Effect of donepezil on motor and cognitive function in Huntington disease," *Neurology* 2006, 67(7), 1268-71.
Czura,: C J et al. J. Intern. Med., (2005) 257(2), 156-66.
Dajas-Bailador, F.A. et al. (2000) The alpha7 nicotinic acetylcholine receptor subtype mediates nicotine protection against NMDA excitotoxicity in primary hippocampal cultures through a Ca(2+) dependent mechanism. Neuropharmacology 39, 2799-2807.
Database Beilstein (Online) Beilstein Institute for Organic Chemistry, Frankfurt-Main, DE; 1995, XP002458036 retrieved from MDL.
Database Registry (Online) Chemical Abstracts Service, Columbus, Ohio, US; Jan. 11, 2006 XP002458035 retrieved from STN.
de Jonge et al. British Journal of Pharmacology (2007) 151, 915-929.
De Tommaso, "Effects of rivastigmine on motor and cognitive impairment in Huntington's disease," *Mov. Disord*. 2004, 19(12), 1516-8.
Donnelly-Roberts, D.L. et al. (1996) In vitro neuroprotective properties of the novel cholinergic channel activator (ChCA), ABT-418. Brain Res. 719, 36-44.
During et al., "Controlled Release of Dopamine from a Polymeric Brain Implant: In Vivo Characterization," *Ann. Neural*. 1989, 25:351-356.
El-Ahmad et al., "Synthesis of 1[ω-[(arylamino)carbonyl]alkyl]-4-(benzocycloalkyl) piperazines," *Heterocycles* 1997,45(4), 723-734.
Emilien, et al., "Prospects for Pharmacological Intervention in Alzheimer Disease," *Arch. Neurol*. 2000, 57:454.
Freedman, R A et al. Am J Med Genet. 2000 Spring; 97(1):58-64.
Friedland, et al., "Functional Imaging, the Frontal Lobes, and Dementia," *Dementia* 1993, 192-203.

Garrido, R. et al. (2001) Nicotine protects against arachidonic-acid-induced caspase activation, cytochrome c release and apoptosis of cultured spinal cord neurons. J. Neurochem. 76, 1395-1403.

Goodson, Medical Applications of Controlled Release, vol. 2, 115-138, 1984.

Gong, Y. and Pauls, H. W. (2000) Synlett 6, 829-831.

Han et al., *Tetrahedron*, 60, 2447-67 (2004).

Hanagasi, et al., "Cognitive impairment in amyotrophic lateral sclerosis: evidence from neuropsychological investigation and event-related potentials," *Brain Res. Cogn. Brain Res.* 2002, 14(2):234-44.

Hansen, et al., "Neocortical morphometry and cholinergic neurochemistry in Pick's disease," *Am. J. Pathol.* 1988, 131(3), 507-18.

Hilmas, C. et al. (2001), The Brain Metabolite Kynurenic Acid Inhibits $\alpha 7$ Nicotinic Receptor Expression: Physiopathological Implications, The Journal of Neuroscience 21(19): 7463-7473.

Holladay et al., "Neuronal nicotinic acetylcholine receptors as targets for drug discovery," *J. Med. Chem.* 1997, 40:26, 4169-94.

Howard et al., "Intracerebral Drug Delivery in Rats with Lesion-Induced Memory Deficits," *J. Neurosurg.* 1989, 71:105-112.

International Search Report for PCT/EP2005/007846, mailed Feb. 10, 2006.

International Search Report for PCT/EP2007/000382 mailed Dec. 7, 2007.

International Search Report for PCT/IB2008/000090 mailed Jun. 30, 2008.

International Search Report for PCT/US2009/030973 mailed Mar. 30, 2009.

International Search Report for PCT/US2009/031003 mailed Mar. 18, 2009.

International Search Report for PCT/US2009/031005 mailed Jun. 8, 2009.

International Search Report for PCT/US2009/050797 mailed Oct. 27, 2009.

Jensen, A. et al. Carbamoylcholine Homologs: Novel and Potent Agonists at Neuronal Nicotinic Acetylcholine Receptors. Molecular Pharmacology, vol. 64, No. 4, Oct. 4, 2003, pp. 865-875.

Johnson et al., J. Med. Chem., 26(2), 185-94 (1983).

Jonnala, R.R. et al. (2002) Nicotine increases the expression of high affinity nerve growth factor receptors in both in vitro and in vivo. Life Sci. 70, 1543-1554.

Kaiser, S. et al. (2000) $\alpha$-Bungarotoxin-Sensitive Nicotinic Receptors Indirectly Modulate [$^3$H]Dopamine Release in Rate Striatal Slices via Glutamate Release, Molecular Pharmacology, 312-318.

Kawashima K, Fujii T., Front Biosci. Sep. 1, 2004; 9:2063-85.

Kanazawa, et al., "Studies on neurotransmitter markers and striatal neuronal cell density in Huntington's disease and dentatorubropal-lidoluysian atrophy," *J. Neurol. Sci.* 1985, 70(2), 151-65.

Kelton, M. C. et al. (2000) The effects of nicotine on Parkinson's disease. Brain Cogn 43, 274-282.

Kem, W. R. (2000) The brain alpha7 nicotinic receptor may be an important therapeutic target for the treatment of Alzheimer's disease: studies with DMXBA (GTS-21). Behav. Brain Res. 113, 169-181.

Bundgaard, H; Kgrogsgaard-Larsen et al. (ed.), "Design and Application of Prodrugs", Textbook of *Drug Design and Development*, Chapter 5, 113-191 (1991).

Kihara, T. et al. (1997) Nicotinic receptor stimulation protects neurons against beta-amyloid toxicity. Ann. Neurol. 42, 159-163.

Kihara, T. et al. (2001) alpha 7 nicotinic receptor transduces signals to phosphatidylinositol 3-kinase to block A beta-amyloid induced neurotoxicity. J. Biol. Chem. 276, 13541-13546.

Kopelman, "The Korsakoff syndrome," *Br. J. Psychiatry* 1995, 166(2), 154-73.

Lange, et al., "Brain muscarinic cholinergic receptors in Huntington's disease," *J. Neurol.* 1992, 239(2), 103-4.

Langer, "New Methods of Drug Delivery," *Science* 1990, 249: 1527-1533.

Langer and Peppas, J. Macromol. Sci. Rev., Macromol. Chem. 1983, 23:61.

Leadbeater, N. E., Marco, M (2002) Org. Lett. 4 (17) 2973-2976.

Levin, E D et al. Eur J Pharmacol, vol. 393 (1-3): 141-6, 2000.

Levin, E D, et.al. Behav Pharmacol, vol. 10 (6-7): 675-80, 1999.

Levy et al., "Inhibition of Calcification of Bioprosthetic Heart Valves by Local Controlled-Release Diphosphonate," *Science* 1985, 228:190-192.

Little et al., *JOC* 1994, 59,24, 7299.

Lopez-Berestein, "Treatment of Systemic Fungal Infections with Liposomal-Amphotericin B," in *Liposomes in the Therapy of Infectious Disease and Cancer*, (Lopez-Berestein and Fidler eds.), Alan R. Liss, Inc., New York, 317-327, 1989.

Manyam, et al., "Cerebrospinal fluid acetylcholinesterase and choline measurements in Huntington's disease," *J. Neurol.* 1990, 237(5), 281-4.

Messi, et al., "Activation of alpha7 nicotinic acetylcholine receptor promotes survival of spinal cord motoneurons," *FEBS Lett.* 1997, 411(1), 32-8.

Meyer, E.M. et al. (1998) Neuroprotective and memory-related actions of novel alpha-7 nicotinic agents with different mixed agonist/antagonist properties. J. Pharnzacol. Exp. Ther. 284, 1026-1032.

Mizukami, "Neuropathological study on the nucleus basalis of Meynert in Pick's disease," *Acta. Neuropathol.* 1989, 78(1), 52-6.

Mohammadi, et al., "Interaction of high concentrations of riluzole with recombinant skeletal muscle sodium channels and adult-type nicotinic receptor channels," *Muscle Nerve* 2002, Oct. 26(4):539-45.

Murray, P.J. et al. (1995) Bioorg. Med Chem. Lett. 5 (3), 219-222.

Nakamizo, et al., "Stimulation of nicotinic acetylcholine receptors protects motor neurons," *Biochem. Biophys. Res. Commun.* 2005, 330(4), 1285-9.

Nishikawa, Y. et al. (1989) Chem. Pharm. Bull. 37 (I), 100-105.

Pascal, J. C. et el. (1990) Eur. J. Med. Chem. 25, 291-293.

Pauly, J.R. et al. (2004) Nicotinic Receptor Modulation for Neuroprotection and Enhancement of Functional Recovery Following Brain Injury or Disease, Ann. N.Y. Acad. Sci. 1035: 316-334.

Prendergast, M.A. et al. (2001) Nicotine exposure reduces N-methyl-D-aspartate toxicity in the hippocampus: relation to distribution of the alpha7 nicotinic acetylcholine receptor subunit. Med. Sci. Monit. 7, 1153-1160.

Procter, et al., "Neurochemical features of frontotemporal dementia," *Dement. Geriatr. Cogn. Disord.* 1999, 10 Suppl 1, 80-4.

Quik M. et al. (1997). Modulation of alpha7 nicotinic receptor-mediated calcium influx by nicotinic agonists. Mol. Pharmacol., 51, 499-506.

Rusted, J.M. et al. (2000) Nicotinic treatment for degenerative neuropsychiatric disorders such as Alzheimer's disease and Parkinson's disease. Behav. Brain Res. 113, 121-129.

Saudek et al., "A Preliminary Trial of the Programmable Implantable Medication System for Insulin Delivery," *N. Engl. J. Med.* 1989, 321:574-579.

Saxena, et al., J. Ind. Chem. Soc., 60(6), 575-77 (1983).

Schmitt et al., *Annual Reports Med. Chem.*, Chapter 5, 41-51 (2000).

Sefton, "Implantable Pumps," *CRC Crit. Ref. Biomed. Eng.* 1987, 14:201-240.

Semba, J. et al. (1996) Nicotine protects against the dexamethasone potentiation of kainic acid-induced neurotoxicity in cultured hippocampal neurons. Brain Res. 735, 335-338.

Shimohama, S. et al. (1998) Nicotinic alpha 7 receptors protect against glutamate neurotoxicity and neuronal ischemic damage. Brain Res. 779, 359-363.

Shimohama, S. et al.(1996) Nicotine-induced protection against glutamate cytotoxicity. Nicotinic cholinergic receptor-mediated inhibition of nitric oxide formation. Ann. N.Y. Acad. Sci. 777, 356-361.

Shytle et al., "Nicotinic acetylcholine receptors as targets for antidepressants," *Molecular Psychiatry* 2002, 7, 525-535.

Smith, et al. "Cholinergic neuronal defect without cell loss in Huntington's disease," *Hum. Mol. Genet.* 2006, 15(21), 3119-31.

Socci, D. J., Arendash, G. W. (1996) Chronic nicotine treatment prevents neuronal loss in neocortex resulting from nucleus basalis lesions in young adult and aged rats. Mol. Chem. Neuropathol. 27, 285-305.

Solinas, et al., "Nicotinic $\alpha_7$ Receptors as a New Target for Treatment of Cannabis Abuse," *Journal of Neuroscience* 2007, 27(21), 5615-5620.

Son, J.-H. and Meizel, S., "Evidence Suggesting That the Mouse Sperm Acrosome Reaction Initiated by the Zona Pellucida Involves an {alpha}7 Nicotinic Acetylcholine Receptor," *Biol. Reproduct.* 2003, 68(4), 1348-1353.

Sparks, "Altered serotoninergic and cholinergic synaptic markers in Pick's disease," *Arch. Neurol.* 1991, 48, 796-9.

Stevens et al., "Selective $\alpha_7$-nicotinic agonists normalize inhibition of auditory response in DBA mice," *Psychopharmacology* (1998) 136: 320-27.

Stevens, T.R. et al. (2003) Neuroprotection by nicotine in mouse primary cortical cultures involves activation of calcineurin and L-type calcium channel inactivation. J. Neuroscience 23, 10093-10099.

Still, C., et al., "Rapid Chromatographic Technique for Preparative Separations with Moderate Resolution," *J. Org. Chem.* 1978, 43, 2923.

Strahlendorf, J.C. et al. (2001) Choline blocks AMPA-induced dark cell degeneration of Purkinje neurons: potential role of the alpha7 nicotinic receptor. Brain Res. 901, 71-78.

Tariq, M. et al. (2005) Neuroprotective effect of nicotine against 3-nitropropionic acid (3-NP)-induced experimental Huntington's disease in rats, Brain Research Bulletin 67: 161-168.

Thompson et al., Proc. Natl. Acad. Sci. USA, 1995, 92:7667-7671.

Tohgi, "Cerebrospinal fluid acetylcholine and choline in vascular dementia of Binswanger and multiple small infarct types as compared with Alzheimer-type dementia," *J. Neural. Transm.* 1996, 103(10), 1211-20.

Tomimoto, "Loss of cholinergic pathways in vascular dementia of the Binswanger type," *Dement. Geriatr. Cogn. Disord.* 2005, 19(5-6), 282-8.

Treat et al., "Liposome Encapsulated Doxorubicin Preliminary Results of Phase I and II Trials," in *Liposomes in the Therapy of Infectious Disease and Cancer*, (Lopez-Berestein and Fidler eds.), Alan R. Liss, Inc., New York, 353-365, 1989.

Utsugisawa, K. et al. (2002) Overexpression of alpha7 nicotinic acetylcholine receptor prevents G1-arrest and DNA fragmentation in PC12 cells after hypoxia. J. Neurochem. 81, 497-505.

Vetter, "Mice transgenic for exon 1 of Huntington's disease: properties of cholinergic and dopaminergic pre-synaptic function in the striatum," *J. Neurochem.* 2003, 85(4), 1054-63.

Wang H. et al. (2003) Nicotinic acetylcholine receptor alpha7 subunit is an essential regulator of inflammation. Nature, 421: 384-388.

Warren, "Cholinergic systems in progressive supranuclear palsy," *Brain* Feb. 2005:128(Pt 2):239-49.

Weiland, S. et al. Behav Brain Res, vol. 113 (1-2): 43-56, 2000.

Whitehouse, "Nicotinic and muscarinic cholinergic receptors in Alzheimer's disease and related disorders," *J. Neural. Transm. Suppl.* 1987, 24:175-82.

Whitehouse, "Nicotinic receptors and neurodegenerative dementing diseases: Basic research and clinical implications," *Alzheimer Dis. Assoc. Disord.* 1995, 9 (Suppl 2):3-5.

Whitehouse, "Reductions in acetylcholine and nicotine binding in several degenerative diseases," *Arch. Neurol.* 1988, 45(7), 722-4.

Yamada, et al., "Benzothiadiazides inhibit rapid glutamate receptor desensitization and enhance glutamatergic synaptic currents," *J. Neurosci.* 1993, 13:3904-3915.

Yamashita, H. et al. (1996) Nicotine rescues PC12 cells from death induced by nerve growth factor deprivation. Neurosci. Lett. 213, 145-147.

Ziegler et al., *J. Am. Chem. Soc.* 1990, 112(7), 2749-58.

Zivkovic et al., "7-Chloro-3-methyl-3-4-dihydro-2H-1,2,4 benzothiadiazine S,S-dioxide (IDRA 21): a benzothiadiazine derivative that enhances cognition by attenuating DL-alpha-amino-2,3-dihydro-5-methyl-3-oxo-4-isoxazolepropanoic acid (AMPA) receptor desensitization," *J. Pharmacol. Exp. Therap.*, 1995, 272(1), 300-309.

International Search Report for PCT/US2009/050797 mailed on Oct. 27, 2009.

* cited by examiner

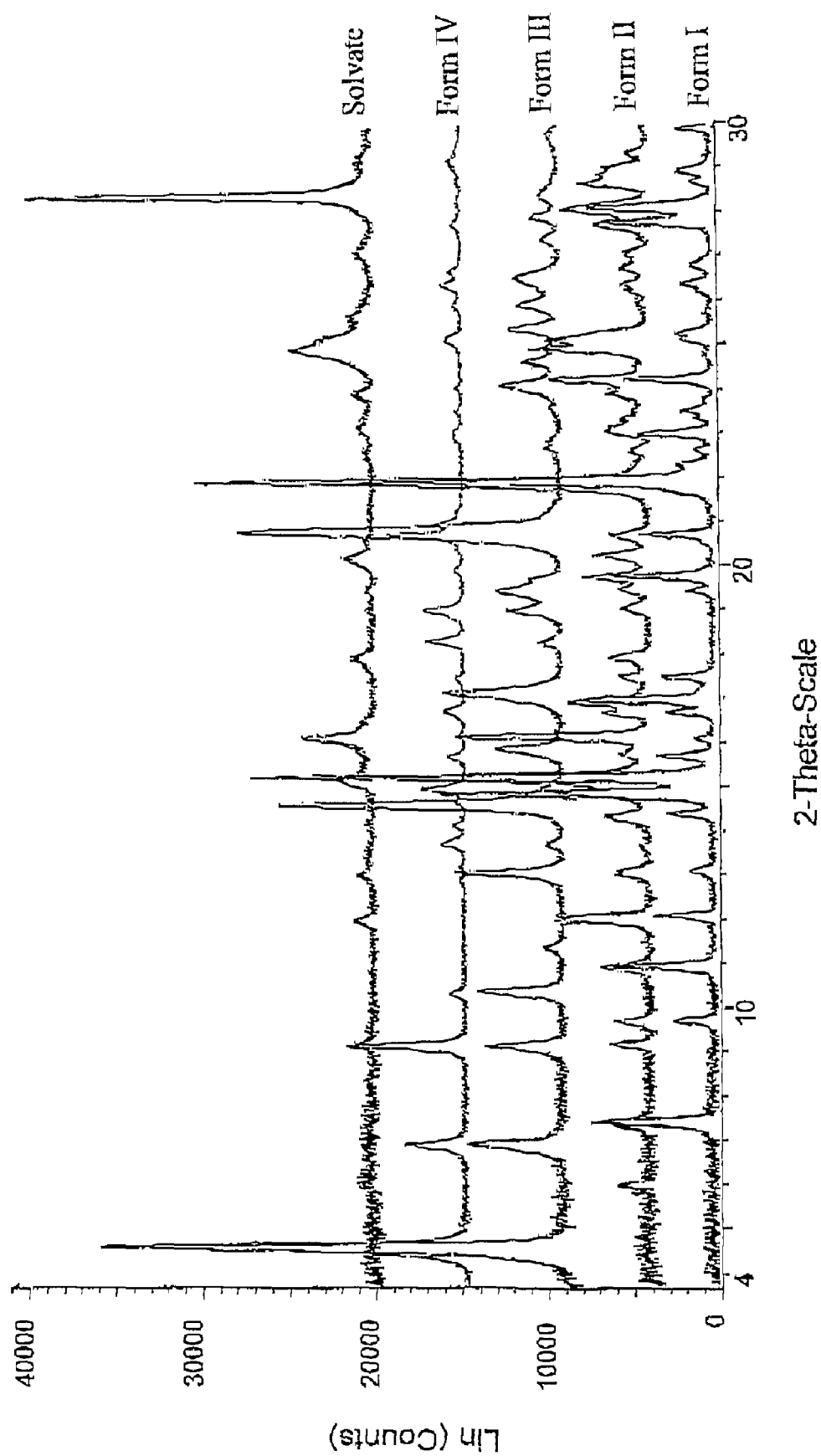
Figure 1. X-ray patterns of various crystal forms of hydrochloric salt

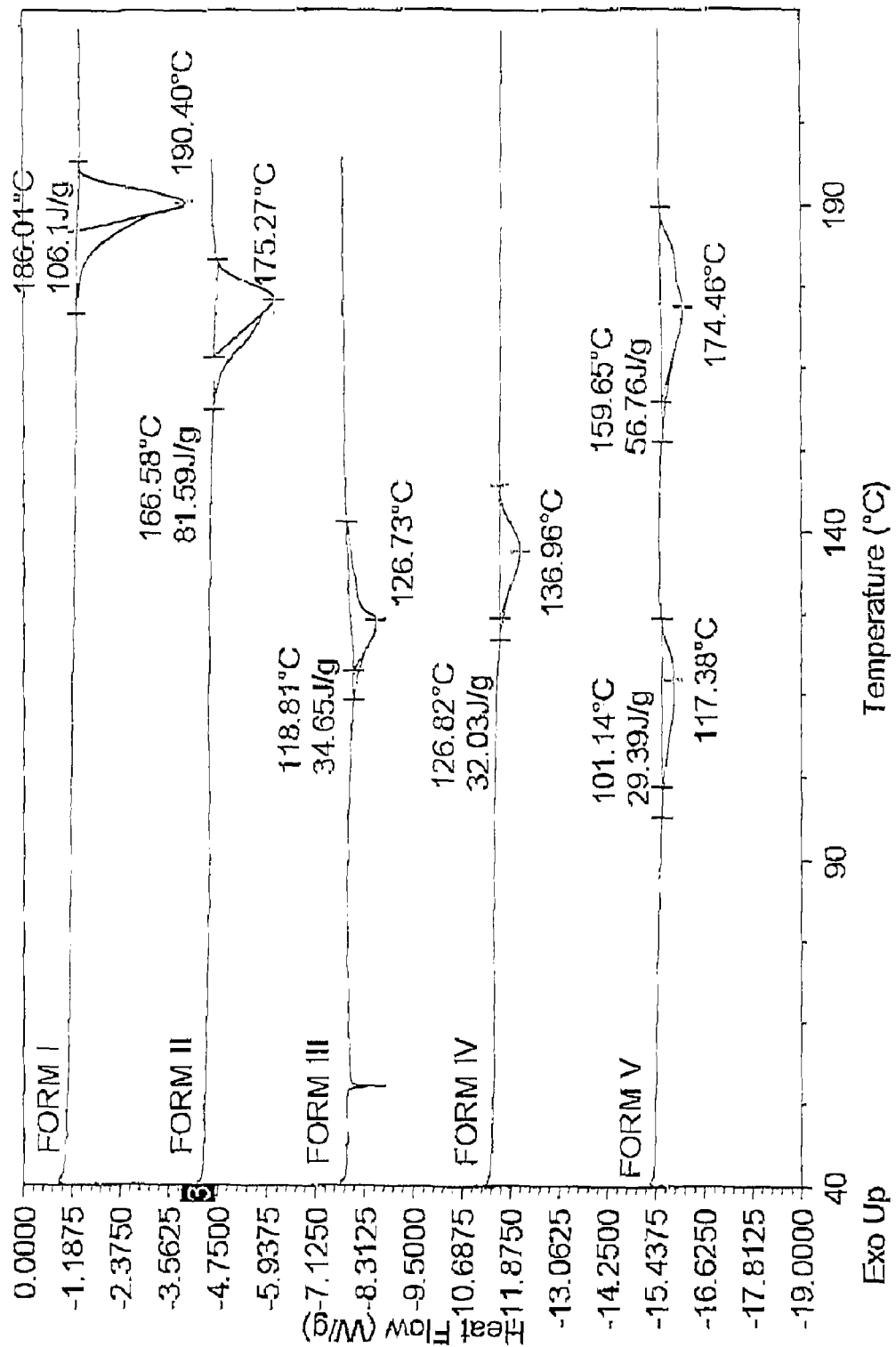
Figure 2- DSC scan of various crystal forms of hydrochloric salt

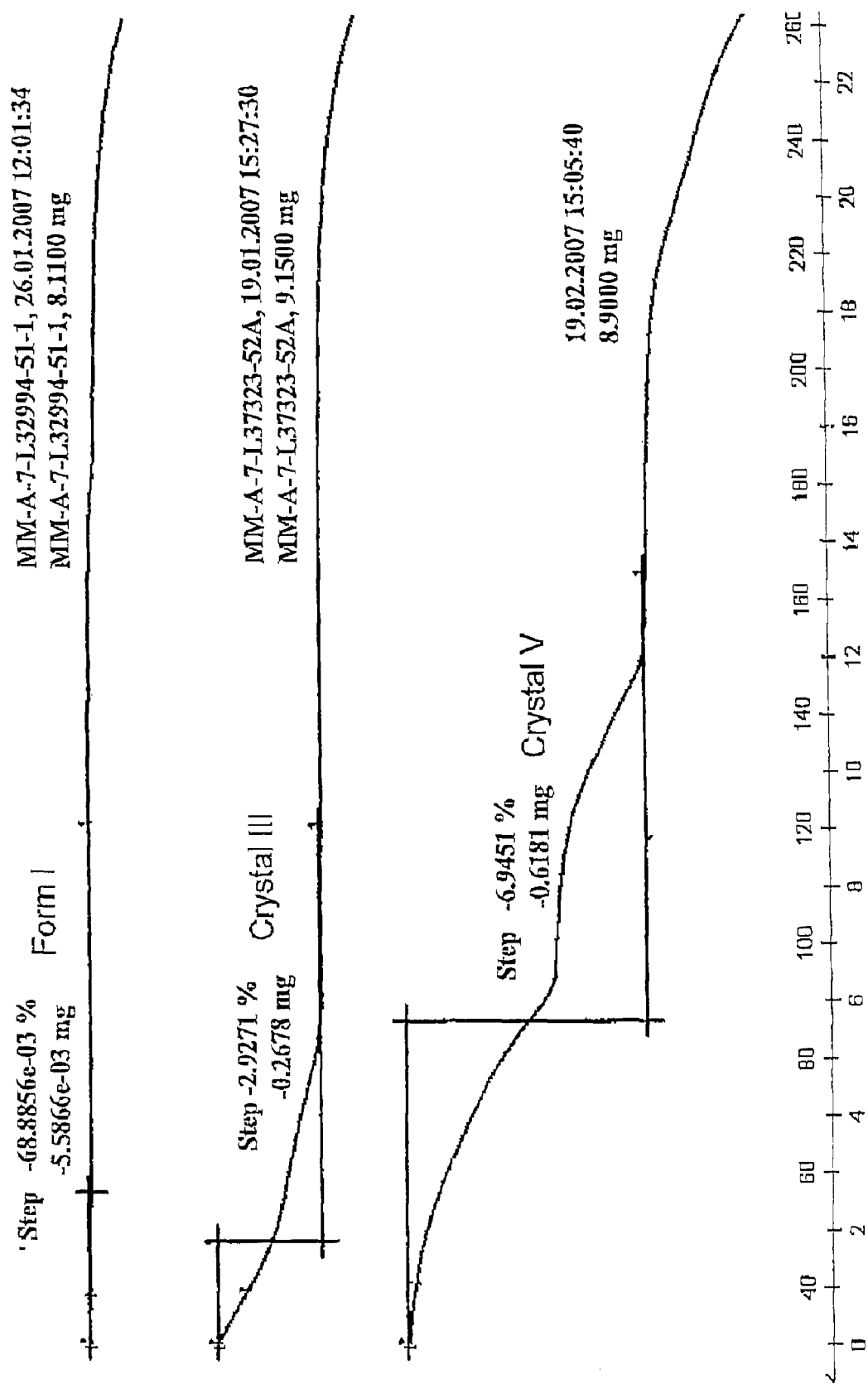
Figure 3- TGA of various crystal forms of hydrochloric salt

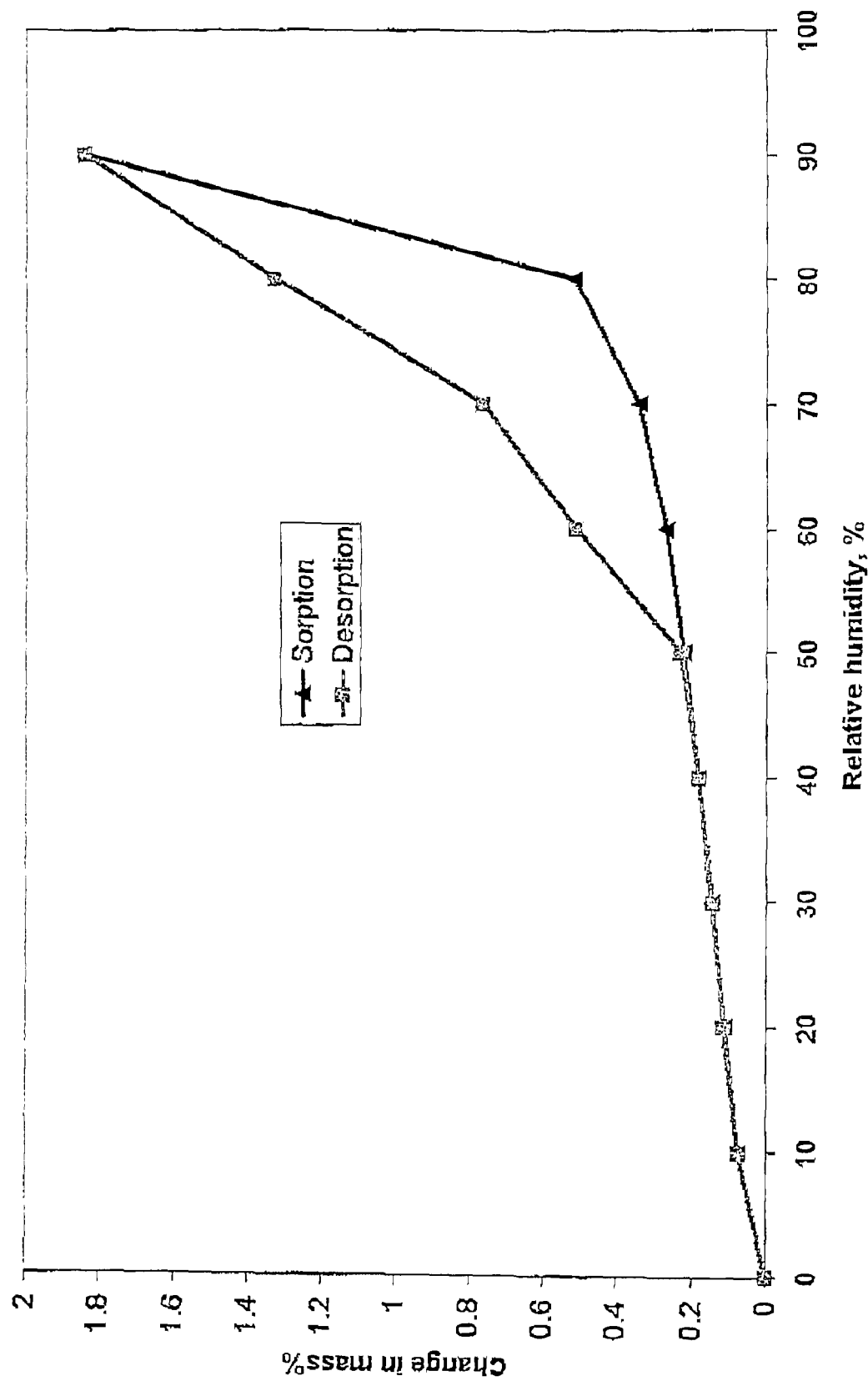
Figure 4- DVS of mono-HCl salt (NO form change after DVS test)

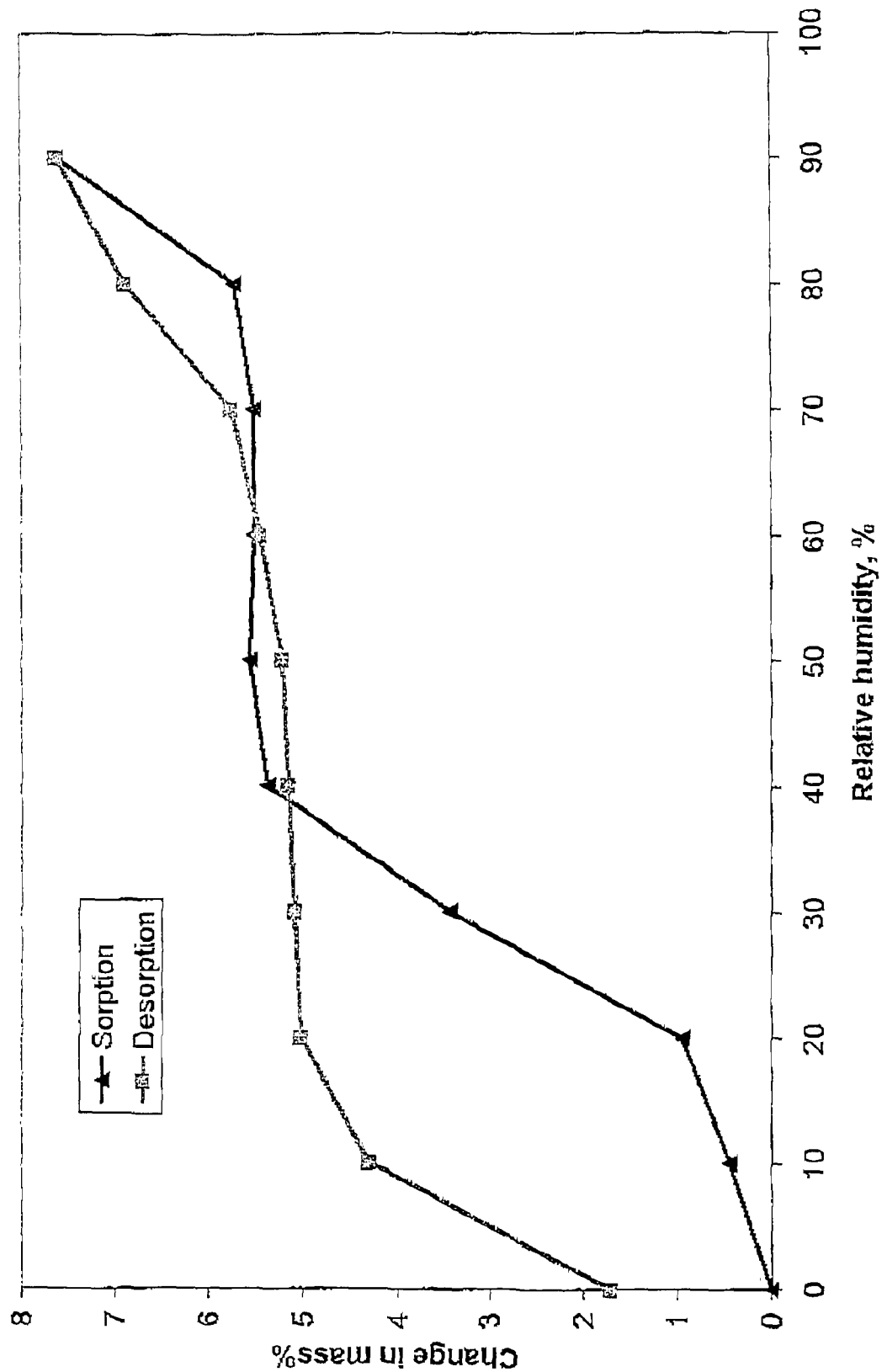
Figure 5- DVS of hydrochloric salt (crystal II) (NO form change after DVS)

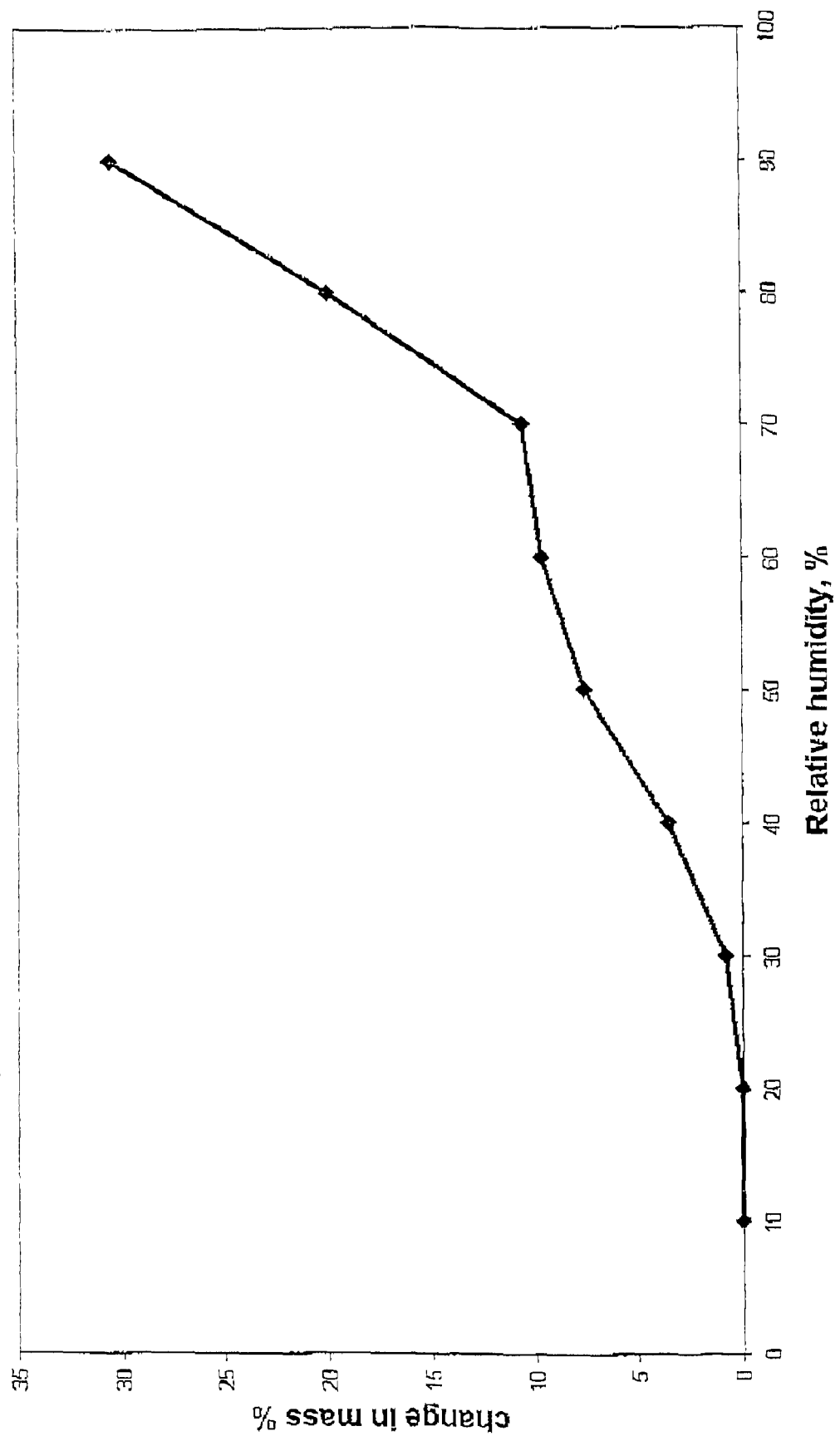
Figure 6- DVS of hydrochloric salt (crystal III) (data from pre-selection minute)

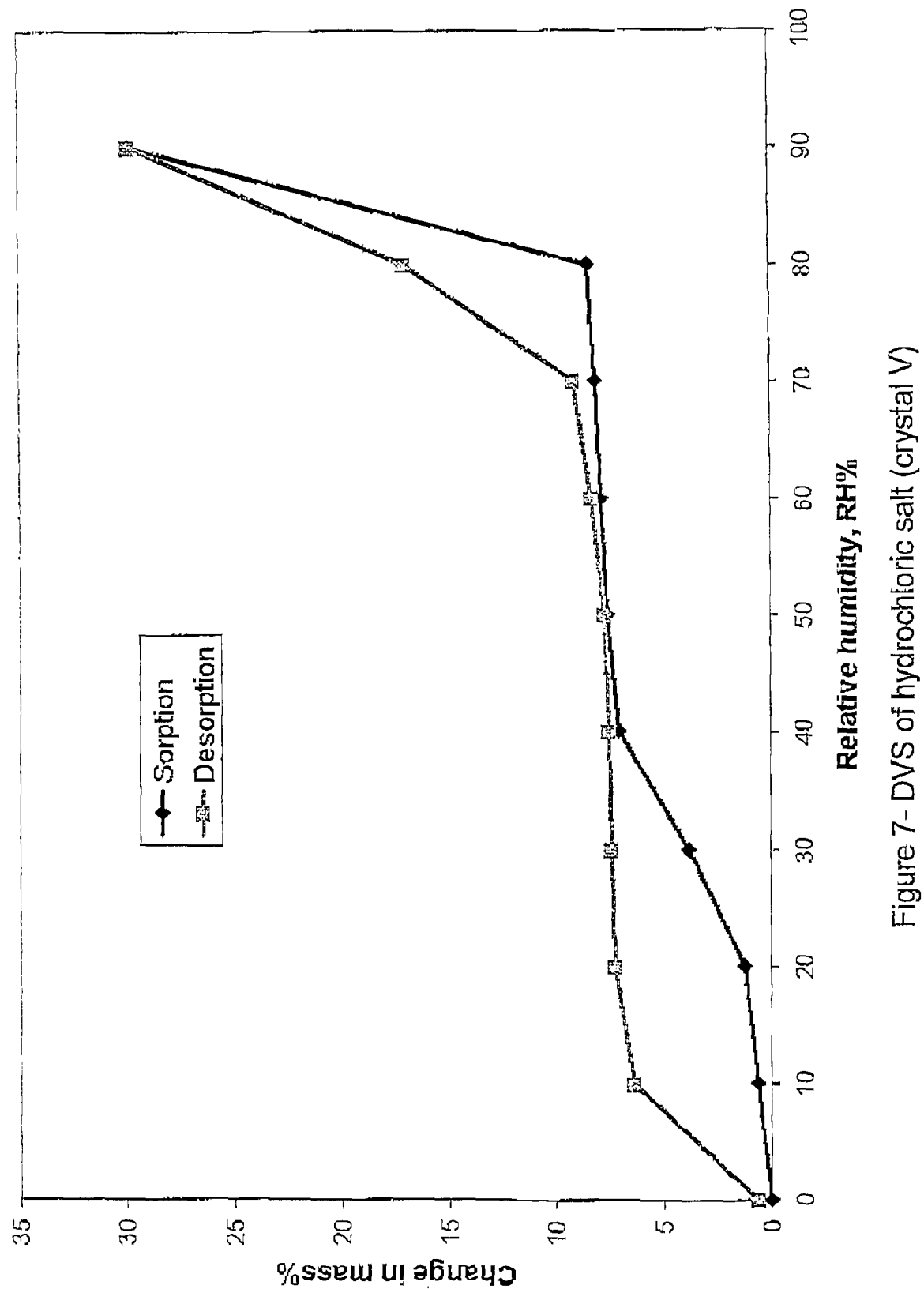
Figure 7- DVS of hydrochloric salt (crystal V)

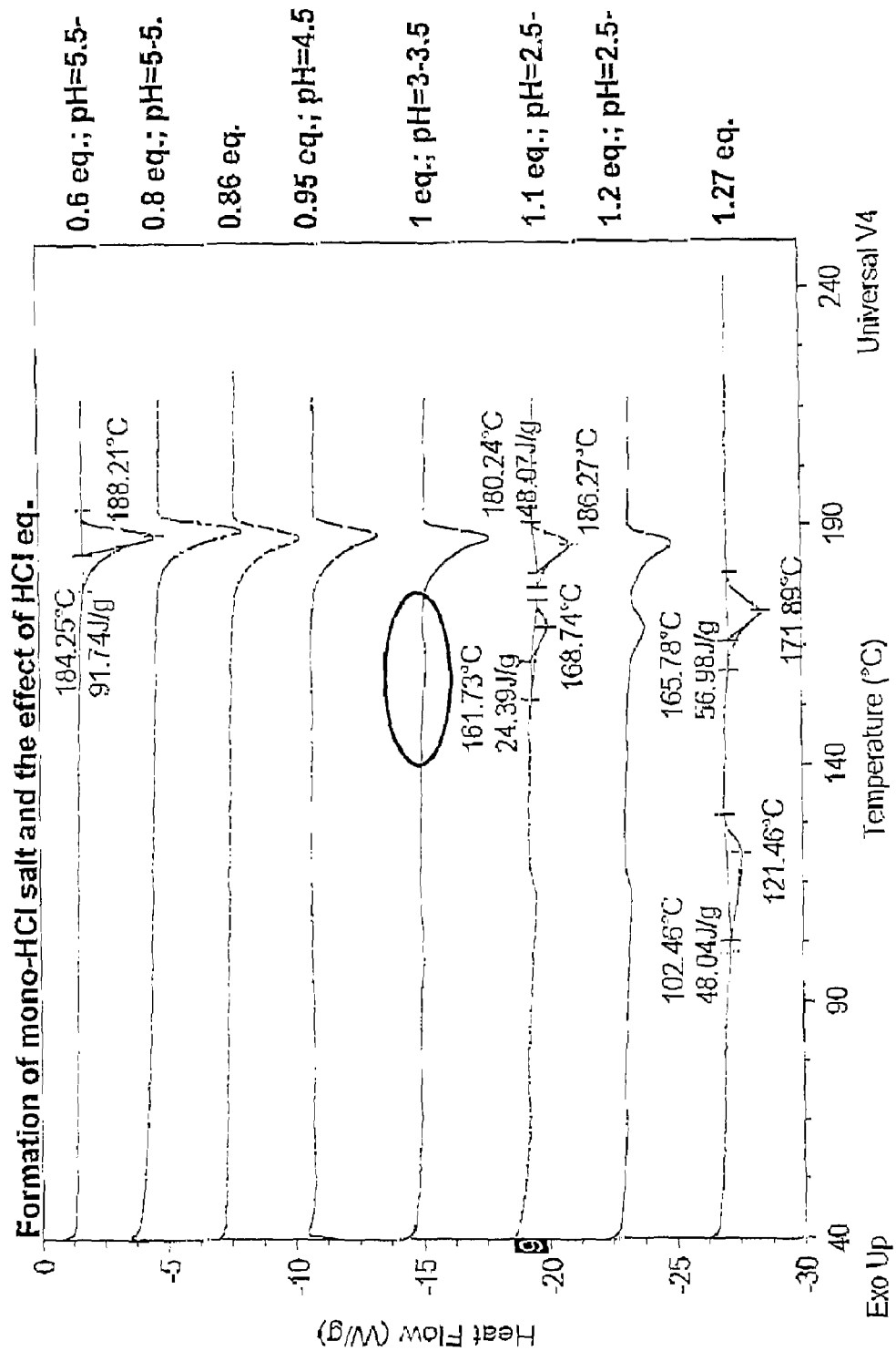
Figure 8- Effect of pH and HCl equivalence on HCl salt formation

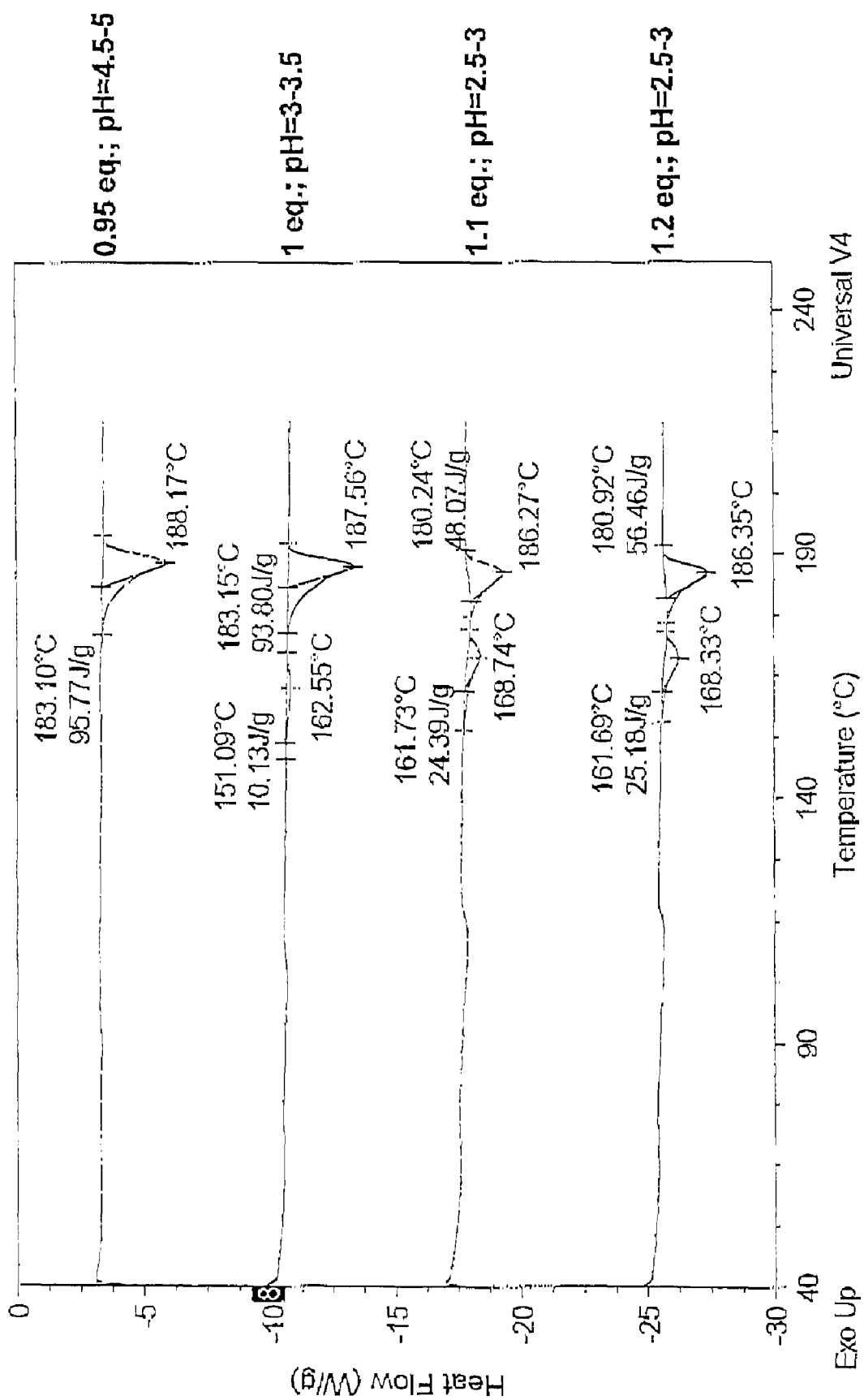
Figure 9- Effect of pH and HCl equivalence on HCl salt formation

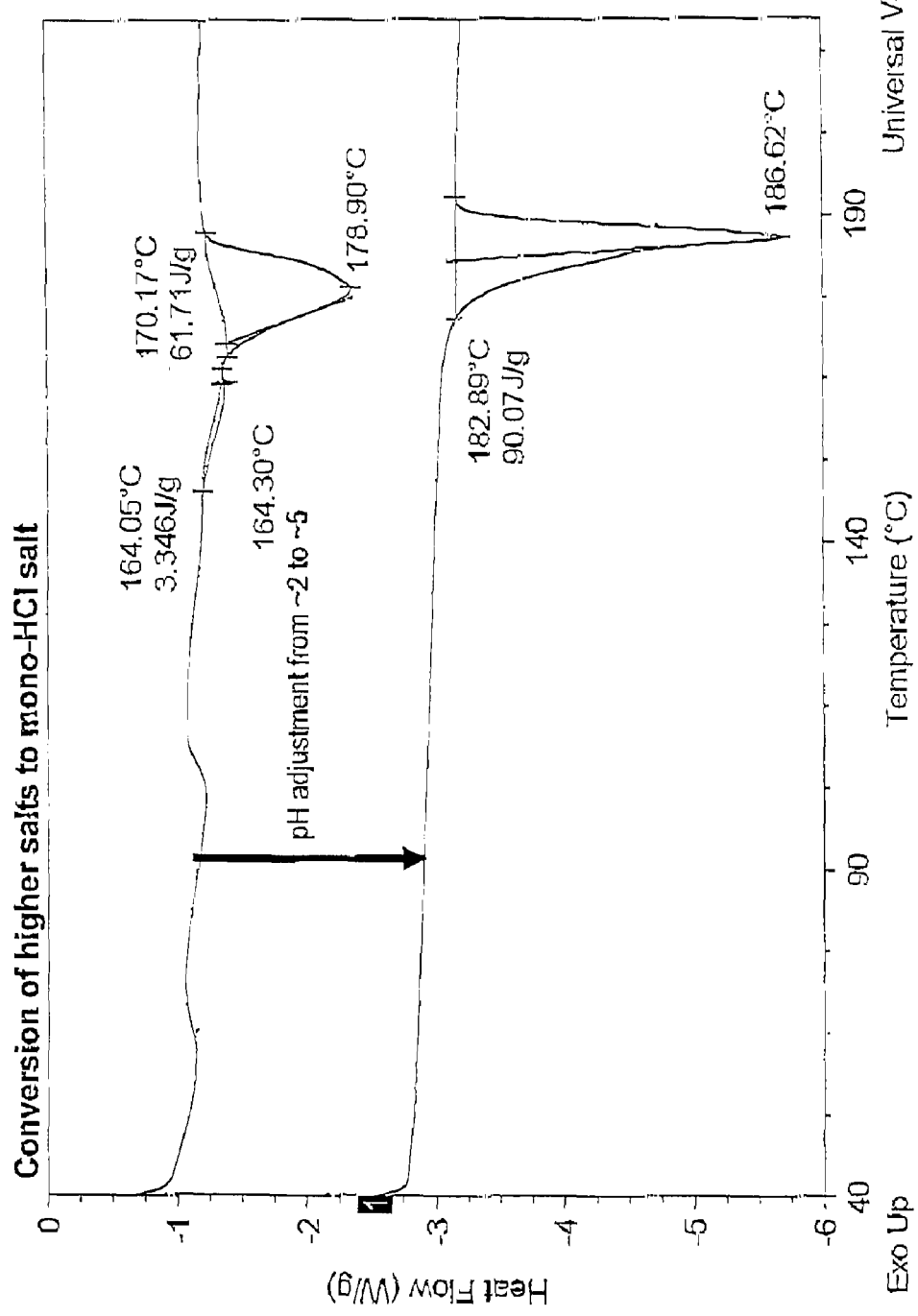
Figure 10- Conversion of higher salts to mono-HCl crystal I 259 mg di-HCl salt was slurried in 4 volumes acetone + 0.5 volume ethanol ASDQ at room temperature. The resulting slurry gave a pH of ~2. To increase the pH, 0.02 mL NaOH 30% was added which increased the pH to 5-5.5. The slurry was stirred overnight and converted to mono-HCl. 173 mg mono-HCl was obtained.

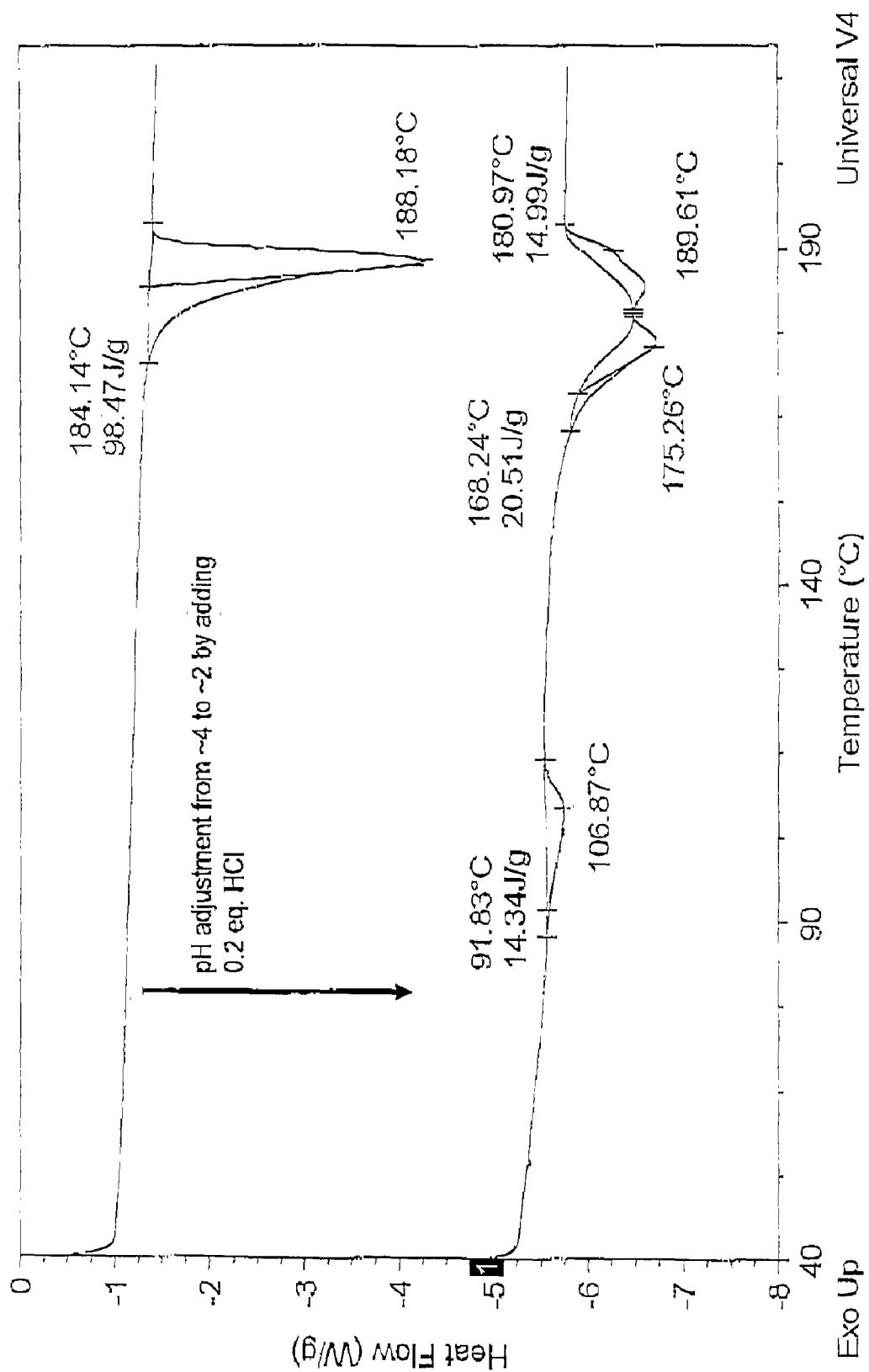
Figure 11 - Conversion of mono-HCl to Form II by decreasing the pH (slurried overnight)

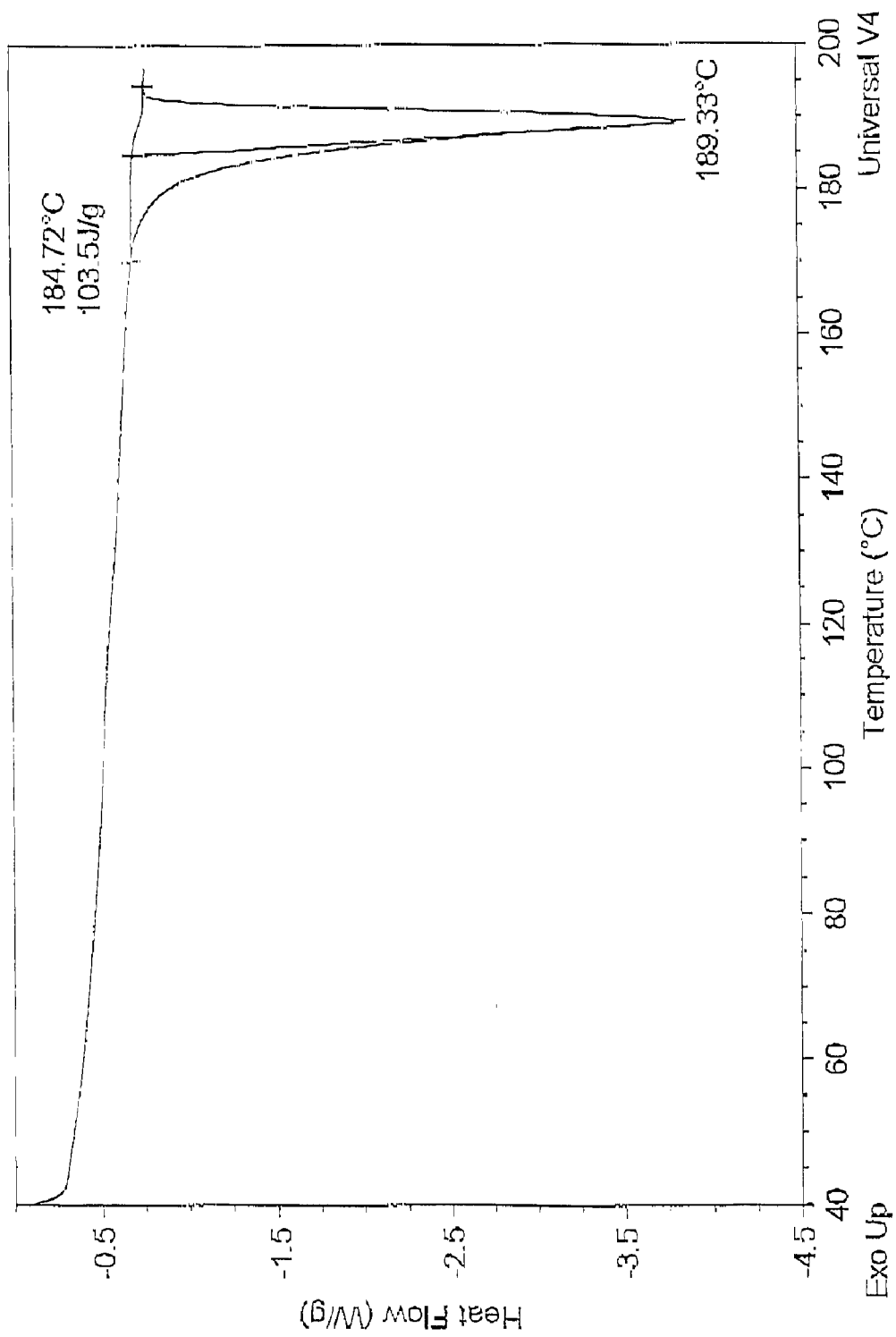
Figure 12- DSC scan of 5-(4-acetyl-1,4-diazepan-1-yl)-N-(5-(4-methoxyphenyl)-1H-pyrazol-3-yl)pentanamide hydrochloric salt Form I

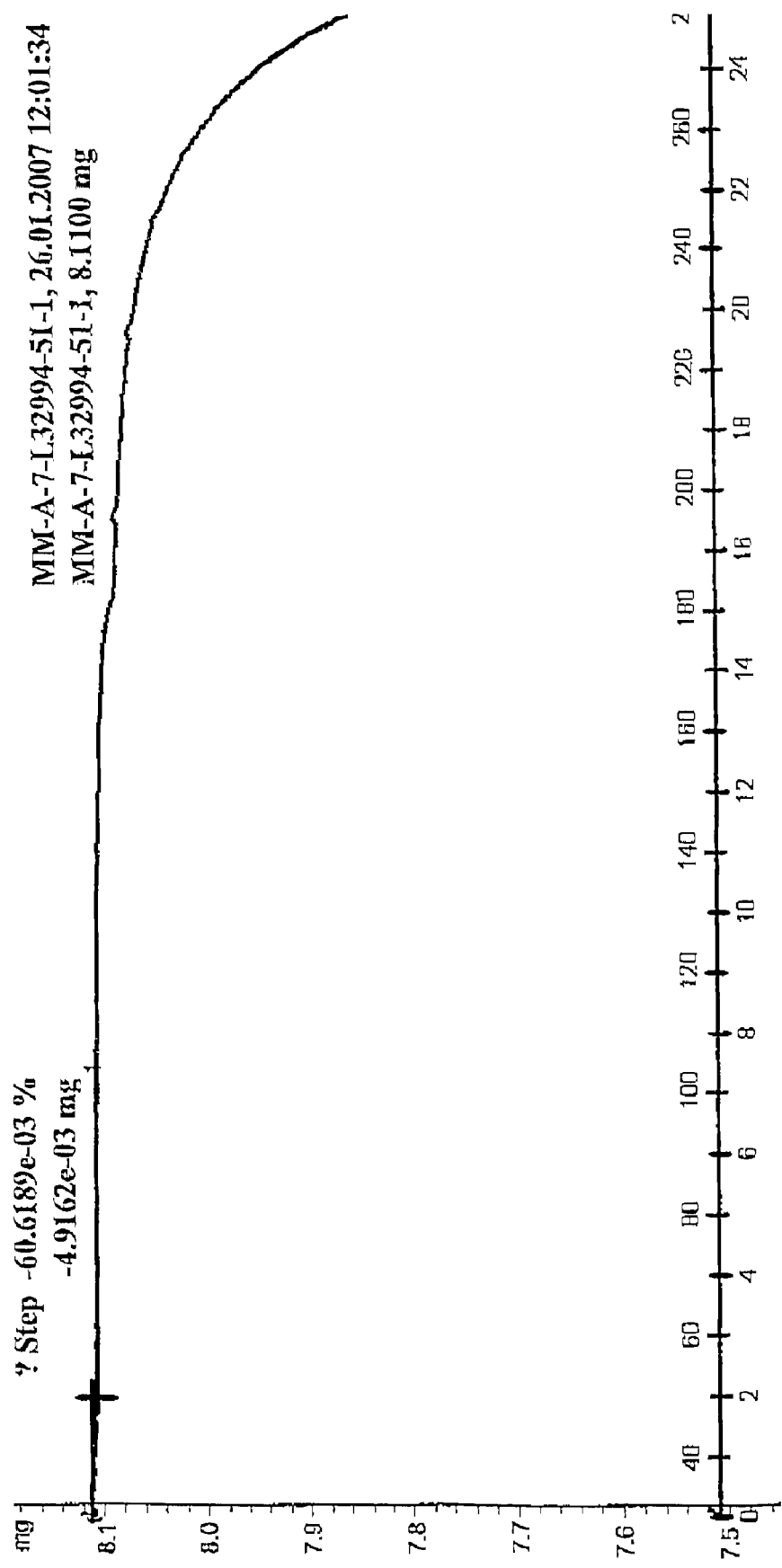
Figure 13- TGA thermogram of 5-(4-acetyl-1,4-diazepan-1-yl)-N-(5-(4-methoxyphenyl)-1H-pyrazol-3-yl)pentanamide hydrochloric salt Form I

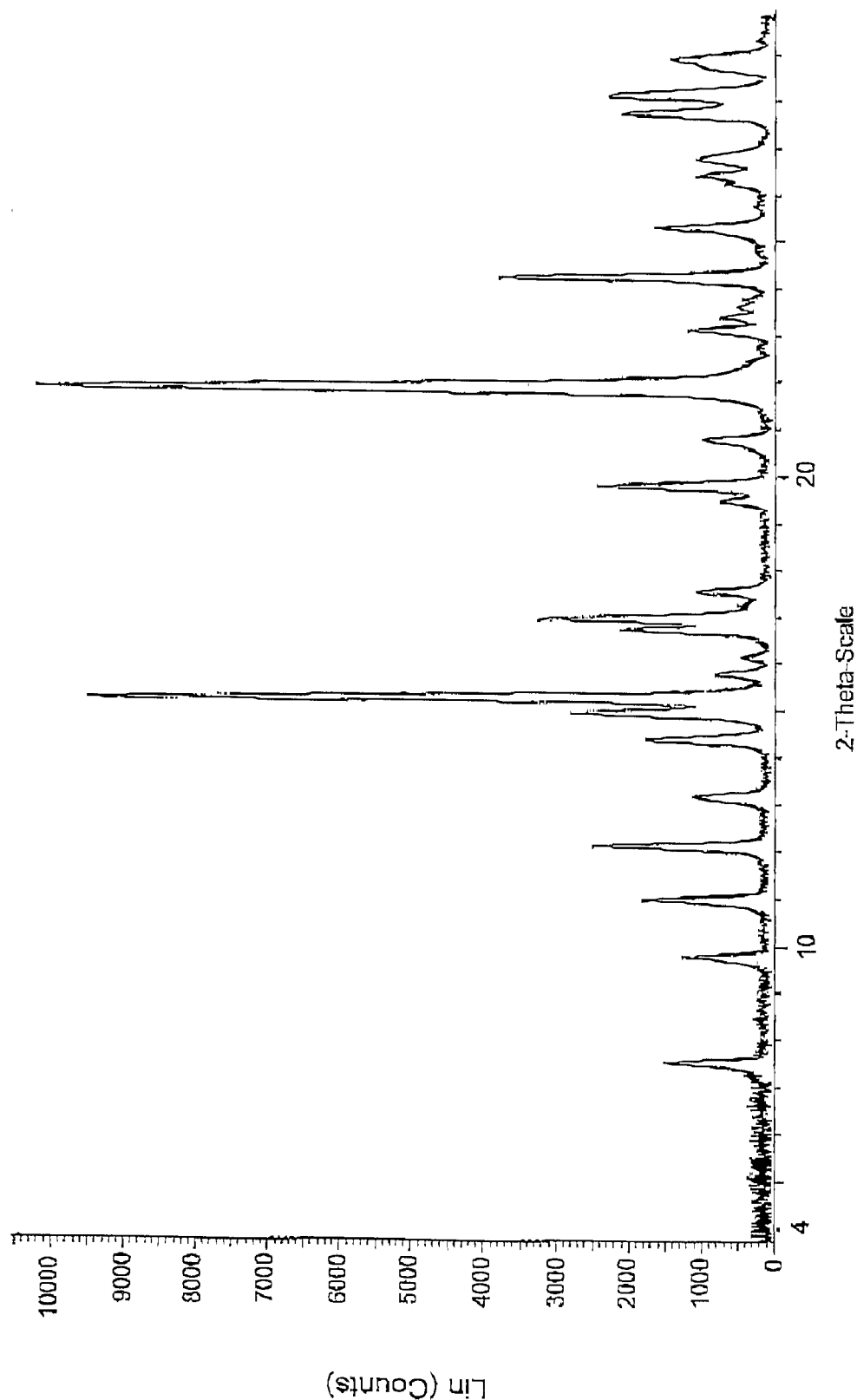
Figure 14 - X-ray diffraction pattern of 5-(4-acetyl-1,4-diazepan-1-yl)-N-(5-(4-methoxyphenyl)-1H-pyrazol-3-yl)pentanamide hydrochloric salt Form I

Figure 14 continued

Table 1 - X-ray diffraction data of 5-(4-acetyl-1,4-diazepan-1-yl)-N-(5-(4-methoxyphenyl)-1H-pyrazol-3-yl)pentanamide hydrochloric salt Form I

| Angle, 2-Theta ° | d value, Angstrom | Intensity, Count | Intensity % |
|---|---|---|---|
| 7.5 | 11.8 | 1484 | 14.5 |
| 9.7 | 9.1 | 1252 | 12.2 |
| 11.0 | 8.1 | 1795 | 17.5 |
| 12.1 | 7.3 | 2502 | 24.5 |
| 13.1 | 6.7 | 1122 | 11.0 |
| 14.4 | 6.2 | 1750 | 17.1 |
| 14.9 | 5.9 | 2814 | 27.5 |
| 15.3 | 5.8 | 9510 | 93.0 |
| 15.8 | 5.6 | 789 | 7.7 |
| 16.1 | 5.5 | 437 | 4.3 |
| 16.7 | 5.3 | 2108 | 20.6 |
| 17.0 | 5.2 | 3257 | 31.8 |
| 17.5 | 5.1 | 1075 | 10.5 |
| 19.5 | 4.6 | 740 | 7.2 |
| 19.8 | 4.5 | 2439 | 23.8 |
| 20.8 | 4.3 | 967 | 9.5 |
| 21.9 | 4.1 | 10228 | 100.0 |
| 23.1 | 3.8 | 1184 | 11.6 |
| 23.4 | 3.8 | 712 | 7.0 |
| 24.3 | 3.7 | 3787 | 37.0 |
| 25.3 | 3.5 | 1634 | 16.0 |
| 26.4 | 3.4 | 1000 | 9.8 |
| 26.8 | 3.3 | 1058 | 10.3 |
| 27.8 | 3.2 | 2091 | 20.4 |
| 28.1 | 3.2 | 2278 | 22.3 |
| 28.7 | 3.1 | 934 | 9.1 |
| 28.9 | 3.1 | 1433 | 14.0 |

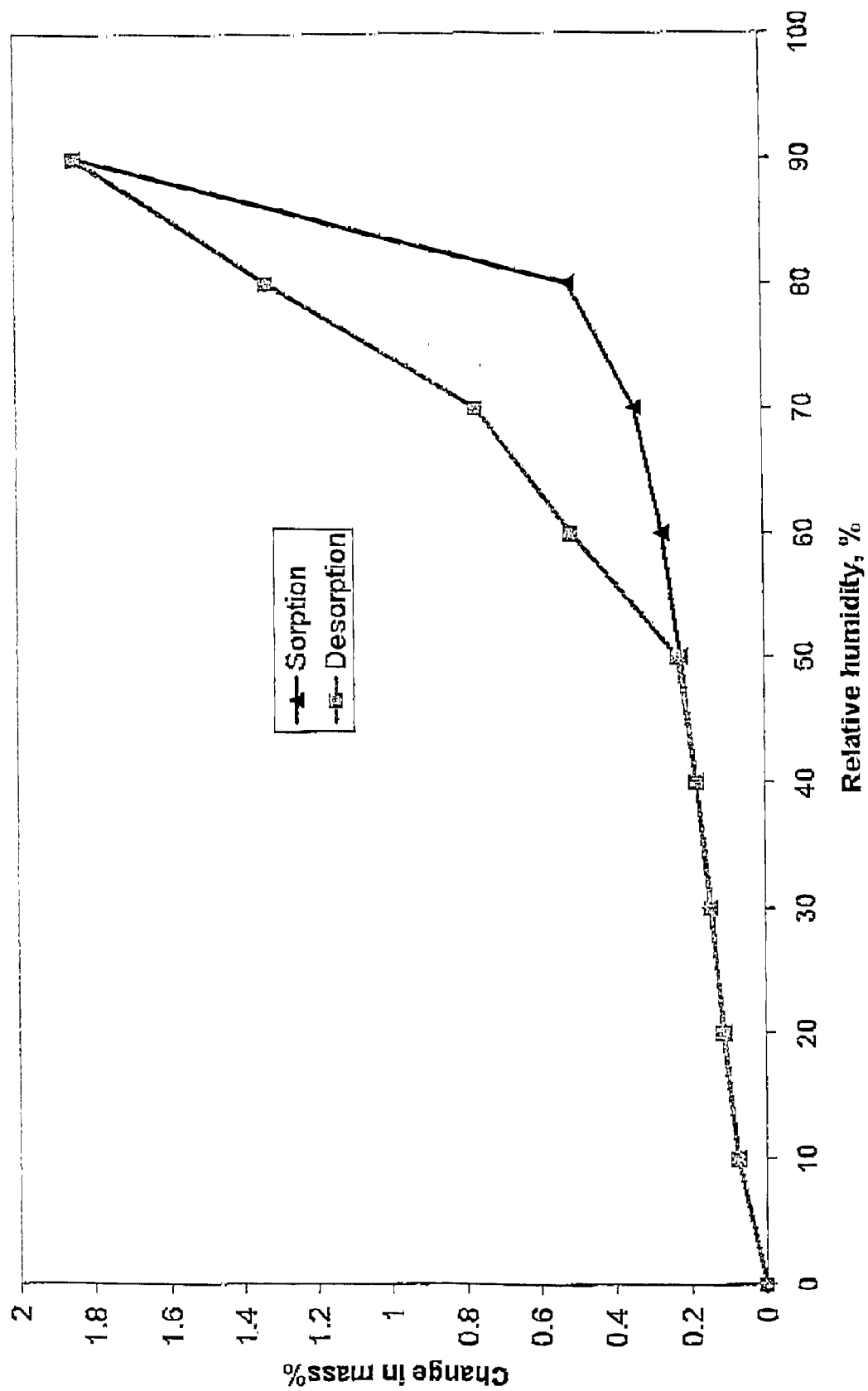
Figure 15- DVS isothermal analysis of 5-(4-acetyl-1,4-diazepan-1-yl)-N-(5-(4-methoxyphenyl)-1H-pyrazol-3-yl)pentanamide hydrochloric salt Form I

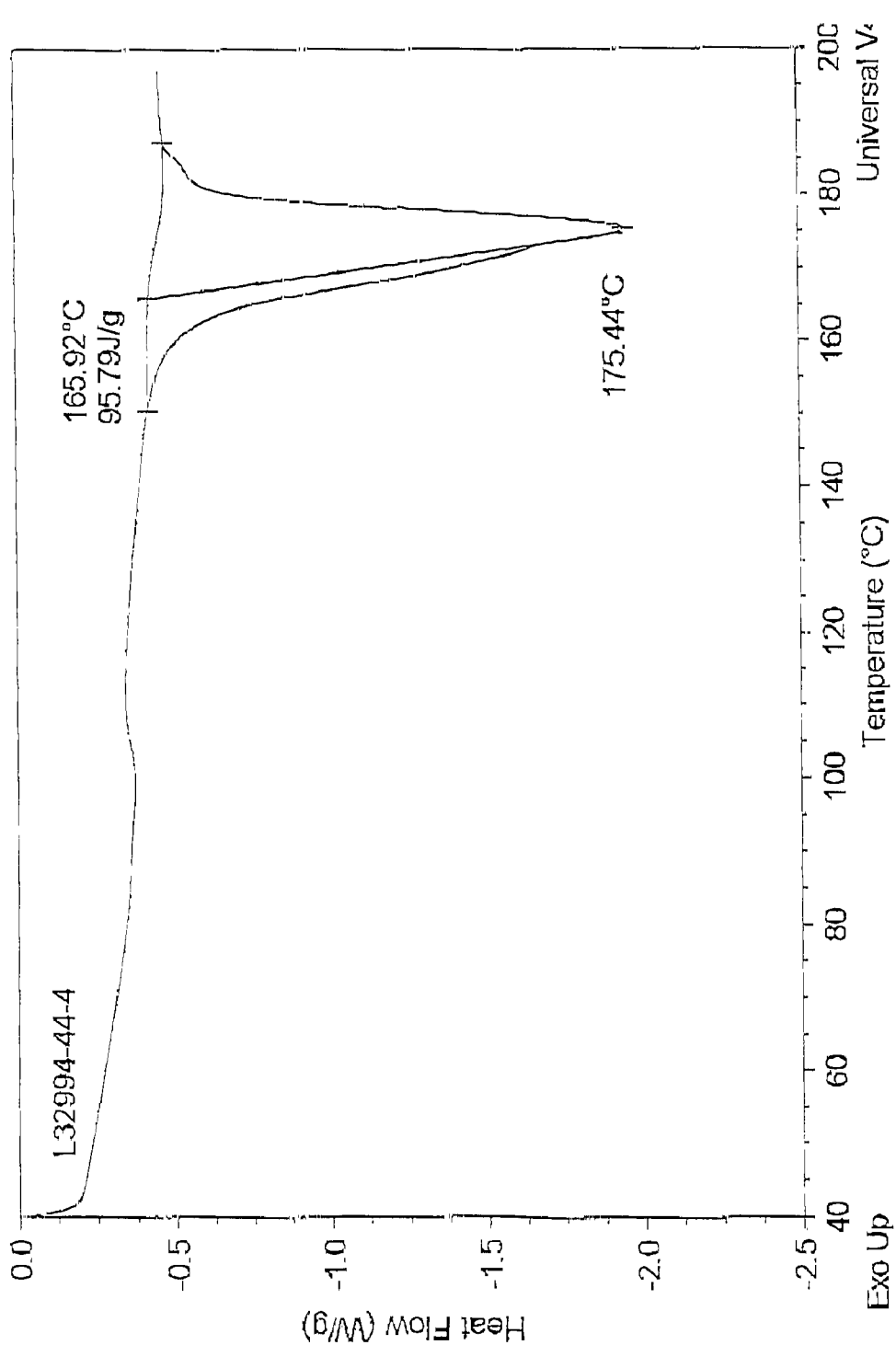
Figure 16- DSC scan of 5-(4-acetyl-1,4-diazepan-1-yl)-N-(5-(4-methoxyphenyl)-1H-pyrazol-3-yl)pentanamide hydrochloric salt Form II

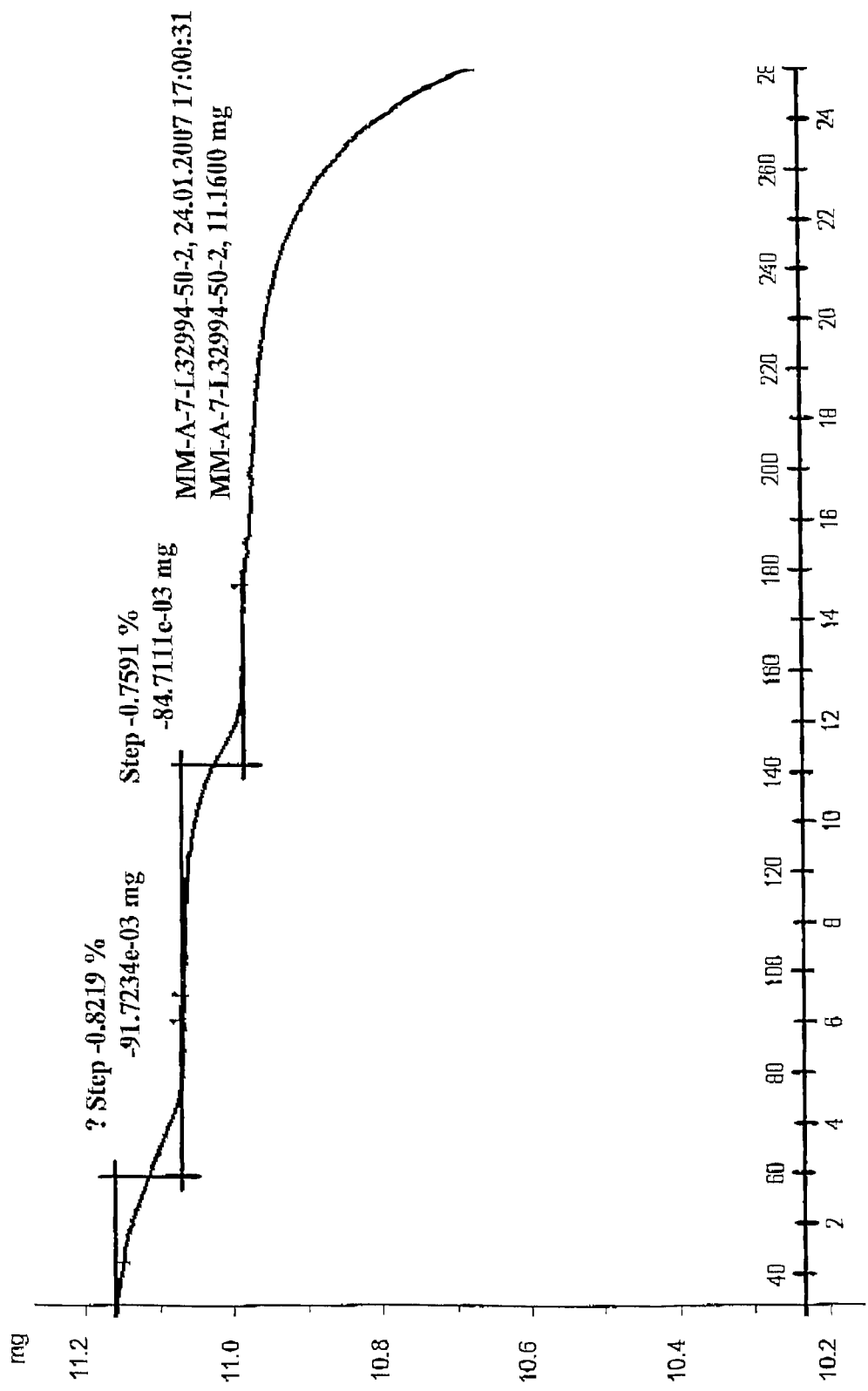
Figure 17 - TGA thermogram of 5-(4-acetyl-1,4-diazepan-1-yl)-N-(5-(4-methoxyphenyl)-1H-pyrazol-3-yl)pentanamide hydrochloric salt Form II

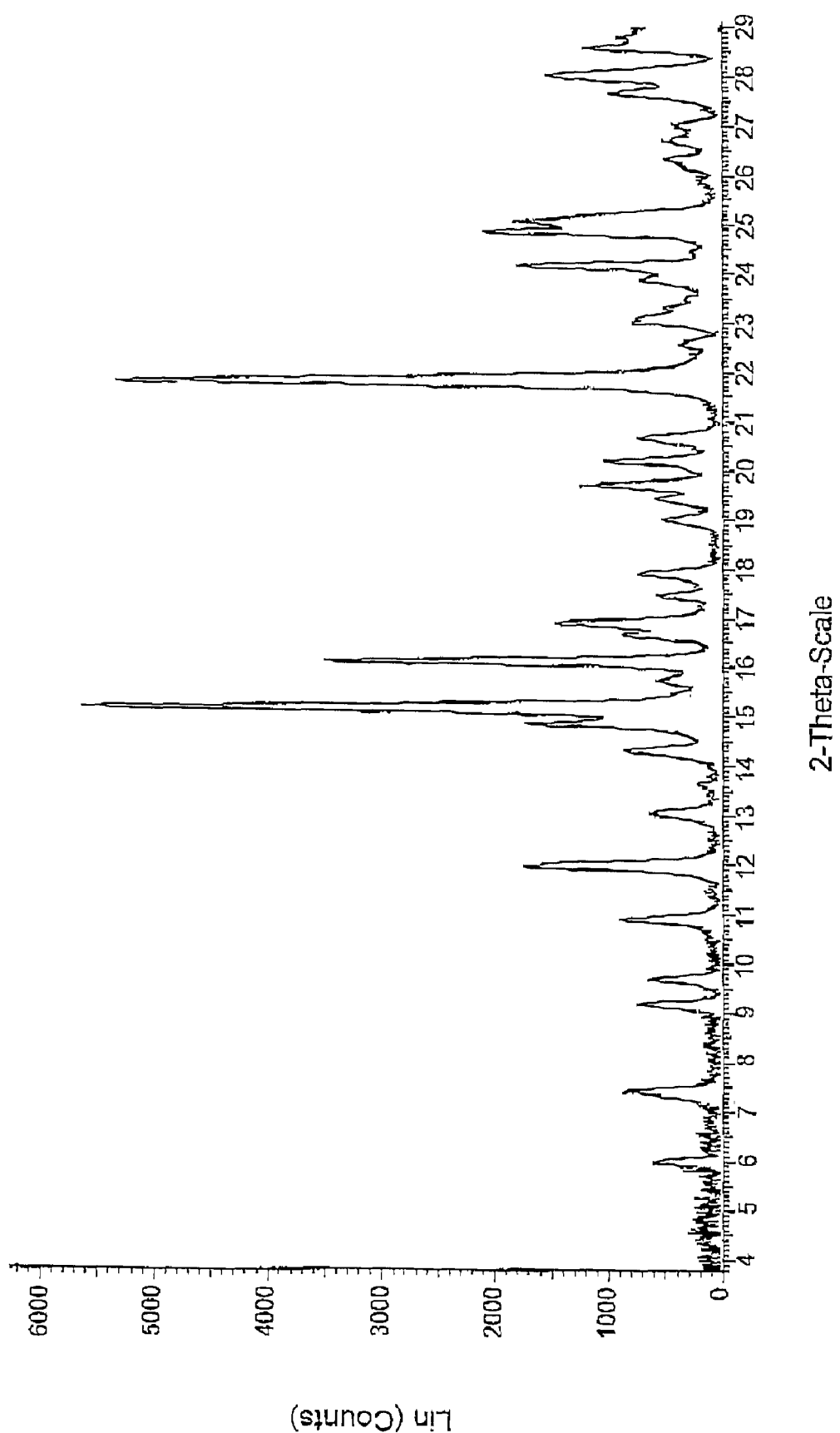
Figure 18- X-ray diffraction pattern of 5-(4-acetyl-1,4-diazepan-1-yl)-N-(5-(4-methoxyphenyl)-1H-pyrazol-3-yl)pentanamide hydrochloric salt Form II

Figure 18 continued

Table 2 - X-ray diffraction data of 5-(4-acetyl-1,4-diazepan-1-yl)-N-(5-(4-methoxyphenyl)-1H-pyrazol-3-yl)pentanamide hydrochloric salt Form II

| Angle, 2-Theta ° | d value, Angstrom | Intensity, Count | Intensity % |
|---|---|---|---|
| 6.0 | 14.8 | 588 | 10.4 |
| 7.4 | 11.9 | 827 | 14.6 |
| 9.2 | 9.6 | 735 | 13.0 |
| 9.7 | 9.1 | 636 | 11.3 |
| 10.9 | 8.1 | 888 | 15.7 |
| 12.0 | 7.4 | 1741 | 30.8 |
| 13.0 | 6.8 | 625 | 11.1 |
| 14.3 | 6.2 | 849 | 15.0 |
| 14.9 | 6.0 | 1723 | 30.5 |
| 15.2 | 5.8 | 5647 | 100.0 |
| 16.1 | 5.5 | 3506 | 62.1 |
| 16.7 | 5.3 | 855 | 15.1 |
| 16.9 | 5.2 | 1454 | 25.7 |
| 17.5 | 5.1 | 542 | 9.6 |
| 17.9 | 4.9 | 730 | 12.9 |
| 19.0 | 4.7 | 491 | 8.7 |
| 19.5 | 4.6 | 576 | 10.2 |
| 19.7 | 4.5 | 1239 | 21.9 |
| 20.2 | 4.4 | 1032 | 18.3 |
| 20.7 | 4.3 | 727 | 12.9 |
| 21.9 | 4.1 | 5332 | 94.4 |
| 22.6 | 3.9 | 358 | 6.3 |
| 23.1 | 3.8 | 747 | 13.2 |
| 23.9 | 3.7 | 706 | 12.5 |
| 24.2 | 3.7 | 1791 | 31.7 |
| 24.9 | 3.6 | 2089 | 37.0 |
| 25.1 | 3.5 | 1828 | 32.4 |
| 26.4 | 3.4 | 495 | 8.8 |
| 26.7 | 3.3 | 500 | 8.9 |
| 27.7 | 3.2 | 989 | 17.5 |
| 28.1 | 3.2 | 1527 | 27.0 |
| 28.7 | 3.1 | 1204 | 21.3 |
| 29.0 | 3.1 | 762 | 13.5 |
| 29.8 | 3.0 | 390 | 6.9 |

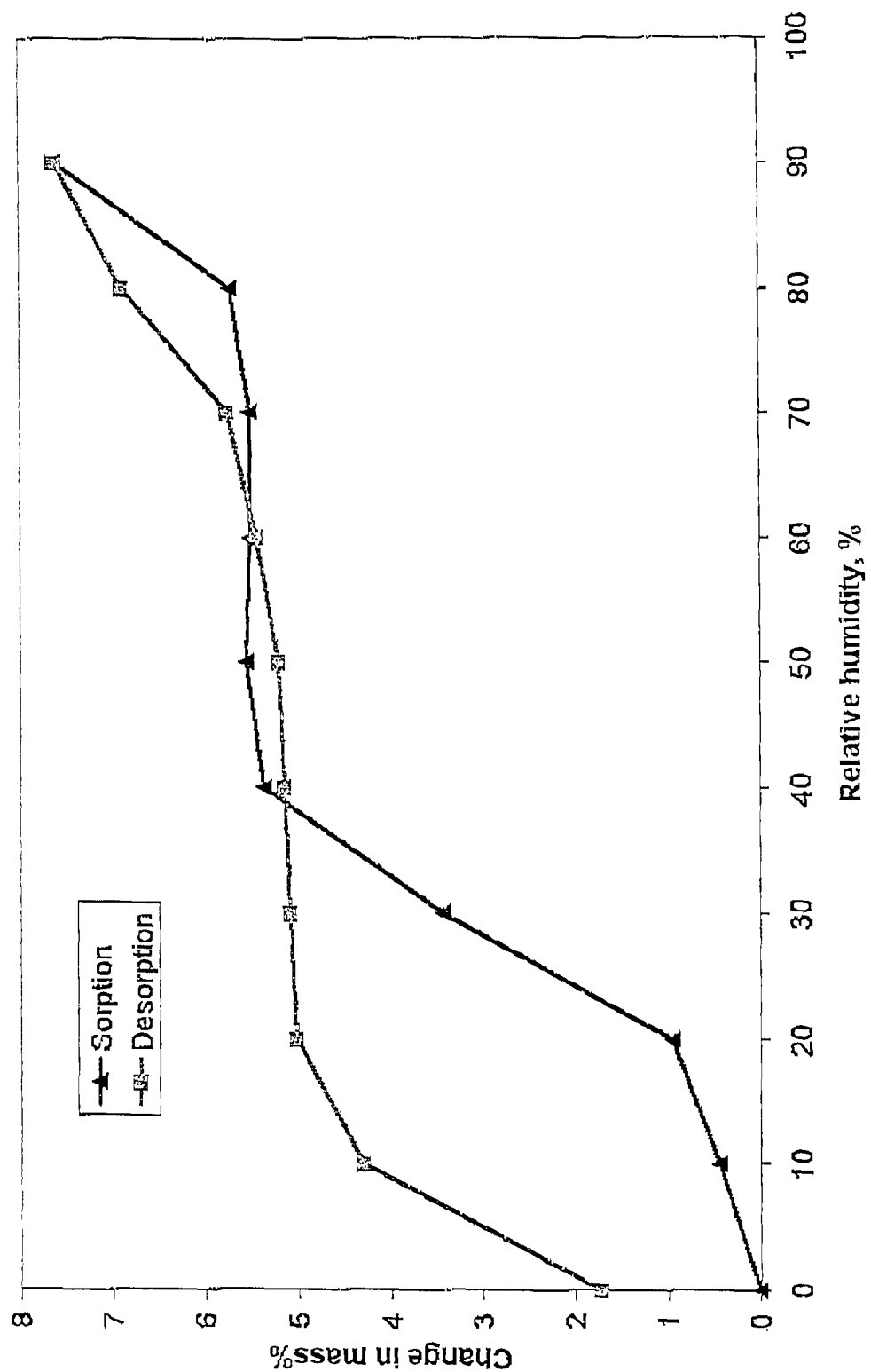
Figure 19- DVS isothermal analysis of 5-(4-acetyl-1,4-diazepan-1-yl)-N-(5-(4-methoxyphenyl)-1H-pyrazol-3-yl)pentanamide hydrochloric salt Form II

US 8,163,729 B2

MODULATORS OF α7 NICOTINIC ACETYLCHOLINE RECEPTORS AND THERAPEUTIC USES THEREOF

RELATED APPLICATIONS

The present application is a U.S. national phase application under 35 U.S.C. §371 of international PCT application no. PCT/IB08/00090, filed Jan. 16, 2008, which claims the benefit of priority of prior-filed United States patent application Ser. No. 60/880,629, filed Jan. 16, 2007, the entire contents of which is incorporated herein by reference.

FIELD OF THE INVENTION

The present invention relates to compounds with α7 nicotinic acetylcholine receptor (α7 nAChR) agonistic activity, processes for their preparation, pharmaceutical compositions containing the same and the use thereof for the treatment of neurological, psychiatric, inflammatory diseases.

BACKGROUND OF THE INVENTION

Agents that bind to nicotinic acetylcholine receptors have been indicated as useful in the treatment and/or prophylaxis of various diseases and conditions, particularly psychotic diseases, neurodegenerative diseases involving a dysfunction of the cholinergic system, and conditions of memory and/or cognition impairment, including for example, schizophrenia, anxiety, mania, depression, manic depression, Tourette's syndrome, Parkinson's disease, Huntington's disease, cognitive disorders (such as Alzheimer's disease, Levy Body Dementia, Amyotrophic Lateral Sclerosis, memory impairment, memory loss, cognition deficit, attention deficit, Attention Deficit Hyperactivity Disorder), and other uses such as treatment of nicotine addiction, inducing smoking cessation, treating pain (e.g. analgesic use), providing neuroprotection, and treating jetlag. See for example WO 97/30998; WO 99/03850; WO 00/42044; WO 01/36417; Holladay et al., *J. Med. Chem.*, 40:26, 4169-94 (1997); Schmitt et al., *Annual Reports Med. Chem.*, Chapter 5, 41-51 (2000); Stevens et al., *Psychopharmacology*, (1998) 136: 320-27; and Shytle et al., *Molecular Psychiatry*, (2002), 7, pp. 525-535.

Different heterocyclic compounds carrying a basic nitrogen and exhibiting nicotinic and muscarinic acetylcholine receptor affinity or claimed for use in Alzheimer disease have been described, e.g. 1H-pyrazole and pyrrole-azabicyclic compounds (WO2004013137); nicotinic acetylcholine agonists (WO2004039366); ureido-pyrazole derivatives (WO0112188); oxadiazole derivatives having acetylcholinesterase-inhibitory activity and muscarinic agonist activity (WO9313083); pyrazole-3-carboxylic acid amide derivatives as pharmaceutical compounds (WO2006077428); arylpiperidines (WO2004006924); ureidoalkylpiperidines (U.S. Pat. No. 6,605,623); compounds with activity on muscarinic receptors (WO9950247). In addition, modulators of alpha7 nicotinic acetylcholine receptor are disclosed in WO06008133, in the name of the same applicant.

SUMMARY

Among other things, the invention provides novel compounds acting as full or partial agonists at the α7 nicotinic acetylcholine receptor (α7 nAChR), pharmaceutical compositions containing the same compounds and the use thereof for the treatment of diseases that may benefit from the activation of the alpha 7 nicotinic acetylcholine receptor such as neurological, neurodegenerative, psychiatric, cognitive, immunological, inflammatory, metabolic, addiction, nociceptive, and sexual disorders, in particular Alzheimer's disease, schizophrenia, and/or others.

BRIEF DESCRIPTION OF THE DRAWING

FIG. 1: X-ray patterns of various crystal forms of hyrochloric salt.
FIG. 2: DSC scan of various crystal forms of hydrochloric salt.
FIG. 3: TGA of various crystal forms of hydrochloric salt.
FIG. 4: DVS of mono-HCl salt (NO form change after DVS test).
FIG. 5: DVS of hydrochloric salt (crystal II) (NO form change after DVS).
FIG. 6: DVS of hydrochloric salt (crystal III) (data from pre-selection minute);
FIG. 7: DVS of hydrochloric salt (crystal V).
FIG. 8: Effect of pH and HCl equivalence on HCl salt formation.
FIG. 9: Effect of pH and HCl equivalence on HCl salt formation.
FIG. 10: Conversion of higher salts to mono-HCl crystal I 259 mg di-HCl salt was slurried in 4 volumes acetone +0.5 volume ethanol ASDQ at room temperature. The resulting slurry gave a pH of 2. To increase the pH, 0.02 mL NaOH 30% was added which increased the pH to 5-5.5. The slurry was stirred overnight and converted to mono-HCl. 173 mg mono-HCl was obtained.
FIG. 11: Conversion of mono-HCl to Form II by decreasing the pH (slurried overnight).
FIG. 12: DSC scan of 5-(4-acetyl-1,4-diazepan-1-yl)-N-(5-(4-methoxyphenyl)-1H-pyrazol-3-yl)pentanamide hydrochloric salt Form I.
FIG. 13: TGA thermogram of 5-(4-acetyl-1,4-diazepan-1-yl)-N-(5-(4-methoxyphenyl)-1H-pyrazol-3-yl)pentanamide hydrochloric salt Form I.
FIG. 14: X-ray diffraction pattern of 5-(4-acetyl-1,4-diazepan-1-yl)-N-(5-(4-methoxyphenyl)-1H-pyrazol-3-yl)pentanamide hydrochloric salt Form I.
FIG. 15: DVS isothermal analysis of 5-(4-acetyl-1,4-diazepan-1-yl)-N-(5-(4-methoxyphenly)-1H-pyrazol-3-yl)pentanamide hydrochloric salt Form I.
FIG. 16: DSC scan of 5-(4-acetyl-1,4-diazepan-1-yl)-N-(5-(4-methoxyphenyl)-1H-pyrazol-3-yl)pentanamide hydrochloric salt Form II.
FIG. 17: TGA thermogram of 5-(4-acetyl-1,4-diazepan-1-yl)-N-(5-(4-methoxyphenyl)-1H-pyrazol-3-yl)pentanamide hydrochloric salt Form II.
FIG. 18: X-ray diffraction pattern of 5-(4-acetyl-1,4-diazepan-1-yl)-N-(5-(4-methoxyphenly)-1H-pyrazol-3-yl)pentanmide hydrochloric salt Form II.
FIG. 19: DVS isothermal analysis of 5-(4-acetyl-1,4-diazepan-1-yl)-N-(5-(4-methoxyphenyl)-1H-pyrazol-3-yl)pentanamide hydrochloric salt Form II.

DESCRIPTION OF CERTAIN PARTICULAR EMBODIMENTS

Compounds
In a first aspect, the invention provides a compound of Formula (I):

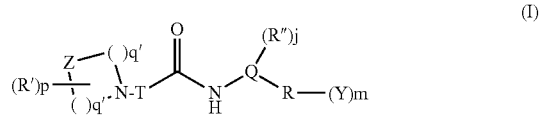

wherein

T is a (C3-C5) alkane-α,ω-diyl or alkene-α,ω-diyl, optionally carrying an oxo group and optionally substituted with one or more halogens; hydroxy groups; (C1-C5) alkyl, alkoxy, fluoroalkyl, hydroxyalkyl, alkylidene, fluoroalkylidene groups; (C3-C6) cycloalkane-1,1-diyl, oxacycloalkane-1,1-diyl groups; (C3-C6) cycloalkane-1,2-diyl, oxacycloalkane-1,2-diyl groups, where the bonds of the 1,2-diyl radical form a fused ring with the T chain; and with the proviso that when T carries an oxo group this is not part of an amide bond;

z is CH$_2$, N, O, S, S(═O), or S(═O)2;

q and q' are, independently from one another, integers from 1 to 4, with the proviso that the sum of q+q' is no greater than 6;

p is 0, 1, or 2;

R', independently from one another for p=2, is selected from the group consisting of mono- or di- [linear, branched or cyclic (C1-C6) alkyl]aminocarbonyl; linear, branched or cyclic (C1-C6) alkyl, alkoxy, acyl;

Q is a group of Formula

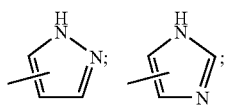

R" is C1-C3 alkyl;

j is 0 or 1;

R is a 5- to 10-member aromatic or heteroaromatic ring;

m is 0, 1, 2, or 3;

Y represents, independently from one another when m is greater than 1, halogen; hydroxy; mercapto; cyano; nitro; amino; linear, branched or cyclic (C1-C6) alkyl, trihaloalkyl, di- or trihaloalkoxy, alkoxy, or alkylcarbonyl; (C3-C6) cycloalkyl-(C1-C6) alkoxy; (C3-C6) cycloalkyl-(C1-C6) alkyl; linear, branched, or cyclic (C1-C6) alkylcarbonylamino; mono- or di-, linear, branched, or cyclic (C1-C6) alkylaminocarbonyl; carbamoyl; linear, branched, or cyclic (C1-C6) alkylsulphonylamino; linear, branched, or cyclic (C1-C6) alkylsulphonyl; mono- or di-, linear, branched, or cyclic (C1-C6) alkylsulphamoyl; linear, branched or cyclic (C1-C6) alkoxy-(C1-C6) alkyl; or, when m=2, two Y substituents, together with the atoms of the R group they are attached to, may form a ring.

In a first preferred embodiment, the invention provides compounds of Formula (I) wherein:

T is butane-1,4-diyl optionally substituted with one or more (C1-C3) alkyl, halogen;

z is N or O;

R', independently from one another for p=2, is selected from the group consisting of mono- or di- [linear, branched or cyclic (C1-C6) alkyl]aminocarbonyl; linear, branched or cyclic (C1-C6) alkyl, alkoxy, acyl;

Q is

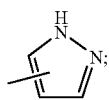

p, q, q', R", j, R, Y and m being as defined under Formula (I);

In this embodiment, particularly preferred compounds of Formula (I) are those in which:

T is butane-1,4-diyl;

z is N or O;

R' is selected from the group consisting of linear, branched or cyclic (C1-C6) alkyl, alkoxy, acyl;

p is 0 or 1;

Q is

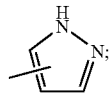

j is 0;

R is a 5- to 10-member aromatic or heteroaromatic ring;

q, q', R, Y and m are as defined under Formula (I);

Another group of particularly preferred compounds are those in which:

T is butane-1,4-diyl;

z is N;

p is 1;

R' is (C1-C6) acyl;

Q is

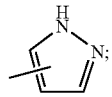

j is 0;

R is phenyl, pyridyl, thienyl; indolyl;

m is 0, 1 or 2;

Y represents, independently from one another when m is greater than 1, halogen; hydroxy; linear, branched or cyclic (C1-C6) alkyl, trihaloalkyl, di- or trihaloalkoxy, alkoxy;(C3-C6) cycloalkyl-(C1-C6) alkyl;

q, q' are as defined under Formula (I);

In a further preferred embodiment, the invention provides compounds, hereafter referred to as G1 of Formula (I), wherein:

T is propane-1,3-diyl optionally substituted with (C1-C3) alkyl, halogen;

z is CH$_2$, N, O;

Q is a group of Formula

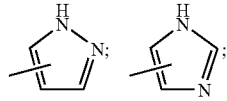

R', p, q, q', R", j, R, Y and m being as defined under Formula (I);

Within G1, particularly preferred compounds of Formula (I) are those in which

T is propane-1,3-diyl optionally substituted with (C1-C3) alkyl, halogen;

z is CH$_2$;

Q is

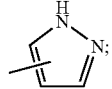

q and q' are, independently from one another, 1 or 2;

p is 0 or 1;

R' is selected from the group consisting of linear, branched or cyclic (C1-C6) alkyl, alkoxy, acyl;
j is 0;
R, Y and m are as defined under Formula (I);
Within G1, another group of particularly preferred compounds are those, in which:
T is propane-1,3-diyl;
z is CH$_2$;
q and q' are, independently from one another, 1 or 2;
p is 0 or 1;
R' is selected from the group consisting of linear, branched or cyclic (C1-C6) alkyl;
Q is

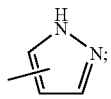

j is 0;
R is phenyl, pyridyl, naphthyl;
m is 1 or 2;
Y represents, independently from one another when m is greater than 1, halogen; hydroxy; linear, branched or cyclic (C1-C6) alkyl, trihaloalkyl, di- or trihaloalkoxy, alkoxy; (C3-C6) cycloalkyl-(C1-C6) alkoxyl.
Within this group, certain inventive compounds are those in which Q-R is

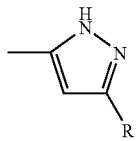

Within G1 falls another group of preferred compounds of formula (I) in which
T is propane-1,3-diyl optionally substituted with (C1-C3) alkyl, halogen;
z is CH$_2$;
Q is

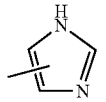

q and q' are, independently from one another, 1 or 2;
p is 0 or 1;
R' is selected from the group consisting of linear, branched or cyclic (C1-C6) alkyl, alkoxy, acyl;
j is 0;
R, Y and m are as defined under Formula (I);
A fourth group of preferred compounds under G1 are those in which
T is propane-1,3-diyl;
z is CH$_2$;
q and q' are, independently from one another, 1 or 2;
p is 0 or 1;
R' is selected from the group consisting of linear, branched or cyclic (C1-C6) alkyl;
Q is

j is 0;
R is phenyl, pyridyl, naphthyl;
m is 1 or 2;

Y represents, independently from one another when m is greater than 1, halogen; hydroxy; linear, branched or cyclic (C1-C6) alkyl, trihaloalkyl, di- or trihaloalkoxy, alkoxy; (C3-C6) cycloalkyl-(C1-C6) alkoxyl.
Within this group, utmost preferred compounds are those in which Q-R is

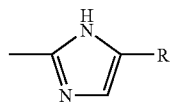

As will be readily apparent to one skilled in the art, the unsubstituted ring nitrogen pyrazoles and imidazoles, as in the compounds of the present invention, are known to rapidly equilibrate in solution, as mixtures of both tautomers:

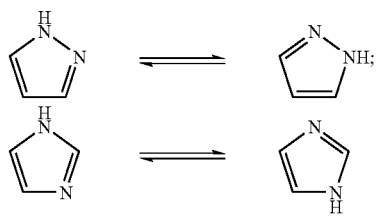

in the following description therefore, where only one tautomer is indicated for compounds of Formula (I), the other tautomer is also intended as within the scope of the present invention.

Compounds of the invention can be in the form of free bases or acid addition salts, preferably salts with pharmaceutically acceptable acids. The invention also provides separated isomers and diastereoisomers of compounds of Formula (I), or mixtures thereof (e.g. racemic and diastereomeric mixtures), as well as isotopic compositions.

Pharmacological activity of a representative group of compounds of Formula (I) was demonstrated in an in vitro assay utilising cells stably transfected with the alpha 7 nicotinic acetylcholine receptor and cells expressing the alpha 1 and alpha 3 nicotinic acetylcholine receptors and 5HT3 receptor as controls for selectivity.

Compounds of Formula (I) may be provided according to the present invention in any of a variety of useful forms, for example as pharmaceutically acceptable salts, as particular crystal forms, etc. In some embodiments, prodrugs of one or more compounds of Formula (I) are provided. Various forms of prodrugs are known in the art, for example as discussed in Bundgaard (ed.), *Design of Prodrugs,* Elsevier (1985); Widder et al. (ed.), *Methods in Enzymology,* vol. 4, Academic Press (1985); Kgrogsgaard-Larsen et al. (ed.); "*Design and Application of Prodrugs*", Textbook of Drug Design and Development, Chapter 5, 113-191 (1991); Bundgaard et al., *Journal of Drug Delivery Reviews,* 8:1-38 (1992); Bundgaard et al., *J. Pharmaceutical Sciences,* 77:285 et seq. (1988); and Higuchi and Stella (eds.), *Prodrugs as Novel Drug Delivery Systems,* American Chemical Society (1975).

Uses

Agents that bind to nicotinic acetylcholine receptors have been indicated as useful in the treatment and/or prophylaxis of various diseases and conditions, particularly psychotic diseases, neurodegenerative diseases involving a dysfunction of the cholinergic system, and conditions of memory and/or cognition impairment, including, for example, schizophrenia, anxiety, mania, depression, manic depression, Tourette's syndrome, Parkinson's disease, Huntington's disease, cognitive disorders (such as Alzheimer's disease, Lewy Body Dementia, Amyotrophic Lateral Sclerosis, memory impairment, memory loss, cognition deficit, attention deficit, Attention Deficit Hyperactivity Disorder), and other uses such as treatment of nicotine addiction, inducing smoking cessation, treating pain (i.e., analgesic use), providing neuroprotection, and treating jetlag. See, e.g., WO 97/30998; WO 99/03850; WO 00/42044; WO 01/36417; Holladay et al., J. Med. Chem., 40:26, 4169-94 (1997); Schmitt et al., Annual Reports Med. Chem., Chapter 5, 41-51 (2000); Stevens et al., Psychopharmatology, (1998) 136: 320-27; and Shytle et al., Molecular Psychiatry, (2002), 7, pp. 55-535.

Thus, in accordance with the invention, there is provided a method of treating a patient, especially a human, suffering from any of psychotic diseases, neurodegenerative diseases involving a dysfunction of the cholinergic system, and/or conditions of memory and/or cognition impairment, including, for example, schizophrenia, anxiety, mania, depression, manic depression, Tourette's syndrome, Parkinson's disease, Huntington's disease, and/or cognitive disorders (such as Alzheimer's disease, Lewy Body Dementia, Amyotrophic Lateral Sclerosis, memory impairment, memory loss, cognition deficit, attention deficit, Attention Deficit Hyperactivity Disorder) comprising administering to the patient an effective amount of a compound according to Formula (I).

Neurodegenerative disorders whose treatment is included within the methods of the present invention include, but are not limited to, treatment and/or prophylaxis of Alzheimer's diseases, Pick's disease (Friedland, Dementia, (1993) 192-203; Procter, Dement Geriatr Cogn Disord. (1999) 80-4; Sparks, Arch Neurol. (1991) 796-9; Mizukami, Acta Neuropathol. (1989) 52-6; Hansen, Am J Pathol. (1988) 507-18), diffuse Lewy Body disease, progressive supranuclear palsy (Steel-Richardson syndrome, see Whitehouse, J Neural Transm Suppl. (1987) 24:175-82; Whitehouse, Arch Neurol. (1988) 45(7):722-4; Whitehouse, Alzheimer Dis Assoc Disord. 1995; 9 Suppl 2:3-5; Warren, Brain. 2005 February; 128(Pt 2):239-49), multisystem degeneration (Shy-Drager syndrome), motor neuron diseases including amyotrophic lateral sclerosis (Nakamizo, Biochem Biophys Res Commun. (2005) 330(4), 1285-9; Messi, FEBS Lett. (1997) 411(1):32-8; Mohammadi, Muscle Nerve. (2002) October; 26(4):539-45; Hanagasi, Brain Res Cogn Brain Res. (2002) 14(2):234-44; Crochemore, Neurochem Int. (2005) 46(5):357-68), degenerative ataxias, cortical basal degeneration, ALS-Parkinson's-Dementia complex of Guam, subacute sclerosing panencephalitis, Huntington's disease (Kanazawa, J Neurol Sci. (1985) 151-65; Manyam, J Neurol. (1990) 281-4; Lange, J Neurol. (1992) 103-4; Vetter, J Neurochem. (2003) 1054-63; De Tommaso, Mov Disord. (2004) 1516-8; Smith, Hum Mol Genet. (2006) 3119-31; Cubo, Neurology. (2006) 1268-71), Parkinson's disease, synucleinopathies, primary progressive aphasia, striatonigral degeneration, Machado-Joseph disease/spinocerebellar ataxia type 3, olivopontocerebellar degenerations, Gilles De La Tourette's disease, bulbar, pseudobulbar palsy, spinal muscular atrophy, spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, prion diseases (such as Creutzfeldt-Jakob, Gerstmann-Straussler-Scheinker disease, Kuru and fatal familial insomnia), and neurodegenerative disorders resulting from cerebral ischemia or infarction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

In addition, α7nACh receptor agonists, such as the compounds of the present invention can be used to treat age-related dementia and other dementias and conditions with memory loss including age-related memory loss, senility, vascular dementia, diffuse white matter disease (Binswanger's disease), dementia of endocrine or metabolic origin, dementia of head trauma and diffuse brain damage, dementia pugilistica, alcoholism related dementia (Korsakoff Syndrome) and frontal lobe dementia. See, e.g., WO 99/62505., Tomimoto Dement Geriatr Cogn Disord. (2005), 282-8; Tohgi—J Neural Transm. (1996), 1211-20; Casamenti, Neuroscience (1993) 465-71, Kopelman, Br J Psychiatry (1995) 154-73; Cochrane, Alcohol Alcohol. (2005) 151-4).

Amyloid precursor protein (APP) and Aβ peptides derived therefrom, e.g., Aβ1-42 and other fragments, are known to be involved in the pathology of Alzheimer's disease. The Aβ1-42 peptides are not only implicated in neurotoxicity but also are known to inhibit cholinergic transmitter function. Further, it has been determined that Aβ peptides bind to α7nACh receptors. The inflammatory reflex is an autonomic nervous system response to an inflammatory signal. Upon sensing an inflammatory stimulus, the autonomic nervous system responds through the vagus nerve by releasing acetylcholine and activating nicotinic α7 receptors on macrophages. These macrophages in turn release cytokines. Dysfunctions in this pathway have been linked to human inflammatory diseases including rheumatoid arthritis, diabetes and sepsis. Macrophages express the nicotinic α7 receptor and it is likely this receptor that mediates the cholinergic anti-inflammatory response. See for example Czura, C J et al., J. Intern. Med., (2005) 257(2), 156-66; Wang, H. et al Nature (2003) 421: 384-388; de Jonge British Journal of Pharmacology, (2007) 151, 915-929. The mammalian sperm acrosome reaction is an exocytosis process important in fertilization of the ovum by sperm. Activation of an α7 nAChR on the sperm cell has been shown to be essential for the acrosome reaction (Son, J.-H. and Meizel, S. Biol. Reproduct. 68: 1348-1353, 2003). In addition, nicotinic receptors have been implicated as playing a role in the body's response to alcohol ingestion. α7nACh receptor agonists such as compounds provided herein, therefore, are also useful in the treatment of these disorders, diseases, and conditions.

For example, agonists for the α7nACh receptor subtypes can also be used in the treatment of nicotine addiction, inducing smoking cessation, treating pain, and treating jetlag, obesity, diabetes, sexual and fertility disorders (eg. Premature ejaculation or vaginal dryness, see U.S. Pat. No. 6,448,276), drug abuse (Solinas, Journal of Neuroscience (2007) 27(21), 5615-5620), and inflammation (Wang H, et al. (2003) Nature 421:384-388).

A number of recent observations point to a potential neuroprotective effect of nicotine in a variety of neurodegeneration models in animals and in cultured cells, involving excitotoxic insults (Prendergast, M. A., et al. Med. Sci. Monit. (2001), 7, 1153-1160; Garrido, R., et al. (2001), J. Neurochem. 76, 1395-1403; Semba, J., et al. (1996) Brain Res. 735, 335-338; Shimohama, S., et al.(1996), Ann. N.Y. Acad. Sci. 777, 356-361; Akaike, A., et al. (1994) Brain Res. 644, 181-187), trophic deprivation (Yamashita, H., Nakamura, S. (1996) Neurosci. Lett. 213, 145-147), ischemia (Shimohama, S. (1998) *Brain Res.* 779, 359-363), trauma (Socci, D. J., Arendash, G. W. (1996) *Mol. Chem. Neuropathol.* 27, 285-305), Aβ-mediated neuronal death (Rusted, J. M., et al. (2000) *Behav. Brain Res.* 113, 121-129; Kihara, T., et al. (1997) *Ann. Neurol.* 42, 159-163; Kihara, T., et al. (2001) *J. Biol. Chem.* 276, 13541-13546) and protein-aggregation mediated neuronal degeneration (Kelton, M. C. et al. (2000) *Brain Cogn* 43, 274-282). In many instances where nicotine displays a neuroprotective effect, a direct involvement of receptors comprising the α7 subtype has been invoked (Shimohama, S. et al. (1998) *Brain Res.* 779, 359-363; Kihara, T., et al. (2001) *J. Biol. Chem.* 276, 13541-13546; Kelton, M. C., et al. (2000) *Brain Cogs* 43, 274-282; Kem, W. R. (2000) *Behav. Brain Res.* 113, 169-181; Dajas-Bailador, F. A., et al. (2000) Neuropharmacology 39, 2799-2807; Strahlendorf, J. C., et al. (2001) Brain Res. 901, 71-78) suggesting that activation of α7 subtype-containing nicotinic acetylcholine receptors may be instrumental in mediating the neuroprotective effects of nicotine. Available data suggest that the α7 nicotinic acetylcholine receptor represents a valid molecular target for the development of agonists/positive modulators active as neuroprotective molecules. Indeed, α7 nicotinic receptor agonists have already been identified and evaluated as possible leads for the development of neuroprotective drugs (Jonnala, R. R., et al. (2002) *Life Sci.* 70, 1543-1554; Bencherif, M., et al. (2000) *Eur. J. Pharmacol.* 409, 45-55; Donnelly-Roberts, D. L., et al. (1996) *Brain Res.* 719, 36-44; Meyer, E. M., et al. (1998) *J. Pharmacol. Exp. Ther.* 284, 1026-1032; Stevens, T. R., et al. (2003) *J. Neuroscience* 23, 10093-10099). Compounds described herein can be used to treat such diseases.

In accordance with the invention, there is provided a method of treating a patient, especially a human, suffering from age-related dementia and other dementias and conditions with memory loss comprising administering to the patient an effective amount of a compound according to Formula (I).

The present invention includes methods of treating patients suffering from memory impairment due to, for example, mild cognitive impairment due to aging, Alzheimer's disease, schizophrenia, Parkinson's disease, Huntington's disease, Pick's disease, Creutzfeldt-Jakob disease, depression, aging, head trauma, stroke, CNS hypoxia, cerebral senility, multiinfarct dementia and other neurological conditions, as well as HIV and cardiovascular diseases, comprising administering an effective amount of a compound according to Formula (I).

In accordance with an embodiment of the invention there is provided a method of treating and/or preventing dementia in an Alzheimer's patient which comprises administering to the subject a therapeutically effective amount of a compound according to Formula (I) to inhibit the binding of an amyloid beta peptide (preferably, Aβ1-42) with nACh receptors, preferable α7nACh receptors, most preferably, human α7nACh receptors (as well as a method for treating and/or preventing other clinical manifestations of Alzheimer's disease that include, but are not limited to, cognitive and language deficits, apraxias, depression, delusions and other neuropsychiatric symptoms and signs, and movement and gait abnormalities).

The present invention also provides methods for treating other amyloidosis diseases, for example, hereditary cerebral angiopathy, nonneuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis anthropathy, and Finnish and Iowa amyloidosis.

In addition, nicotinic receptors have been implicated as playing a role in the body's response to alcohol ingestion. Thus, agonists for α7nACh receptors can be used in the treatment of alcohol withdrawal and in anti-intoxication therapy. Thus, in accordance with an embodiment of the invention there is provided a method of treating a patient for alcohol withdrawal or treating a patient with anti-intoxication therapy comprising administering to the patient an effective amount of a compound according to Formula (I).

Agonists for the α7nACh receptor subtypes can also be used for neuroprotection against damage associated with strokes and ischemia and glutamate-induced excitotoxicity. Thus, in accordance with an embodiment of the invention there is provided a method of treating a patient to provide for neuroprotection against damage associated with strokes and ischemia and glutamate-induced excitotoxicity comprising administering to the patient an effective amount of a compound according to Formula (I).

Agonists for the α7nACh receptor subtypes can also be used in the treatment of nicotine addiction, inducing smoking cessation, treating pain, and treating jetlag, obesity, diabetes, sexual and fertility disorders (eg. Premature ejaculation or vaginal dryness, see U.S. Pat. No. 6,448,276), drug abuse (Solinas, Journal of Neuroscience (2007) 27(21), 5615-5620), and inflammation. Thus, in accordance with an embodiment of the invention there is provided a method of treating a patient suffering from nicotine addiction, pain, jetlag, obesity and/or diabetes, or a method of inducing smoking cessation in a patient comprising administering to the patient an effective amount of a compound according to Formula (I).

The inflammatory reflex is an autonomic nervous system response to an inflammatory signal. Upon sensing an inflammatory stimulus, the autonomic nervous system responds through the vagus nerve by releasing acetylcholine and activating nicotinic α7 receptors on macrophages. These macrophages in turn release cytokines. Dysfunctions in this pathway have been linked to human inflammatory diseases including rheumatoid arthritis, diabetes and sepsis. Macrophages express the nicotinic α7 receptor and it is likely this receptor that mediates the cholinergic anti-inflammatory response. Therefore, compounds with affinity for the α7nACh receptor on macrophages may be useful for human inflammatory diseases including rheumatoid arthritis, diabetes and sepsis. See, e.g., Czura, C J et al., J. Intern. Med., (2005) 257(2), 156-66, Wang, H. et al Nature (2003) 421: 384-388; de Jonge British Journal of Pharmacology (2007) 151, 915-929.

Thus, in accordance with an embodiment of the invention there is provided a method of treating a patient (e.g., a mammal, such as a human) suffering from an inflammatory disease, such as, but not limited to, rheumatoid arthritis, diabetes or sepsis, comprising administering to the patient an effective amount of a compound according to Formula (I).

The mammalian sperm acrosome reaction is an exocytosis process important in fertilization of the ovum by sperm. Activation of an α7 nAChR on the sperm cell has been shown to be essential for the acrosome reaction (Son, J. -H. and Meizel, S. Biol, Reproduct. 68: 1348-1353 2003). Consequently, selective α7 agents demonstrate utility for treating fertility disorders.

In addition, due to their affinity to α7nACh receptors, labeled derivatives of the compounds of Formula (I) (for example C11 or F18 labeled derivatives), can be used in neuroimaging of the receptors within, e.g., the brain. Thus, using such labeled agents in vivo imaging of the receptors can be performed using, for example PET imaging.

The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntingdon's disease, Pick's disease, Creutzfeldt-Jakob disease, HIV, cardiovascular disease, and head trauma as well as age-related cognitive decline.

Thus, in accordance with an embodiment of the invention there is provided a method of treating a patient suffering from, for example, mild cognitive impairment (MCI), vascular dementia (VaD), age-associated cognitive decline (AACD), amnesia associated w/open-heart-surgery, cardiac arrest, and/or general anesthesia, memory deficits from early exposure of anesthetic agents, sleep deprivation induced cognitive impairment, chronic fatigue syndrome, narcolepsy, AIDS-related dementia, epilepsy-related cognitive impairment, Down's syndrome, Alcoholism related dementia (Korsakoff Syndrome), drug/substance induced memory impairments, Dementia Puglistica (Boxer Syndrome), and animal dementia (e.g., dogs, cats, horses, etc.) comprising administering to the patient an effective amount of a compound according to Formula (I).

Dosage of the compounds for use in therapy may vary depending upon, for example, the administration route, the nature and severity of the disease. In general, an acceptable pharmacological effect in humans may be obtained with daily dosages ranging from 0.01 to 200 mg/kg.

In some embodiments of the present invention, one or more compounds of formula (I) are administered in combination with one or more other other pharmaceutically active agents. The phrase "in combination", as used herein, refers to agents that are simultaneously administered to a subject. It will be appreciated that two or more agents are considered to be administered "in combination" whenever a subject is simultaneously exposed to both (or more) of the agents. Each of the two or more agents may be administered according to a different schedule, it is not required that individual doses of different agents be administered at the same time, or in the same composition. Rather, so long as both (or more) agents remain in the subject's body, they are considered to be administered "in combination".

For example, compounds of Formula (I), in forms as described herein, may be administered in combination with one or more other modulators of α7 nicotinic acetylcholine receptors. Alternatively or additionally, compounds of Formula (I), in forms as described herein, may be administered in combination with one or more other anti-psychotic agents, pain relievers, anti-inflammatories, or other pharmaceutically active agents.

Effective amounts of a wide range of other pharmaceutically active agents are well known to those skilled in the art. However, it is well within the skilled artisan's purview to determine the other pharmaceutically active agent's optimal effective amount range. The compound of Formula (I) and the other pharmaceutically active agent can act additively or, in some embodiments, synergistically. In some embodiments of the invention, where another pharmaceutically active agent is administered to an animal, the effective amount of the compound of Formula (I) is less than its effective amount would be where the other pharmaceutically active agent is not administered. In this case, without being bound by theory, it is believed that the compound of Formula (I) and the other pharmaceutically active agent act synergistically. In some cases, the patient in need of treatment is being treated with one or more other pharmaceutically active agents. In some cases, the patient in need of treatment is being treated with at least two other pharmaceutically active agents.

In some embodiments, the other pharmaceutically active agent is selected from the group consisting of one or more anti-depressant agents, anti-anxiety agents, anti-psychotic agents, or cognitive enhancers. Examples of classes of anti-depressants that can be used in combination with the active compounds of this invention include norepinephrine reuptake inhibitors, selective serotonin reuptake inhibitors (SSRIs), NK-1 receptor antagonists, monoamine oxidase inhibitors (MAOs), reversible inhibitors of monoamine oxidase (RIMAs), serotonin and noradrenaline reuptake inhibitors (SNRIs), corticotropin releasing factor (CRF) antagonists, α-adrenoreceptor antagonists, and atypical antidepressants. Suitable norepinephrine reuptake inhibitors include tertiary amine tricyclics and secondary amine tricyclics. Suitable tertiary amine tricyclics and secondary amine tricyclics include amitriptyline, clomipramine, doxepin, imipramine, trimipramine, dothiepin, butriptyline, iprindole, lofepramine, nortriptyline, protriptyline, amoxapine, desipramine and maprotiline. Suitable selective serotonin reuptake inhibitors include fluoxetine, citolopram, escitalopram, fluvoxamine, paroxetine and sertraline. Examples of monoamine oxidase inhibitors include isocarboxazid, phenelzine, and tranylcypromine. Suitable reversible inhibitors of monoamine oxidase include moclobemide. Suitable serotonin and noradrenaline reuptake inhibitors of use in the present invention include venlafaxine, nefazodone, milnacipran, and duloxetine. Suitable CRF antagonists include those compounds described in International Patent Publication Nos. WO 94/13643, WO 94/13644, WO 94/13661, WO 94/13676 and WO 94/13677. Suitable atypical anti-depressants include bupropion, lithium, nefazodone, trazodone and viloxazine. Suitable NK-1 receptor antagonists include those referred to in International Patent Publication WO 01/77100.

Anti-anxiety agents that can be used in combination with the compounds of Formula (I) include without limitation benzodiazepines and serotonin 1A (5-HT$_{1A}$) agonists or antagonists, especially 5-HT$_{1A}$ partial agonists, and corticotropin releasing factor (CRF) antagonists. Exemplary suitable benzodiazepines include alprazolam, chlordiazepoxide, clonazepam, chlorazepate, diazepam, halazepam, lorazepam, oxazepam, and prazepam. Exemplary suitable 5-HT$_{1A}$ receptor agonists or antagonists include buspirone, flesinoxan, gepirone and ipsapirone.

Anti-psychotic agents that are used in combination with the compounds of Formula (I) include without limitation aliphatic phethiazine, a piperazine phenothiazine, a butyrophenone, a substituted benzamide, and a thioxanthine. Additional examples of such drugs include without limitation haloperidol, olanzapine, clozapine, risperidone, pimozide, aripiprazol, and ziprasidone. In some cases, the drug is an anticonvulsant, e.g., phenobarbital, phenytoin, primidone, or carbamazepine.

Cognitive enhancers that are used in combination with the compounds of Formula (I) include, without limitation, drugs that modulate neurotransmitter levels (e.g., acetylcholinesterase or cholinesterase inhibitors, cholinergic receptor agonists or serotonin receptor antagonists), drugs that modulate the level of soluble Aβ, amyloid fibril formation, or amyloid plaque burden (e.g., γ-secretase inhibitors, β-secretase inhibitors, antibody therapies, and degradative enzymes), and drugs that protect neuronal integrity (e.g., antioxidants, kinase inhibitors, caspase inhibitors, and hormones). Other representative candidate drugs that are co-administered with the compounds of the invention include cholinesterase inhibitors, (e.g., tacrine (COGNEX®), donepezil (ARICEPT®), rivastigmine (EXELON®) galantamine (REMINYL®), metrifonate, physostigmine, and Huperzine A), N-methyl-D-aspartate (NMDA) antagonists and agonists (e.g., dextromethorphan, memantine, dizocilpine maleate (MK-801), xenon, remacemide, eliprodil, amantadine, D-cycloserine, felbamate, ifenprodil, CP-101606 (Pfizer), Delucemine, and compounds described in U.S. Pat. Nos. 6,821,985 and 6,635,270), ampakines (e.g., cyclothiazide, aniracetam, CX-516 (Ampalex®), CX-717, CX-516, CX-614, and CX-691 (Cortex Pharmaceuticals, Inc. Irvine, Calif.), 7-chloro-3-methyl-3-4-dihydro-2H-1,2,4-benzothiadiazine S,S-dioxide (see Zivokovic et al., 1995, *J. Pharmacol. Exp. Therap.*, 272:300-309; Thompson et al., 1995, *Proc. Natl. Acad. Sci. USA*, 92:7667-7671), 3-bicyclo[2,2,1]hept-5-en-2-yl-6-chloro-3,4-dihydro-2H-1,2,4-benzothiadiazine-7-sulfonamide-1,1-dioxide (Yamada, et al., 1993, *J. Neurosc.* 13:3904-3915); 7-fluoro-3-methyl-5-ethyl-1,2,4-benzothiadiazine-S,S-dioxide; and compounds described in U.S. Pat. No. 6,620,808 and International Patent Application Nos. WO 94/02475, WO 96/38414, WO 97/36907, WO 99/51240, and WO 99/42456), benzodiazepine (BZD)/GABA receptor complex modulators (e.g., progabide, gengabine, zaleplon, and compounds described in U.S. Pat. Nos. 5,538,956, 5,260,331, and 5,422,355); serotonin antagonists (e.g., 5HT receptor modulators, $5HT_{1A}$ antagonists or agonists (including without limitation lecozotan and compounds described in U.S. Pat. Nos. 6,465,482, 6,127,357, 6,469,007, and 6,586,436, and in PCT Publication No. WO 97/03982) and $5\text{-}HT_6$ antagonists (including without limitation compounds described in U.S. Pat. Nos. 6,727,236, 6,825,212, 6,995,176, and 7,041,695)); nicotinics (e.g., niacin); muscarinics (e.g., xanomeline, CDD-0102, cevimeline, talsaclidine, oxybutin, tolterodine, propiverine, tropsium chloride and darifenacin); monoamine oxidase type B (MAO B) inhibitors (e.g., rasagiline, selegiline, deprenyl, lazabemide, safinamide, clorgyline, pargyline, N-(2-aminoethyl)-4-chlorobenzamide hydrochloride, and N-(2-aminoethyl)-5(3-fluorophenyl)-4-thiazolecarboxamide hydrochloride); phosphodiesterase (PDE) IV inhibitors (e.g., roflumilast, arofylline, cilomilast, rolipram, RO-20-1724, theophylline, denbufylline, ARIFLO, ROFLUMILAST, CDP-840 (a tri-aryl ethane) CP80633 (a pyrimidone), RP 73401 (Rhone-Poulenc Rorer), denbufylline (SmithKline Beecham), arofylline (Almirall), CP-77,059 (Pfizer), pyrid[2,3d]pyridazin-5-ones (Syntex), EP-685479 (Bayer), T-440 (Tanabe Seiyaku), and SDZ-ISQ-844 (Novartis)); G proteins; channel modulators; immunotherapeutics (e.g., compounds described in U.S. Patent Application Publication No. US 2005/0197356 and US 2005/0197379); anti-amyloid or amyloid lowering agents (e.g., bapineuzumab and compounds described in U.S. Pat. No. 6,878,742 or U.S. Patent Application Publication Nos. US 2005/0282825 or US 2005/0282826); statins and peroxisome proliferators activated receptor (PPARS) modulators (e.g., gemfibrozil (LOPID®), fenofibrate (TRICOR®), rosiglitazone maleate (AVANDIA®), pioglitazone (Actos™), rosiglitazone (Avandia™), clofibrate and bezafibrate); cysteinyl protease inhibitors; an inhibitor of receptor for advanced glycation endproduct (RAGE) (e.g., aminoguanidine, pyridoxaminem carnosine, phenazinediamine, OPB-9195, and tenilsetam); direct or indirect neurotropic agents (e.g., Cerebrolysin®, piracetam, oxiracetam, AIT-082 (Emilieu, 2000, *Arch. Neurol.* 57:454)); beta-secretase (BACE) inhibitors, α-secretase, immunophilins, caspase-3 inhibitors, Src kinase inhibitors, tissue plasminogen activator (TPA) activators, AMPA (alpha-amino-3-hydroxy-5-methyl-4-isoxazolepropionic acid) modulators, M4 agonists, JNK3 inhibitors, LXR agonists, H3 antagonists, and angiotensin IV antagonists. Other cognition enhancers include, without limitation, acetyl-1-carnitine, citicholine, huperzine, DMAE (dimethylaminoethanol), Bacopa monneiri extract, Sage extract, L-alpha glyceryl phosphoryl choline, Ginko biloba and Ginko biloba extract, Vinpocetine, DHA, nootropics including Phenyltropin, Pikatropin (from Creative Compounds, LLC, Scott City, Mo.), besipirdine, linopirdine, sibopirdine, estrogen and estrogenic compounds, idebenone, T-588 (Toyama Chemical, Japan), and FK960 (Fujisawa Pharmaceutical Co. Ltd.). Compounds described in U.S. Pat. Nos. 5,219,857, 4,904,658, 4,624,954 and 4,665,183 are also useful as cognitive enhancers as described herein. Cognitive enhancers that act through one or more of the above mechanisms are also within the scope of this invention.

In some embodiments, the compound of Formula (I) and cognitive enhancer act additively or, in some embodiments, synergistically. In some embodiments, where a cognitive enhancer and a compound of Formula (I) of the invention are co-administered to an animal, the effective amount of the compound or pharmaceutically acceptable salt of the compound of the invention is less than its effective amount would be where the cognitive enhancer agent is not administered. In some embodiments, where a cognitive enhancer and a compound of Formula (I) are co-administered to an animal, the effective amount of the cognitive enhancer is less than its effective amount would be where the compound or pharmaceutically acceptable salt of the invention is not administered. In some embodiments, a cognitive enhancer and a compound of Formula (I) of the invention are co-administered to an animal in doses that are less than their effective amounts would be where they were no co-administered. In these cases, without being bound by theory, it is believed that the compound of Formula (I) and the cognitive enhancer act synergistically.

In some embodiments, the other pharmaceutically active agent is an agent useful for treating Alzheimer's disease or conditions associate with Alzheimer's disease, such as dementia. Exemplary agents useful for treating Alzheimer's disease include, without limitation, donepezil, rivastigmine, galantamine, memantine, and tacrine.

In some embodiments, the compound of Formula (I) is administered together with another pharmaceutically active agent in a single administration or composition.

In some embodiments, a composition comprising an effective amount of the compound of Formula (I) and an effective amount of another pharmaceutically active agent within the same composition can be administered.

In another embodiment, a composition comprising an effective amount of the compound of Formula (I) and a separate composition comprising an effective amount of another pharmaceutically active agent can be concurrently administered. In another embodiment, an effective amount of the compound of Formula (I) is administered prior to or subsequent to administration of an effective amount of another pharmaceutically active agent. In this embodiment, the compound of Formula (I) is administered while the other pharmaceutically active agent exerts its therapeutic effect, or the other pharmaceutically active agent is administered while the compound of Formula (I) exerts its preventative or therapeutic effect.

Thus, in some embodiments, the invention provides a composition comprising an effective amount of the compound of Formula (I) of the present invention and a pharmaceutically acceptable carrier. In some embodiments, the composition further comprises a second pharmaceutically active agent.

In another embodiment, the composition further comprises a pharmaceutically active agent selected from the group consisting of one or more other antidepressants, anti-anxiety agents, anti-psychotic agents or cognitive enhancers. Antidepressants, anti-anxiety agents, anti-psychotic agents and cognitive enhancers suitable for use in the composition include the antidepressants, anti-anxiety agents, anti-psychotic agents and cognitive enhancers provided above.

In another embodiment, the pharmaceutically acceptable carrier is suitable for oral administration and the composition comprises an oral dosage form.

In some embodiments, one or more compounds of Formula (I) is administered in combination with antidepressant drug treatment, antipsychotic drug treatment, and/or anticonvulsant drug treatment.

In certain embodiments, a compound of Formula (I) is administered in combination with one or more selective serotonin reuptake inhibitors (SSRIs) (for example, fluoxetine, citalopram, escitalopram oxalate, fluvoxamine maleate, paroxetine, or sertraline), tricyclic antidepressants (for example, desipramine, amitriptyline, amoxipinie, clomipramiiine, doxepin, imipramine, nortriptyline, protriptyline, trimipramine, dothiepin, butriptyline, iprindole, or lofepramine), aminoketone class compounds (for example, bupropion); in some embodiments, a compound of Formula (I) is administered in combination with a monoamine oxidase inhibitor (MAOI) (for example, phenelzine, isocarboxazid, or tranylcypromine), a serotonin and norepinepherine reuptake inhibitor (SNRI) (for example, venlafaxine, nefazodone, milnacipran, duloxetine), a norepinephrine reuptake inhibitor (NRI) (for example, reboxetine), a partial $5\text{-HT}_{1A}$ agonist (for example, buspirone), a $5\text{-HT}_{2A}$ receptor antagonist (for example, nefazodone), a typical antipsychotic drug, or an atypical antipsychotic drug. Examples of such antipsychotic drugs include aliphatic phethiazine, a piperazine phenothiazine, a butyrophenone, a substituted benzamide, and a thioxanthine. Additional examples of such drugs include haloperidol, olanzapine, clozapine, risperidone, pimozide, aripiprazol, and ziprasidone. In some cases, the drug is an anticonvulsant, e.g., phenobarbital, phenytoin, primidone, or carbamazepine. In some cases, the compound of Formula (I) is administered in combination with at least two drugs that are antidepressant drugs, antipsychotic drugs, anticonvulsant drugs, or a combination thereof.

Pharmaceutical Compositions

In yet a further aspect, the invention refers to a pharmaceutical composition containing one or more compounds of Formula (I), in association with pharmaceutically acceptable carriers and excipients. The pharmaceutical compositions can be in the form of solid, semi-solid or liquid preparations, preferably in form of solutions, suspensions, powders, granules, tablets, capsules, syrups, suppositories, aerosols or controlled delivery systems. The compositions can be administered by a variety of routes, including oral, transdermal, subcutaneous, intravenous, intramuscular, rectal and intranasal, and are preferably formulated in unit dosage form, each dosage containing from about 1 to about 1000 mg, preferably from 1 to 600 mg of the active ingredient. The compounds of the invention can be in the form of free bases or as acid addition salts, preferably salts with pharmaceutically acceptable acids. The invention also includes separated isomers and diastereomers of compounds I, or mixtures thereof (e.g. racemic mixtures). The principles and methods for the preparation of pharmaceutical compositions are described for example in Remington's Pharmaceutical Science, Mack Publishing Company, Easton (Pa.).

When administered to an animal, one or more compounds of Formula (I), in any desirable form (e.g., salt form, crystal form, etc)., can be administered neat or as a component of a pharmaceutical composition that comprises a physiologically acceptable carrier or vehicle. Such a pharmaceutical composition of the invention can be prepared using standard methods, for example admixing the compound(s) and a physiologically acceptable carrier, excipient, or diluent. Admixing can be accomplished using methods well known for admixing a compound of Formula (I) and a physiologically acceptable carrier, excipient, or diluent.

Provided pharmaceutical compositions (i.e., comprising one or more compounds of Formula (I), in an appropriate form, can be administered orally. Alternatively or additionally, provided pharmaceutical compositions can be administered by any other convenient route, for example, parenterally (e.g., subcutaneously, intravenously, etc., by infusion or bolus injection, etc), by absorption through epithelial or mucocutaneous linings (e.g., oral, rectal, vaginal, and intestinal mucosa, etc.), etc. Administration can be systemic or local. Various known delivery systems, including, for example, encapsulation in liposomes, microparticles, microcapsules, and capsules, can be used.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. In some instances, administration will result of release of the compound (and/or one or more metabolites thereof) into the bloodstream. The mode of administration may be left to the discretion of the practitioner.

In some embodiments, provided pharmaceutical compositions are administered orally; in some embodiments, provided pharmaceutical compositions are administered intravenously.

In some embodiments, it may be desirable to administer provided pharmaceutical compositions locally. This can be achieved, for example, by local infusion during surgery, topical application, e.g., in conjunction with a wound dressing after surgery, by injection, by means of a catheter, by means of a suppository or edema, or by means of an implant, said implant being of a porous, non-porous, or gelatinous material, including membranes, such as sialastic membranes, or fibers.

In certain embodiments, it can be desirable to introduce a compound of Formula (I) into the central nervous system, circulatory system or gastrointestinal tract by any suitable route, including intraventricular, intrathecal injection, paraspinal injection, epidural injection, enema, and by injection adjacent to the peripheral nerve. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compound of Formula (I) can be formulated as a suppository, with traditional binders and excipients such as triglycerides.

In some embodiments, one or more compounds of Formula (I) can be delivered in a vesicle, in particular a liposome (see Langer, *Science* 249:1527-1533, 1990 and Treat et al., *Liposomes in the Therapy of Infectious Disease and Cancer* 317-327 and 353-365, 1989).

In some embodiments, one or more compounds of Formula (I) can be delivered in a controlled-release system or sustained-release system (see, e.g., Goodson, in *Medical Applications of Controlled Release,* vol. 2, pp. 115-138, 1984). Other controlled or sustained-release systems discussed in the review by Langer, *Science* 249:1527-1533, 1990 can be used. In some embodiments, a pump can be used (Langer, *Science* 249:1527-1533, 1990; Sefton, *CRC Crit. Ref. Biomed. Eng.* 14:201, 1987; Buchwald et al., *Surgery* 88:507, 1980; and Saudek et al., *N. Engl. J Med.* 321:574, 1989). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 2:61, 1983; Levy et al., *Science* 228:190, 1935; During et al., *Ann. Neural.* 25:351, 1989; and Howard et al., *J. Neurosurg.* 71:105, 1989).

As noted above, provided pharmaceutical compositions can optionally comprise a suitable amount of a physiologically acceptable excipient. Exemplary physiologically acceptable excipients can be liquids, such as water and oils, including those of petroleum, animal, vegetable, or synthetic origin, such as peanut oil, soybean oil, mineral oil, sesame oil and the like. For example, useful physiologically acceptable excipients can be saline, gum acacia, gelatin, starch paste, talc, keratin, colloidal silica, urea and the like. Alternatively or additionally, auxiliary, stabilizing, thickening, lubricating, and coloring agents can be used.

In some embodiments, a physiologically acceptable excipient that is sterile when administered to an animal is utilized. Such physiologically acceptable excipients are desirably stable under the conditions of manufacture and storage and will typically be preserved against the contaminating action of microorganisms. Water is a particularly useful excipient when a compound of Formula (I) is administered intravenously. Saline solutions and aqueous dextrose and glycerol solutions can also be employed as liquid excipients, particularly for injectable solutions. Suitable physiologically acceptable excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Provided pharmaceutical compositions, if desired, can also contain minor amounts of wetting or emulsifying agents, or pH buffering agents.

Liquid carriers may be used in preparing solutions, suspensions, emulsions, syrups, and elixirs. A compound of Formula (I) can be dissolved or suspended in a pharmaceutically acceptable liquid carrier such as water, an organic solvent, a mixture of both, or pharmaceutically acceptable oils or fat. Such a liquid carrier can contain other suitable pharmaceutical additives including solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g., cellulose derivatives, including sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Provided pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, pharmaceutical compositions in the form of a capsule are provided. Other examples of suitable physiologically acceptable excipients are described in *Remington's Pharmaceutical Sciences* 1447-1676 (Alfonso R. Gennaro, ed., 19th ed. 1995).

In some embodiments, a compound of Formula (I) (in an appropriate form) is formulated in accordance with routine procedures as a composition adapted for oral administration to humans. Compositions for oral delivery can be in the form of tablets, lozenges, buccal forms, troches, aqueous or oily suspensions or solutions, granules, powders, emulsions, capsules, syrups, or elixirs, for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. In powders, the carrier can be a finely divided solid, which is an admixture with the finely divided compound or pharmaceutically acceptable salt of the compound. In tablets, the compound or pharmaceutically acceptable salt of the compound is mixed with a carrier having the necessary compression properties in suitable proportions and compacted in the shape and size desired. The powders and tablets can contain up to about 99% of the compound or pharmaceutically acceptable salt of the compound.

Capsules may contain mixtures of one or more compounds of Formula (I) with inert fillers and/or diluents such as pharmaceutically acceptable starches (e.g., corn, potato, or tapioca starch), sugars, artificial sweetening agents, powdered celluloses (such as crystalline and microcrystalline celluloses), flours, gelatins, gums, etc.

Tablet formulations can be made by conventional compression, wet granulation, or dry granulation methods and utilize pharmaceutically acceptable diluents, binding agents, lubricants, disintegrants, surface modifying agents (including surfactants), suspending or stabilizing agents (including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins.) Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine.

Moreover, when in a tablet or pill form, provided pharmaceutical compositions can be coated to delay disintegration and absorption in the gastrointestinal tract, thereby providing a sustained action over an extended period of time. Selectively permeable membranes surrounding an osmotically active driving compound are also suitable for orally administered compositions. In these latter platforms, fluid from the environment surrounding the capsule can be imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In some embodiments, the excipients are of pharmaceutical grade.

In some embodiments, one or more compounds of Formula (I) (in an appropriate form) can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where a compound of Formula (I) is to be administered by infusion, it can be dispensed, for example, with an infusion bottle containing sterile pharmaceutical grade water or saline. Where a compound of Formula (I) is administered by injection, an ampule of sterile water for injection or saline can be provided so that the ingredients can be mixed prior to administration.

In some embodiments, one or more compounds of Formula (I) (in an appropriate form) can be administered transdermally through the use of a transdermal patch. Transdermal administrations include administrations across the surface of the body and the inner linings of the bodily passages including epithelial and mucosal tissues. Such administrations can be carried out using the present in lotions, creams, foams, patches, suspensions, solutions, and suppositories (e.g., rectal or vaginal).

Transdermal administration can be accomplished through the use of a transdermal patch containing one or more compounds of Formula (I) (in an appropriate form) and a carrier that is inert to the compound or pharmaceutically acceptable salt of the compound, is non-toxic to the skin, and allows delivery of the agent for systemic absorption into the blood stream via the skin. The carrier may take any number of forms such as creams or ointments, pastes, gels, or occlusive devices. The creams or ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the compound or pharmaceutically acceptable salt of the compound into the blood stream, such as a semi-permeable membrane covering a reservoir containing a compound of Formula (I) with or without a carrier, or a matrix containing the active ingredient.

One or more compounds of Formula (I) (in an appropriate form) may be administered rectally or vaginally in the form of a conventional suppository. Suppository formulations may be made from traditional materials, including cocoa butter, with or without the addition of waxes to alter the suppository's melting point, and glycerin. Water-soluble suppository bases, such as polyethylene glycols of various molecular weights, may also be used.

One or more compounds of Formula (I) (in an appropriate form) can be administered by controlled-release or sustained-release means or by delivery devices that are known to those of ordinary skill in the art. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

In some embodiments a controlled- or sustained-release composition comprises a minimal amount of a compound of Formula (I) to treat or prevent one or more disorders, diseases or conditions associated with activity of α7 nicotinic acetylcholine receptors. Advantages of controlled- or sustained-release compositions include extended activity of the drug, reduced dosage frequency, and increased compliance by the animal being treated. In addition, controlled- or sustained-release compositions can favorably affect the time of onset of action or other characteristics, such as blood levels of the compound or a pharmaceutically acceptable salt of the compound, and can thus reduce the occurrence of adverse side effects.

Controlled- or sustained-release compositions can initially release an amount of one or more compounds of Formula (I) that promptly produces a desired therapeutic or prophylactic effect, and gradually and continually release other amounts of the compound to maintain this level of therapeutic or prophylactic effect over an extended period of time. To maintain a constant level of the compound a body, the compound can be released from the dosage form at a rate that will replace the amount of the compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

In certain embodiments, provided pharmaceutical compositions deliver an amount of a compound of Formula (I) that is effective in the treatment of one or more disorders, diseases, or conditions associated with activity (or inactivity) of α7 nicotinic acetylcholine receptors. According to the present invention, in vitro or in vivo assays can optionally be employed to help identify optimal dosage ranges. The precise dose to be employed can also depend on the route of administration, the condition, the seriousness of the condition being treated, as well as various physical factors related to the individual being treated, and can be decided according to the judgment of a health-care practitioner. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy will be determined according to the judgment of a health-care practitioner. Effective dosage amounts described herein typically refer to total amounts administered; that is, if more than one compound of Formula (I) is administered, the effective dosage amounts correspond to the total amount administered.

The effective amount of a compound of Formula (I) for use as described herein will typically range from about 0.001 mg/kg to about 600 mg/kg of body weight per day, in some embodiments, from about 1 mg/kg to about 600 mg/kg body weight per day, in another embodiment, from about 10 mg/kg to about 400 mg/kg body weight per day, in another embodiment, from about 10 mg/kg to about 200 mg/kg of body weight per day, in another embodiment, from about 10 mg/kg to about 100 mg/kg of body weight per day, in another embodiment, from about 1 mg/kg to about 10 mg/kg body weight per day, in another embodiment, from about 0.001 mg/kg to about 100 mg/kg of body weight per day, in another embodiment, from about 0.001 mg/kg to about 10 mg/kg of body weight per day, and in another embodiment, from about 0.001 mg/kg to about 1 mg/kg of body weight per day.

In some embodiments, pharmaceutical compositions are provided in unit dosage form, e.g., as a tablet, capsule, powder, solution, suspension, emulsion, granule, or suppository. In such form, the composition is sub-divided in unit dose containing appropriate quantities of the active ingredient; the unit dosage form can be packaged compositions, for example, packeted powders, vials, ampoules, prefilled syringes or sachets containing liquids. A unit dosage form can be, for example, a capsule or tablet itself, or it can be the appropriate number of any such compositions in package form. Such unit dosage form may contain, for example, from about 0.01 mg/kg to about 250 mg/kg, and may be given in a single dose or in two or more divided doses. Variations in the dosage will necessarily occur depending upon the species, weight and condition of the patient being treated and the patient's individual response to the medicament.

In some embodiments, the unit dosage form is about 0.01 to about 1000 mg. In another embodiment, the unit dosage form is about 0.01 to about 500 mg; in another embodiment, the unit dosage form is about 0.01 to about 250 mg; in another embodiment, the unit dosage form is about 0.01 to about 100 mg; in another embodiment, the unit dosage form is about 0.01 to about 50 mg; in another embodiment, the unit dosage form is about 0.01 to about 25 mg; in another embodiment, the unit dosage form is about 0.01 to about 10 mg; in another embodiment, the unit dosage form is about 0.01 to about 5 mg; and in another embodiment, the unit dosage form is about 0.01 to about 10 mg;

A compound of Formula (I) can be assayed in vitro or in vivo for the desired therapeutic or prophylactic activity prior to use in humans. Animal model systems can be used to demonstrate safety and efficacy.

Synthesis and Preparation

The compounds of Formula (I) or their precursors can be prepared through a number of synthetic routes amongst which the ones illustrated in Schemes 1-5 below:

Scheme 1

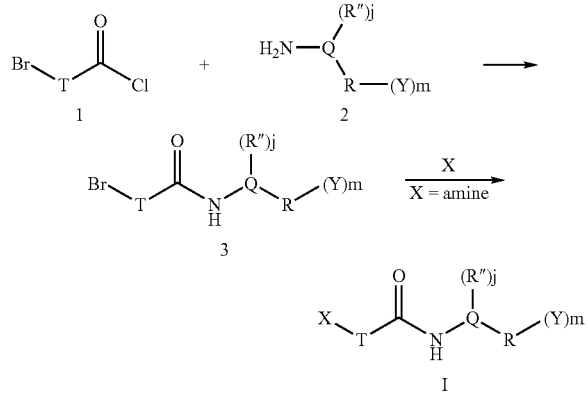

According to Scheme 1, an ω-haloalkanoylchloride 1 (hereby exemplified by a co-bromoalkanoyl chloride) is reacted with a suitable heterocyclic amine 2 in a solvent such as for example but not limited to dichloromethane, dimethylformamide, dimethylacetamide, tetrahydrofurane, ethyl acetate and the like, or mixtures thereof, in the presence of a base such as for example but not limited to triethylamine, Hunig's base (diisopropylethylamine) or an inorganic base such as for example potassium carbonate, to afford the coupling amide product 3 which may or may be not isolated and purified. Amide 3 is then reacted in a suitable solvent such as but not limited to dichloromethane, dimethylformamide, or dimethylacetamide with an amine X, which may be or may not be used in excess, in the presence or absence of an additional base such as triethylamine or Hunig's base to afford subject matter compounds of Formula (I).

Scheme 2

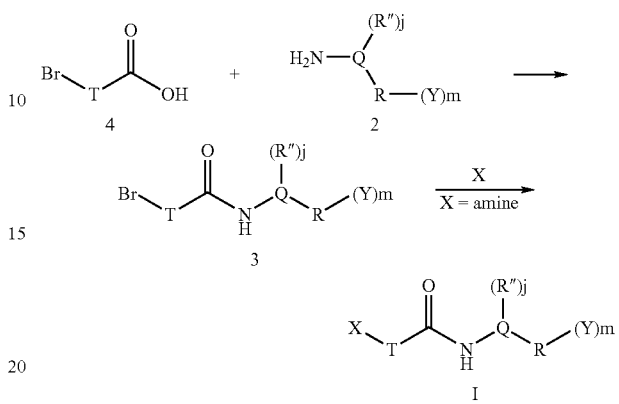

According to Scheme 2, an ω-haloalkanoic acid is suitably activated using an agent such for example but not limited to as 1,1'-carbonyldiimidazole in a solvent such as for example dichloromethane, dimethylformamide or mixtures thereof and reacted with a suitable heterocyclic amine to afford the intermediate ω-haloalkanoic acid amide 3, which may or may be not isolated and purified. Amide 3 is then reacted in a suitable solvent such as but not limited to dichloromethane, dimethylformamide, or dimethylacetamide with an amine X, which may be or may not be used in excess, in the presence or absence of an additional base such as triethylamine or Hunig's base to afford subject matter compounds of Formula (I).

Scheme 3

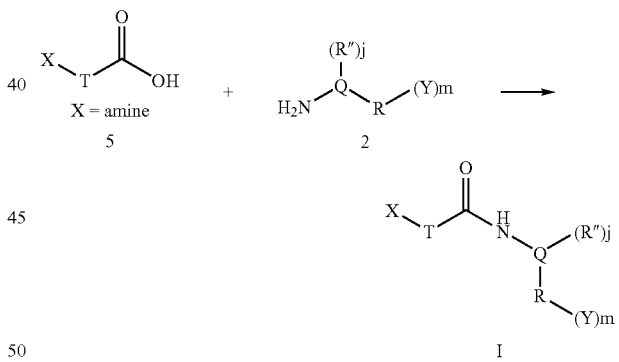

According to Scheme 3, an ω-aminoalkanoic acid is suitably activated using an agent such for example but not limited to as 1,1'-carbonyldiimidazole in a solvent such as for example dichloromethane, dimethylformamide or mixtures thereof and reacted with a suitable heterocyclic amine to afford subject matter compounds of Formula (I).

Scheme 4 d)

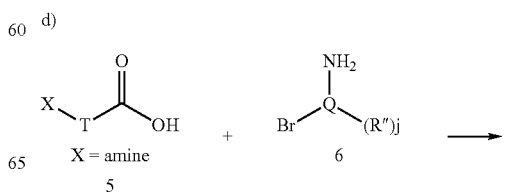

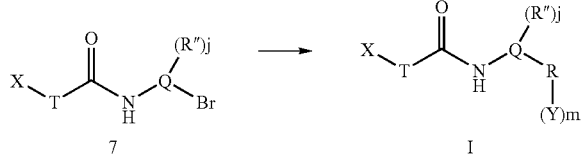

According to Scheme 4, an ω-aminoalkanoic acid 5 is suitably activated using an agent such for example but not limited to as 1,1'-carbonyldiimidazole in a solvent such as for example dichloromethane, dimethylformamide or mixtures thereof and reacted with a suitable bromoheterocyclic amine to afford bromoheteroarylamides of formula 7, which are then reacted further under cross-coupling conditions, for example Suzuki conditions, to afford subject matter compounds of Formula (I).

Scheme 5 shows one possible route towards the synthesis of chain-substituted acids 5, precursors to compounds of Formula (I)

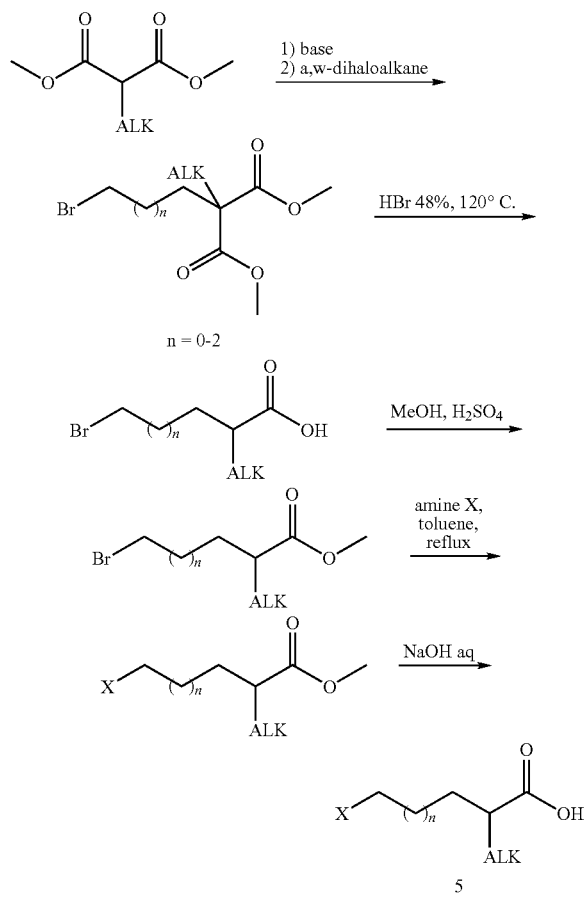

According to Scheme 5, an alkyl-substituted malonic acid diester it treated with base, such as for example but not limited to sodium hydride in a solvent such as tetrahydrofurane or dimethylformamide and reacted with an α,ω-dihaloalkane. The disubstituted malonic acid diester thus obtained is hydrolysed and mono-decarboxylated by treatement with a strong acid, such as for example hydrobromic acid. Esterification is then carried out, for example by treatement with methanol and a catalytic amount of acid. Substitution of the ω-halogen may be accomplished by the use of a suitable amine heating in a solvent like toluene, but not limited to this solvent. Finally, hydrolysis of the ester function with an aqueous base affords intermediates of formula 5 which can be activated as described to afford compounds of Formula (I).

The compounds of Formula (I), their optical isomers or diastereomers can be purified or separated according to well-known procedures, including but not limited to chromatography with a chiral matrix and fractional crystallisation.

EXEMPLIFICATION

Experimetal Procedures—Synthesis of Compounds

General

Unless otherwise specified all nuclear magnetic resonance spectra were recorded using a Varian Mercury Plus 400 MHz spectrometer equipped with a PFG ATB Broadband probe.

HPLC-MS analyses were performed with a Waters 2795 separation module equipped with a Waters Micromass ZQ (ES ionisation) and Waters PDA 2996, using a Waters XTerra MS C18 3.5 µm 2.1×50 mm column.

Preparative HLPC was run using a Waters 2767 system with a binary Gradient Module Waters 2525 pump and coupled to a Waters Micromass ZQ (ES) or Waters 2487 DAD, using a Supelco Discovery HS C18 5.0 µm 10×21.2 mm column Gradients were run using 0.1% formic acid/water and 0.1% formic acid/acetonitrile with gradient 5/95 to 95/5 in the run time indicated in the Examples.

All column chromatography was performed following the method of Still, C.; J. Org Chem 43, 2923 (1978). All TLC analyses were performed on silica gel (Merck 60 F254) and spots revealed by UV visualisation at 254 nm and KMnO4 or ninhydrin stain.

When specified for array synthesis, heating was performed on a Buchi Syneore® system.

All microwave reactions were performed in a CEM Discover oven.

Abbreviations Used Throughout the Experimental Procedures

| | |
|---|---|
| AcOEt | ethyl acetate |
| DCM | dichloromethane |
| DCE | 1,2-dichloroethane |
| DMEA | N,N-dimethylethylamine |
| DMF | N,N-dimethylformamide |
| DMSO, dmso | dimethylsulphoxide |
| DAM | N,N-dimethylacetamide |
| SCX | strong cation exchanger |
| TEA | triethylamine |
| TFA | trifluoroacetic acid |
| THF | tetrahydrofuran |
| TLC | thin layer chromatography |
| LC-MS | liquid chromatography-mass spectrometry |
| HPLC | high performance liquid chromatography |

General 3-amino-5-aryl/Heteroaryl Pyrazole Synthesis

The 3-amino-5-aryl/heteroaryl pyrazoles used in the Examples were either commercially available or synthesised using the routes shown in the scheme below:

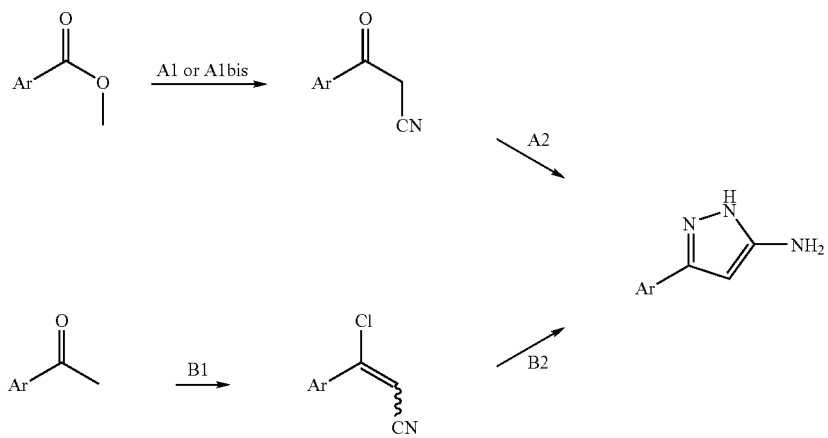

General Procedure for Aryl/Heteroaryl β-ketonitrile Synthesis (A1):

Aryl or heteroaryl methyl carboxylate were commercially available or were synthesized according to the following standard procedure: the aryl or heteroaryl carboxylic acid (32 mmol) was dissolved in MeOH (40 mL) and sulfuric acid (1 mL) was added. The mixture was refluxed overnight, after which the solvent was evaporated under reduced pressure; the crude was dissolved in DCM and washed with saturated aqueous NaHCO3 solution. The organic phase was dried and evaporated under reduced pressure, and the crude was used without further purification.

To a solution of an aryl or heteroaryl methyl carboxylate (6.5 mmol) in dry toluene (6 mL) under $N_2$, NaH (50-60% dispersion in mineral oil, 624 mg, 13 mmol) was carefully added. The mixture was heated at 80° C. and then dry $CH_3CN$ was added dropwise (1.6 mL, 30.8 mmol). The reaction was heated for 18 hours and generally the product precipitated from the reaction mixture as Na salt.

The reaction was then allowed to cool down to room temperature and the solid formed was filtered and then dissolved in water. The solution was then acidified with 2N HCl solution and at pH between 2-6 (depending on the ring substitution on the aryl/heteroaryl system) the product precipitated and was filtered off. If no precipitation occurred, the product was extracted with DCM.

After work-up, the products were generally used in the following step without further purification. The general yield was between 40 and 80%.

General Procedure for Aryl/Heteroaryl β-ketonitrile Synthesis (Route A1 bis).

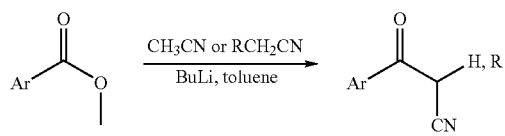

Aryl- or heteroaryl-carboxylic acid methyl esters are commercially available or were synthesized under the standard procedure, as described in general procedure A1.

To a solution of dry alkanenitrile in toluene (1 mmol/mL, 5 eq.) cooled down to −78° C. under nitrogen, a solution of n-butyllithium in n-hexane (1.6 N, 3.5 eq) was added dropwise. The mixture was left stirring at −78° C. for 20 minutes and then a solution of the aryl or heteroaryl methyl carboxylate in toluene (0.75 mmol/mL, 1 eq.) was added and the reaction allowed to reach room temperature. Upon reaction completion, after about 20 minutes, the mixture was cooled down to 0° C. and HCl 2N was added to pH 2. The organic phase was recovered, dried over $Na_2SO_4$ and concentrated under reduced pressure, affording the title product which was generally used without further purification.

General Procedure for Aryl Aminopyrazole Synthesis (Route A2):

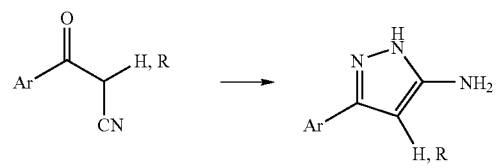

To a solution of the β-ketonitrile (7.5 mmoL), in absolute EtOH (15 mL) hydrazine monohydrate (0.44 mL, 9.0 mmol) was added and the reaction was heated at reflux for 18 hrs. The reaction mixture was allowed to cool to room temperature and the solvent was evaporated under reduced pressure. The residue was dissolved in DCM and washed with water.

The organic phase was concentrated under reduced pressure to give a crude product that was purified by $SiO_2$ column or by precipitation from $Et_2O$.

Yields were generally between 65 and 90%.

Hydroxy-aryl- or Hydroxy/Heteroaryl-carboxylic Acid to Methyl Ester—General Procedure 4-hydroxy-benzoic acid (usually 24.0 mmol) was dissolved in MeOH (50 mL) and sulfuric acid (1 mL/g substrate) was added. The mixture was refluxed overnight, after which the solvent was evaporated under reduced pressure; the crude was dissolved in DCM and washed with saturated $NaHCO_3$ to basic pH. The organic phase was dried and evaporated under reduced pressure, and the product was used without further purification. The yields were between 80 and 90%.

Hydroxy-aryl- or Hydroxy-heteroaryl-carboxylic Acid Methyl Ester to F₂CHO-aryl- or Heteroarylcarboxylic Acid Methyl Ester—General Procedure Under a N₂ atmosphere, 4-hydroxy-benzoic acid methyl or ethyl ester (1.0 eq) and sodium chlorodifluoroacetate (1.2 eq) were dissolved in DMF (20-25 mL) in a two neck round bottom flask; potassium carbonate (1.2 eq) was added and the mixture was heated at 125° C. until complete conversion of the starting material was observed by LC-MS. The mixture was then diluted with water and extracted with DCM; the organic phase was dried and removed under reduced pressure, and the crude was purified through Si column to obtain the product (Yields from 20 to 70%).

The following Table 1 reports yields and analytical data obtained in the preparation of a series of F₂CHO-aryl- or F₂CHO-heteroaryl-carboxylic acid methyl esters prepared according to the general procedures described above

TABLE 1

| Starting material | Methyl ester —OH | Methyl ester —OCHF2 |
|---|---|---|
| 3-Fluoro-4-hydroxy-benzoic acid | C8H7FO3<br>Yield = 85%<br>1H NMR (DMSO-d6) δ 3.78 (3H, s), 7.00-7.05 (1H, m), 7.60-7.65 (2H, m) | C9H7F3O3<br>Yield = 66%<br>1H NMR (DMSO-d6) δ 3.78 (3H, s), 6.24 (1H, m), 7.61 (1H, m), 7.64 (1H, m), 10.89 (1H, bs) |
| 2,6-Difluoro-4-hydroxy-benzoic acid | C8H6F2O3<br>Yield = 85%<br>1H NMR (DMSO-d6) δ 3.79 (s, 3H, s), 6.53 (2H, d, J = 10.8 Hz), 11.13 (1H, s) | C9H6F4O3<br>Yield = 34%<br>1H NMR (DMSO-d6) δ 3.86 (3H, s), 7.18-7.24 (2H, m), 7.42 (1H, t, J = 72.4 Hz). |
| 3,5-Dichloro-4-hydroxy-benzoic acid | Commercially available | C9H6Cl2F2O3<br>Yield = 74%<br>1H NMR (DMSO-d6) δ 3.31 (3H, s), 7.22 (1H, t, J = 71.6 Hz), 8.05 (2H, s). |
| 3-Chloro-4-hydroxy-benzoic acid | Commercially available | C9H7ClF2O3<br>Yield = 85%<br>1H NMR (DMSO-d6) δ 3.85 (3H, s), 7.39 (1H, t, J = 72.4 Hz), 7.50 (1H, t, J = 8.4 Hz), 7.82-7.89 (2H, m). |
| 4-Hydroxy-3-methoxy-benzoic acid | Commercially available | C10H10F2O4<br>Yield = 85%<br>1H NMR (DMSO-d6) 3.84 (3H, s), 3.87 (3H, s); 7.22 (1H, t, J = 73.6 Hz), 7.29 (1H, d, J = 8.4 Hz), 7.57-7.60 (2H, m). |
| 4-Hydroxy-2-methyl-benzoic acid | C9H10O3<br>Yield = 95%<br>1H NMR (DMSO-d6) 2.43 (3H, br s), 3.72 (3H, s); 6.61-6.64 (2H, m); 7.71-7.73 (1H, m), 10.10 (1H, s). | C10H10F2O3<br>Yield = 85%<br>1H NMR (DMSO-d6) 2.52 (3H, br s), 3.80 (3H, s); 7.07-7.13 (2H, m); 7.34 (1H, t, J = 73.6 Hz), 7.89 (1H, d, J = 8.8 Hz). |

3-Imidazo [1,2-a]pyridin-6-yl-3-oxo-propionitrile

The product was obtained starting from imidazo[1,2-a]pyridine-6-carboxylic acid methyl ester according to general procedure A1
Yield 39%
C10H7N3O Mass (calculated) [185]; (found) [M+H+]=186 [M−H]=184
LC Rt=0.23, 100% (3 min method)
1H-NMR: (dmso-d6): 4.72 (2H,s), 7.61-7.65 (2H, m), 7.70 (1H, m), 8.07 (1H, s), 9.40 (s, 1H).

5-Imidazo[1,2-a]pyridin-6-yl-1H-pyrazol-3-ylamine

The title compound was synthesized according to general procedure A2 starting from 3-imidazo [1,2-a]pyridin-6-yl-3-oxo-propionitrile
Yield: 84%
C10H9N5 Mass (calculated) [199]; (found) [M+1]=200
LCMS, (5 min method, RT=0.21 min,
NMR (1H, 400 MHz, MeOH-d₄) 3.34 (s, 2H), 5.90 (br s, 1H), 7.57 (s, 1H), 7.63 (br s, 1H), 7.86 (s, 1H), 8.73 (s, 1H)

Chlorocynnamonitrile Synthesis (Route B1)

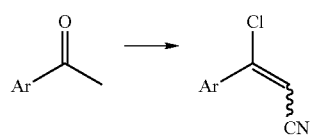

POCl₃ (2 eq with respect to the aryl/heteroaryl acetophenone) were added dropwise to 4 molar equivalents of anhydrous DMF cooled down to 0° C., at such a rate that the temperature did not exceed 10° C. The acetophenone (1 eq) was then added dropwise and the reaction was allowed to reach room temperature.

The reaction was then stirred for further 30' and then 0.4 mmol of hydroxylamine hydrochloride were added. The reaction was then heated up to 50° C., after which heating was removed and additional 4 eq. of hydroxylamine hydrochloride were added portionwise (at such a rate that the temperature never exceeded 120° C.). The reaction was then stirred until the temperature of the mixture spontaneously decreased to 25° C. Water (100 mL) were then added and the mixture was extracted with diethyl ether. The organic phase was dried over Na$_2$SO$_4$ and concentrated under reduced pressure. The crude product was used for the next step without further purification.

Aryl Aminopyrazole Synthesis (Route B2)

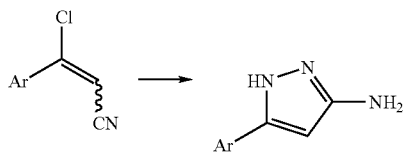

To a solution of the chlorocynnamonitrile (0.5 mmol/mL, 1 eq) in absolute EtOH 2 eq of hydrazine monohydrate were added and the reaction was heated at reflux for 4 hrs. The reaction mixture was allowed to cool to room temperature and the solvent was evaporated under reduced pressure. The residue was triturated with Et$_2$O, allowing to recover the title compound which was generally used without further purification.

5-(2-Trifluoromethyl-phenyl)-2H-pyrazol-3-ylamine a) 3-Oxo-3-(2-trifluoromethyl-phenyl)-propionitrile The product was prepared according to the general procedure for aminopyrazole synthesis (route A1) from 2-trifluoromethyl-benzoic acid methyl ester (3.1 g, 14.0 mmol, 1.0 eq). The crude was precipitated from HCl to give the title product as a yellow solid (2.8 g, yield: 94%).
C10H6F3NO
$^1$H-NMR (CD$_3$OD): 4.90 (2H, br s); 7.52-7.86 (4H, m).

b) 5-(2-Trifluoromethyl-phenyl)-2H-pyrazol-3-ylamine

The product was prepared according to general procedure for aminopyrazole synthesis (route A2). The crude was purified through Si column (eluent: DCM) and dried to give the title product (0.6 g, 20% Yield).
C10H8F3N3

5-(2,6-Dimethyl-phenyl)-2H-pyrazol-3-ylamine a) 3-(2,6-Dimethyl-phenyl)-3-oxo-propionitrile The product was prepared according to the general procedure for aminopyrazole synthesis (route A1), refluxing the mixture overnight and then for 2 h at 110° C. The crude product was extracted with DCM and used in the following step without further purification (2.2 g, yield: 76%).
C11H11NO b) 5-(2,6-Dimethyl-phenyl)-2H-pyrazol-3-ylamine The product was prepared according to general procedure for aminopyrazole synthesis (route A2). The crude was purified through Si column (eluent: DCM) and washed with water, extracted and dried to give the title product (0.25 g, yield 10%).
C11H13N3
$^1$H-NMR (CD$_3$OD): 2.09-2.23 (6H, m); 7.04-7.12 (2H, m); 7.18-7.26 (2H, m).

5-(2-Chloro-4-fluoro-phenyl)-2H-pyrazol-3-ylamine a) 3-(2-Chloro-4-fluoro-phenyl)-3-oxo-propionitrile The product was prepared according to the general procedure for aminopyrazole synthesis (route A1) from 2-chloro-4-fluoro-benzoic acid methyl ester (0.7 g, 3.7 mmol, 1.0 eq). The crude product was extracted with DCM and used in the following step without further purification (0.4 g, yield: 60%).
C9H5ClFNO b) 5-(2-Chloro-4-fluoro-phenyl)-2H-pyrazol-3-ylamine The product was prepared according to general procedure for aminopyrazole synthesis (route A2). The crude was dissolved in DCM, washed with sat NaHCO3, extracted and dried to give the title product (0.12 g, yield 26%).
C9H7ClFN3
$^1$H-NMR (dmso-d6): 7.03-7.53 (4H, m).

5-(5-tert-Butyl-thiophen-2-yl)-2H-pyrazol-3-ylamine a) 3-(5-tert-Butyl-thiophen-2-yl)-3-oxo-propionitrile The product was prepared according to the general procedure for aminopyrazole synthesis (route A1) from 5-tert-Butyl-thiophene-2-carboxylic acid methyl ester (3.0 g, 15.0 mmol, 1.0 eq). The crude product was extracted with DCM and used in the following step without further purification (2.7 g, yield: 86%).
C11H13NOS b) 5-(5-tert-Butyl-thiophen-2-yl)-2H-pyrazol-3-ylamine The product was prepared according to general procedure for aminopyrazole synthesis (route A2). The crude was washed with water and precipitated to give the title product (2.7 g, yield 91%).
C11H15N3S
Mass (calculated) [221]; (found) [M+H$^+$]=222.
LC Rt=2.53 min, 94% (10 min method)
$^1$H-NMR (dmso-d6): 1.26-1.29 (9H, m); 4.87 (2H, br s); 5.47 (1H, br s); 6.66-6.79 (1H, m); 6.97-7.02 (1H, m)

5-(3-Chloro-2-methyl-phenyl)-2H-pyrazol-3-ylamine a) 2-Ethyl-benzoic acid methyl ester 2-Ethyl-benzoic acid (3.0 g, 17.6 mmol) was dissolved in MeOH (20 mL) and sulfuric acid (1 mL) was added. The mixture was refluxed overnight, after which the solvent was evaporated under reduced pressure; the crude was dissolved in DCM and washed with saturated Na2CO3 to basic pH. The organic phase was dried and evaporated under reduced pressure, and the product (3.1 g, yield 96%) was used without further purification.
C9H9ClO2
$^1$H-NMR (dmso-d6): 2.48 (3H, br s); 3.82 (3H, s); 7.31 (1H, t, J=7.6 Hz); 7.63-7.67 (2H, m).

b) 3-(3-Chloro-2-methyl-phenyl)-3-oxo-propionitrile

The product was prepared according to the general procedure for aminopyrazole synthesis (route A1) from 3-Chloro- 2-methyl-benzoic acid methyl ester (3.1 g, 16.8 mmol, 1.0 eq). The crude product was precipitated form water and used in the following step without further purification (2.4 g, yield: 74%).

C10H8ClNO
$^1$H-NMR (dmso-d6): 2.31 (3H, br s); 4.64 (2H, br s); 7.27-7.36 (2H, m); 7.54-7.77 (1H, m).

c) 5-(3-Chloro-2-methyl-phenyl)-2H-pyrazol-3-ylamine

The product was prepared according to general procedure for aminopyrazole synthesis (route A2). The crude product was purified through SiO$_2$ column (20 g) with gradient elution from 100% EtOAc to EtOAc-MeOH 80:20. The title product (1.3 g, yield 50%) was obtained.

C10H10ClN3
Mass (calculated) [207]; (found) [M+H$^+$]=208.
LC Rt=1.96 min, 85% (10 min method)
$^1$H-NMR (CDCl$_3$): 2.41 (3H, s); 5.74 (1H, s); 7.16 (1H, t, J=8.0 Hz); 7.20-7.26 (1H, m); 7.38-7.40 (1H, m).

5-(2-Ethyl-phenyl)-2H-pyrazol-3-yl-amine a) 2-Ethyl-benzoic acid methyl ester

2-Ethyl-benzoic acid (3.0 g, 20.0 mmol) was dissolved in MeOH (20 mL) and catalytic quantity of sulfuric acid (1 mL) was added. The mixture was refluxed overnight, after that the solvent was evaporated under reduced pressure; the crude was dissolved in DCM and washed with saturated Na$_2$CO$_3$ to basic pH. The organic phase was dried and evaporated under reduced pressure, and the product (2.9 g, yield 88%) was used without further purification C10H12O2
$^1$H-NMR (dmso-d6): 1.12 (3H, t, J=7.2 Hz); 2.86 (2H, q, J=7.2 Hz); 3.81 (3H, s); 7.27-7.34 (2H, m); 7.46-7.51 (1H, m); 7.73-7.75 (1H, m).

b) 3-(2-Ethyl-phenyl)-3-oxo-propionitrile

The product was prepared according to the general procedure for aminopyrazole synthesis (route A1) from 2-ethyl-benzoic acid methyl ester (2.9 g, 17.6 mmol, 1.0 eq). The crude product was extracted with DCM as a yellow oil and used in the following step without further purification (2.8 g, yield: 92%).

C11H11NO
1H-NMR (dmso-d6): 1.10-1.18 (3H, m); 2.78 (2H, q, J=7.2 Hz); 4.67 (1H, s); 7.23-7.53 (3H, m); 7.73-7.78 (1H, m).

c) 5-(2-Ethyl-phenyl)-2H-pyrazol-3-yl-amine

The product was prepared according to general procedure for aminopyrazole synthesis (route A2). The crude product was purified through SiO$_2$ column (20 g) with gradient elution from 100% EtOAc to EtOAc-MeOH 80:20. The title product (1.2 g, yield 40%) was obtained C11H13N3
Mass (calculated) [187]; (found) [M+H$^+$]=188.
LC Rt=1.58 min, 90% (10 min method)
$^1$H-NMR (CDCl$_3$): 1.15 (3H, t, J=7.6 Hz); 2.71 (2H, q, J=7.6 Hz); 5.72 (1H, s); 7.20-7.26 (1H, m); 7.29-7.35 (3H, m).

5-(4-Methoxy-phenyl)-4-Methyl-2H-pyrazol-3-ylamine a) 3-(4-Methoxy-phenyl)-2-methyl-3-oxo-propionitrile

The product was prepared according to the general procedure for aminopyrazole synthesis (route A1) from 4-methoxy-benzoic acid methyl ester (3.0 mL, 18.0 mmol, 1.0 eq), NaH (1.4 g, 36.0 mmol, 2.0 eq) and propionitrile (6.1 mL, 84.9 mmol, 4.7 eq). The crude was purified through Si-column (eluent exane/ethyl acetate) to give 2.1 g of title product (yield: 62%).

C11H11NO2 b) 5-(4-Methoxy-phenyl)-4-methyl-2H-pyrazol-3-ylamine

The product was prepared according to general procedure for aminopyrazole synthesis (route A2). The crude product was washed with basic water and dried, and the title product (1.8 g, yield 80%) was used without further purification C11H13N3O
Mass (calculated) [203]; (found) [M+H$^+$]=204.
LC Rt=1.34 min, 91% (10 min method)
$^1$H-NMR (CDCl$_3$): 2.03 (3H, s); 3.84 (3H, s); 6.96-6.98 (2H, m); 7.37-7.39 (2H, m).

a) 2-Methyl-3-oxo-3-(4-trifluoromethyl-phenyl)-propionitrile

The product was prepared according to the general procedure for aminopyrazole synthesis (route A1) from 4-trifluoromethyl-benzoic acid methyl ester (3.0 g, 14.7 mmol, 1.0 eq), NaH (1.2 g, 29.4 mmol, 2.0 eq) and propionitrile (4.9 mL, 69.4 mmol, 4.7 eq). The crude product was extracted with DCM and used in the following step without further purification (3.2 g, yield: 96%).

C11H8F3NO b) 4-Methyl-5-(4-trifluoromethyl-phenyl)-2H-pyrazol-3-ylamine

The product was prepared according to general procedure for aminopyrazole synthesis (route A2). The crude product was washed with basic water and dried, and the title product (2.8 g, yield 84%) was used without further purification C11H10F3N3
Mass (calculated) [241]; (found) [M+H$^+$]=242.
LC Rt=2.34 min, 92% (10 min method)
$^1$H-NMR (CDCl$_3$): 2.05 (3H, s); 7.56 (2H, d, J=8.4 Hz); 7.64 (2H, d, J=8.4 Hz).

5-(4-Cyclopropylmethoxy-2-methyl-phenyl)-2H-pyrazol-3-ylamine a) 4-Hydroxy-2-methyl-benoic acid methyl ester

4-Hydroxy-2-methyl-benzoic acid (4.8 g, 32.0 mmol) was dissolved in MeOH (40 mL) and catalytic quantity of sulfuric acid (1 mL) was added. The mixture was refluxed overnight, after which the solvent was evaporated under reduced pressure; the crude was dissolved in DCM and washed with saturated NaHCO$_3$ to basic pH. The organic phase was dried and evaporated under reduced pressure, and the product (5.0 g, yield 95%) was used without further purification.

C9H10O3
$^1$H-NMR (dmso-d6): 2.43 (3H, s); 3.72 (3H, s); 6.62-6.64 (2H, m); 7.71-7.73 (1H, m); 10.10 (1H, s).

b) 4-Cyclopropylmethoxy-2-methyl-benzoic acid methyl ester

4-Hydroxy-2-methyl-benzoic acid methyl ester (1.0 g, 6.0 mmol, 1.0 eq) was dissolved in acetone (14 mL), NaI (0.45 g, 3.0 mmol, 0.5 eq) and $K_2CO_3$ (1.66 g, 12.0 mmol, 2.0 eq) were added ad the mixture was stirred at room temperature for 20 min. (Bromomethyl)cyclopropane (0.53 mL, 5.4 mmol, 0.9 eq) was added, and the mixture was refluxed for 2 days. The solvent was concentrated under reduced pressure, NaOH 10% was added, and the crude was extracted with DCM and dried. 0.42 g of title product (yield 32%) were recovered and used without further purification.
C13H16O3
$^1$H-NMR (CDCl$_3$): 0.23-0.34 (2H, m); 0.52-0.64 (2H, m); 1.15-1.24 (1H, m); 2.52 (3H, s); 3.75 (2H, d, J=7.2 Hz); 3.77 (3H, s); 6.64-6.66 (1H, m); 7.83-7.85 (2H, m).

c) 3-(4-Cyclopropylmethoxy-2-methyl-phenyl)-3-oxo-propionitrile

The product was prepared according to the general procedure for aminopyrazole synthesis from 4-cyclopropylmethoxy-2-methyl-benzoic acid methyl ester (route A1bis). 0.54 g of the title product was extracted from water and dried (yield 69%) and used directly for the next step.
C14H15NO2 d) 5-(4-Cyclopropylmethoxy-2-methyl-phenyl)-2H-pyrazol-3-ylamine

The product was prepared according to general procedure for aminopyrazole synthesis (route A2). The crude product was purified through SiO$_2$ column with gradient elution from 100% EtOAc to EtOAc-MeOH 90:10. The title product (206 mg, yield 36%) was obtained.
C14H17N3O
$^1$H-NMR (CD$_3$OD): 0.29-0.36 (2H, m); 0.54-0.63 (2H, m); 1.18-1.28 (1H, m); 2.33 (3H, s); 3.81 (2H, d, J=7.2 Hz); 5.67 (1H,s); 6.74-6.80 (2H, m); 7.25 (1H, d, J=8.8 Hz).

5-(3-Chloro-4-cyclopropylmethoxy-phenyl)-2H-pyrazol-3-ylamine a) 3-Chloro-4-cyclopropylmethoxy-benzoic acid methyl ester

3-Chloro-4-hydroxy-benzoic acid methyl ester (1.1 g, 6.0 mmol, 1.0 eq) was dissolved in acetone (14 mL), NaI (0.45 g, 3.0 mmol, 0.5 eq) and $K_2CO_3$ (1.66 g, 12.0 mmol, 2.0 eq) were added ad the mixture was stirred at room temperature for 20 min. (Bromomethyl)cyclopropane (0.53 mL, 5.4 mmol, 0.9 eq) was added, and the mixture was refluxed for 2 days. The solvent was concentrated under reduced pressure, NaOH 10% was added, and the crude was extracted with DCM and dried. The title product (0.88 g, yield 32%) was recovered and used without further purification.
C12H13ClO3
$^1$H-NMR (dmso-d6): 0.33-0.37 (2H, m); 0.55-0.60 (2H, m); 1.25-1.27 (1H, m); 3.80 (3H, s); 3.99 (2H, d, J=7.2 Hz); 7.21 (1H, s, J=8.8 Hz); 7.85-7.91 (2H, m).

b) 3-(3-Chloro-4-cyclopropylmethoxy-phenyl)-3-oxo-propionitrile

The product was prepared according to the general procedure from 3-Chloro-4-cyclopropylmethoxy-benzoic acid methyl ester (route A1 bis). 0.74 g of the title product was extracted from water and dry (yield 81%) and used directly for the next step.
C13H12ClNO2 c) 5-(3-Chloro-4-cyclopropylmethoxy-phenyl)-2H-pyrazol-3-ylamine

The product was prepared according to general procedure for aminopyrazole synthesis (route A2). The crude product was purified through SiO$_2$ column (gradient elution from 100% EtOAc to EtOAc-MeOH 90:10). 521 mg of the title product (yield 67%) were obtained.
Mass (calculated) [263]; (found) [M+H$^+$]=264.
LC Rt=2.51 min, 90% (10 min method)
$^1$H-NMR (CD$_3$OD): 0.25-0.29 (2H, m); 0.52-0.55 (2H, m); 1.10-1.18 (1H, m); 3.81 (2H, d, J=6.8 Hz); 5.74 (1H, s); 6.95-6.99 (1H, m); 7.24-7.30 (2H, m).

5-(4-Cyclopropylmethoxy-2-trifluoromethyl-phenyl)-2H-pyrazol-3-ylamine a) 4-hydroxy-2-trifluoromethyl-benzoic acid methyl ester 4-hydroxy-2-trifluoromethyl-benzoic acid (5.0 g, 24.0 mmol) was dissolved in MeOH (50 mL) and a catalytic quantity of sulfuric acid was added. The mixture was refluxed overnight, after which the solvent was evaporated under reduced pressure; the crude was dissolved in DCM and washed with saturated NaHCO$_3$. The organic phase was dried and evaporated under reduced pressure, and the product was used without further purification.
C9H7F3O3 b) 4-Cyclopropylmethoxy-2-trifluoromethyl-benzoic acid methyl ester 4-hydroxy-2-trifluoromethyl-benzoic acid methyl ester (1.1 g, 4.8 mmol, 1.0 eq) was dissolved in acetone (14 mL), NaI (0.5 eq) and K2CO3 (1.04 g, 2.0 eq) were added and the mixture was stirred at room temperature for 30 min. (Bromomethyl)cyclopropane (0.42 mL, 4.3 mmol, 0.9 eq) was added, and the mixture was refluxed for 2 days. The solvent was concentrated under reduced pressure, NaOH 10% was added, and it was extracted with DCM and dried. The title product (1.21 g, yield 92%) was recovered and used without further purification.
C13H13F3O3 c) 3-(4-Cyclopropylmethoxy-2-trifluoromethyl-phenyl)-3-oxo-propionitrile

The product was prepared according to the general procedure (route A1 bis). The mixture was acidified with HCl 1M and the organic phase separated and dried, to give 1.2 g of the title product (yield 94%) which was used directly for the next step.
C14H12F3NO2
Mass (calculated) [283]; (found) [M+H$^+$]=284
LC Rt=3.86 min, 98% (10 min method)

d) 5-(4-Cyclopropylmethoxy-2-trifluoromethyl-phenyl)-2H-pyrazol-3-ylamine

The product was prepared according to general procedure for aminopyrazole synthesis (route A2). The crude product was purified through SiO$_2$ column (gradient elution from Ethyl Acetate-cycloexane 1:1 to Ethyl Acetate-MeOH 90:10). 650 mg of the title product (yield 52%) were obtained.
C14H14F3N3O
Mass (calculated) [297]; (found) [M+H$^+$]=298.
LC Rt=2.78 min, 59% (10 min method)
$^1$H-NMR (CDCl$_3$): 032-0.44 (2H, m); 0.64-0.62 (2H, m); 1.22-1.37 (1H, m); 3.80-3.92 (2H, m); 5.78 (1H, s); 7.04-7.07 (1H, m); 7.24-7.26 (1H, m); 7.38-7.40 (1H, m)

5-(4-Cyclopropylmethoxy-2,3-difluoro-phenyl)-2H-pyrazol-3-ylamine a) 4-hydroxy-2,3-difluoro-benzoic acid methyl ester 4-hydroxy-2,3-difluoro-benzoic acid (2.0 g, 11.5 mmol) was dissolved in MeOH (20 mL) and catalytic quantity of sulfuric acid was added. The mixture was refluxed overnight, after that the solvent was evaporated under reduced pressure; the crude was dissolved in DCM and washed with saturated NaHCO$_3$. The organic phase was dried and evaporated under reduced pressure, and the product was used without further purification.
C8H6F2O3 b) 4-Cyclopropylmethoxy-2,3-difluoro-benzoic acid in ethyl ester

4-Hydroxy-2,3-difluoro-benzoic acid methyl ester (0.9 g, 4.8 mmol, 1.0 eq) was dissolved in acetone (14 mL), NaI (0.5 eq) and K$_2$CO$_3$ (1.03 g, 2.0 eq) were added and the mixture was stirred at room temperature for 30 min. (Bromomethyl)cyclopropane (0.42 mL, 0.9 eq) was added, and the mixture was refluxed for 2 days. The solvent was concentrated under reduced pressure, NaOH 10% was added, and it was extracted with DCM and dried. The title product (0.97 g, yield 84%) was recovered and used without further purification.
C12H12F2O3 c) 3-(4-Cyclopropylmethoxy-2,3-difluoro-phenyl)-3-oxo-propionitrile

The product was prepared according to the general procedure (route A1 bis). The mixture was acidified with HCl 1M and the organic phase separated and dried, to give 0.79 g of the title product (yield 79%) which was used directly for the next step.
C13H11F2NO2
Mass (calculated) [251]; (found) [M+H$^+$]=252.
LC Rt=3.53 min, 82% (10 min method)

d) 5-(4-Cyclopropylmethoxy-2,3-difluoro-phenyl)-2H-pyrazol-3-ylamine

The product was prepared according to general procedure for aminopyrazole synthesis (route A2). The crude product was purified through SiO$_2$ column (gradient elution from EtOAc-cycloexane 1:1 to EtOAc:MeOH 90:10). 810 mg of the title product (yield 97%) were obtained.
C13H13F2N3O
Mass (calculated) [265]; (found) [M+H$^+$]=266.
LC Rt=2.59 min, 75% (10 min method)
$^1$H-NMR (CDCl$_3$): 032-0.47 (2H, m); 0.64-0.75 (2H, m); 1.19-1.38 (1H, m); 3.67-4.15 (4H, m); 5.95 (1H, s); 6.74-6.88 (1H, m); 7.17-7.26 (1H, m);

5-(3,5-Dichloro-4-cyclopropylmethoxy-phenyl)-2H-pyrazol-3ylamine a) 3,5-Dichloro-4-Cyclopropylmethoxy-benzoic acid methyl ester 3,5-Dichloro-4-hydroxy-benzoic acid ethyl ester (1.0 g, 4.5 mmol, 1.0 eq) was dissolved in acetone (14 mL), NaI (0.5 eq) and K$_2$CO$_3$ (0.98 g, 9.0 mmol, 2.0 eq) were added ad the mixture was stirred at room temperature for 30 min. (Bromomethyl)cyclopropane (0.39 mL, 4.1 mmol, 0.9 eq) was added, and the mixture was refluxed for 2 days. The solvent was concentrated under reduced pressure, NaOH 10% was added, and it was extracted with DCM and dried. The title product (0.98 g, yield 79%) was recovered and used without further purification.
C12H12Cl2O3 b) 3(3,5-Dichloro-4-cyclopropylmethoxy-phenyl)-3-oxo-propionitrile

The product was prepared according to the general procedure (route A1 bis). The mixture was acidified with HCl 1M and the organic phase separated and dried, to give 0.91 g of the title product (yield 90%) which was used directly for the next step.
C13H13Cl2N3O
Mass (calculated) [283]; (found) [M+H$^+$]=284.
LC Rt=4.06 min, 99% (10 min method)

c) 5-(3,5-Dichloro-4-cyclopropylmethoxy-phenyl)-2H-pyrazol-3ylamine

The product was prepared according to general procedure for aminopyrazole synthesis (route A2). The crude product was purified through SiO$_2$ column (gradient elution from EtOAc-cycloexane 1:1 to Ethyl Acetate:MeOH 90:10). 750 mg of the title product (yield 79%) were obtained.
C13H13Cl2N3O
Mass (calculated) [297]; (found) [M+H$^+$]=298.
LC Rt=3.23 min, 93% (10 min method)
$^1$H-NMR (CDCl$_3$): 023-0.46 (2H, m); 0.64-0.74 (2H, m); 1.30-1.48 (1H, m); 3.60-4.04 (4H, m); 5.86 (1H, s); 7.48 (2H, s)

5-(4-Cyclopropylmethoxy-3-methoxy-phenyl)-2H-pyrazol-3-ylamine a) 4-Cyclopropylmethoxy-3-methoxy-benzoic acid methyl ester 4-hydroxy-3-methoxy-benzoic acid methyl ester (1.0 g, 5.5 mmol, 1.0 eq) was dissolved in acetone (14 mL), NaI (0.5 eq) and K$_2$CO$_3$ (1.0 g, 2.0 eq) were added and the mixture was stirred at room temperature for 30 min. (Bromomethyl)cyclopropane (0.53 mL, 0.9 eq) was added, and the mixture was refluxed for 2 days. The solvent was concentrated under reduced pressure, NaOH 10% was added, and it was extracted with DCM and dried. The title product (1.21 g, yield 93%) was recovered and used without further purification.
C13H16O4 b) 3(4-Cyclopropylmethoxy-3-methoxy-phenyl)-3-oxo-propionitrile

The product was prepared according to the general procedure (route A1 bis). The mixture was acidified with HCl 1M and the organic phase separated and dried, to give 1.24 g of the title product (yield 99%) which was used directly for the next step.
C14H15NO3
Mass (calculated) [245]; (found) [M+H$^+$]=246.
LC Rt=3.03 min, 100% (10 min method)

c) 5-(4-Cyclopropylmethoxy-3-methoxy-phenyl)-2H-pyrazol-3-ylamine

The product was prepared according to general procedure for aminopyrazole synthesis (route A2). The crude product was purified through SiO$_2$ column (gradient elution from EtOAc-cycloexane 1:1 to Ethyl Acetate:MeOH 90:10). 220 mg of the title product (yield 50%) were obtained.
C14H17N3O2
Mass (calculated) [259]; (found) [M+H$^+$]=260.
LC Rt=1.86 mine 93% (10 min method)
$^1$H-NMR (CDCl$_3$): 027-0.43 (2H, m); 0.56-0.72 (2H, m); 1.23-1.40 (1H, m); 348 (2H, m); 3.87 (3H, s); 3.98 (2H, br s); 5.82 (1H, s); 6.85-6.89 (1H, m); 7.05-7.10 (2H, m);

3-Amino-5-(3-fluoro-phenyl)-pyrazole-1-carboxylic acid tert-butyl ester

3-Amino-5-(3-fluoro-phenyl)-pyrazole (5.0 g, 28.0 mmol, 1.0 eq) and KOH 4.5 M (50 mL, 226 mmol, 8 eq) were dissolved in DCM (200 mL), and di-tert-butyl dicarbonate (6.5 g, 30.0 mmol, 1.1 eq) was added; the mixture was stirred at room temperature until complete conversion was observed by LC-MS analysis. The organic phase was washed with saturated brine and evaporated; the crude was crystallized with MeOH, to give 7.4 g of title product (yield 95%).
C14H16FN3O2
$^1$H-NMR (dmso-d6): 1.57 (9H, s), 5.80 (1H, s), 6.43 (2H, br s), 7.16-7.21 (1H, m), 7.41-7.47 (1H, m); 7.50-7.54 (1H, m); 7.58-7.60 (1H, m).

3-Amino-5-o-tolyl-pyrazole-1-carboxylic acid tert-butyl ester

3-Amino-5-o-tolyl-pyrazole (0.5 g, 2.89 mmol, 1.0 eq) and KOH 4.5 M (5.1 mL, 23.1 mmol, 8.0 eq) were dissolved in DCM (20 mL), and Di-tert-butyl dicarbonate (0.66 g, 3.0 mmol, 1.1 eq) was added; the mixture was stirred at room temperature until complete conversion was observed by LC-MS analysis. The organic phase was washed with saturated brine and evaporated, to give 0.6 g of title product (yield 76%).
C15H19N3O2
Mass (calculated) [273]; (found) [M+H$^+$]=274.
LC Rt=2.34 min, 96% (5 min method)

3-Amino-5-(4-trifluoromethyl-phenyl)-pyrazole-1-carboxylic acid tert-butyl ester 3-Amino-5-(4-trifluoromethyl-phenyl)-pyrazole (2.0 g, 8.8 mmol, 1.0 eq) and KOH 4.5 M (15.7 mL, 70.5 mmol, 8.0 eq) were dissolved in DCM (70 mL), and di-tert-butyl dicarbonate (2.02 g, 9.2 mmol, 1.1 eq) was added; the mixture was stirred at room temperature until complete conversion was observed by LC-MS analysis. The organic phase was washed with saturated brine and evaporated; the crude was crystallized with CH$_3$CN, to give 1.9 g of title product (yield 69%).
C15H16F3N3O2
Mass (calculated) [327]; (found) [M+H$^+$]=328.
LC Rt=2.59 min, 100% (5 min method)
$^1$H-NMR (dmso-d6): 1.57 (9H, s), 5.83 (1H, s), 6.46 (2H, s), 7.74 (2H, d, J=8.4 Hz), 7.95 (2H, d, J=8.8 Hz)

5-Pyridin-2-yl-2H-pyrazol-3-ylamine a) Oxo-pyridin-2-yl-acetonitrile

The product was prepared according to the general procedure for aminopyrazole synthesis (route A1) from pyridine-2-carboxylic acid methyl ester (3.0 g, 21.9 mmol, 1.0 eq). The crude was precipitated from HCl to give the title product as a solid (2.2 g, yield: 69%) which was used directly for the next step.
C8H6N2O b) 5-Pyridin-2-yl-2H-pyrazol-3-ylamine

The product was prepared according to general procedure for aminopyrazole synthesis (route A2). The crude product was dissolved in EtOAc, washed with NaHCO$_3$, dried and evaporated. NMR analysis showed that a major portion of the crude mixture was still in the opened form: the mixture was then dissolved in CH$_3$COOH and heated at 80° C. overnight, to allow for ring closure of the opened form. The product was then recovered as the acylated form, which was de-acylated stirring with HCl 6N at 60° C. overnight obtaining the title product (0.816 g, yield 60%).
C8H8N4
$^1$H-NMR (dmso-d6): 4.81 (2H, bs), 5.92 (1H, s), 7.21-7.24 (1H, m), 7.76 (2H, d), 8.51 (1H, d), 11.96 (1H, bs)

5-(3-Difluoromethoxy-phenyl)-2H-pyrazol-3-ylamine a) 3-Difluoromethoxy-benzoic acid methyl ester

Difluoromethoxy-benzoic acid (2.0 g, 10.6 mmol, 1.0 eq) was dissolved in MeOH (15 mL) and a catalytic quantity of sulfuric acid was added. The mixture was refluxed overnight, after which the solvent was evaporated under reduced pressure; the crude was dissolved in DCM and washed with saturated NaHCO$_3$ to basic pH. The organic phase was dried and evaporated under reduced pressure, and the title product was used without further purification (1.9 g, yield 90%).
C9H8F2O3
$^1$H-NMR (dmso-d6): 3.86 (3H, s), 7.33 (1H, t, J=73.6 Hz), 7.46-7.50 (1H, m), 7.59 (1H, t, J=8.0 Hz), 7.67 (1H, s); 7.82 (1H, d, J=7.6 Hz).

b) 3-(3-Difluoromethoxy-phenyl)-3-oxo-propionitrile

The product was prepared according to the general procedure for aminopyrazole synthesis (route A1 bis) from 3-difluoromethoxy-benzoic acid methyl ester (1.5 g, 7.4 mmol, 1.0 eq). The crude was precipitated by addition of aqueous HCl to give the product which was used directly for the next step.
C10H7F2NO2 c) 5-(3-Difluoromethoxy-phenyl)-2H-pyrazol-3-ylamine

The product was prepared according to general procedure for aminopyrazole synthesis (route A2). The crude product was purified through Si-column with gradient elution from 100% EtOAc to EtOAc-MeOH 90:10. 1.45 g of title product (yield 87%) was obtained.
C10H9F2N3O
$^1$H-NMR (dmso-d6): 4.89 (2H, br s), 5.75 (1H, s), 7.02 (1H, d), 7.25 (1H, t, J=74.0 Hz), 7.36-7.42 (2H, m), 7.48-7.50 (1H, d), 11.76 (1H, br s)

5-Pyrazolo[1,5-a]pyridin-3-yl-2H-pyrazol-3-ylamine a) 3-Oxo-3-pyrazolo[1,5-a]pyridin-3-yl-propionitrile

To a solution of dry acetonitrile in toluene (0.66 mL, 13 mmol, 5 eq) cooled down to −78° C. under nitrogen, a solution of n-butyllithium in n-hexane (5.2 mL, 13 mmol, 5 eq) was added dropwise. The mixture was left stirring at −78° C. for 20 minutes and then a solution of pyrazolo[1,5-a]pyridine-3-carboxylic acid methyl ester (0.46 g, 2.6 mmol, 1 eq, prepared according to the reported procedure (Anderson et al. *Journal of Heterocyclic Chemistry* 1981, 18, 1149-1152) in toluene was added and the reaction allowed to reach room temperature. Upon reaction completion, after about 20 minutes, the mixture was cooled down to 0° C. and HCl 2N was added to pH 2. The organic phase was recovered, dried over $Na_2SO_4$ and concentrated under reduced pressure, affording the title product which was used without further purification in the following step.

C10H7N3O b) 5-Pyrazolo[1,5-a]pyridin-3-yl-2H-pyrazol-3-ylamine

To a solution of the 3-oxo-3-pyrazolo[1,5-a]pyridin-3-yl-propionitrile (0.66 g, 3.6 mmol), in absolute EtOH (25 mL) hydrazine monohydrate (0.44 mL, 9.0 mmol) was added and the reaction was heated at reflux for 18 hours. The reaction mixture was allowed to cool to room temperature and the solvent was evaporated under reduced pressure. The residue was dissolved in DCM and washed with water.

The organic phase was concentrated under reduced pressure to give a crude product that was purified by $SiO_2$ column (DCM to DCM:MeOH 95:5 to 85:15 gradient), yielding the title compound in 41% Yield (0.29 g, 1.48 mmol).

C10H9N5

$^1$H-NMR (dmso-d6): 8.68 (s, 1H); 8.21 (s, 1H); 7.92 (s, 1H); 7.28 (s, 1H); 6.90 (s, 1H); 5.75 (s, 1H); 5.10 (s, 2H).

Mass (calculated) [199]; (found) [M+H$^+$]=200.

LC Rt=0.86 min, 92% (5 min method).

The following Table 2 shows analytical data obtained for a series of aminopyrazoles synthesised following procedures A1/A2 outlined in the general section

TABLE 2

| Name | % yield | MF | MW | Mass found | LC Purity | LC Rt | LC Method (min) | NMR |
|---|---|---|---|---|---|---|---|---|
| 5-(2-Methoxy-phenyl)-2H-pyrazol-3-ylamine | 79 | C10H11N3O | 189.22 | 190 | 96 | 1.08 | 5 | MeOD 3.92 (3H, s); 6.04 (1H, s); 6.96-7.00 (1H, m); 7.07-7.09 (1H, m); 7.28-7.32 (1H, m); 7.57-7.59 (1H, m) |
| 5-Quinolin-6-yl-2H-pyrazol-3-ylamine | 63 | C12H10N4 | 210.24 | 211 | 100 | 0.45 | 5 | MeOD 6.08 (1H, s); 7.52-7.55 (1H, m); 8.02-8.08 (2H, m); 8.18 (1H, s); 8.35-8.37 (1H, m); 8.79-8.81 (1H, m) |
| 5-(3-Bromo-4-methoxy-phenyl)-2H-pyrazol-3-ylamine | 61 | C10H10BrN3O | 268.11 | — | — | — | — | 1H NMR (DMSO-d6, 400 MHz) δ 3.84 (s, 1H), 6.29 (s, 1H), 7.11 (d, 1H, J = 8.6 Hz), 7.59 (dd, 1H, J = 2.0 Hz, J = 8.6 Hz), 7.83 (d, 1H, J = 2.0 Hz), 12.50 (s, 1H). |
| 5-Pyridin-3-yl-2H-pyrazol-3-ylamine | 27 | C8H8N4 | 160.18 | 161 | 100 | 0.22 | 5 | DMSO 5.9 (2H, s, broad); 7.45-7.47 (2H, m); 8.08-8.1 (1H, m), 8.45 (1H, m, broad), 8.84 (1H, s) |
| 5-[6-(Tetrahydro-pyran-2-yloxy)-pyridin-3-yl]-2H-pyrazol-3-ylamine | 99 | C13H16N4O2 | 260.3 | 260.2 | 94 | 1.93 | 10 | 1H NMR (DMSO-d6, 400 MHz) δ 1.67 (m, 6H), 3.53 (m, 1H), 5.45 (m, 1H), 5.65 (bs, 1H), 6.99 (d, 2H, J = 8.8 Hz), 7.53 (d, 2H, J = 8.8 Hz). |
| 5-(2-Fluoro-4-trifluoromethyl-phenyl)-2H-pyrazol-3-ylamine | 44 | C10H7F4N3 | 245.18 | — | — | — | — | 1H NMR (CDCl3, 400 MHz) δ 6.10 (s, 1H), 7.42 (d, 1H, J = 12.6 Hz), 7.45 (d, 1H, J = 7.7 Hz), 7.73 (dd, 1H, J = 7.7 Hz). |
| 5-(3-Fluoro-4-trifluoromethyl-phenyl)-2H-pyrazol-3-ylamine | 67 | C10H7F4N3 | 245.18 | — | — | — | — | 1H NMR (CDCl3, 400 MHz) δ 5.96 (s, 1H), 7.40 (d, 1H, J = 11.4 Hz), 7.44 (d, 1H, J = 7.8 Hz), 7.62 (d, 1H, J = 7.8 Hz). |
| 5-(2-Methyl-3-trifluoromethyl-phenyl)-2H-pyrazol-3-ylamine | 42 | C11H10F3N3 | 241.22 | — | — | — | — | 1H NMR (CDCl3, 400 MHz) δ 2.45 (s, 1H), 5.75 (s, 1H), 7.30 (dd, 1H, J = 7.7 Hz), 7.49 (d, 1H, J = 7.7 Hz), 7.66 (d, 1H, J = 7.7 Hz). |
| 5-(4-Chloro-3-trifluoromethyl-phenyl)-2H-pyrazol-3-ylamine | 44 | C10H7ClF3N3 | 261.64 | — | — | — | — | 1H NMR (CDCl3, 400 MHz) δ 5.93 (s, 1H), 7.50 (d, 1H, J = 8.34 Hz), 7.66 (dd, 1H, J = 8.34 Hz, J = 2.0 Hz), 7.88 (d, 1H, J = 2.0 Hz). |
| 5-(3-Fluoro-phenyl)-2H-pyrazol-3-ylamine | 33 | C9H8FN3 | 177.18 | 178 | 69% | 1.13 | 5 | — |
| 5-(2-Difluoromethoxy-phenyl)-2H-pyrazol-3-ylamine | 76 | C10H9F2N3O | 225.20 | — | — | — | — | DMSO 4.82 (2H, bs), 5.79 (1H, s), 7.00-7.37 (4H, m), 7.79 (1H, d), 11.74 (1H, bs) |
| 5-(3-Difluoromethoxy-phenyl)-2H-pyrazol-3-ylamine | 87 | C10H9F2N3O | 225.20 | — | — | — | — | DMSO 4.89 (2H, bs), 5.75 (1H, s), 7.02 (1H, d), 7.25 (1H, t, J = 74.0), 7.36-7.42 (2H, m), 7.48-7.50 (1H, d), 11.76 (1H, bs) |

TABLE 2-continued

| Name | % yield | MF | MW | Mass found | LC Purity | LC Rt | LC Method (min) | NMR |
|---|---|---|---|---|---|---|---|---|
| 5-(2-Trifluoromethoxy-phenyl)-2H-pyrazol-3-ylamine | 57 | C10H8F3N3O | 243.19 | — | — | — | — | CDCl3 4.45 (2H, bs), 5.86 (1H, s), 7.10 (1H, d), 7.32 (2H, t), 7.41 (1H, d) |
| 5-(3-Trifluoromethoxy-phenyl)-2H-pyrazol-3-ylamine | 59 | C10H8F3N3O | 243.19 | — | — | — | — | CDCl3 3.71 (2H, bs), 5.96 (1H, s), 7.24-7.30 (3H, m), 7.55 (1H, dd) |
| 5-(4-Trifluoromethoxy-phenyl)-2H-pyrazol-3-ylamine | 74 | C10H8F3N3O | 243.19 | — | — | — | — | DMSO 4.90 (2H, bs), 5.72 (1H, s), 7.32 (2H, d, J = 8), 7.73 (2H, d, J = 8.4), 11.74 (1H, bs) |
| 5-(2,4-Difluoro-phenyl)-2H-pyrazol-3-ylamine | 53 | C9H7F2N3 | 195.17 | — | — | — | — | DMSO 4.97 (2H, bs), 5.67 (1H, s), 7.17 (2H, d), 7.82 (1H, bs), 11.74 (1H, bs) |
| 5-(4-Difluoromethoxy-3-fluoro-phenyl)-2H-pyrazol-3-ylamine | 35 | C10H8F3N3O | 243.19 | 244 | 98% | 1.56 | 5 | CDCl3 3.64 (2H, bs), 5.82 (1H, s), 6.50 (1H, t, J = 73.2), 7.20-7.27 (2H, m), 7.30 (1H, dd, J = 11.2, J = 2.0) |
| 5-(4-Difluoromethoxy-2,6-difluoro-phenyl)-2H-pyrazol-3-ylamine | 14 | C10H7F4N3O | 261.18 | 262 | 92% | 1.56 | 5 | DMSO 4.88 (2H, bs), 5.61 (1H, s), 7.11 (2H, d, J = 8), 7.35 (1H, t, J = 73.2), 11.76 (1H, bs) |
| 5-(3,5-Dichloro-4-difluoromethoxy-phenyl)-2H-pyrazol-3-ylamine | 66 | C10H7Cl2F2N3O | 294.09 | 294 | 86% | 1.99 | 5 | CDCl3 3.63 (2H, bs), 5.82 (1H, s), 6.53 (1H, t, J = 60.0), 7.54 (2H, s) |
| 5-(3-Chloro-4-difluoromethoxy-phenyl)-2H-pyrazol-3-ylamine | 90 | C10H8C1F2N3O | 259.64 | 260 | 97% | 1.69 | 5 | CDCl3 4.02 (2H, bs), 5.83 (1H, s), 6.48 (1H, t, J = 81.2), 81.2), 7.20 (1H, d, J = 8.0), 7.38 (1H, dd, J = 8.4, J = 2.0), 7.58 (1H, d, J = 2.0) |
| 5-(4-Difluoromethoxy-3-methoxy-phenyl)-2H-pyrazol-3-ylamine | 78 | C11H11F2N3O2 | 255.23 | 256 | 100% | 1.46 | 5 | CDCl3 3.51 (2H, bs), 3.86 (3H, s), 5.83 (1H, s), 6.50 (1H, t, J = 74.8), 7.02 (1H, dd, J = 8.4, J = 2.0), 7.07 (1H, d, J = 2.0), 7.13 (1H, d, J = 8.4) |
| 5-(4-Difluoromethoxy-2-methyl-phenyl)-2H-pyrazol-3-ylamine | 48 | C11H11F2N3O | 239.23 | 240 | 95% | 1.43 | 5 | DMSO 2.38 (3H, s), 4.72 (2H, bs), 5.53 (1H, s), 7.00 (1H, dd, J = 8.4, J = 2.4), 7.05 (1H, s), 7.21 (1H, t, J = 74.0), 7.42 (1H, d, J = 8.4), 11.56 (1H, s) |
| 5-(5-Methyl-pyridin-3-yl)-2H-pyrazol-3-ylamine | 60 | C9H10N4 | 174.21 | 175.21 | 100 | 0.23 | 5 | MeOD 2.39 (3H, s); 5.96 (1H, s); 7.92-7.95 (1H, m); 7.30-7.33 (1H, m); 8.63-8.65 (1H, m) |
| 5-(2-Methyl-quinolin-6-yl)-2H-pyrazol-3-ylamine | 81 | C13H12N4 | 224.27 | 225.27 | 100 | 0.23-0.42 | 5 | MeOD 2.72 (3H, s); 6.09 (1H, s); 7.43-7.45 (1H, m); 7.94-7.97 (1H, m); 8.00-8.07 (1H, m); 8.13-8.15 (1H, m); 8.24-8.27 (1H, m) |
| 5-(6-Methoxy-naphthalen-2-yl)-2H-pyrazol-3-ylamine | 83 | C14H13N3O | 239.28 | 240.28 | 88 | 1.49 | 5 | MeOD 3.91 (3H, s); 6.01 (1H, s); 7.12-7.17 (1H, m); 7.21-7.25 (1H, m); 7.67-7.81 (3H, m); 8.03-8.05 (1H, m |
| 5-(2-Methoxy-phenyl)-2H-pyrazol-3-ylamine | 60 | C10H11N3O | 189.22 | 190 | 100 | 1.07 | 10 | |
| 5-(4-Trifluoromethyl-phenyl)-2H-pyrazol-3-ylamine | 43 | C10H8F3N3 | 227.19 | 228.19 | 98 | 1.64 | 5 | MeOD 5.91 (1H, s); 7.57-7.63 (2H, m); 7.38-7.58 (1H, m); 7.99-8.03 (1H, m) |
| 5-Pyridin-4-yl-2H-pyrazol-3-ylamine | 28 | C8H8N4 | 160.18 | 161.18 | 100 | 0.21 | 5 | |
| 5-(2-Fluoro-phenyl)-2H-pyrazol-3-ylamine | 45 | C9H8FN3 | 177.18 | 178 | 100 | 1.06 | 5 | $^1$H-NMR (dmso-d6): 4.83 (2H, bs); 5.75 (1H, s); 7.14-7.45 (2H, m); 7.65-7.88 (1H, m) |
| 5-(5-Chloro-2-methyl-phenyl)-2H-pyrazol-3-ylamine | 72 | C10H10C1N3 | 207.66 | — | — | — | — | $^1$H-NMR (cdcl3): 2.36 (3H, s); 3.73 (2H, bs); 5.78 (1H, s); 7.19 (1H, bs); 7.22-7.23 (1H, m); 7.34-7.35 (1H, m) |
| 5-(2-Methyl-3-trifluoromethyl-phenyl)-2H-pyrazol-3-ylamine | 33 | C11H10F3N3 | 241.22 | — | — | — | — | $^1$H-NMR (cdcl3): 2.45 (3H, s); 3.72 (2H, bs); 5.76 (1H, s); 7.28-7.34 (1H,m); 7.46-7.51 (1H, m); 7.64-7.68 (1H, m) |

TABLE 2-continued

| Name | % yield | MF | MW | Mass found | LC Purity | LC Rt | LC Method (min) | NMR |
|---|---|---|---|---|---|---|---|---|
| 5-(4-Fluoro-2-methyl-phenyl)-2H-pyrazol-3-ylamine | 61 | C10H10FN3 | 191.21 | — | — | — | — | ¹H-NMR (cdcl3): 2.38 (3H, s); 3.72 (2H, bs); 5.75 (1H, s); 6.89-7.08 (2H, m); 7.28-7.36 (1H, m) |
| 5-(2,4-Dimethyl-phenyl)-2H-pyrazol-3-ylamine | 66 | C11H13N3 | 187.25 | — | — | — | — | ¹H-NMR (cdcl3): 2.35 (3H, s); 2.37 (3H, s); 3.67 (2H, bs); 5.77 (1H, s); 7.02-7.10 (2H, m) 7.23-7.25 (1H, m) |
| 5-(4-Chloro-2-methyl-phenyl)-2H-pyrazol-3-ylamine | 62 | C10H10C1N3 | 187.25 | — | — | — | — | ¹H-NMR (cdcl3): 2.36 (3H, s); 5.74 (1H, s); 7.17-7.20 (1H, m); 7.24-7.26 (2H, m). |
| 5-(4-Fluoro-3-trifluoromethyl-phenyl)-2H-pyrazol-3-ylamine | 33 | C10H7F4N3 | 245.18 | — | — | — | — | 1H NMR (CDCl3, 400 MHz) δ 5.84 (s, 1H), 7.19 (m, 1H), 7.67 (m, 1H), 7.75 (m, 1H). |
| 5-(4-Difluoromethoxy-phenyl)-1H-pyrazol-3-ylamine | 46 | C10H9F2N3O | 225.2 | 226 | 100% | 1.34 | 5 | DMSO 4.82 (2H, bs), 5.71 (1H, s), 7.15 (2H, d, J = 8.4), 7.22 (1H, t, J = 74.0), 7.67 (2H, d, J = 8.8) 11.58 (1H, bs) |
| 5-(1-Ethyl-1H-indol-5-yl)-2H-pyrazol-3-ylamine | 82 | C13H14N4 | 226.28 | 227 | 87 | 1.3 | 5 | |
| 5-(1-Ethyl-1H-indol-6-yl)-2H-pyrazol-3-ylamine | 53 | C13H14N4 | 226.28 | 227 | 90 | 1.35 | 5 | |
| 5-(2-Methyl-quinolin-6-yl)-2H-pyrazol-3-ylamine | 56 | C13H12N4 | 224.27 | 225 | 90 | 0.21 | 3 | ¹H-NMR (dmso-d6): 2.62 (3H, s); 4.89 (2H, bs); 5.85 (1H, s); 7.35-7.40 (1H, m); 7.83-7.89 (1H, m); 7.85-7.87 (1H, m); 8.11 (1H, bs); 8.18-8.21 (1H, m) |
| 5-Quinolin-3-yl-2H-pyrazol-3-ylamine | 84 | C12H10N4 | 210.24 | 211 | 100 | 83 | 3 | ¹H-NMR (dmso-d6): 5.03 (2H, bs), 5.92 (1H, s); 7.52-7.61 (1H, m); 7.66-7.64 (1H, m); 7.92-7.99 (2H, m); 8.50 (1H, s); 9.25 (1H, s) |
| 5-Quinolin-6-yl-2H-pyrazol-3-ylamine | 85 | C12H10N4 | 210.24 | 211 | 90 | 0.21 | 5 | ¹H-NMR (dmso-d6): 4.94 (2H, bs); 5.88 (1H, s); 7.44-7.54 (1H, m); 7.93-8.01 (1H, m); 8.08-8.15 (1H, m); 8.16-8.20 (1H, m); 8.30-8.35 (1H, m); 8.80-8.84 (1H, m). |
| 5-(2-Methyl-5-trifluoromethyl-phenyl)-2H-pyrazol-3-ylamine | 41 | C11H10F3N3 | 241.22 | — | — | — | — | 1H NMR (CDCl3, 400 MHz) δ 5.81 (s, 1H), 7.37 (d, 1H, J = 8.0 Hz), 7.51 (dd, 1H, J = 8.0 Hz, J = 1.6 Hz), 7.61 (d, 1H, J = 1.6 Hz). |
| 5-(2-Methyl-6-trifluoromethyl-pyridin-3-yl)-1H-pyrazol-3-ylamine | 36 | C10H9F3N4 | 242.21 | 242.9 | 95 | 1.89 | 5 | |
| 5-(6-Trifluoromethyl-pyridin-3-yl)-1H-pyrazol-3-ylamine | 40 | C9H7F3N4 | 228.18 | 228 | 95 | 1.37 | 5 | 1H NMR (DMSO-d6, 400 MHz) δ 5.13 (s, 1H), 7.85 (d, 1H, J = 7.9 Hz), 8.25 (dd, 1H, J = 7.7 Hz, J = 1.63 Hz), 9.03 (d, 1H, J = 1.63 Hz), 11.89 (s, 1H). |

General method for the synthesis of ω-bromo-alkanoic acid (1H-pyrazol-3-yl-5-aryl)-amides

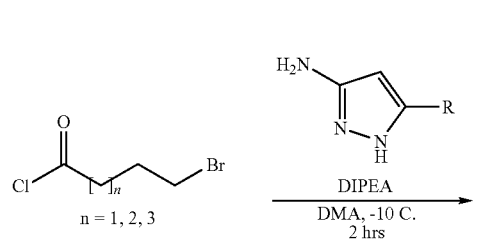

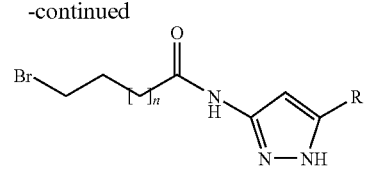

A solution of ω-bromoalkanoyl chloride (15.7 mmol, 1 eq) in dry DMA (35 mL) was cooled to −10° C. (ice/water bath) under N₂; a solution of 5-aryl/heteroaryl-1H-pyrazol-3-ylamine (15.7 mmol, 1 eq) and diisopropylethylamine (15.7 mmol, 1 eq) in dry DMA (15 mL) is added over 30'. After 2 hrs at −10° C., completion of the reaction as monitored by LC-MS was generally observed (acylation on the pyrazole ring is also detected). The reaction is then quenched by addition of H₂O (ca. 50 mL); the thick white precipitate formed upon addition of water was recovered by filtration. Washing with Et₂O (3×10 mL) usually efficiently removed the byproduct of acylation on the pyrazole ring.

General method for the synthesis of
ω-amino-alkanoic acid
(1H-pyrazol-3-yl-5-aryl)-amides

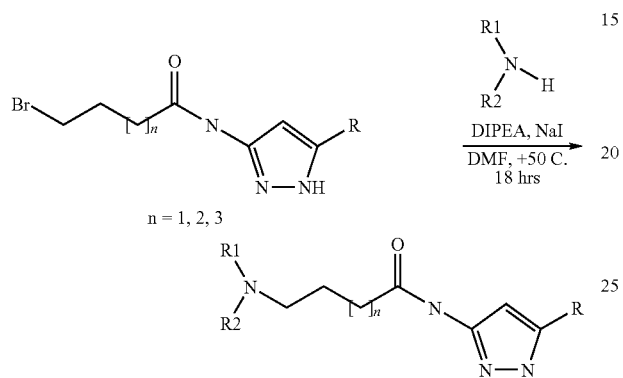

ω-Bromo-alkanoic acid [5-aryl-1H-pyrazol-3-yl]-amide (0.6 mmol, 1 eq) is dissolved in DMF (4 mL), sodium iodide (0.6 mmol, 1.0 eq) is added followed by the secondary amine (1.5 mmol, 2.5 eq) and diisopropylethylamine (0.6 mmol, 1 eq). The reaction is then stirred under $N_2$ at +50° C. for 18 hrs.

Upon reaction completion (as monitored by LC-MS), the solvent is removed at reduced pressure and the resulting oily residue is dissolved in DCM (20 mL), washed with sat. $Na_2CO_3$ (2×20 mL) and sat. NaCl (2×20 mL); the organic layer is dried over $Na_2SO_4$ and the solvent removed under reduced pressure. The title compounds were purified either by silica column or preparative HPLC.

General Synthetic Method for the One-Pot Synthesis
of ω-amino-alkanoic acid (1H-pyrazol-3-yl-5-aryl)-
amides: acylation-nucleophilic Substitution

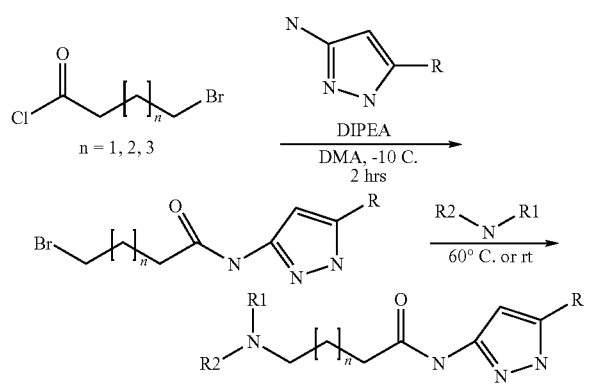

To a solution of ω-bromoalkanoyl chloride (0.94 mmol, 1 eq) in DMA (1 mL) cooled at 0° C. is added a solution of 3-amino-5-aryl/heteroarylpyrazole (0.94 mmol, 1 eq) and diisopropylethylamine (1.88 mmol, 2 eq) in DMA (2 mL) and the reaction is stirred for 1 hour at 0° C. The secondary amine (2.35 mmol, 2.5 eq) and NaI (0.94 mmol, 1 eq) are then added. For 3-carbon chain derivatives the reaction was generally complete after 2 hours at room temperature. For 4-carbon chain derivatives the reaction mixture was generally heated at 60° C. for 24-48 hours. Upon complete conversion of the bromo-intermediate (as monitored by LC-MS), the solvent was removed under reduced pressure. The residue was taken up in DCM (2 mL) and washed with $Na_2CO_3$ saturated water solution. The organic phase was concentrated under reduced pressure and the crude products were either recrystallised from $CH_3CN$, or purified by $SiO_2$ column (gradient from 100% DCM to DCM-NH3MeOH 2N solution 8:2) or by preparative HPLC (standard acidic conditions).

General Method for the Synthesis of
ω-amino-alkanoic acid
(1H-pyrazol-3-yl-5-aryl)-amides via the amino acid
Route

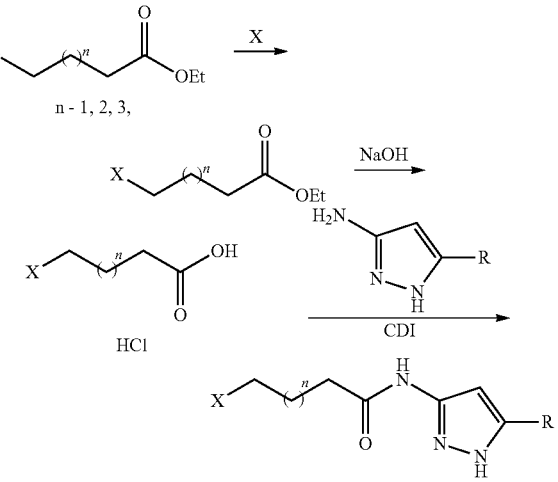

General Method for the Sythesis of ω-aminoester
(Route C1)

To a solution of amine X (65 mmol) in toluene (15 mL) ethyl ω-bromoalkanoate (26 mmol) was added and the reaction mixture was refluxed for 10 hours. The mixture was allowed to cool to room temperature and any solid present was filtered off and washed with ether. The filtrate was concentrated under reduced pressure to give the ω-aminoester which was used in the next step without further purification.

General Method for the Synthesis of ω-aminoacid
(Route C2)

To a suspension of crude ethyl ω-aminoalkanoate from the previous step (about 25 mmol) in 15 mL of water, NaOH (1.4 g, 25 mmol) was added and the mixture was heated at reflux for 16 hours. The reaction was then allowed to cool down to room temperature, the solution was acidified at 0° C. with HCl 6N and concentrated under reduced pressure. The residue was treated with EtOH and the sodium chloride which precipitated was filtered off. Evaporation of the solvent under reduced pressure afforded the ω-aminoacid as a white solid or as a colourless oil.

4-(2-Methyl-piperidin-1-yl)-butyric acid a) 4-(2-Methyl-piperidin-1-yl)-butyric acid ethyl ester

The title product was prepared according to the general procedure for ω-aminoester synthesis (route C1). After filtration of the excess 2-methylpiperidine, the organic phase was concentrated under reduced pressure to give the 4.6 g of the aminoester (yield 99%) which was used in the next step without further purification.
$C_{12}H_{23}NO_2$
$^1$H-NMR (dmso-d6): 0.94 (3H, d, J=6.0 Hz); 1.11-1.19 (4H, m); 1.31-1.40 (1H, m); 1.46-1.62 (5H, m); 1.97-2.02 (1H, m); 2.12-2.28 (5H, m); 2.52-2.59 (1H, m); 2.68-2.73 (1H, m); 4.02 (2H, q, J=7.2 Hz).

b) 4-(2-Methyl-piperidin-1-yl)-butyric acid

The product was prepared according to the general procedure for ω-aminoacid synthesis (route C2). Evaporation of water under reduced pressure afforded 4.1 g of the title compound (99% Yield).
$C_{10}H_{19}NO_2$
$^1$H-NMR (dmso-d6): 1.01 (3H, d, J=6.4 Hz); 1.19-1.27 (2H, m); 1.40-1.49 (2H, m); 1.54-1.61 (4H, m); 2.10-2.13 (2H, m); 2.18-2.25 (1H, m); 2.28-2.35 (1H, m); 2.42-2.48 (1H, m); 2.62-2.69 (1H, m); 2.69-2.84 (1H, m).

4-(2-Methyl-pyrrolidin-1-yl)-butyric acid a) 4-(2-Methly-pyrrolidin-1-yl)-butyric acid ethyl ester

The product was prepared according to the general procedure for ω-aminoester synthesis (route C1). After filtration of the excess 2-methylpyrrolidine, the organic phase was concentrated under reduced pressure to give 4.1 g of the aminoester as an oil (yield 99%) which was used in the next step without further purification.
$C_{11}H_{21}NO_2$
1H-NMR (CDCl3): 1.09-1.11 (3H, m); 1.23 (3H, t, J=6.8 Hz); 1.41-1.48 (2H, m); 1.63-1.95 (6H, m); 2.10-2.14 (2H, m); 2.78-2.81 (1H, m); 3.17-3.21 (2H, m); 4.10 (2H, q, J=7.2 Hz)

b) 4-(2-Methyl-pyrrolidin-1-yl)-butyric acid

The product was prepared according to the general procedure for ω-aminoacid synthesis (route C2). Evaporation of water under reduced pressure and crystallization from acetone afforded 1.4 g of the title compound (49% Yield).
$C_9H_{17}NO_2$
1H-NMR (dmso-d6): 1.31 (3H, d, J=6.4 Hz); 1.51-1.60 (1H, m); 1.81-1.91 (4H, m); 2.03-2.17 (1H, m); 2.24-2.37 (2H, m); 2.82-2.95 (1H, m); 2.97-3.02 (1H, m); 3.19-3.32 (2H, m), 3.49-3.57 (1H, m); 10.06 (1H, br s).

4((S)-2-Methyl-piperidin-1-yl)-butyric acid a) 4-((S)-(2-Methyl-piperidin-1-yl)-butyric acid ethyl ester

The product was prepared according to the general procedure for ω-aminoester synthesis (route C1). After filtration of the excess (S)-2-methylpiperidine, the organic phase was concentrated under reduced pressure to give the 2.4 g of the aminoester (yield 92%) which was used in the next step without further purification.
$C_{12}H_{23}NO_2$
$^1$H-NMR (CDCl$_3$): 0.93 (3H, d, J=6.0 Hz); 1.10-1.21 (5H, m); 1.31-1.39 (1H, m); 1.44-1.64 (5H, m); 1.97-2.03 (1H, m); 2.11-2.25 (4H, m); 2.53-2.59 (1H, m); 2.68-2.72 (1H, m); 4.01 (2H, q, J=6.8 Hz).

b) 4((S)-2-Methyl-piperidin-1-yl)-butyric acid

The product was prepared according to the general procedure for ω-aminoacid synthesis (route C2). Evaporation of water under reduced pressure afforded 1.9 g of the title compound (85% Yield).
$C_{10}H_{19}NO_2$
$^1$H-NMR (dmso-d6): 1.22 (3H, d, J=6.4 Hz); 1.40-1.43 (1H, m); 1.50-1.70 (4H, m); 1.76-1.83 (3H, m); 2.26-2.33 (2H, m); 2.80-2.89 (2H, m); 2.95-3.00 (1H, m); 3.11-3.19 (2H, m).

4-((R)-2-Methyl-pyrrolidin-1-yl)-butyric acid a) 4-((R)-2-Methyl-pyrrolidin-1-yl)-butyric acid ethyl ester (R)-2-methyl-pyrrolidine hydrochloride (1.0 g, 8.2 mmol, 1.1 eq) was dissolved in 2-butanone (25 mL) and potassium carbonate (2.2 g, 15.7 mmol, 2.1 eq) was added. Ethyl 4-bromobutyrate (1.07 mL, 7.5 mmol, 1.0 eq) was added and the reaction mixture was refluxed for 2 days. The mixture was allowed to cool to room temperature and solid was filtered off and washed with ether. The filtrate was concentrated under reduced pressure to give 1.5 g of the title compound (yield 99%) which was used in the next step without further purification.
$C_{11}H_{21}NO_2$
1H-NMR (dmso-d6): 0.95 (3H, d, J=6.0 Hz); 1.15 (3H, t, J=7.2 Hz); 1.20-1.27 (1H, m); 1.56-1.64 (4H, m); 1.77-1.86 (1H, m); 1.91-1.99 (2H, m); 2.15-2.22 (1H, m); 2.25-2.30 (2H, m); 2.62-2.69 (1H, m); 2.97-3.01 (1H, m); 4.01 (2H, q, J=7.2 Hz).

b) 4-((R)-2-Methyl-pyrrolidin-1-yl)-butyric acid

The product was prepared according to the general procedure for ω-aminoacid synthesis (route C2). Evaporation of water under reduced pressure afforded 1.4 g of the title compound (88% Yield) as its hydrochloride salt.
$C_9H_{17}NO_2$
$^1$H-NMR (dmso-d6 of HCl salt): 1.34 (3H, d, J=6.4 Hz); 1.56-1.61 (1H, m); 1.83-1.92 (3H, m); 2.11-2.14 (1H, m); 2.31-2.39 (2H, m); 2.81-2.90 (1H, m); 2.95-3.04 (1H, m); 3.19-3.44 (3H, m); 3.51-3.58 (1H, m); 10.20 (1H, br s); 12.29 (1H, br s).

2-Methyl-4-(pyrrolidin-1-yl)-2-butyric acid a) 4-Bromo-2-methyl-butyryl bromide 2-methylbutyrolactone (50 mmol, 5.0 g) and phosphorous tribromide (41 mmol, 3.7 mL) were heated at 140° C. for 2.5 hours. The reaction mixture was transferred into a Kugelrohr distillation apparatus and distilled under reduced pressure (40 mmHg, T=128° C.) to obtain 6.21 g (yield: 51%) of 4-bromo-2-methyl-butyryl bromide as a clear oil.
$C_5H_8Br_2O$
$^1$H-NMR (CDCl$_3$): 3.45 (2H, t, J=6.8 Hz); 3.22-3.18 (1H, m); 2.42-2.36 (1H, m); 1.99-1.94 (1H, m); 1.32 (3H, d, J=7.2 Hz).

b) 4-Bromo-2-methyl-butyric acid methyl ester

A solution of 4-bromo-2-methyl-butyryl bromide (6.2 g, 43.0 mmol, 1.0 eq) in $CHCl_3$ (10 mL) was cooled at 0° C. MeOH (10 mL) was slowly added and the resulting mixture stirred at room temperature for 16 hours. The solvent was evaporated and the residue dissolved in $CHCl_3$ and washed with water and brine. The organic layer was collected and dried with $Na_2SO_4$. Evaporation of the solvent gave 4-bromo-2-methyl-butyric acid methyl ester as thick oil (4.3 g, yield 51%).

$C_6H_{11}BrO_2$ $^1$H-NMR (dmso-d6): 1.19 (3H, d, J=7.2 Hz); 1.94-1.89 (2H, m); 2.29-2.23 (2H, m); 3.43-3.40 (1H, m); 3.69 (3H, s).

c) 2-Methyl-4-(pyrrolidin-1yl)-2-butyric acid

Pyrrolidine (5.4 mL, 66 mmol) was dissolved in toluene (40 mL). 4-Bromo-2-methyl-butyric acid methyl ester (4.3 g, 22.0 mmol) was added and the reaction stirred at reflux for 2.5 hours. Removal of the solvent and of the excess amine at reduced pressure gave 2-methyl-4-(pyrrolidin-1-yl)-butyric acid methyl ester as a thick oil. The crude product was diluted with MeOH (3 mL) and 1.0M NaOH aq solution (22 mL) was added and the reaction stirred at reflux for 18 hours.

After cooling to room temperature, the mixture was concentrated at reduced pressure to remove the organic solvent and the water. HCl 6N was added to reach pH 4.5; subsequently EtOH was added to precipitate NaCl. After filtration the solvent was evaporated at reduced pressure (keeping the water bath at room temperature to avoid esterification) to give 4-pyrrolidin-2-methyl-butyric acid as yellow oil (3.58 g, yield 90%).

$C_9H_{17}NO_2$

Mass (calculated) [199]; (found) [M+H$^+$]=200.

LC Rt=1.12 min; 90% (5 min method):

$^1$H-NMR (dmso-d6): 2.79 (4H, m); 2.73 (2H, m); 2.37 (1H, m); 1.84 (2H, m); 1.81-1.75 (3H, br m); 1.57 (1H, m); 1.5 (3H, d, J=7.2 Hz)

2-Methyl-4-piperidin-1-yl-butyric acid

Piperidine (1.1 mL, 20.0 mmol, 3.0 eq) was dissolved in toluene (15 mL). 4-Bromo-2-methyl-butyric acid methyl ester (1.3 g, 6.6 mmol, 1.0 eq) was added and the reaction stirred at reflux for 3 hours. Removal of the solvent and of the excess amine at reduced pressure gave 4-pyrrolidin-2-methyl-butyric acid methyl ester as a thick oil. The crude product was diluted with MeOH (2 mL) and 1.0M NaOH aq solution (14 mL, 7.0 eq) was added and the reaction stirred at reflux for 16 hours. After cooling to room temperature, the mixture was concentrated at reduced pressure to remove the organic solvent and the water. HCl 6N was added to reach pH 4.5; subsequently EtOH was added to precipitate NaCl. After filtration the solvent was evaporated at reduced pressure (bath at room temperature to avoid esterification) to give 4-pyrrolidin-2-methyl-butyric acid as yellow oil (0.9 g, yield 66%).

$C_{10}H_{19}NO_2$

Mass (calculated) [171]; (found) [M+H$^+$]=172.

LC Rt=0.22 min; 90% (5 min method).

1H-NMR (CDCl3): 3.66 (m, 1H); 3.59 (m, 1H); 3.53 (m, 2H); 3.45 (m, 2H); 2.93 (m, 1H); 1.62-1.51 (br m, 8H); 1.10 (d, 3H, J=7.2)

5-[1,4]-Oxazepan-4-yl-butyric acid

Homomorpholine (1.0 g, 7.3 mmol, 1.2 eq) was dissolved in toluene (15 mL) and 4-bromo-2-methyl-butyric acid methyl ester (0.9 g, 6.1 mmol, 1.0 eq) was added and the reaction stirred at reflux for 3 hours. Removal of the solvent and of the excess amine at reduced pressure gave the methyl ester as an oil. The crude product was diluted with H2O (10 mL) and MeOH (2 mL) and 1.0M NaOH aq solution (0.3 g, 7.0 eq) was added and the reaction stirred at reflux for 18 hours. After cooling to room temperature, the mixture was concentrated at reduced pressure to remove the organic solvent and the water. HCl 6N was added to reach pH 4; subsequently EtOH was added to precipitate NaCl. After filtration the solvent was evaporated at reduced pressure at room temperature to give 4-pyrrolidin-2-methyl-butyric acid as yellow oil (0.9 g, yield 66%).

$C_9H_{17}NO_3$ $^1$H-NMR (dmso-d6): 3.73 (m, 2H); 3.68 (m, 2H); 3.16-3.11 (m, 2H); 2.93 (m, 2H); 2.28 (m, 2H); 2.23 (m, 2H); 1.96 (m, 2H); 1.79 (m, 2H).

4-Pyrrolidin-1-yl-butyric acid a) 4-Pyrrolidin-1-yl-butyric acid ethyl ester

To a solution of pyrrolidine (8.42 mL, 102 mmol, 4.0 eq) in toluene (30 mL), ethyl 4-bromobutyrate (3.8 mL, 26 mmol, 1.0 eq) was added and the reaction mixture was refluxed for 10 hours. The mixture was allowed to cool down to room temperature, the white solid present was filtered off and washed with $Et_2O$. The filtrate was concentrated under reduced pressure to give the title product which was used in the next step without further purification.

b) 4-Pyrrolidin-1-yl-butyric acid hydrochloride

4-Pyrrolidin-1-yl-butyric acid ethyl ester (about 25 mmol) was suspended in 100 mL of NaOH 10% and the mixture was heated at reflux for 10 hours. The reaction mixture was then allowed to cool to room temperature and was washed with AcOEt. The aqueous layer was recovered by extraction and acidified at 0° C. with HCl 37% to pH 4 and concentrated under reduced pressure. The residue was treated with EtOH and the sodium chloride which precipitated was filtered off. The crude was treated with $Et_2O$ and filtered; evaporation of the solvent under reduced pressure afforded 2.5 g of the title compound as a white solid in 61% overall yield of steps a) and b).

$C_8H_{15}NO_2$

Mass (calculated) [157]; (found) [M+H$^+$]=158.

LC Rt=0.21 min, 100% (5 min method)

$^1$H-NMR (dmso-d6 for HCl salt): 1.80-1.93 (6H, m); 2.31 (2H, t, J=14.8); 3.03-3.11 (2H, m); 3.18-3.32 (4H, m, broad)

4-Morpholin-4-yl-butyric acid a) 4-Morpholin-4-yl-butyric acid ethyl ester

To a solution of morpholine (8.96 mL, 102 mmol, 4.0 eq) in toluene (30 mL) ethyl 4-bromobutyrate (3.8 mL, 2-6 mmol, 1.0 eq) was added and the reaction mixture was refluxed for 10 hours. The mixture was allowed to cool to room temperature; the white solid present was filtered off and washed with $Et_2O$. The filtrate was concentrated under reduced pressure to give the title product which was used in the next step without further purification.

b) 4-Morpholin-4-yl-butyric acid

4-Morpholin-4-yl-butyric acid ethyl ester (about 25 mmol) was suspended in 100 mL of NaOH 10%, and the mixture was heated at reflux for 10 hours. The reaction mixture was then allowed to cool down to room temperature and washed with AcOEt. The aqueous layer was recovered by extraction and acidified at 0° C. with HCl 37% to pH 4 and concentrated under reduced pressure. The residue was treated with EtOH and the sodium chloride which precipitated was filtered off. The crude was treated with acetone and filtered; evaporation of the solvent under reduced pressure afforded 3.2 g of the title compound as a white solid in 72% overall yield of steps a) and b).

C8H15NO3

Mass (calculated) [173]; (found) [M+H$^+$]=174.

LC Rt=0.30 min, 100% (5 min method)

$^1$H-NMR (dmso-d6 of HCl salt): 1.86-1.95 (2H, m); 2.29-2.34 (2H, m); 2.94-3.08 (4H, m); 3.34-3.38 (2H, m); 3.74-3.83 (2H, m); 3.88-3.91 (2H, m); 11.24 (1H, s)

General Method for Amide Coupling

To a suspension of ω-aminoacid (7.93 mmol) in 12,2-dichloroethane (20 mL), N,N'-carbonyldiimidazole (1.2 g, 7.4 mmol) was added and the mixture was stirred at room temperature for 2 hours (when all the aminoacid was activated complete dissolution of the suspension was generally observed). The 3-amino-5-aryl/heteroarylpyrazole (5.29 mmol) was then added and the reaction was stirred for further 10 hours. Upon reaction completion (as monitored by LC-MS) if the formation of two isomers was observed, the mixture was heated at 50° C. until the conversion of the less stable isomer to the title compound was observed (as monitored by LC-MS). The solvent was washed with sat. Na$_2$CO$_3$ solution, extracted and removed under reduced pressure. The crude products were either recrystallised from CH$_3$CN, or purified by SiO$_2$ column or by preparative HPLC.

4-(4-Trifluoromethoxy-phenyl)-1H-imidazol-2-ylamine a) N-[4-(4-Trifluoromethoxy-phenyl)-1H-imidazol-2-yl]-acetamide Acetyl guanidine (2.6 g, 25.7 mmol, 3.0 eq) was dissolved in anhydrous DMF (40 mL) and 2-bromo-1-(4-trifluoromethoxy-phenyl)-ethanone (2.4 g, 8.6 mmol, 1.0 eq) was added; the mixture was stirred at room temperature for 4 days. DMF was removed under reduced pressure, the residue was washed with water, filtered and dried over sodium sulphate; after crystallization from MeOH 0.7 g of the title compound were recovered (yield 30%).

C12H10F3N3O2

$^1$H-NMR (dmso-d6): 2.14 (3H, s); 7.37-7.40 (3H, m); 7.88-7.91 (2H, m); 11.33 (1H, s); 11.78 (1H, br s).

b) 4-(4- Trifluoromethoxy-phenyl)-1H-imidazol-2-ylamine

N-[4-(4-Trifluoromethoxy-phenyl)-1H-imidazol-2-yl]-acetamide (0.7 g, 2.6 mmol, 1.0 eq) was dissolved in water (18 mL) and methanol (18 mL), and 20 drops of sulfuric acid were added. The reaction was refluxed for 2 days, then the mixture was dried; the residue was diluted with water, the pH adjusted to 8 with NaOH 2N, the product was extracted with DCM and concentrated under reduced pressure to give 0.6 g of the title compound (yield 98%)

C10H8F3N3O $^1$H-NMR (dmso-d6): 5.73 (2H, br s); 7.10 (1H, s); 7.26 (2H, d, J=8.0 Hz); 7.67-7.69 (2H, m).

EXAMPLE 1

5-Azepan-1-yl-pentanoic acid [5-(4-methoxy-phenyl)-1H-pyrazol-3-yl]-amide 5-(4-Methoxy-phenyl)-1H-pyrazol-3-yl-amine (0.089 g, 0.45 mmol) is dissolved in DCE:DMF 4:1 (2.5 mL) and 5-bromovaleryl chloride (0.057 mL, 0.43 mmol) is added followed by diisopropylethylamine (0.078 mL, 0.45 mmol). The reaction is stirred under N$_2$ at 0° C. for 1 hr. Azepane (0.152 mL, 1.35 mmol) is then added together with more disopropylethylamine (0.078 mL, 0.45 mmol). The reaction is stirred at +50° C. for 18 hrs. Upon reaction completion (as monitored by LC-MS), the solvent is removed under reduced pressure and the resulting oily residue is dissolved in DCM (20 mL), washed with sat. Na$_2$CO$_3$ (2×20 mL) and sat. NaCl (2×20 mL); the organic layer is dried over Na$_2$SO$_4$.

Purification by preparative HPLC (standard acidic conditions) gives 0.046 g of the title compound as formate salt (0.11 mmol, 25% yield)

C$_{21}$H$_{30}$N$_4$O$_2$ Mass (calculated) [370.50]; (found) [M+H$^+$]=371

LC Rt=1.97, 96% (10 min method)

NMR (400 MHz, dmso-d6): 1.79-1.71 (6H, m); 1.89 (6H, m); 3.17 (2H, t); 3.34 (2H, m); 3.82 (3H, s); 6.7 (1H, s); 6.98 (2H, d); 7.58 (2H, d); 8.26 (1H, HCOOH,s); 10.21 (1H, s).

EXAMPLE 2

5-(4-Methyl-piperidin-1-yl)-pentanoic acid [5-(4-methoxy-phenyl)-1H-pyrazol-3-yl]-amide 5-Bromo-pentanoic acid [5-(4-methoxy-phenyl)-1H-pyrazol-3-yl]-amide (0.106 g, 0.6 mmol) is dissolved in DMF (2 mL), sodium iodide (0.045 g, 0.6 mmol) is added followed by 4-methylpiperidine (0.054 mL, 1.5 mmol) and diisopropylethylamine (0.052 mL, 0.6 mmol, 1 eq). The reaction is stirred under N$_2$ at +50° C. for 18 hrs.

Upon reaction completion (as monitored by LC-MS), the solvent is removed at reduced pressure and the resulting oily residue is dissolved in DCM (20 mL), washed with sat. Na$_2$CO$_3$ (2×20 mL) and sat. NaCl (2×20 mL); the organic layer is dried over Na$_2$SO$_4$.

Purification by preparative HPLC (standard acidic conditions) gives 0.057 g of the title compound as formate salt (0.14 mmol, 45% yield).

C$_{21}$H$_{30}$N$_4$O$_2$ Mass (calculated) [370.50]; (found) [M+H$^+$]=371.26

LC Rt=1.73, 100% (10 min method)

NMR (400 MHz, dmso-d6): 0.84 (3H, d, J=6.23 Hz); 1.13-1.07 (2H, m); 1.33-1.27 (4H, m); 1.45 (1H, m); 1.50 (2H, m); 1.96 (2H, m); 2.26 (2H, m); 2.35 (2H, m); 2.88 (2H, m); 3.14 (3H, s); 6.71 (1H, s); 6.96 (2H, d); 7.6 (2H, d); 8.17 (1H, s, HCOOH); 10.13 (1H, s).

EXAMPLE 3

5-(4-Acetyl-[1,4]diazepan-1-yl)-pentanoic acid (5-thiophen-2-yl-1H-pyrazol-3-yl)-amide Bromovaleryl chloride (1.62 mL, 12.12 mmol) was dissolved in DMA (50 mL). To this, a solution of 5-thiophen-2-yl-2H-pyrazol-3-ylamine (2 g, 12.12 mmol) and DIEA (2.1 mL, 12.12 mmol) was added portionwise at 0° C. The reaction mixture was left stirring 1 hour at 0° C. and then for 2 hours at room temperature. After a total of 3 hours, PS-Trisamine (1 g, ~4 mmol/g) was added to the mixture and left stirring for 2 hours. Then, N-acetylhomopiperazine (4.3 g, 30.3 mmol) was added and the mixture was left stirring at room temperature for a further 60 hours. After DMA evaporation under reduced pressure, water was added (50 mL) and this was extracted with ethyl acetate (3×30 mL). The aqueous layer was basified with solid NaOH and extracted with ethyl acetate at pH=10 and then again at pH=11. All the organic phases were reunited, dried and evaporated. The residue was purified by silica chromatography eluting with a gradient of ethyl acetate/methanol 9:1 up to ethyl acetate/methanol 8:2, to give the title compound as yellowish oil (800 mg, 17%).

$C_{19}H_{27}N_5O_2S$ Mass (calculated) [389.52]; (found) [M+H$^+$]=390.11

NMR (400 MHz, CDCl$_3$): 1.52 (2H, m); 1.77 (2H, m); 1.82 (2H, m); 2.13+2.09 (3H, s); 2.44 (2H, m); 2.56 (2H, m); 2.62 (1H, m); 2.76-2.70 (3H, m); 3.51 (2H, m); 3.61 (1H, m); 3.64 (1H, m); 6.48 (1H, s); 6.56 (1H, s); 7.05-7.02 (2H, m); 6.9-7.26 (2H, m); 8.94 (1H, s); 9.53 (1H, s).

The title compound was converted in its hydrochloride salt by adding a solution of HCl (1.05 mL, 2N) in diethyl ether to (5-(4-Acetyl-[1,4]diazepan-1-yl)-pentanoic acid (5-thiophen-2-yl-2H-pyrazol-3-yl)-amide (800 mg, 2.05 mmol) suspended in MeOH (10 mL). The solution was left stirring at room temperature for 1 hour, then evaporated to dryness to yield the title compound as a yellowish powder (750 mg, 86%)

EXAMPLE 4

5-(4-Acetyl-[1,4]diazepan-1-yl)-pentanoic acid [5-(4-methoxy-phenyl)-2H-pyrazol-3-yl]-amide a) First Approach ai) 5-Bromo-pentanoic acid [5-(4-methoxy-phenyl)-1H-pyrazol-3-yl]-amide A solution of 5-bromovaleryl chloride (2.1 mL, 15.7 mmol, 1 eq) in dry DMA (35 mL) was cooled to −10° C. (ice/water bath) under N$_2$; a solution of 5-(4-methoxy-phenyl)-1H-pyrazol-3-ylamine (3.0 g, 15.7 mmol, 1 eq) and diisopropylethylamine (2.74 mL, 15.7 mmol, 1 eq) in dry DMA (15 mL) was added over 30 min. After 2 hrs at −10° C., LC-MS shows completion of the reaction which was quenched by addition of H$_2$O (ca. 50 mL). The solid which precipitates was filtered and washed with Et$_2$O, to give 4.68 g of 5-bromo-pentanoic acid [5-(4-methoxy-phenyl)-1H-pyrazol-3-yl]-amide as a white powder (13.3 mmol, 85% yield).

mp=149.5-151.5° C.

$C_{15}H_{18}BrN_3O_2$ Mass (calculated) [352.23]; (found) [M+H$^+$]=352.09/354.10

LC Rt=2,07, 95% (5 min method)

NMR (400 MHz, dmso-d6): 1.69-1.63 (2H, m); 1.81-1.75 (2H, m); 2.29 (2H, t); 3.52 (2H, t); 3.75 (3H, s); 6.75 (1H, bs); 6.96 (2H, d); 7.6 (2H, d); 10.28 (1H, s); 12.57 (1H, s)

aii) 5-(4-Acetyl-[1,4]diazepan-1-yl)-pentanoic acid [5-(4-methoxy-phenyl)-2H-pyrazol-3-yl]-amide To 750 mg (1.96 mmol) of 5-bromo-pentanoic acid [5-(4-methoxy-phenyl)-2H-pyrazol-3-yl]-amide in 7 mL of DMA, N-acetyl-diazepine (278 mg, 1.96 mmol) and NaI (240 mg, 1.96 mmol) were added and the reaction heated at 60° C. for 18 hours. Upon complete conversion (as monitored by LC-MS) the mixture was diluted with 20 mL of DCM and washed with water. The organic phase was concentrated under reduced pressure to afford a residue which was purified with SiO2 column (10 g) eluting with a gradient from DCM to DCM-MeOH 90:10. The title compound (380 mg) was recovered pure (yield 46%).

$C_{22}H_{31}N_5O_3$ Mass (calculated) [413]; (found) [M+H$^+$]=414

LC Rt=1.91, 100% (10 min method)

$^1$H-NMR (400 MHz, dmso-d$_6$): 1.53-1.75 (4H, m), 1.90-2.15 (5H, m), 2.28-2.42 (2H, m), 2.90-3.26 (3H, m), 3.34-3.58 (3H, m), 3.71-3.88 (7H, m)

b) Second Approach bi) 5-(4-Acetyl-[1,4]diazepan-1-yl)-pentanoic acid [5-(4-methoxy-phenyl)-1H-pyrazol-3-yl]-amide (mono hydrochloride salt)

To a solution of 5-(4-methoxyphenyl)-1H-pyrazol-3-ylamine (12 g, 62.8 mmol) and N,N-diisopropylethylamine (10.96 mL, 62.8 mmol) in dry N,N-dimethylformamide (150 mL) at −10° C. was added a solution of 5-bromovaleryl chloride (8.4 mL, 62.8 mmol) in dry N,N-dimethylformamide (50 mL) slowly (~40 min) and the reaction mixture was allowed to stir at −10 to 0° C. for 8 hrs. Sodium iodide (9.44 g, 62.8 mmol) was added at 0° C. and followed by N-acetylhomopiperazine (8.24 mL, 62.8 mmol) and N,N-diisopropylethylamine (10.96 mL, 62.8 mmol) and the reaction mixture was allowed to stir at 50° C. for 18 hrs. The solvent was removed in vacuo. The residue was dissolved in methylene chloride (500 mL) and saturated aqueous sodium bicarbonate (500 mL) and the mixture was stirred at room temperature for 30 minutes. The organic layer was separated, dried over sodium sulfate, and the solvent was removed in vacuo to provide 25.8 g (99%) of 5-(4-acetyl-1,4-diazepan-1-yl)-N-(5-(4-methoxyphenyl)-1H-pyrazol-3-yl)pentanamide as a thick light yellow oil (crude).

Then to a solution of the crude 5-(4-acetyl-1,4-diazepan-1-yl)-N-(5-(4-methoxyphenyl)-1H-pyrazol-3-yl)pentanamide (as a free base) in methylene chloride (270 mL) at room temperature was added hydrogen chloride (65 mL, 1.0 M in ethyl ether) slowly. The resulting suspension was allowed to stir at room temperature for 1 hour. The solvent was removed in vacuo to afford 33 g as a yellow foam, mono hydrochloride salt. The foam was dissolved in solvents (330 mL, acetonitrile: methanol=33:1) at 60-70° C. and the crystal seed was added. The mixture was slowly cooled down to the room temperature and allowed to stir at room temperature for 15 hours. The resulting precipitate was filtered and dried to give 20.5 g (72%) of the title compound as a white crystal, mono hydrochloride salt. MS [M−H]$^-$ m/z 412.3; mp. 132-133° C.

c) Third Approach ci) 3-(4-methoxyphenyl)-3-oxopropanenitrile

A solution of methyl p-anisate in acetonitrile was cooled to −10° C. Lithium bis(trimethylsilyl)amide (1 M in THF) was added dropwise over a minimum of 3 hr. The mixture was held at −10 to 0° C. until reaction completion. The reaction mixture was quenched with water and the pH adjusted to 3-4 with conc HCl. The mixture was stirred for 1 hr. The product was isolated by filtration, washed with water and dried in a vacuum oven. The yield was 73%.

cii) 5-(4-methoxyphenyl)-1H-pyrazol-3-amine

A suspension of 3-(4-methoxyphenyl)-3-oxopropanenitrile in ethanol was heated to 60° C. Hydrazine hydrate was added dropwise over a minimum of 30 min at 60° C. The resulting solution was held at 60° C. until reaction completion, generally 15-18 hr. The reaction mixture was quenched with water. Ethanol was removed by distillation to about 5 volumes. The product was isolated by filtration, washed with water and dried in a vacuum oven. The yield was 88-95%.

ciii) 5-bromo-N-(5-(4-methoxyphenyl)-1H-pyrazol-3-yl)pentanamide

A solution of 5-(4-methoxyphenyl)-1H-pyrazol-3-amine and diisopropylethylamine in 10 volumes of a 9:1 mixture of acetonitrile:DMF was cooled to −10° C. 5-Bromovaleryl chloride was added dropwise over a minimum of 3 hr at −10° C. The resulting solution was held at −10° C. until reaction completion, generally 2 hr. The reaction mixture was quenched with water. The product was isolated by filtration, washed with water, TBME and suction dried. The product-wet cake was purified by re-slurrying in TBME at 35° C. for a minimum of 2 hr. The yield was 70-80%.

civ) 5-(4-acetyl-1,4-diazepaz-1-yl)-N-(5-(4-methoxyphenyl)-1H-pyrazol-3-yl)pentanamide Bromopyrazole is mixed with $K_2CO_3$ and KI in 10 volumes of acetone at room temperature and N-acetylhomopiperazine was added over 1 hr. The reaction mixture was stirred until the reaction was complete. The mixture was filtered, removing the inorganics, washed with acetone and distilled to 2 volumes. The freebase was extracted into methyl THF/EtOH and washed with NaCl and $NaHCO_3$. The solvent was replaced with EtOH, a strength of the solution was determined, and 0.93 eq of HCl based on the available freebase was added to a mixture of acetone, ethanol and water. Careful monitoring of the pH yielded crystalline product in a 70% overall yield and the desired form 1.

d) Fourth Approach di) 5-(4-methoxy-phenyl-1H-pyrazol-3-ylamine

The intermediate 5-(4-methoxy-phenyl)-1H-pyrazol-3-ylamine is commercially available from Sigma-Airich (USA), but can be made using the following general procedure:

Aryl β-Ketonitrile Synthesis

To a solution of an aromatic ester (6.5 mmol) in dry toluene (6 mL), under $N_2$, NaH (50-60% dispersion in mineral oil, 624 mg, 13 mmol) was carefully added. The mixture was heated at 80° C. and then dry $CH_3CN$ was added dropwise (1.6 mL, 30.8 mmol). The reaction was heated for 18 h and generally the product precipitated from the reaction mixture as a salt. The reaction was allowed to cool to room temperature and the solid formed was filtered and then dissolved in water. The solution was acidified with 2N HCl solution, and upon reaching a pH between 2-4, the product precipitated and was filtered. If no precipitation occurred, the product was extracted with DCM. After aqueous workup, the products were generally pure enough to be used in the next step without further purification. The isolated yield was generally 40-80%.

Aryl Aminopyrazole Synthesis

To a solution of β-ketonitrile (7.5 mmol) in absolute EtOH (15 mL), hydrazine monohydrate (0.44 mL, 9.0 mmol) was added and the reaction was heated at reflux for 18 hrs. The reaction mixture was allowed to cool to room temperature and the solvent was evaporated under reduced pressure. The residue was dissolved in 20 mL of DCM and washed with water. The organic phase was concentrated to give a crude product that was purified by $SiO_2$ column or by precipitation from $Et_2O$. For example, the 2-methoxy derivative was purified by $SiO_2$ chromatography, eluting with a DCM/MeOH gradient (from 100% DCM to 90/10 DCM/MeOH); the 3-methoxy derivative was triturated with $Et_2O$. Yields were generally 65-90%.

dii) 5-bromo-pentanoic acid [5-(4-methoxy-phenyl)-1H-pyrazol-3-yl]amide

A solution of 5-bromovaleryl chloride (2.1 mL, 15.7 mmol) in dry dimethylacetamide (DMA) (35 mL) was cooled to −10° C. (ice water bath) under $N_2$; a solution of 5-(4-methoxy-phenyl)-1H-pyrazol-3-ylamine (3.0 g, 15.7 mmol) and diisopropylethylamine (2.74 mL, 15.7 mmol) in dry DMA (15 mL) was added over 30 min. After two hours at −10° C., LCMS shows completion of the reaction (acylation on the pyrazole ring was also detected). The reaction was quenched by addition of $H_2O$ (ca. 50 mL), and the thick white precipitate formed upon addition of water is recovered by filtration. When the reaction was allowed to reach room temperature before quenching, a putative exchange of Br with Cl caused reactivity problems in subsequent steps. Washing with $Et_2O$ (3×10 mL) efficiently removed the byproduct (acylation on pyrazole ring). 4.68 g of the title compound was obtained as a white powder (13.3 mmol, 85% yield). Mp=149.5-151.5° C.

diii) 5-(4-acetyl-[1,4]diazepan-1-yl)-pentanoic acid [5-(4-methoxy)-phenyl)-1H-pyrazol-3-yl]-amide 5-bromo-pentanoic acid [5-(4-methoxy-phenyl)-1H-pyrazol-3-yl]amide (1.5 g, 4.26 mmol) was dissolved in DMF (15 mL), and sodium iodide (0.64 g, 4.26 mmol) was added followed by N-acetylhomopiperazine (0.56 mL, 4.26 mmol) and diisopropylethylamine (0.74 mL, 4.26 mmol). The reaction was stirred under $N_2$ at 50° C. for 18 hrs. Upon reaction completion (as monitored by LCMS), the solvent was removed at reduced pressure and the resulting oily residue was dissolved in DCM (20 mL), washed with sat. $Na_2CO_3$ (2×20 mL) and sat. NaCl (2×20 mL), and dried over $Na_2SO_4$. Upon solvent removal, 1.7 g of crude product as a thick oil were obtained. The product was purified by $SiO_2$ chromatography (10 g cartridge-flash SI II from IST) employing DCM and DCM:MeOH 9:1 to yield 0.92 g of pure product and 0.52 g of less pure product. A second purification of the impure fractions using a 5 g $SiO_2$ cartridge was performed using the same eluent. Overall, 1.09 g of 5-(4-acetyl-[1,4]diazepan-1-yl)-pentanoic acid [5-(4-methoxy-phenyl)-1H-pyrazol-3-yl]-amide were obtained (2.64 mmol, 62% yield) as a thick light yellow oil. MS (ES+): 414.26 (M+H)+.

div) 5-(4-acetyl-[1,4]diazepan-1-yl)-pentanoic acid [5-(4-methoxy)-phenyl)-1H-pyrazol-3-yl]-amide hydrochloride 5-(4-acetyl-[1,4]diazepan-1-yl)-pentanoic acid [5-(4-methoxy-phenyl)-1H-pyrazol-3-yl]-amide (1.05 g, 2.54 mmol) was dissolved in a minimum amount of DCM (5 mL) and cooled to 0° C. HCl (2.0 M in $Et_2O$, 1.4 mL, 2.89 mmol) was added and the mixture stirred at rt until precipitation of the salt was complete (about 10 min.). The solid was filtered, washed with Et$_2$O several times, and dried in a dessicator to yield 1.09 g of the hydrochloride salt (2.42 mmol, 95% yield). Melting point was not determined due to the extreme hygroscopicity of the sample. MS (ES+): 414.26 (M+H)$^+$.

e) Fifth Approach ei) 5-(4-acetyl-[1,4]diazepan-1-yl)-N-[5-(4-methoxy-phenyl)-1H-pyrazol-3-yl]-pentanamide To a cylindrical, jacketed 3 L reactor equipped with nitrogen inerting, agitator, condenser/distillation head, and temperature control, 5-bromo-pentanoic acid [5-(4-methoxy-phenyl)-1H-pyrazol-3-yl]amide (0.15 kg, 0.426 mol), potassium carbonate (0.059 kg, 0.426 mol), potassium iodide (0.071 kg, 0.426 mol), and acetone (1.18 kg, 1.5 L) were added (at 20° C.) to form a white mixture. The mixture was stirred (235 rpm) at 25-30° C. for a minimum of 15 min. N-acetylhomopiperazine (0.062 kg, 0.057 L, 0.434 mol) was added via addition funnel to the reactor over a minimum of 45 min., maintaining the temperature in the range of 25-30° C. The addition funnel was rinsed with 0.05 L acetone. A white mixture persisted. The mixture was stirred (235 rpm) in the range of 25-30° C. for a minimum of 16 h, forming a white/yellow mixture. The reaction progress was monitored by HPLC and was considered complete when there was ≦2% of the starting material (bromopyrazole) and ≦2% of the iodopyrazole present.

The reactor contents were cooled to 5-15° C. over a minimum of 15 min with agitation (295 rpm) to form a white/yellow mixture that was stirred for a minimum of 1 h. To remove inorganics, the mixture was then filtered on a Buchner funnel with filter paper using house vacuum for 1.5 min. The cake was washed twice with acetone (total of 0.24 kg, 0.30 L) at 5-15° C. The wash was combined with the mother liquor from the prior filtration and used to rinse the reactor. The filtrate was concentrated to a volume of approximately 0.45 L to form a clear solution.

eii) Aqueous Workup

To a reactor containing the material from step i, 1.5 L of a freshly made homogeneous solution of methyl THF (1.22 kg, 1.42 L) and ethanol (0.059 kg, 0.075 L) was added at 25° C., forming a hazy solution. To this, 0.45 L of a 5% solution of sodium chloride (0.022 kg) in water (0.43 L) was added at 25° C. The resulting mixture was heated with stirring to 30-35° C. over a minimum of 15 min., forming a clear biphasic solution. The agitation was stopped to allow the layers to settle, the product being in the upper layer. The layers were separated, keeping any emulsion in the upper organic layer. The organic layer was retained. A homogeneous 5% solution of sodium bicarbonate (0.03 kg) in water (0.57 L) at 25° C. was used to wash organic layer, stirring for a minimum of 5 min. at 10-15° C. The agitation was stopped to allow the layers to settle, the product being in the upper layer. The layers were separated, keeping any emulsion in the upper organic layer. The organic layer was retained and concentrated to a volume of 0.35 L, forming a hazy solution. The mixture was chased with ethanol to remove residual water.

eiii) 5-(4-acetyl-[1,4]diazepan-1-yl)-N-[5-(4-methoxy-phenyl)-1H-pyrazol-3-yl]-pentanamide HCl To a reactor containing the material from step ii, 0.47 kg (0.60 L) of acetone was added. The resulting mixture was heated with stirring to 25-30° C. over a minimum of 10 min., forming a hazy solution. The contents of the reactor were clarified through a polypropylene pad into a tared 2 L suction flask using vacuum, maintaining the contents of the reactor at 25-30° C. Suction was maintained until filtration stopped. The reactor and filter pad were rinsed with acetone (0.05 L) at 20-25° C. The filtrates from the suction flask were transferred to the reactor and rinsed using acetone (0.05 L). A solution of 5% HCl (0.042 kg, 0.036 L) in acetone (0.174 L) and alcohol solution (0.0174 L of ethanol:acetone (91:9) v/v) was prepared and stirred until homogeneous at 10° C. To the reactor, 0.05 L of water was added to form a clear solution. One third of the 5% HCl solution (0.076 L) was added to the reactor over a minimum of 20 min., maintaining the temperature in the range of 20-25° C. A second third of the 5% HCl solution (0.076 L) was then added to the reactor over a minimum of 20 min., maintaining the temperature in the range of 20-25° C. The contents of the reactor were seeded with 75 mg of 5-(4-acetyl-[1,4]diazepan-1-yl)-N-[5-(4-methoxy-phenyl)-1H-pyrazol-3-yl]-pentanamide HCl (e.g., Form 1), followed by the addition of the last third of 5% HCl solution (0.076 L) over a minimum of 20 min., maintaining the temperature in the range of 20-25° C. Another 0.08 equiv. of the 5% HCl solution (0.023 L) was then added to the reactor over a minimum of 30 min., maintaining the temperature in the range of 20-25° C. Judicious monitoring of pH was performed to attain the desired pH range of 5.2-5.8.

The mixture was stirred at 20-25° C. for a minimum of 1 h, forming a thin suspension. Acetone (0.6 L) was added over a minimum of 60 min., maintaining the temperature in the range of 20-25° C. The mixture was stirred at 20-25° C. for a minimum of 60 min. Acetone (1.5 L) was added to the reactor over a minimum of 3 hr., maintaining the temperature in the range of 20-25° C., forming a thick suspension. The mixture was then stirred at 20-25° C. for a minimum of 12 h. Crystallization was considered complete when there was ≦20% of the product present in the mother liquor.

The mixture was then filtered on a Buchner funnel (polypropylene pad) using house vacuum. A solution of water (0.009 L), acetone (0.23 L) and 0.06 L alcohol (ethanol:acetone (91:9) v/v) was stirred until homogeneous (20% ethanol, 3% water, 77% acetone overall). This solution was used to wash the filter cake twice (0.15 L×2). A solution of water (0.009 L), acetone (0.171 L) and 0.12 L alcohol (ethanol:acetone (91:9) v/v) was stirred until homogeneous (40% ethanol, 3% water, 57% acetone overall). This solution was used to wash the filter cake (0.30 L). The wet cake was subjected to suction under nitrogen using house vacuum and held for 30 min. after dripping stopped. Product purity was checked by HPLC and additional washing was performed if total impurities were not ≦2%. Product was oven dried in a vacuum oven with nitrogen bleed at 38-45° C., maintaining vacuum at 20 torr for a minimum of 12 h until loss on drying of less than 1% was obtained. Following drying, 0.119 kg of the title compound was obtained in 62% yield (67% adjusted for aliquots removed during process; 60% when corrected for strength or purity). Melting point=185° C., crystal form=form 1; particle size=D90<89.4 um, D50<19.2 um.

J) Hydrochloride salt of 5-(4-Acetyl-[1,4]diazepan-1-yl)-pentanoic acid [5-(4-methoxy-phenyl)-2H-pyrazol-3-yl]-amide The present Example describes the preparation of the hydrochloride salt form of 5-(4-Acetyl-[1,4]diazepan-1-yl)-pentanoic acid [5-(4-methoxy-phenyl)-2H-pyrazol-3-yl]-amide. The hydrochloric acid salt form readily adopted a solid form. Indeed, at least four different crystalline forms (i.e., polymorphs) were observed for the hydrochloric acid salt form (see below).

| Counter Ion Used | Solid Obtained | Melting Onset | Hygroscopicity |
|---|---|---|---|
| Hydrochloric acid | Crystalline solid | 185° C. | No |
| | | 165° C. | Somewhat |
| | | 125° C. | Yes |
| | | 125° C. | ? |
| | | three peaks: about 100 about 180; and about 200° C. | Yes |

Differential scanning calorimetry data were collected for each solid form achieved using a DSC (TA instruments, model Q1000) under the following parameters: 50 mL/min purge gas($N_2$); scan range 40 to 200° C., scan rate 10° C./min. Thermogravimetric analysis data were collected using a TGA instruments (Mettler Toledo, model TGA/SDTA 851e) under the following parameters: 40 ml/min purge gas($N_2$); scan range 30 to 250° C., scan rate 10° C./min. X-ray data were acquired using an X-ray powder diffractometer (Bruker-axs, model D8 advance) having the following parameters: voltage 40 kV, current 40.0 mA, scan range (2θ) 5 to 30°, scan step size 0.01°, total scan time 33 minutes, VANTEC detector, and antiscattering slit 1 mm. FIGS. 1-7 show characterization data for hydrochloride salt forms.

The hydrochloride salt was polymorphic, adopting crystalline forms exhibiting DSC endotherins at 119° C. (Form III), 127° C. (Form IV), 167° C. (Form II), and 186° C. (Form I). Another form, potentially an ethanol solvate, exhibited multiple endotherms, corresponding to 1) desolvation at about 100° C., 2) Form I at about 183° C., and 3) possibly another polymorph at about 200° C. The Crystal Form Table below illustrates certain characteristics of observed hydrochloride salt crystal forms:

| Crystal Form Table | | | | |
|---|---|---|---|---|
| Crystal Form I Mono-hydrochloride (8% HCl) | Crystal Form II | Crystal Form III | Crystal Form IV | Crystal Form V |
| Melting: 180-186° C. | Melting: 165° C. | Melting: 125° C. | Melting: 125° C. | Three peaks: About 100° C. About 180° C. About 200° C. |
| Non-hygroscopic (see FIG. 4) | Somewhat hygroscopic (5% water at RH 50%; see FIG. 10) | Hygroscopic (10% water at RH 50%; see FIG. 11) | Not tested | Hygroscopic (7% at RH 50%; see FIG. 12) |

Of the various observed hydrochloride forms, only Form I (186° C.) is relatively non-hygroscopic, gaining only about 0.5% moisture when equilibrated at RH less than or equal to 70%. At 70-100% RH, Form I gains at least about 12% moisture, but loses it without significant hysteresis on decreasing RH. Evidence of a hydrochloride hydrate was not observed.

Higher degrees of hydrochloride salt were formed, depending on the amount of hydrochloric acid present in the solution during reactive crystallization. The conversion of higher degrees of hydrochloride salt to mono-hydrochloride salt can be achieved by adjusting the pH of the solution to about pH 4-5. Further adjustment, however, can result in formation of inorganic salts. In some embodiments, pure mono-hydrochloride salt forms are produced with hydrochloride equivalence and slurry pH of <0.95 eq. (e.g., 0.93) and pH.5, respectively (see, for example, FIGS. 8-11).

g) Characterization of Certain Crystal Forms of Hydrochloride Salt

The present Example describes characterization of two surprisingly non-hygroscopic crystal forms (Forms I and II, as described above) of a hydrochloride salt of 5-(4-Acetyl-[1,4]diazepan-1-yl)-pentanoic acid [5-(4-methoxy-phenyl)-2H-pyrazol-3-yl]-amide:

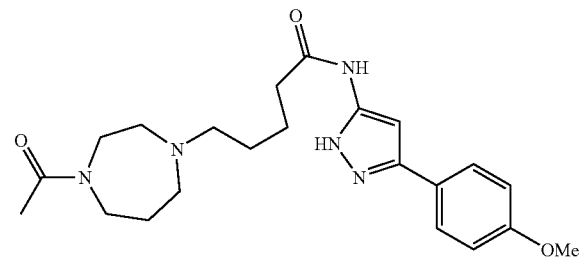

Both forms are considerably soluble in water. The melting point of Form I is 185° C. (plus or minus 2 degrees); the melting point of Form II is 166° C. (plus or minus 2 degrees).

Form I picks up moisture at relative humidity (RH) of about 50% and absorbs up to about 2% water eventually (90% RH) and loses the water as RH decreases (<50%). Form I also exhibits characteristic X-ray peaks at 2θ of 15.3° and 21.9°, plus or minus about 0.3°, depending upon the machine and measurement method utilized.

Form II picks up moisture at RH of about 20% and absorbs up to 7% water eventually (RH of 90%) and holds 2% at low RH (0%). Form II also exhihbits characteristic X-ray peaks at 2θ of 20.2° and 24.9°, plus or minus about 0.3°, depending upon the machine and measurement method utilized. Differential scanning calorimetry data were collected for each solid form achieved using a DSC (TA instruments, model Q1000) under the following parameters: 50 mL/min purge gas($N_2$); scan range 40 to 200° C., scan rate 10° C./min.

Thermogravimetric analysis data were collected using a TGA instruments (Mettler Toledo, model TGA/SDTA 851e) under the following parameters: 40 ml/min purge gas($N_2$); scan range 30 to 250° C., scan rate 10° C./min.

X-ray data were acquired using an X-ray powder diffractometer (Bruker-axs, model D8 advance) having the following parameters: voltage 40 kV, current 40.0 mA, scan range (2θ) 3.7 to 30°, scan step size 0.01°, total scan time 33 minutes, VANTEC detector, and antiscattering slit 1 mm.

Dynamic Vapor Sorption (DVS) was done at 26° C.

Results of thermal studies on Crystal Forms I and II are shown in FIGS. 12-19.

h) Preparation of Crystal Form I of the Hydrochloride Salt of 5-(4-Acetyl-[1,4]diazepan-1-yl)-pentanoic acid [5-(4-methoxy-phenyl)-2H-pyrazol-3-yl]-amide The present Example describes the preparation of crystal form I of the hydrochloride salt of 5-(4-Acetyl-[1,4]diazepan-1-yl)-pentanoic acid [5-(4-methoxy-phenyl)-2H-pyrazol-3-yl]-amide.

First procedure: 611.7 mg of the free base form of 5-(4-Acetyl-[1,4]diazepan-1-yl)-pentanoic acid [5-(4-methoxy-phenyl)-2H-pyrazol-3-yl]-amide was dissolved in 1.97 mL acetone at 35° C. A solution of 5% HCl in acetone-water was prepared by diluting 37.5% aq. HCL using acetone. 0.6 ml of 5% HCl was added slowly. 1.2 ml EtOH ASDQ (100:10 ethanol:methanol) was added slowly. The solution became milky in a few minutes; stirring was performed for around 5 minutes. 0.25 ml of 5% HCl was added slowly. After 5 minutes, 0.25 ml of 5% HCl was added slowly. After 5 minutes, 0.087 ml of 5% HCl was added slowly. The mixture was heated to about 40-50° C. The mixture was left at room temperature while stirring overnight. Crystals were filtered and washed with 2 ml acetone, and were dried at 45° C. for about 7 hours. 505 mg of solid were recovered.

Second procedure: 377 mg of the free base form of 5-(4-Acetyl-[1,4]diazepan-1-yl)-pentanoic acid [5-(4-methoxy-phenyl)-2H-pyrazol-3-yl]-amide was dissolved in 1.2 ml acetone at 35° C. 0.754 ml ethanol ASDQ (100:10 ethanol:methanol) was added. A solution of 5% HCl in acetone-water was prepared by diluting 37.5% aq HCl using acetone. 0.18 ml diluted HCl solution was added slowly. A seed of crystal form I of the hydrochloride salt of 5-(4-Acetyl-[1,4]diazepan-1-yl)-pentanoic acid [5-(4-methoxy-phenyl)-2H-pyrazol-3-yl]-amide was added. 0.18 ml diluted HCl solution was added slowly. Around two minutes later, 0.18 ml diluted HCl solution was added slowly. Around two minutes later, another 0.18 ml diluted HCl solution was added slowly. The mixture was heated to about 40-50° C., and then was left at room temperature while stirring overnight. The crystals were filtered and washed with 1.5 ml acetone, and were dried at 45° C. for about 6 hours.

EXAMPLE 5

5-Piperidin-1-yl-pentanoic acid [5-(3-bromo-phenyl)-2H-pyrazol-3-yl]-amide a) 3-(3-Bromo-phenyl)-3-chloro-acrylonitrile To 30.9 mL of dry DMF (400 mmol) cooled down to 0° C. 18.3 mL of POCl$_3$ (200 mmol) were added dropwise so that the temperature was always under 10° C. To the mixture 19.9 g (100 mmol) of 1-(3-bromophenyl)ethanone were added dropwise and the reaction was allowed to reach room temperature.

When the addition was complete the reaction was stirred for further 30 minutes and then 2.7 g (40 mmol) of hydroxylamine hydrochloride were added and the reaction heated up to 50° C. The heating was then removed and other 27 g (400 mmol) of hydroxylamine hydrochloride were added portionwise (so that the temperature did never exceed 120° C.).

After the last addition the reaction was left stirring until the temperature of the mixture spontaneously decreased to 25° C. Water (100 mL) was then added and the mixture was extracted with diethyl ether. The organic phase was dried over Na$_2$SO$_4$ andconcentrated under reduced pressure.

The crude product was used for the next step without further purification.

$C_9H_5BrClN$
$^1$H-NMR (400 MHz, dmso-d$_6$): 7.03 (s, 1H), 7.44-7.54 m, 1H), 7.72-7.84 (m, 2H), 8.00 (br s, 1H)
Yield 68% b) 5-(3-Bromo-phenyl)-2H-pyrazol-3-ylamine

To a solution of 3-(3-bromo-phenyl)-3-chloro-acrylonitrile (10 mmoL), in absolute EtOH (20 mL) hydrazine monohydrate (1 mL, 20 mmol) was added and the reaction was heated at reflux for 4 hrs. The reaction mixture was then allowed to cool to room temperature and the solvent was evaporated under reduced pressure. The residue was triturated with Et$_2$O, allowing to recover 1.8 g of the title compound as pure product (yield 54%).

$C_9H_8BrN_3$
$^1$H-NMR(400 MHz, dmso-d$_6$): 4.58, 5.03 (1H, 2 tautomeric peaks), 5.64, 5.84 (1H, 2 tautomeric peaks), 7.28 (1H, s), 7.35 (1H, s), 7.53-7.65 (1H, m), 7.77 (1H, s), 11.56, 11.97 (1H, 2 tautomeric peaks).

c) 5-Piperidin-1-pentanoic acid [5-(3-bromo-phenyl)-2H-pyrazol-3-yl]-amide

To a solution of 5-bromo-valeryl chloride (500 μL, 3.74 mmol) in 5 mL of DMA, cooled at 0° C., a solution of 5-(3-bromo-phenyl)-2H-pyrazol-3-ylamine (890 mg, 3.74 mmol) in 3 mL of DMA was added and the reaction left stirring for 1 h at 0° C. Upon reaction completion the reaction was diluted with 5 mL and the product was extracted with 20 mL of DCM. The organic phase was dried over Na2SO4 and concentrated under reduced pressure. The oily product, wet of DMA, was used for the next step without further purification, assuming 100% yield.

To a solution of 5-bromo-pentanoic acid [5-(3-bromo-phenyl)-2H-pyrazol-3-yl]-amide (about 3.74 mmol) in 10 mL of DMF, Na2CO3 1.23 g, 7.48 mmol), piperidine (738 μL, 7.48 mmol), and NaI (561 mg, 3.74 mmol) were added and the mixture was heated at 60° C. for 5 hours. When the reaction was complete the solvent was removed under reduced pressure and the residue was diluted with DCM and washed with a saturated solution of NaHCO3. The organic phase was dried over Na2SO4 and concentrated under reduced pressure. The crude was purified with SiO2 column (10 g) with gradient elution from 100% DCM to DCM-NH3 (2N MeOH solution) 95:5 to afford the title compound (1.2 g, yield 79%).

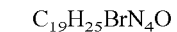
$C_{19}H_{25}BrN_4O$
Mass (calculated) [405]; (found) [M+H$^+$]=405-407
LC Rt=2.48, 100% (10 min method)
$^1$H-NMR (400 MHz, dmso-d$_6$): 1.24-1.70 (10H, m), 2.06-2.41 (6H, m), 3.15-3.17 (2H, m), 6.96 (1H, s), 7.29-7.45 (1H, m), 7.46-7.57 (1H, m), 7.63-7.83 (1H, m), 7.94 (1H, s), 10.43 (1H, s), 12.89 (1H, s).

EXAMPLE 6

5-Piperidin-1-yl-pentanoic acid [5-(1H-indol-5-yl)-2H-pyrazol-3-yl]-amide a) 1-Triisopropylsilanyl-1H-indole-5-carboxylic acid methyl ester To a solution of 1 g of methyl indole-5-carboxylate (5.7 mmol) in 10 mL of dry DMF 273 mg of NaH (mineral oil dispersion 50-60%, 5.7 mmol) were added and the mixture cooled to 0° C. Triisopropylchlorosilane (1.06 g, 5.7 mmol) were added drop wise and after 1 hour LC-MS showed complete conversion of the starting material to the title product. The mixture was diluted with 30 mL of DCM and washed with saturated Na2CO3. The organic phase was dried over Na$_2$SO$_4$ and concentrated under reduced pressure. The crude was purified with SiO$_2$ column eluting with n-hexane. The title compound was obtained (500 mg, yield 26%)

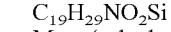
$C_{19}H_{29}NO_2Si$
Mass (calculated) [331]; (found) [M+H$^+$]=332
LC Rt=3.39, 100% (5 min method)
$^1$H-NMR: (dmso-d$_6$): 1.06 (d, 18H, J=7.52), 1.75 (quin, 3H, J=7.52), 6.75 (m, 1H), 7.48 (m, 1H), 7.60 (m, 1H), 7.72 (m, 1H), 8.25 (s, 1H).

b) 3-Oxo-3-(1-triisopropylsilanyl-1H-indol-5-yl)-propionitrile

To a solution of 393 μL of anhydrous CH₃CN (7.5 mmol) in 6 mL of dry toluene cooled down to −78° C., 5.35 mL of butyllithium in hexane solution (1.6 N) were added dropwise. The mixture was left stirring at −78° C. for 20 minutes and then a solution of 500 mg of 1-triisopropylsilanyl-1H-indole-5-carboxylic acid methyl ester (1.5 mmol) in 2 mL of dry toluene were added and the reaction allowed to reach room temperature. Upon reaction completion after about 20 minutes the mixture was cooled down to 0° C. and HCl 2N was added to pH 2. The organic phase was separated, dried over Na₂SO₄ and concentrated under reduced pressure, affording 490 mg of title product which was used in the next step without further purification (yield=96%).

$C_{20}H_{28}N_2OSi$

Mass (calculated) [340]; (found) [M+H⁺]=341 [M−H⁺]=339

LC Rt=3.10, 89% (5 min method)

¹H-NMR: (dmso-d₆): 1.06 (18H, d, J=7.52), 1.76 (3H, quin, J=7.52), 4.76 (1H, d), 7.78-7.81 (1H, m), 7.48-7.52 (1H, m), 7.60-7.73 (2H, m), 8.25 (s, 1H).

c) 5-(1H-Indol-5-yl)-2H-pyrazol-3-ylamine

To a solution of 3-Oxo-3-(1-triisopropylsilanyl-1H-indol-5-yl)-propionitrile (490 mg, 1.44 mmol) in 15 mL of absolute EtOH, 720 μL of hydrazine monohydrate (14.4 mmol) were added and the reaction refluxed for 18 hours. LC-MS showed complete conversion to the aminopyrazole and also silyl deprotection. The mixture was concentrated under reduced pressure, and purified with SiO2 column (eluent gradient from 100% DCM to DCM:MeOH 9:1) to afford the title compounds (120mg, yield: 41%)

$C_{11}H_{10}N_4$

Mass (calculated) [198]; (found) [M+H⁺]=199

LC Rt=0.84, 100% (3 min method)

d) 5-Piperidin-1-yl-pentanoic acid [5-(1H-indol-5-yl)-2H-pyrazol-3-yl]-amide To a solution of 5-bromovaleryl chloride (80 μL, 0.60 mmol) in DMA (1 mL) cooled at 0° C. a solution of 5-(1H-Indol-5-yl)-2H-pyrazol-3-ylamine (120 mg, 0.60 mmol) and diisopropylethylamine (104 μL, 1.20 mmol) in DMA (2 mL) was added. The reaction was left stirring for 1 hour at 0° C. and then piperidine (119 μL, 1.20 mmol) and NaI (90 mg, 0.60 mmol) were added and the mixture heated at 60° C. for 5 hours, when LC-MS showed complete conversion of the bromo-intermediate and the solvent was removed under reduced pressure.

The residue was dissolved in DCM (2 mL) and washed with Na₂CO₃ saturated water solution. The organic phase was concentrated under reduced pressure and the crude product was purified by prep HPLC.

Yield:22%

$C_{21}H_{27}N_5O$

Mass (calculated) [365]; (found) [M+H⁺]=366

LC Rt=1.49, 100% (10 min method)

¹H-NMR (400 MHz, MeOH-d₄): 1.47-1.91 (10H, m), 2.44-2.56 (2H, m), 2.80-3.01 (2H, m), 3.07-3.17 (2H, m), 3.40-3.60 (2H, m), 6.48-6.51 (1H, m), 6.76 (1H, s), 7.26-7.30 (1H, m), 7.40-7.44 (2H, m), 7.86 (1H, s), 8.28 (1H, s, HCOOH)

Example 7

5-(4-Acetyl-[1,4]diazepan-1-yl)-pentanoic acid (5-pyridin-3-yl-2H-pyrazol-3-yl)-amide a) 3-Oxo-3-pyridin-3-yl-propionitrile

The product was prepared according to the general procedure for aminopyrazole synthesis (route A1)

¹H-NMR (400 MHz, MeOH-d₄): 9.07 (1H, d), 8.81 (2H, dd), 8.26 (1H, dt), 7.59 (1H, dd), 4.79 (2H, s).

b) 5-Pyridin-3-yl-2H-pyrazol-3-ylamine

The product was prepared according to general procedure for aminopyrazole synthesis (route A2)

The crude product was purified with SiO2 column (5 g) with gradient elution from 100% DCM to DCM-NH3 (2N MeOH solution) 95:5. The title product (371 mg, 68% yield) was obtained.

¹H-NMR (400 MHz, MeOH-d₄): 8.82 (1H, d), 8.41 (1H, dd), 7.98 (1H, dt), 7.37 (1H, dd), 5.82 (2H, s)

c) 5-(4-Acetyl-[1,4]diazepan-1-yl)-pentanoic acid (5-pyridin-3-yl-2H-pyrazol-3-yl)-amide The product was prepared according to the general synthetic method for the one-pot synthesis of ω-amino-alkanoic acid (1H-pyrazol-3-yl-5-aryl)-amides. The crude product was purified with SiO2 column (5 g) with gradient elution from 100% DCM to DCM-NH3 (2N MeOH solution) 95:5.

The crude was further purified by preparative HPLC to give 772 mg of pure product (yield 25%).

$C_{20}H_{28}N_6O_2$

Mass (calculated) [384]; (found) [M−H⁺]=385

LC Rt=1.91, 100% (10 min method)

¹H-NMR (400 MHz, MeOH-d₄): 8.89 (1H, d), 8.49 (1H, dd), 8.12 (1H, d), 7.48 (1H, dd), 6.81 (1H, broad), 3.60 (1H, m), 3.55 (3H, m), 2.72 (3H, m), 2.63 (1H, m), 2.55 (2H, m), 2.43 (2H, m), 2.07 (3H, s), 1.90 (1H, m), 1.80 (1H, m), 1.70 (m, 2H), 1.57 (2H, m).

Example 8

5-Piperidin-1-yl-pentanoic acid [5-(4-methoxy-phenyl)-4-methyl-2H-pyrazol-3-yl]-amide a) 3-(4-Methoxy-phenyl)-2-methyl-3-oxo-propionitrile

The product was prepared according to the general procedure for aminopyrazole synthesis (route A1).

The crude product was purified with SiO2 column (10 g) with gradient elution from 100% Hexane to Hexane-AcOEt 7:3 to give 1.43 g of pure product (yield 31%).

¹H-NMR (400 MHz, MeOH-d₄): 7.97 (2H, d), 6.98 (1H, d), 4.31 (1H, q, J=7.3 Hz), 3.89 (3H, s), 1.63 (3H, d, J=7.3 Hz).

b) 5-(4-Methoxy-phenyl)-4-methyl-2H-pyrazol-3-ylamine

The product was prepared according to the general procedure for aminopyrazole synthesis (route A2)

The crude product was purified with SiO2 column (10 g) with gradient elution from 100% DCM to DCM-MeOH 8:2. 1.0 g of pure product were obtained (yield 65%).

¹H-NMR (400 MHz, CDCl3): 7.37 (2H, d), 6.97 (2H, d), 3.84 (3H, s), 2.03 (3H, s).

c) 5-Piperidin-1-yl-pentanoic acid [5-(4-methoxy-phenyl)-4-methyl-2H-pyrazol-3-yl]-amide The product was prepared according to the general synthetic method for the one-pot synthesis of ω-amino-alkanoic acid (1H-pyrazol-3-yl-5-aryl)-amides.

The crude product was purified with SiO2 column (2 g) with gradient elution from 100% DCM to DCM-NH3 (2N MeOH solution) 95:5.

The obtained crude was then purified again by prep-HPLC to give 54 mg of pure product (yield 7%).

$C_{21}H_{30}N_4O_2$
Mass (calculated) [370]; (found) [M+H$^+$]=371
LC Rt=1.61, 100% (10 min method)
$^1$H-NMR (400 MHz, dmso-d$_6$): 9.57 (1H, s), 8.12 (1H, s), 7.47 (2H, d), 7.02 (2H, d), 3.78 (3H, s), 2.41 (4H, broad), 2.37 (2H, m), 2.29 (2H, t), 1.91 (3H, s), 1.57 (2H, m), 1.50 (6H, m), 1.38 (2H, m).

Example 9

5-Piperidin-1-yl-pentanoic acid (5-furan-2-yl-2H-pyrazol-3-amide

The product was prepared according to the general synthetic method for the one-pot synthesis of ω-amino-alkanoic acid (1H-pyrazol-3-yl-5-aryl)-amides.

The crude product was purified by prep-HPLC (yield 15%).

$C_{17}H_{24}N_4O_2$
Mass (calculated) [316]: (found) [M+H$^+$]=317
LC Rt=1.53, 100% (10 min method)
$^1$H-NMR (400 MHz, MeOH-d$_4$): 8.48 (1H, s), 7.56 (1H, s), 6.70 (1H, s), 6.66 (1H, s), 6.52 (1H, m), 5.49 (1H, s), 4.88 (1H, s), 3.10 (2H, m), 2.48 (2H, m), 1.77 (10, m).

Example 10

N-[5-(4-Methoxy-phenyl)-2H-pyrazol-3-yl]-4-piperidin-1-yl-butyramide a) 4-Piperidin-1-yl-butyric acid ethyl ester

To a solution of piperidine (5.4 g, 65 mmol) in toluene (15 mL) ethyl 4-bromobutyrate (3.8 mL, 26 mmol) was added and the reaction mixture was refluxed for 10 hours. The mixture was allowed to cool down to room temperature and the white solid present (piperidium bromide) was filtered off and washed with ether. The filtrate was concentrated under reduced pressure to give the title product which was used in the next step without further purification.

$C_{11}H_{21}NO_2$
Mass (calculated) [199]; (found) [M+H$^+$]=200
LC Rt=0.2, 100% (5 min method)
$^1$H-NMR (400 MHz, MeOH-d$_4$): 1.22-1.25 (3H, m), 1.46-1.47 (2H, m), 1.57-1.63 (4H, m), 1.78-1.84 (2H, m), 2.30-2.35 (4H, m), 2.42 (4H, m, broad), 4.08-4.14 (2H, m).

b) 4-Piperidin-1-yl-butyric acid

To a suspension of crude 4-piperidin-1-yl-butyric acid ethyl ester from the previous step (about 25 mmol) in 15 mL of water, NaOH (1.4 g, 25 mmol) was added and the mixture was heated at reflux for 16 hours. The reaction was then allowed to cool down to room temperature, the solution was acidified at 0° C. with HCl 6N and concentrated under reduced pressure. The residue was treated with EtOH and the sodium chloride which precipitated was filtered off. Evaporation of the solvent under reduced pressure afforded 2.8 g of the title compound as a white solid in 58% overall yield of steps a) and b)

$C_9H_{17}NO_2$
Mass (calculated) [171]; (found) [M+H$^+$]=172
LC Rt=0.23, 100% (5 min method)
$^1$H-NMR (400 MHz, dmso-d$_6$): 1.44-1.51 (2H, m); 1.64-1.80 (6H, m); 2.22-2.25 (2H, m); 2.75-2.78 (2H, m, broad); 2.91-2.94 (2H, m, broad); 3.30-3.40 (2H, m).

c) N-[5-(4-Methoxy-phenyl)-2H-pyrazol-3-yl]-4-piperidin-1-yl-butyramide

To a suspension of 4-piperidin-1-yl-butyric acid (1.32 g, 7.93 mmol) in 12,2-dichloroethane (20 mL), N,N'-carbonyl-diimidazole (1.2 g, 7.4 mmol) was added and the mixture was stirred at room temperature for 2 hours (when all the aminoacid was activated complete dissolution of the suspension was generally observed). 3-Amino-5-(4-methoxyphenyl) pyrazole (1 g, 5.29 mmol) was then added and the reaction was stirred for further 10 hours. Upon reaction completion (as monitored by LC-MS) the formation of two isomers was observed, and the mixture was heated at 50° C. until the conversion of the less stable isomer to the title compound was observed (as monitored by LC-MS). The solvent was washed with sat. Na$_2$CO$_3$ solution, extracted and removed under reduced pressure. The crude was crystallised from acetonitrile to give 1.2 g of the title compound (Yield: 70%).

$C_{19}H_{26}N_4O_2$
Mass (calculated) [342]; (found) [M+H$^+$]=343
LC Rt=1.54, 100% (10 min method)
$^1$H-NMR (400 MHz, dmso-d$_6$): 1.34-1.40 (1H, m); 1.52-1.55 (1H, m); 1.62-1.75 (6H, m); 1.94-1.98 (2H, m); 2.37-2.40 (2H, m); 2.81-2.88 (2H, m); 2.97-3.03 (2H, m); 3.39-3.42 (2H, m); 3.77 (3H, s); 6.77 (1H, s); 6.98 (2H, d, J=8.8 Hz); 7.61 (2H, d, J=8.8 Hz); 10.47 (1H, s), 12.66 (1H, s).

Example 11

N-[5-(3-Methoxy-phenyl)-1H-pyrazol-3-yl]-4-morpholin-4-yl-butyramide a) 3-(3-Methoxy-phenyl)-3-oxo-propionitrile

To a solution of commercially available 3-methoxy-benzoic acid ethyl ester (3.2 g, 18 mmol) in dry toluene (25 mL), under N$_2$, NaH (50-60% dispersion in mineral oil, 1.44 g, 36 mmol) was carefully added. The mixture was heated at 90° C. and anhydrous CH$_3$CN was added dropwise (4.45 mL, 85.2 mmol). The reaction was heated for 18 hours and the product precipitated from the reaction mixture as Na salt. The reaction was allowed to cool down to room temperature and the solid formed was filtered and washed with ether, then it was redissolved in water and the solution acidified with 2N HCl solution to pH 3 when precipitation of title compound was observed. Filtration of the solid from the aqueous solution afforded 1.57 g of title product (50% yield).

$C_{10}H_9NO_2$
Mass (calculated) [175]; (found) [M+H$^+$]=176
LC Rt=1.69, 94% (5 min method)

b) 5-(3-Methoxy-phenyl)-2H-pyrazol-3-ylamine

To a solution of 3-(3-methoxy-phenyl)-3-oxo-propionitrile (8.96 mmoL) in absolute EtOH (20 mL) hydrazine monohydrate (0.52 mL, 15 mmol) was added and the reaction was heated at reflux for 18 hrs. The reaction mixture was then allowed to cool to room temperature and the solvent was evaporated under reduced pressure.

The crude was treated with ether and filtered, to give 1.4 g of title product (83% of yield)

$C_{10}H_{11}N_3O$
Mass (calculated) [189]; (found) [M+H$^+$]=190
LC Rt=1.13, 100% (5 min method)
$^1$H-NMR (400 MHz, MeOH-d$_4$): 3.82 (3H, s): 5.93 (1H, s); 6.86-6.88 (1H, m); 7.19-7.31 (3H, m).

c) N-[5-(3-Methoxy-phenyl)-1H-pyrazol-3-yl]-4-morpholin-4-yl-butyramide

A solution of 4-bromobutyryl chloride chloride (0.104 mL, 0.9 mmol) in dry DMA (1 mL) was cooled to −10° C. (ice/water bath) under N$_2$; 5-(3-methoxy-phenyl)-2H-pyrazol-3-ylamine (170 mg, 0.9 mmol) and diisopropylethylamine (0.315 mL, 1.8 mmol) in dry DMA (1 ml) were added. Upon complete conversion to the intermediate 4-bromo-N-[5-(3-methoxy-phenyl)-1H-pyrazol-3-yl]-butyramide (as monitored by LC-MS), morpholine (0.079 mL, 0.9 mmol) was added and the mixture was heated at 60° C. for 16 hours. The residue was dissolved in DCM (2 mL) and washed with sat. Na$_2$CO$_3$ solution, The organic phase was concentrated under reduced pressure and the crude product was purified by SiO$_2$ column (gradient from Acetonitrile 100% to MeCN/MeOH, NH$_3$ 90/10). The fractions containing the title compound were collected to afford 17 mg (5.5% of yield).

$C_{18}H_{24}N_4O_3$
Mass (calculated) [344]; (found) [M+H$^+$]=345
LC Rt=1.36, 95% (10 min method)
$^1$H-NMR (400 MHz, MeOH-d$_4$): 1.77-1.85 (2H, m); 2.34-2.40 (8H, m); 3.59-3.62 (4H, m); 3.76 (3H, s); 6.79-6.85 (2H, m); 7.15-7.29 (3H, m).

Example 12

4-Azepan-1-yl-N-[5-(3-methoxy-phenyl)-1-pyrazol-3-yl]-butyramide

A solution of 4-bromobutyryl chloride (0.104 mL, 0.9 mmol) in dry DMA (1 mL) was cooled to −10° C. (ice/water bath) under N$_2$; 5-(3-Methoxy-phenyl)-2H-pyrazol-3-3-ylamine (170 mg, 0.9 mmol) and diisopropylethylamine (0.315 mL, 1.8 mmol) in dry DMA (1 ml) was added. Upon complete conversion to the ω-bromoamide intermediate (as monitored by LC-MS) 0.101 mL of azepine were added to the solution and the mixture was left stirring at 60° C. for 16 hours.

The residue was dissolved in DCM (2 mL) and washed with saturated Na$_2$CO$_3$ solution. The organic phase was concentrated under reduced pressure and the crude product was purified by SiO$_2$ column (gradient from acetonitrile 100% to MeCN/MeOH, NH$_3$ 90/10). The fractions containing the title product were collected and a further purification by preparative HPLC was carried out to afford 20 mg of the title compound as its formate salt (5.5% yield).

$C_{20}H_{28}N_4O_2$
Mass (calculated) [356]; (found) [M+H$^+$]=357
LC Rt=1.71, 99% (10 min method)
$^1$H-NMR (400 MHz, MeOH-d$_4$): 1.65-1.68 (4H, m); 1.80-1.90 (4H, m); 1.97-2.04 (2H, m); 2.49-2.52 (2H, m); 3.12-3.16 (2H, m); 3.24-3.30 (4H, m, broad); 3.75 (3H, s); 6.76 (1H, s); 6.82-6.85 (1H, m); 6.13-6.15 (2H, m); 6.23-6.27 (1H, m); 8.37 (1H, s, formate)

Example 13

4-Azepan-1-yl-N-[5-(4-fluoro-phenyl)-2H-pyrazol-3-yl]-butyramide

Prepared following the general synthetic method for the one-pot synthesis of ω-amino-alkanoic acid (1H-pyrazol-3-yl-5-aryl)-amides. Starting from commercially available 5-(4-fluoro-phenyl)-2H-pyrazol-3-ylamine and following the procedure, 25 mg of title compound were recovered as its formate salt after preparative HPLC purification (7% yield).

C19H25NT4OF
Mass (calculated) [344]; (found) [M+H$^+$]=345
LC Rt=1.69, 100% (10 min method).
$^1$H-NMR (400 MHz, MeOH-d$_4$): 1.66-1.69 (4H, m); 1.80-1.90 (4H, m, broad); 1.97-2.05 (2H, n); 2.52-2.54 (2H, m); 3.12-3.18 (2H, m); 3.25-3.30 (4H, m, broad); 6.67 (1H, s, broad); 7.08-7.12 (2H, m); 7.59-7.63 (2H, m); 8.43 (1H, s, formate)

Example 14

N-[5-(6-Methyl-pyridin-3-yl)-1H-pyrazol-3-yl]-4-piperidin-1-yl-butyramide a) 3-(6-Methyl-pyridin-3-yl)-3-oxo-propionitrile The oxopropionitrile was synthesised following the general method for 3-oxopropionitriles (route A1)

$C_9H_8N_2O$
Mass (calculated) [160]; (found) [M+H$^+$]=161
LC Rt=0.63, 100% (5 min method)
$^1$H-NMR (400 MHz, dmso-d$_6$): 2.55 (3H, s); 4.65 (2H, s); 7.43-7.45 (m, 1); 8.13-8.16 (1H, m); 8.94-8.95 (1H, m).

b) 5- (6-Methyl-pyridin-3-yl)-1H-pyrazol-3-ylamine

The aminopyrazole was synthesised following the general method described in route A2

$C_9H10N_4$
Mass (calculated) [174]; (found) [M+H$^+$]=175
LC Rt=0.23, 100% (5 min method)

c) N-[5-(6-Methyl-pyridin-3-yl)-1H-pyrazol-3-yl]-4-piperidin-1-yl-butyramide

Prepared following the general synthetic method for the one-pot synthesis of ω-amino-alkanoic acid (1H-pyrazol-3-yl-5-aryl)-amides to afford 19 mg (6% yield) of title compound as its formate salt after preparative HPLC purification.

$C_{18}H_{25}N_5O$
Mass (calculated) [327]; (found) [M+H$^+$]=328
LC Rt=0.33, 100% (10 min method)
$^1$H-NMR (400 MHz. MeOH-d$_4$): 1.40-1.90 (6H, m); 2.30-2.54 (5H, m); 3.05-3.09 (4H, m); 3.20-3.24 (2H, m); 6.72 (1H, s, broad); 7.30 (1H, d J=8.0 Hz); 7.92-7.94 (1H, m); 8.35 (1H, s, formate); 8.67 (1H, s).

Example 15

N-[5-(5-Methyl-pyridin-3-yl)-1H-pyrazol-3-yl]-4-piperidin-1-yl-butyramide a) 3-(5-Methyl-pyridin-3-yl)-3-oxo-propionitrile The oxopropionitrile was synthesised following the general method for 3-oxopropionitriles (route A1)

$C_9H_8N_2O$
Mass (calculated) [160]; (found) [M+H$^+$]=161
LC Rt=0.63, 100% (5 min method)
$^1$H-NMR (400 MHz, MeOH-d$_4$): 2.55 (3H, s); 4.65 (2H, s); 7.43-7.45 (m, 1H); 8.13-8.16 (1H, m); 8.94-8.95 (1H, m).

b) 5-(5-Methyl-pyridin-3-yl)-1H-pyrazol-3-ylamine

The aminopyrazole was synthesised following the general method described in route A2
$C_9H_{10}N_4$
Mass (calculated) [174]; (found) [M+H$^+$]=175
LC Rt=0.23, 100% (5 min method)

c) N-[5-(5-Methyl-pyridin-3yl)-1H-pyrazol-3-yl]-4-piperidin-1-yl-butyramide

Prepared following the general synthetic method for the one-pot synthesis of ω-amino-alkanoic acid (1H-pyrazol-3-yl-5-aryl)-amides to afford 25 mg of the title compound as its formate salt (7.4% yield) after preparative HPLC purification.
$C_{18}H_{25}N_5O$
Mass (calculated) [327]; (found) [M+H$^+$]=328
LC Rt=0.33, 100% (10 min method)
$^1$H-NMR (400 MHz, MeOH-d$_4$): 1.52-1.70 (2H, m, broad); 1.72-1.84 (4H, m, broad); 1.98-2.06 (2H, m); 2.45 (3H, s); 2.48-2.54 (2H, m); 3.04-3.10 (4H, m); 3.20-3.24 (2H, m, broad); 6.74 (1H, s, broad); 7.88 (1H, s); 7.28 (1H, s); 8.37 (1H, s, formate); 8.67 (1H, s).

Example 16

4-(4-Acetyl-[1,4]diazepan-1-yl)-N-[5-(6-methoxy-naphthalen-2-yl)-1H-pyrazol-3-yl]-butyramide a) 6-Methoxy-naphthalene-2-carboxylic acid methyl ester To a solution of 6-methoxy-naphthalene-2-carboxylic acid (1.01 g, 5 mmol) in methanol (10 mL), a catalytic amount of sulphuric acid was added. The mixture was then heated at 80° C. for 8 hours. Upon reaction completion (as monitored by LcMS), the solution was slowly cooled and the precipitation of the product was observed. Filtration of the white solid afforded 1.01 g (94% yield) of title compound
$C_{13}H_{12}O_3$
Mass (calculated) [216]; (found) [M+H$^+$]=217
LC Rt=2.43, 100% (5 min method)

b) 3-(6-Methoxy-naphthalen-2-yl)-3-oxo-propionitrile

To a solution of 6-methoxy-naphthalene-2-carboxylic acid methyl ester (1.0 g, 4.7 mmol) in dry toluene (8 mL), NaH (0.55 mg, 9.4 mmol) were added and the mixture was heated at 90° C. To the hot solution, acetonitrile (1.2 mL) was added dropwise. The reaction was then heated for 18 hours and the product precipitated from the reaction mixture as its sodium salt.
The reaction was allowed to cool down to room temperature and the solid formed was first filtered and washed with ether, then it was dissolved in water and the solution was acidified with HCl 2N to pH 3, upon which precipitation of the title compound was observed. Filtration of the solid from the aqueous solution afforded 1.1 g of title compound (100% of yield).
$C_{13}H_{12}O_3$
Mass (calculated) [225]; (found) [M+H$^+$]=226
LC Rt=2.13, 90% (5 min method)

c) 5-(6-Methoxy-naphthalen-2-yl)-1H-pyrazol-3-ylamine

To a solution of 3-(6-methoxy-naphthalen-2-yl)-3-oxo-propionitrile (1.1 g, 4.8 mmoL) in absolute EtOH (10 mL) hydrazine monoltydrate (0.96 mL, 19.2 mmol) was added and the reaction was heated at reflux for 18 hrs. The reaction mixture was allowed to cool to room temperature and the solvent was evaporated under reduced pressure. The crude was treated with ether and filtered to afford 0.95 g of title compound (83% of yield).
$C_{14}H_{13}N_3O$
Mass (calculated) [239]; (found) [M+H$^+$]=240
LC Rt=1.49, 90% (5 mim method)

d) 4-(4-Acetyl-[1,4]diazepan-1-yl)-N-[5-(6-methoxy-naphthalen-2-yl)-1H-pyrazol-3-yl]-butyramide Following the general method for the synthesis of ω-bromo-alkanoic acid (1H-pyrazol-3-yl-5-aryl)-amides and the general method for the synthesis of ω-amino-alkanoic acid (1H-pyrazol-3-yl-5-aryl)-amides, purification by preparative HPLC afforded 15 mg (3% yield) of title compound as its formate salt.
$C_{25}H_{31}N_5O_3$
Mass (calculated) [449]; (found) [M+H$^+$]=450
LC Rt=1.91, 100% (10 min method)
$^1$H-NMR (400 MHz, MeOH-d$_4$): 1.88-2.0 (4H, m); 2.06 (3H, s); 2.48-2.52 (2H, m); 2.94-3.02 (2H, m); 3.08-3.18 (4H, m); 3.52-3.58 (2H, m); 3.64-3.72 (2H, m); 3.82 (3H, s); 6.78-6.82 (1H, m); 7.04-7.10 (1H, m); 7.16-7.18 (1H, m); 7.62-7.78 (3H, m); 7.98-8.02 (1H, m); 8.28 (1H, s, formate).

Example 17

5-Piperidin-1-yl-pentanoic acid [5-(3-fluoro-phenyl,)-1H-pyrazol-3yl]-amide a) 3-(3-Fluoro-phenyl)-3-oxo-propionitrile The product was prepared according to a modification of general route A1. To a solution of methyl-3-fluorobenzoate (3 g, 18 mmol) in dry toluene (25 mL) under N$_2$, NaH (50-60% dispersion in mineral oil, 1.44 g, 36 mmol) was carefully added.
The mixture was heated at 90° C. and then dry CH$_3$CN was added dropwise (4.45 mL, 85.2 mmol). The reaction was heated for 18 hours and the product precipitated from the reaction mixture as its sodium salt. The reaction was allowed to cool down to room temperature and the solid formed was filtered, then redissolved in water, and the solution was acidified with 2N HCl to pH 5-6, upon which precipitation was observed. Filtration of the solid from the aqueous solution afforded 2.12 g of the title compound (72% yield) which was used directly in the following step.

b) 5-(3-Fluoro-phenyl)-1H-pyrazol-3-yl-amine

The product was prepared according to a slight modification of route A2. To a solution of 3-(3-fluoro-phenyl)-3-oxo-propionitrile (1.92 g, 11.77 mmoL) in absolute EtOH (32 mL) hydrazine monohydrate (0.685 mL, 14.12 mmol) was added and the reaction was heated at reflux for 2 hrs. The reaction mixture was allowed to cool to room temperature and the solvent was evaporated under reduced pressure. The crude was treated with ether and filtered to give 1.71 g of title compound were recovered (82% yield).
$C_9H_8FN_3$
Mass (calculated) [177]; (found) [M+H$^+$]=190
LC Rt=1.13, 69% (5 min method)

c) 5-Piperidin-1-yl-pentanoic acid [5-(3-fluoro-phenyl)-1H-pyrazol-3-yl]-amide The product was prepared according to the general synthetic method for the one-pot synthesis of ω-amino-alkanoic acid (1H-pyrazol-3-yl-5-aryl)-amides. A solution of 5-bromovaleryl chloride (0.125 mL, 0.94 mmol) in dry DMA (1 mL) was cooled to −10° C. (ice/water bath) under $N_2$; 5-(3-Fluoro-phenyl)-2H-pyrazol-3-ylamine (177 mg, 0.94 mmol) and diisopropylethylamine (0.324 mL, 1.88 mmol) in dry DMA (1 ml) were added.

The reaction was left stirring for 1 h at 0° C. and then piperidine (0.232 mL, 2.35 mmol) and NaI (141 mg, 0.94 mmol) were added. The reaction mixture was heated at 60° C., until LC-MS analysis showed complete conversion of the bromo-intermediate, upon which the reaction was cooled, the solvent was removed under reduced pressure and the residue was dissolved in DCM (2 mL) and washed with sat. $Na_2CO_3$ solution. The organic phase was concentrated under reduced pressure and the crude product was purified by $SiO_2$ column (gradient from 100% DCM to DCM-NH3MeOH 2N solution 8:2) followed by preparative HPLC. The fractions containing the title product were collected to afford 15 mg (4.4% of yield) as its formate salt.

$C_{19}H_{25}FN_4O$
Mass (calculated) [344]; (found) [M+H$^+$]=345
LC Rt=1.64, 100% (10 min method)
$^1$H-NMR (400 MHz, dmso-d6): 1.37-1.58 (10H, m); 2.27-2.31 (2H, m); 2.35-2.44 (6H, m); 6.85 (1H, s); 7.14 (1H, t, J=8.6 Hz); 7.45 (1H, m), 7.53-7.55 (2H, m); 8.21 (1H, s, formate); 10.47 (1H, s).

Example 18

5-Azepan-1-yl-pentanoic acid (5-pyridin-4-yl-1H-pyrazol-3-yl)-amide

3-Oxo-3-pyridin-4-yl-propionitrile

The product was prepared according to a modification of route A1. To a solution of 3 g (22 mmol) of isonicotinic acid methyl ester in dry toluene (30 mL) under $N_2$, NaH (50-60% dispersion in mineral oil, 1.75 g, 44 mmol) was carefully added.

The mixture was heated at 90° C. and then dry $CH_3CN$ was added dropwise (5.39 mL, 103 mmol). The reaction was heated for 18 hours and the product precipitated from the reaction mixture as the sodium salt. The reaction was allowed to cool down to room temperature and the solid formed was filtered, then it was dissolved in water and the solution was acidified with 6N HCl solution to pH 5-6 and the product extracted with DCM. The pH of the aqueous phase was adjusted again to 4-5 and another extraction with DCM afforded more product.

The organic phases were combined, dried and evaporated. The product was used directly in the following step. Yield of crude product: 58% b) 5-Pyridin-4-yl-1H-pyrazol-3-ylamine

The product was prepared according to a modification of route A2. To a solution of 3-oxo-3-pyridin-4-yl-propionitrile (1.86 g, 12.74 mmoL) in absolute EtOH (35 mL) hydrazine monohydrate (0.74 mL, 15.29 mmol) was added and the reaction was heated at reflux for 2 hours. The reaction mixture was then allowed to cool to room temperature and the solvent was evaporated under reduced pressure. The crude product obtained was washed with ether to afford the title compound (yield: 39%).

$C_8H_8N_4$
Mass (calculated) [160]; (found) [M+H$^+$]=161
LC Rt=0.23, 100% (5 min method)
$^1$H-NMR (400 MHz, dmso-d6): 5.02 (2H, s); 5.85 (1H, s); 7.59 (2H, d, J=6 Hz); 8.50 (2H, d, J=6 Hz); 11.93 (1H, s).

c) 5-Azepan-1-yl-pentanoic acid (5-pyridin-4-yl-1H-pyrazol-3-yl)-amide

The product was prepared according to the general synthetic method for the one-pot synthesis of ω-amino-alkanoic acid (1H-pyrazol-3-yl-5-aryl)-amides. A solution of 5-bromovaleryl chloride (0.125 mL, 0.94 mmol) in dry DMA (1 mL) was cooled to −10° C. (ice/water bath) under $N_2$; 5-Pyridin-4-yl-1H-pyrazol-3-ylamine (151 mg, 0.94 mmol) and diisopropylethylamine (0.324 mL, 1.88 mmol) in dry DMA (1 ml) were added. The reaction was left stirring for 1 h at 0° C. and then azepane (0.265 mL, 2.35 mmol) and NaI (0.94 mmol, 1 eq) were added.

The reaction mixture was heated at 60° C. until LC-MS analysis showed complete conversion of the bromo-intermediate, at which point the reaction was cooled down and the solvent was removed under reduced pressure. The residue was dissolved in DCM (2 mL) and washed with saturated $Na_2CO_3$ solution. The organic phase was concentrated under reduced pressure and the crude product was purified by $SiO_2$ column (gradient from 100% DCM to DCM-NH3MeOH 2N solution 8:2); the fractions containing the title compound were collected (30 mg, 8.8% of yield).

$C_{19}H_{27}N_5O$
Mass (calculated) [341]; (found) [M+H$^+$]=342
LC Rt=0.23, 100% (10 min method)
$^1$H-NMR (400 MHz, dmso-d6): 1.58-1.75 (12H, m); 2.34-2.37 (2H, t, J=6.6 Hz); 3.05-3.09 (4H, m); 3.31 (2H, m); 7.09 (1H, s); 7.68 (2H, d, J=4.8 Hz); 8.59 (2H, d, J=4 Hz); 9.14 (1H, s); 10.52 (1H, s); 13.17 (1H, s).

Example 19

6-(4-Acetyl-[1,4]diazepan-1-yl)-hexanoic acid [5-(4-methoxy-phenyl)-1H-pyrazol-3-yl]-amide The product was prepared according to the general synthetic method for the one-pot synthesis of ω-amino-alkanoic acid (1H-pyrazol-3-yl-5-aryl)-amides. A solution of 5-bromohexanoyl chloride (0.144 mL, 0.94 mmol) in dry DMA (1 mL) was cooled to −10° C. (ice/water bath) under $N_2$; 5-(4-methoxy-phenyl)-1H-pyrazol-3-ylamine (178 mg, 0.94 mmol) and diisopropylethylamine (0.324 mL, 1.88 mmol) were added in dry DMA (1 ml).

The reaction was left stirring for 1 h at 0° C. and then 1-[1,4]diazepan-1-yl-ethanone (0.310 mL, 2.35 mmol) and NaI (0.94 mmol, 1 eq) were added.

The reaction mixture was heated at 60° C. until LC-MS. analysis showed complete conversion of the bromo-intermediate, at which point the reaction was cooled down and the solvent was removed under reduced pressure. The residue was dissolved in DCM (2 mL) and washed with saturated $Na_2CO_3$ solution.

The organic phase was concentrated under reduced pressure and half of the crude was purified by $SiO_2$ column (gradient from 100% DCM to DCM-NH3MeOH 2N solution 8:2). The fractions containing the title compound were collected (35 mg).

C23H33N5O3
Mass (calculated) [427]; (found) [M+H$^+$]=428
LC Rt=1.61, 96% (10 min method)
$^1$H-NMR (400 MHz, dmso-d6): 1.24-1.29 (2H, m); 1.36-1.44 (2H, m); 1.54-1.58 (2H, m); 1.62-1.76 (2H, m); 1.94-1.96 (3H, m); 2.25-2.28 (2H, m); 2.35-2.41 (2H, m); 2.51-2.54 (2H, m); 2.60-2.62 (1H, m); 3.38-3.44 (5H, m); 3.77 (3H, s); 6.73 (1H, s); 6.98 (2H, d, J=8.8 Hz); 7.61 (2H, d, J=8.8); 10.32 (1H, s)

Example 20

N-[5-(4-Methoxy-phenyl)-2H-pyrazol-3-yl]-2-methyl-4-piperidin-1-yl-butyramide a) 4-Bromo-2-methyl-butyric acid methyl ester 4-Bromo-2-methyl-butyric acid (2.16 g, 1 eq, prepared according to the procedure described in *J. Am. Chem. Soc.* 1990, 112, 2755) was dissolved in MeOH (10 mL) and a few drops of conc. H$_2$SO$_4$ were added. The reaction was stirred at reflux for 16 hours. After reaction completion, as monitored by LC-MS, MeOH was removed under reduced pressure, the oily residue was diluted with water, the pH adjusted to 9 with 10% NaOH, and the product was extracted with Et$_2$O (2×20 mL) and dried over Na$_2$SO$_4$. The title compound was obtained as a colourless oil (1.29 g, 55% yield) after solvent removal.
C6H11BrO2
NMR (400 MHz, CDCl3); 1.19 (3H, d); 1.94-1.89 (2H, m); 2.29-2.23 (2H, m); 3.43-3.40 (1H, m); 3.69 (3H, s).

b) 2-Methyl-4-piperidin-1-yl-butyric acid. HCl

Methyl-4-bromo-2-methyl-butyric acid (1.29 g, 1 eq) was dissolved in toluene (15 mL) and piperidine (1.07 mL, 3 eq) was added; the reaction was stirred for 3 hours. After reaction completion, as monitored by LC-MS, toluene was removed under reduced pressure and the crude ester was dissolved in 1M NaOH (14 mL, 1.1 eq) and MeOH (2 mL). The reaction was stirred at reflux for 16 hours; after hydrolysis was complete, the reaction was concentrated under reduced pressure and the pH adjusted to 4 with 6N HCl. EtOH was added to help precipitation of NaCl. The organic phase was filtered and EtOH removed under reduced pressure. The resulting oil was treated with 2M HCl in Et$_2$O to obtain 2-methyl-4-piperidin-1-yl-butyric acid. HCl (0.96 g, 66% yield)
C$_{10}$H$_{19}$NO$_2$
Mass (calculated) [185.27]; (found) [M+H$^+$]=186.27
LC Rt=0.23, 95% (5 min method)

c) N-[5-(4-Methoxy-phenyl)-2H-pyrazol-3-yl]-2-methyl-4-piperidin-1-yl-butyramide 2-Methyl-4-piperidin-1-yl-butyric acid. HCl (0.45 g, 1.2 eq) was suspended in 1,2-DCE (15 mL) and triethylamine (0.29 mL, 1.2 eq) was added; 1,1'-carbonyldiimidazole (0.303 g, 1.1 eq) was added in one portion and the reaction was stirred at room temperature for 2 hours. 5-(4-Methoxyphenyl)-2H-pyrazol-3-ylamine (0.325 g, 1 eq) was then added and the reaction stirred at room temperature for further 16 hours. After reaction completion, as monitored by LC-MS, the solvent was removed under reduced pressure and the crude amide was purified by column chromatography (Flash-SI 10 g; CH$_3$CN:MeOH 9:1, CH$_3$CN:2N NH$_3$ MeOH 9:1) to give the title compound as thick colourless oil (0.120 g, 0.33 mmol)
C$_{20}$H$_{28}$N$_4$O$_2$
Mass (calculated) [356.48]; (found) [M+H$^+$]=357.25
LC Rt=1.67, 97% (10 min method)
NMR (400 MHz, dmso-d6); 1.18 (3H, d); 1.35-1.31 (2H, m); 1.46-1.41 (4H, m); 1.77-1.72 (1H, m); 2.19-2.16 (2H, m); 2.27-2.23 (4H, m); 2.61-2.58 (2H, m); 3.76 (3H, s); 6.76 (1H, s); 6.92 (2H, d); 7.61 (2H, d); 10.33 (1H, s).

Example 21

N-[4-(4-Methoxy-phenyl)-1H-imidazol-2-yl]-4-piperidin-1-yl-butyramide

To a suspension of 4-piperidin-1-yl-butyric acid (200 mg, 1.17 mmol, 1.0 eq) in 1,2-dichloroethane (2 mL), N,N'-carbonyldiimidazole (179.9 mg, 1.11 mmol, 0.95 eq) was added and the mixture was stirred at room temperature for 1 hour until complete activation of the aminoacid and dissolution of the suspension. 4-(4-Methoxy-phenyl)-1H-imidazol-2-ylamine (prepared according to the procedure reported in JOC 1994, 59, 24, 7299; 110.5 g, 0.58 mmol, 0.50 eq) was added and the reaction stirred for 1 day at 50° C. The slow conversion was monitored by LC-MS. Another aliquote of activated acid (4-piperidin-1-yl-butyric acid, 200 mg and carbonyldiimidazole, 179.9 mg in 2 mL of 1,2-dichloroethane) were added and the reaction stirred for further two days at 50° C.

The solvent was evaporated under reduced pressure and the crude mixture purified by preparative HPLC to obtain a 9:1 mixture of the product and unreacted 4-(4-methoxy-phenyl)-1H-imidazol-2-ylamine. The crude was purified by treatment with isocyanate resin and SCX column to give 78.0 mg (Yield: 39%) of the title compound as a white solid
C19H26N4O2 Mass (calculated) [342]; (found) [M+H$^+$]=343
LC Rt=1.00 (and solvent front), 99% (10 min method)
$^1$H-NMR (400 MHz, DMSO): 1.30-1.36 (2H, m); 1.43-1.49 (4H, m); 1.67-1.75 (2H, m); 2.22-2.34 (8H, m); 3.73 (3H, s, —OCH3); 6.87 (2H, d, J=8.8 Hz); 7.10 (1H, s); 7.60 (2H, d, J=8.8 Hz); 11.26 (1H, s, NHCO), 11.52 (1H, s, NH).
$^{13}$C-NMR (400 MHz, DMSO): 21.54 (1C); 23.63 (1C); 24.92 (2C); 33.24 (1C); 53.6 (1C, —OCH3); 55.02 (2C); 57.46 (1C); 113.88 (2C); 125.18 (2C), 141.13 (1C); 157.67 (1C); 162.33 (2C); 163.66 (1C); 171.15 (1C, CO).

Example 22

N-(4-Methyl-5-o-tolyl-2H-pyrazol-3-yl)-4-pyrrolidin-1-yl-butyramide a) 2-Methyl-3-oxo-3-o-tolyl-propionitrile The product was prepared according to the general procedure for aminopyrazole synthesis (route A1). The mixture of methyl 2-methylbenzoate (3.0 mL, 20.0 mmol, 1.0 eq) and NaH (1.6 g, 40.0 mmol, 2.0 eq) in dry toluene (20 mL) was heated at 80° C. and then propionitrile (6.7 mL, 94.4 mmol. 4.7 eq) was added dropwise; the reaction was heated for 18 hours. The crude product was dissolved in water and extracted with DCM, and it was used in the following step without further purification (3.04 g, yield: 88%).
C11H11NO
$^1$H-NMR (dmso-d6): 1.82 (3H, s); 2.26 (3H, s); 2.48-2.49 (1H, m); 7.10-7.42 (4H, m).

b) 4-Methyl-5-o-tolyl-2H-pyrazol-3-ylamine

The product was prepared according to general procedure for aminopyrazole synthesis (route A2). The crude product was purified through SiO2 column (20 g) with gradient elution from 100% ethyl acetate (EtOAc) to EtOAc-MeOH 80:20. The title product (1.2 g, 37% yield) was obtained.

C11H13N3

Mass (calculated) [187]; (found) [M+H$^+$]=188.

LC Rt=1.33 min, 100% (10 min method)

$^1$H-NMR (dmso-d6): 1.68 (3H, s); 2.17 (3H, s); 4.36 (2H, br s); 7.14 (1H,d, J=7.2 Hz); 7.20-7.26 (3H, m); 11.24 (1H, br s).

c) N-(4-Methyl-5-o-tolyl-2H-pyrazol-3-yl)-4-pyrrolidin-1-yl-butyramide

To a suspension of 4-pyrrolidin-1-yl-butyric acid (118.0 mg, 0.8 mmol, 1.5 eq) in 1,2-dichloroethane (3 mL), N,N'-carbonyldiimidazole (113.0 mg, 0.7 mmol, 1.4 eq) was added and the mixture was stirred at room temperature for 1 hour, then N,N-diisopropyl ethyl amine (87 μL, 0.5 mmol, 1.0 eq) was added and the mixture was stirred at room temperature for further 1 hour until complete dissolution of the suspension. 4-Methyl-5-o-tolyl-2H-pyrazol-3-ylamine (93.5 mg, 0.5 mmol, 1.0 eq) was added and the reaction was stirred for 18 hours, then at 50° C. for 1 day, until the conversion of the less stable ring nitrogen-acylated isomer to the title compound was observed (as monitored by LC-MS). The solvent was removed under reduced pressure, the crude was purified by SiO$_2$ column to give 44.0 mg of the title compound (yield: 27%).

C19H26N4O

Mass (calculated) [326]; (found) [M+H$^+$]=327, [M+2/2]=164.

LC Rt=1.56 min, 95% (10 min method)

$^1$H-NMR (CD$_3$OD): 1.83 (3H, s); 2.07-2.11 (6H,m); 2.22 (3H, s); 2.62 (2H,t, J=7.2 Hz); 3.27-3.39 (6H,m); 7.22-7.28 (2H, m); 7.32-7.34 (2H, m).

Example 23

N-[5-(4-Cyclopropylmethoxy-3-fluoro-phenyl)-2H-pyrazol-3-yl]-4-pyrrolidin-1-yl-butyramide a) 3-Fluoro-4-hydroxy-benzoic acid methyl ester 3-Fluoro-4-hydroxy-benzoic acid (5 g, 32.0 mmol) was dissolved in MeOH (50 mL) and catalytic quantity of sulfuric acid (1 mL) was added. The mixture was refluxed overnight, after which the solvent was evaporated under reduced pressure; the crude was dissolved in DCM and washed with saturated NaHCO$_3$ to basic pH. The organic phase was dried and evaporated under reduced pressure, and the residue was used without further purification (yield 85%).

C8H7FO3

$^1$H-NMR (dmso-d6): 3.78 (3H, s); 7.00-7.02 (1H, m); 7.61-7.64 (2H, m); 10.89 (1, br s).

b) 4-Cyclopropylmethoxy-3-fluoro-benzoic acid methyl ester

3-Fluoro-4-hydroxy-benzoic acid methyl ester (1.02 g, 6.0 mmol, 1.0 eq) was dissolved in acetone (14 mL), NaI (0.45 g, 3.0 mmol, 0.5 eq) and K$_2$CO$_3$ (1.66 g, 12.0 mmol, 2.0 eq) were added ad the mixture was stirred at room temperature for 20 min. (Bromomethyl)cyclopropane (0.53 mL, 5.4 mmol, 0.9 eq) was added, and the mixture was refluxed for 2 days. The solvent was concentrated under reduced pressure, NaOH 10% was added, and it was extracted with DCM and dried.

0.91 g of title product (yield 69%) were recovered and used without further purification.

C12H13FO3

$^1$H-NMR (dmso-d6): 0.34-0.37 (2H, m); 0.57-0.62 (2H, m); 1.22-1.26 (1H, m); 3.82 (3H, s); 3.99 (2H, d, J=6.8 Hz); 7.26 (1H, t, J=8.4 Hz); 7.67-7.77 (2H, m).

c) 3-(4-Cyclopropylmethoxy-3-fluoro-phenyl)-3-oxo-propionitrile

The product was prepared according to the general procedure for aminopyrazole synthesis from 4-Cyclopropylmethoxy-3-fluoro-benzoic acid methyl ester (route A1bis). 0.84 g of the title product was extracted from water and dried over sodium sulphate (yield 88%) and used directly for the next step.

C13H12FNO2 d) 5-(4-Cyclopropylmethoxy-3-fluoro-phenyl)-2H-pyrazol-3-ylamine

The product was prepared according to general procedure for aminopyrazole synthesis (route A2). The crude product was purified through SiO2 column with gradient elution from 100% Ethyl Acetate to EtOAc-MeOH 90:10. The title product (576 mg, 65% yield) was obtained.

C13H14FN3O

Mass (calculated) [247]; (found) [M+H$^+$]=248.

LC Rt=2.19 min, 99% (10 min method)

1H-NMR (CD3OD): 0.33-0.38 (2H, m); 0.59-0.65 (2H, m); 1.22-1.31 (1H, m); 2.90-3.92 (2H, m); 7.02-7.20 (2H, m); 7.34-7.40 (2H, m).

N-[5-(4-Cyclopropylmethoxy-3-fluoro-phenyl)-2H-pyrazol-3-yl]-4-pyrrolidin-1-yl-butyramide The product was prepared according to the general synthetic method for the synthesis of ω-amino-alkanoic acid (1H-pyrazol-3-yl-5-aryl)-amides via the amino acid route, starting from 5-(4-Cyclopropylmethoxy-3-fluoro-phenyl)-2H-pyrazol-3-ylamine (123.5 nag, 0.5 mmol, 1.0 eq). 130 mg of title compound were recovered as its formate salt after preparative HPLC purification (67% yield).

C21H27N4O2F

Mass (calculated) [386]; (found) [M+H$^+$]=387.

LC Rt=2.01 min, 100% (10 min method)

1H-NMR (dmso-d6 of HCOOH salt): 0.32-0.36 (2H, m); 0.56-0.61 (2H, m); 1.21-1.28 (1H, m); 1.73-1.84 (5H, m); 2.36 (2H, t, J=7.2 Hz); 2.67-2.77 (6H, m); 3.92 (3H, d, J=7.2 Hz); 6.79 (1H, s); 7.18 (1H, t, J=8.8 Hz); 7.45-7.47 (1H, m); 7.55-7.59 (1H, m); 8.19 (1H, s); 10.49 (1H, s)

Example 24

N-[4-(4-Difluoromethoxy-phenyl)-1H-imidazol-2-yl]-4-pyrrolidin-1-yl-butyramide a) N-[4-(4-Difluoromethoxy-phenyl)-1H-imidazol-2-yl]-acetamide Acetyl guanidine (2.6 g, 25.7 mmol, 3.0 eq) was dissolved in DMF anhydrous (40 mL) and 2-Bromo-1-(4-difluoromethoxy-phenyl)-ethanone (2.3 g, 8.5 mmol, 1.0 eq) was added; the mixture was stirred under nitrogen at room temperature for 4 days. DMF was dried; the residue was washed with water, filtered and dried. The crude was crystallized from methanol to give 1.2 g of the title compound (yield: 53%).

C12H11F2N3O2

$^1$H-NMR (dmso-d6): 3.40 (3H, br s); 7.10-7.47 (4H, m); 7.82 (2H, d, J=8.4 Hz); 11.32 (1H,s); 11.73 (1H, br s).

b) 4-(4-Difluoromethoxy-phenyl)-1H-imidazol-2-ylamine

N-[4-(4-Difluoromethoxy-phenyl)-1H-imidazol-2-yl]-acetamide (1.2 g, 4.5 mmol, 1.0 eq) was dissolved in water (30 mL) and methanol (30 mL), and 30 drops of sulfuric acid were added. The reaction was refluxed for 2 days, then the mixture was dried; the residue was diluted with water, the pH adjusted to 8 with NaOH 2N, the product was extracted with DCM and concentrated under reduced pressure to give 1.0 g of the title compound (yield: 99%)

C10H9F2N3O $^1$H-NMR (dmso-d6): 5.59 (2H, br s); 6.98-7.35 (4H, m); 7.60-7.62 (2H, m).

c) N-[4-(4-Difluoromethoxy-phenyl)-1H-imidazol-2-yl]-4-pyrrolidin-1-yl-butyramide To a suspension of 4-pyrrolidin-1-yl-butyric acid (386 mg, 2.0 mmol, 4.0 eq) in 1,2-dichloroethane (3 mL), N,N'-carbonyldiimidazole (300 mg, 1.8 mmol, 3.7 eq) and N,N-diisopropyl ethyl amine (87 μL, 0.5 mmol, 1.0 eq) were added and the mixture was stirred at room temperature for 1 hour until complete activation of the aminoacid and dissolution of the suspension.

4-(4-Difluoromethoxy-phenyl)-1H-imidazol-2-ylamine (112.5 mg, 0.5 mmol, 1.0 eq) was added; the reaction was stirred for 1 day at room temperature, then for further 2 days at 50° C. (the slow conversion was not complete and was monitored by LC-MS).

The solvent was evaporated under reduced pressure and the crude mixture purified by preparative HPLC to give 80 mg (yield: 44%) of the title compound as a white solid.

C18H22N4O2F2

Mass (calculated) [364]; (found) M+H$^+$=365, [M/2]=183. LC Rt=1.18 min, 100% (10 min method)

1H-NMR (dmso-d6): 1.74-1.84 (6H, m); 2.38 (2H, t, J=7.6 Hz); 2.70-2.79 (6H, m); 6.99-7.37 (4H, m); 7.71 (2H, d, J=8.8 Hz); 8.23 (1H, br s)

Example 25

N-[5-(5-Chloro-2-methoxy-phenyl)-2H-pyrazol-3-yl]-4-cis-2,6-dimethyl-piperidin-1-yl)-butyramide a) 4-(2,6-Dimethyl-piperidin-1-yl)-butyric acid ethyl ester To a solution of cis-2,6-dimethylpiperidine (6.9 mL, 51.3 mmol, 2.5 eq) in toluene (25 mL) ethyl 4-bromobutyrate (2.9 mL, 20.5 mmol, 1 eq) was added and the reaction mixture was refluxed for 2 days. The mixture was allowed to cool down to room temperature and the white solid present was filtered off and washed with ether. The crude was diluted with HCl 1N (8 mL, 1 eq), then washed with EtOAc, treated with NaOH 1N (16 mL, 2 eq) and extracted with ethyl acetate. The title product obtained (1.51 g, yield 32%) was used in the next step without further purification.

C13H25NO2

$^1$H-NMR (CD$_3$OD): 0.99 (6H, d, J=6.0 Hz); 1.07-1.21 (6H, m); 1.45-1.58 (5H, m); 2.20 (2H, t, J=6.8 Hz); 2.30-2.35 (2H, m); 2.53-2.57 (2H, m); 4.02 (2H,q, J=7.2 Hz).

b) 4-(2,6-Dimethyl-piperidin-1-yl)-butyric acid

To a suspension of 4-(2,6-dimethyl-piperidin-1-yl)-butyric acid ethyl ester (1.5 g, 6.7 mmol) in water (5 mL) and MeOH (1 mL), NaOH (266 mg, 6.7 mmol, 1.0 eq) was added and the mixture was heated at reflux for 22 hours. The reaction was then allowed to cool down to room temperature, the pH adjusted to 4 at 0° C. with HCl 2N and the mixture was concentrated under reduced pressure. The residue was treated with EtOH, and the sodium chloride precipitated was filtered off. Evaporation of the solvent under reduced pressure afforded 950 mg of the title compound as a white solid (51% yield).

C11H21NO2

1H-NMR (CD3OD): 1.28-1.34 (6H, m); 1.46-1.74 (5H, m); 1.81-1.91 (4H, m); 2.36-2.40 (2H, m); 3.20-3.27 (3H, m).

c) N-[5-(5-Chloro-2-methoxy-phenyl)-2H-pyrazol-3-yl]-4-((cis)-2,6-dimethyl-piperidin-1-yl)-butyramide Prepared following the general synthetic method for the one-pot synthesis of ω-amino-alkanoic acid (1H-pyrazol-3-yl-5-aryl)-amides, starting from commercially available 5-(5-Chloro-2-methoxy-phenyl)-2H-pyrazol-3-ylamine (111.8 mg, 0.5 mmol, 1.0 eq) and 4-(2,6-Dimethyl-piperidin-1-yl)-butyric acid (149.0 mg, 0.8 mmol, 1.5 eq).

Following the general procedure, 80 mg of title compound were recovered as its formate salt after preparative HPLC purification (40% yield).

C21H29N4O2Cl

Mass (calculated) [404]; (found) [M+H$^+$]=405

LC Rt=2.03 min. 100% (10 min method)

1H-NMR (dmso-d6 of HCOOH salt): 1.12 (6H, d, J=6.4 Hz); 1.27-1.32 (3H, m); 1.57-1.59 (3H, m); 1.68-1.74 (2H, m); 2.27-2.31 (2H, m); 2.72-2.82 (4H,m); 3.87 (3H, s); 6.92 (1H, s); 7.14 (1H, d, J=9.2 Hz); 7.33-7.36 (1H, m); 7.70 (1H, d, J=2.8 Hz); 8.26 (1H,s); 10.48 (1H, br s)

Example 26

N-[5-(4-Difluoromethoxy-phenyl)-2H-pyrazol-3-yl]-4-((S)-2-methyl-pyrrolidin-1-yl)-butyramide a) 4-((S)-2-Methyl-pyrrolidin-1-yl)-butyric acid ethyl ester (S)-2-methyl-pyrrolidine hydrochloride (0.8 g, 6.6 mmol, 1.1 eq) was dissolved in 2-butanone (20 mL) and potassium carbonate (1.7 g, 12.6 mmol, 2.1 eq) was added. Ethyl 4-bromobutyrate (0.86 mL, 6.0 mmol, 1.0 eq) was added and the reaction mixture was refluxed for 2 days. The mixture was allowed to cool to room temperature and any solid present was filtered off and washed with ether. The filtrate was concentrated under reduced pressure to give 1.20 g of the title compound (yield 99%) which was used in the next step without further purification.

C11H21NO2

$^1$H-NMR (dmso-d6): 0.95 (3H, d, J=6.0 Hz); 1.13-1.17 (3H, m); 1.20-1.28 (1H, m); 1.59-1.64 (4H, m); 1.77-1.86 (1H, m); 1.90-2.00 (2H, m); 2.10-2.23 (1H,m); 2.25-2.31 (2H,m); 2.62-2.66 (1H,m); 2.96-2.99 (1H, m); 3.98-4.03 (2H, m).

b) 4-((S)-2-Methyl-pyrrolidin-1-yl)butyric acid

The product was prepared according to the general procedure for ω-aminoacid synthesis (route C2). Evaporation of water under reduced pressure afforded 1.1 g of the title compound (76% yield) as its hydrochloride salt.

C9H17NO2

$^1$H-NMR (dmso-d6 of HCl salt): 1.22-1.27 (3H, m); 1.62-1.64 (1H, m); 2.03-2.09 (6H, m); 2.19-2.28 (1H, m); 2.47-2.58 (1H, m); 2.86-2.92 (1H, m); 3.15-3.40 (1H, m); 3.69-3.75 (2H, m); 7.25 (1H,s).

c) N-[5-(4-Difluoromethoxy-phenyl)-2H-pyrazol-3-yl]-4-((S)-2-methyl-pyrrolidin-1-yl)-butyramide Prepared following the general synthetic method for the one-pot synthesis of ω-amino-alkanoic acid (1H-pyrazol-3-yl-5-aryl)-amides, starting from 5-(4-Difluoromethoxy-phenyl)-2H-pyrazol-3-ylamine (112.5 mg, 0.5 mmol, 1.0 eq) and 4-((S)-2-Methyl-pyrrolidin-1-yl)-butyric acid (155.0 mg, 0.8 mmol, 1.5 eq).

120 mg of title compound were recovered as its formate salt after preparative HPLC purification (69% yield).

C19H24N4O2F2
Mass (calculated) [378]; (found) [M+H$^+$]=379
LC Rt=1.64 min, 98% (10 min method)
1H-NMR (dmso-d6 of HCOOH salt): 1.04 (3H, d, J=6.0 Hz); 1.30-1.37 (1H, m); 1.65-1.89 (5H, m); 2.16-2.26 (2H, m); 2.28-2.40 (2H, m); 2.80-2.82 (1H, m); 3.12-3.17 (2H, m); 6.79 (1H, s); 7.07-7.44 (3H, m); 7.73-7.75 (2H, m); 8.18 (1H,s); 10.44 (1H, br s)

Example 27

N-[5-(1H-Indol-3-yl)-2H-pyrazol-3-yl]-4-piperidin-1-yl-butyramide a) 3-(1H-Indol-3-yl)-3-oxo-propionitrile

In a flask, cyanoacetic acid (5.0 g, 58.8 mmol, 1.2 eq) was dissolved in acetic anhydride (50 mL) and heated at 50° C. Indole (5.8 g, 50.0 mmol, 1.0 eq) was added and the reaction was heated at 80° C. for 5 min. A white precipitate crushed out of the solution; the reaction was cooled to room temperature and then filtered. The solid obtained (620.0 mg, 85% yield) was used for the next step without further purification.

C11H8N2O
1H-NMR (dmso-d6): 4.48 (2H, s); 7.21-7.24 (2H, m); 7.48-7.50 (1H, m); 8.12-8.14 (1H, m); 8.37 (1H, d, J=3.2 Hz); 12.17 (1H, s).

b) 5-(1H-Indol-3-yl)-2H-pyrazol-3-ylamine

To a solution of 3-(1H-indol-3-yl)-3-oxo-propionitrile (6.4 g, 34.7 mmol, 1.0 eq), in absolute EtOH (40 mL), hydrazine monohydrate (5.0 mL, 104.1 mmol, 3.0 eq) was added and the reaction was heated at reflux for 24 hours. The reaction mixture was allowed to cool to room temperature; the solid was filtered and washed with Et$_2$O/EtOAc 10/1 to give 3.0 g of title product (yield 74%).

C11H10N4
Mass (calculated) [198]; (found) [M+H$^+$]=199.
LC Rt=0.98 min, 90% (5 min method)
$^1$H-NMR (dmso-d6): 4.57 (2H, bs); 5.70 (1H, s); 7.00-7.19 (2H, m); 7.33-7.46 (1H, m); 7.59 (1H, s); 7.69-7.90(1H, bs); 11.11-11.36 (1H, bs); 11.37-11.77 (1H, bs).

c) N-[5-(1H-Indol-3-yl)-2H-pyrazol-3-yl]-4-piperidin-1-yl-butyramide

To a suspension of 4-piperidin-1-yl-butyric acid (621.0 mg, 3.0 mmol, 1.5 eq) in 1,2-dichloroethane (6 mL), N,N'-carbonyldiimidazole (453.0 mg, 2.8 mmol, 1.4 eq) was added and the mixture was stirred at room temperature for 1 hour. 5-(1H-indol-3-yl)-2H-pyrazol-3-ylamine (400.0 mg, 2.0 mmol, 1.0 eq) in 1,2-dichloroethane (6 mL) was added; the reaction was stirred at room temperature for 2 days, then 1 day at 70° C., to allow complete migration of the acyl group from the ring nitrogen to the exocyclic nitrogen. The reaction then was allowed to cool down to room temperature and the mixture was washed with saturated Na$_2$CO$_3$ and evaporated under reduced pressure; the crude was purified by preparative HPLC to give 320.0 mg (yield: 41%) of the title compound as formate salt.

C20H25N5O
Mass (calculated) [351]; (found) [M+H$^+$]=352.
LC Rt=1.42 min, 95% (10 min method)
$^1$H-NMR (dmso-d6 of HCOOH salt): 1.37-1.39 (2H, m); 1.50-1.54 (4H, m); 1.72-1.80 (2H, m); 2.30-2.34 (2H, m); 2.40-2.48 (6H, m); 6.78 (1H, s); 7.08-7.17 (2H, m); 7.43 (1H, d, J=7.6 Hz); 7.71 (1H, d, J=2.8 Hz); 7.76 (1H, d, J=7.6 Hz); 8.19 (1H, s); 10.39 (1H, s); 11.39 (1H, s)

Example 28

N-[5-(4-Isopropoxy-phenyl)-2H-pyrazol-3-yl]-4-piperidin-1-yl-butyramide a) 4-Isopropoxy-benzoic acid methyl ester 3.0 g of 4-isopropoxy-benzoic acid (16.7 mmol, 1.0 eq) were dissolved in MeOH (20 mL) and a catalytic quantity of sulfuric acid was added; the mixture was heated at reflux for 2 days. The solvent was then evaporated and the residue was dissolved in DCM and washed with 10% NaOH. The organic phases were dried and evaporated to give 2.2 g of title product (yield 67%).

C11H14O3
$^1$H-NMR (dmso-d6): 1.25 (6H, d, J=6.4 Hz); 3.77 (3H, s); 4.67-4.70 (1H, m); 6.96-6.98 (2H, m); 7.84-7.87 (2H, m).

b) 3-(4-Isopropoxy-phenyl)-3-oxo-propionitrile

To a solution of 4-Isopropoxy-benzoic acid methyl ester (2.2 g, 11.2 mmol, 1.0 eq) in dry toluene (15 mL) under N$_2$, NaH (50-60% dispersion in mineral oil, 1.1 g, 22.4 mmol, 2.0 eq) was added. The mixture was heated at 80° C. and then dry CH$_3$CN was added dropwise (2.8 mL, 56.0 mmol, 5.0 eq). The reaction was heated for 18 hours, then was allowed to cool down to room temperature and acidified with HCl 2N. The organic phase was recovered and 2.0 g of crude were obtained and it was used for cyclization without further purification.

C11H14O3 c) 5-(4-Isopropoxy-phenyl)-2H-pyrazol-3-ylamine

The product was prepared from 3-(4-isopropoxy-phenyl)-3-oxo-propionitrile according to general procedure for aminopyrazole synthesis (route A2). The solvent was removed under reduced pressure, water (10 mL) was added, and the title product (1.0 g, 94% yield) was precipitated as a yellow solid and used for the next step without further purification.

C12H15N3O
Mass (calculated) [217]; (found) [M+H$^+$]=218.
LC Rt=1.36 min, 95% (5 min method)
1H-NMR (dmso-d6): 1.24 (6H, d, J=6.0 Hz); 4.57-4.69 (3H, br m); 5.64 (1H, s); 6.89 (2H, d, J=8.8 Hz); 7.51 (2H, d, J=8.8 Hz)

d) N-[5-(4-Isopropoxy-phenyl)-2H-pyrazol-3-yl]-4-piperidin-1-yl-butyramide

The product was prepared according to the general synthetic method for the synthesis of ω-amino-alkanoic acid (1H-pyrazol-3-yl-5-aryl)-amides via the amino acid route, starting from 5-(4-isopropoxy-phenyl)-2H-pyrazol-3-ylamine (86.0 mg, 0.4 mmol, 1.0 eq). The crude product was purified via preparative HPLC; the title product (56.0 mg, 38% yield) was obtained as formate salt.

C21H30N4O2

Mass (calculated) [370]; (found) [M+H$^+$]=371, [M+2/2]=165.

LC Rt=1.91 min, 96% (10 min method)

$^1$H-NMR (dmso-d6 of HCOOH salt): 1.25 (6H, d, J=6 Hz); 1.33-1.41 (2H, m); 1.48-1.53 (4H, m); 1.71-1.77 (2H, m); 2.29 (2H, t, J=7.2 Hz); 2.35 (2H, t, J=7.2 Hz); 2.42-2.47 (4H, m); 4.60-4.66 (1H, m); 6.71 (1H, s); 6.94 (2H, d, J=8.8 Hz); 7.58 (2H, d, J=8.8 Hz); 8.17 (1H, s); 10.38 (1H, s).

Example 29

N-[5-(1-Ethyl-1H-indol-3-yl]-4-pyrrolidin-1-yl-butyramide a) 1-Ethyl-1H-indole-3-carboxylic acid ethyl ester To a suspension of NaH (50-60% dispersion in mineral oil, 548.0 mg, 11.4 mmol, 2.0 eq) in THF (20 mL), 1H-indole-3-carboxylic acid methyl ester (1.0 g, 5.7 mmol, 1.0 eq) was added and after 20 min also ethyl iodide (507.0 μL, 6.3 mmol, 1.1. eq) was added. The reaction was heated at 70° C. for 1 h. The mixture was cooled down to 0° C. and water (10 mL) was added carefully. AcOEt was added and the organic phase was collected and concentrated, to give the crude compound that was purified through SiO2 column (10 g) with gradient elution from 100% cyclohexane to cyclohexane-EtOAc 80:20. The title product (860 mg, 74% yield) was obtained.

C12H13NO2

$^1$H-NMR (dmso-d6): 1.36 (3H, t, J=7.2 Hz); 3.77 (3H, s); 4.26 (2H, q, J=7.2); 7.16-7.27 (2H, m); 7.55-7.59 (1H, m); 7.97-7.99 (1H, m); 8.15 (1H, s).

b) 3-(1-Ethyl-1H-indol-3-yl)-3-oxo-propionitrile

The product was prepared according to the general procedure for aminopyrazole synthesis (route A1bis) from 1-ethyl-1H-indole-3-carboxylic acid methyl ester (860.0 mg, 4.2 mmol, 1.0 eq). 820.0 mg of the title product (yield 91%) were obtained and used directly for the next step.

C13H12N2O c) 5-(1-Ethyl-1H-indol-3-yl)-2H-pyrazol-3-ylamine

The product was prepared according to general procedure for aminopyrazole synthesis (route A2) starting from 3-(1-ethyl-1H-indol-3-yl)-3-oxo-propionitrile (820 mg, 3.87 mmol, 1.0 eq). The solvent was removed under reduced pressure; the solid residue was washed with EtOH to obtain the title product (612 mg, 70% yield).

C13H14N4

Mass (calculated) [226]; (found) [M+H$^+$]=227.

LC Rt=1.30 min. 69% (5 min method)

d) N-[5-(1-Ethyl-1H-indol-3-yl)-2H-pyrazol-3-yl]-4-pyrrolidin-1-yl-butyramide

The product was prepared according to the general synthetic method for the synthesis of ω-amino-alkanoic acid (1H-pyrazol-3-yl-5-aryl)-amides via the amino acid route, starting from 5-(1-ethyl-1H-indol-3-yl)-2H-pyrazol-3-ylamine (99.0 mg, 0.5 mmol, 1.0 eq) and 4-pyrrolidin-1-yl-butyric acid (118 mg, 0.75 mmol). The crude product was purified via preparative HPLC; the title product (77.0 mg, 42% yield) was obtained as formate salt.

C21H27N5O

Mass (calculated) [365]; (found) [M+H$^+$]=366.

LC Rt=1.83 min, 99% (10 min method)

$^1$H-NMR (dmso-d6 of HCOOH salt): 1.38 (3H, t, J=7.2 Hz); 1.71-1.81 (6H, m); 2.34 (2H, t J=7.2 Hz); 2.59-2.65 (6H, m); 4.23 (2H, q, J=7.2 Hz); 6.76 (1H, s); 7.11-7.22 (2H, m); 7.53 (1H, d, J=8.4 Hz); 7.75-7.79 (2H,m); 8.19 (1H, br s); 10.40 (1H, s).

Example 30

N-[5-(4-Cyclopropylmethoxy-phenyl)-2H-pyrazol-3-yl]-4-pyperidin-1-yl-butyramide a) 4-Cyclopropylmethoxy-benzoic acid methyl ester 4-hydroxy-benzoic acid methyl ester (2.0 g, 13.1 mmol, 1.2 eq) was dissolved in acetone (20 mL), NaI (0.97 g, 6.5 mmol, 0.5 eq) and K$_2$CO$_3$ (3.0 g, 21.8 mmol, 2.0 eq) were added and the mixture was stirred at room temperature for 20 min. (Bromomethyl)cyclopropane (1.1 mL, 10.3 mmol, 1.0 eq) was added, and the reaction was refluxed for 2 days. The solvent was concentrated under reduced pressure, NaOH 10% was added, and the product was extracted with DCM. The organic phase was dried over Na$_2$SO$_4$ and the solvent evaporated under reduced pressure. The title product (1.23 g, yield 79%) was recovered and used without further purification.

Mass (calculated) [206]; (found) [M+H$^+$]=207.

LC Rt=2.38 min, 86% (5 min method)

$^1$H-NMR (dmso-d6): 033-0.34 (2H, m); 0.57-0.59 (2H, m); 1.21-1.25 (1H, m); 3.81 (3H, s); 3.89 (2H, d, J=6.8 Hz); 7.02 (2H, d, J=8.8 Hz); 7.88 (2H, d, J=8.8 Hz).

b) 5-(4-Cyclopropylmethoxy-phenyl)-2H-pyrazol-3-ylamine

The product was prepared according to the general procedure (route A1bis). from 4-cyclopropylmethoxy-benzoic acid methyl ester (1.17 g, 5.9 mmol, 1.0 eq). The reaction was allowed to cool down to room temperature, the solid formed was filtered and dissolved in H$_2$O. The solution was acidified to pH 4 and the solid formed was filtered, affording 1.2 g of 3-(4-cyclopropylmethoxy-phenyl)-3-oxo-propionitrile that was used directly for the next step.

5-(4-Cyclopropylmethoxy-phenyl)-2H-pyrazol-3-ylamine was prepared according to general procedure for aminopyrazole synthesis (route A2). The reaction was concentrated and the residue was precipitated with water: 500 mg of the title product (37% yield) were obtained, and it was used directly for the next step.

c) N-[5-(4-Cyclopropylmethoxy-phenyl)-2H-pyrazol-3-yl]-4-piperidin-1-yl-butyramide The product was prepared according to the general synthetic method for the synthesis of ω-amino-alkanoic acid (1H-pyrazol-3-yl-5-aryl)-amides via the amino acid route, starting from 5-(4-cyclopropylmethoxy-phenyl)-2H-pyrazol-3-ylamine (152.9 mg, 0.7 mmol, 1.0 eq) and 4-piperidin-1-yl-butyric acid (168 mg, 1.0 mmol, 1.5 eq). The crude product was purified via preparative HPLC; 72.0 mg of the title product (28% yield) was obtained as a formate salt.

C22H30N4O2

Mass (calculated) [382]; (found) [M+H$^+$]=383.

LC Rt=1.99 min, 100% (10 min method)

$^1$H-NMR (dmso-d6 of HCOOH salt): 033-0.34 (2H, m); 0.55-0.59 (2H, m); 1.19-1.25 (1H, m); 1.38-1.40 (2H, m); 1.49-1.54 (4H, m); 1.70-1.77 (2H, m); 2.28-2.41 (8H, m); 3.84 (2H, d, J=6.8 Hz); 6.74 (1H, s); 6.97 (2H, d, J=8.8 Hz); 7.60 (2H, d, J=8.8 Hz); 8.19 (1H,s); 10.40 (1H, s).

Example 31

4-Azepan-1-yl-N-[5-(4-difluoromethoxy-phenyl)-2H-pyrazol-3-yl]-butyramide a) 4-Azepan-1-yl-butyric acid ethyl ester

To a solution of azepane (10.2 mL, 102.0 mmol, 4.0 eq) in toluene (30 mL), ethyl 4-bromobutyrate (3.8 mL, 26.0 mmol, 1.0 eq) was added and the reaction mixture was refluxed for 10 hours. The mixture was allowed to cool to room temperature and the solid present was filtered off and washed with ether. The filtrate was concentrated under reduced pressure to give the aminoester which was used in the next step without further purification.

C12H23NO2 b) 4-Azepan-1-yl-butyric acid

The product was prepared according to the general procedure for ω-aminoacid synthesis (route C2). Evaporation of water under reduced pressure afforded 3.8 g of the title compound (80% yield) as its hydrochloride salt.

C10H19NO2

Mass (calculated) [185]; (found) [M+H$^+$]=186.

LC Rt=0.26 min, 100% (5 min method)

$^1$H-NMR (dmso-d6 of HCl salt): 1.53-1.66 (4H, m); 1.77-1.91 (6H, m); 2.30 (2H, t, J=7.2 Hz); 2.98-3.09 (4H, m); 3.27-3.30 (2H, m); 10.42 (1H, br s).

c) 4-Difluoromethoxy-benzoic acid methyl ester

Under N$_2$ flow, 1.3 g of 4-hydroxy-benzoic acid methyl ester (8.3 mmol, 1.0 eq) and 1.5 g of sodium chlorodifluoroacetate (10.0 mmol, 1.2 eq) were dissolved in DMF (25 mL) in a two neck round bottom flask; potassium carbonate (1.4 g, 10.0 mmol, 1.2 eq) was added and the mixture was heated at 125° C. for 3.5 hours. The mixture was then diluted with water and extracted with DCM; organic phases were dried and evaporated, the crude was purified with Si column (eluent: cycloexane/EtOAc 80/20) to obtain 0.77 g of product (yield 46%) which was used directly for the next step.

C9H8F2O3 d) 3-(4-Difluoromethoxy-phenyl)-3-oxo-propionitrile

The product was prepared according to the general procedure for aminopyrazole synthesis from 872.0 mg (4.3 mmol, 1.0 eq) of 4-difluoromethoxy-benzoic acid methyl ester (route A1bis). 818.5 mg of the title product (yield 90%) were used directly for the following step.

C10H7F2NO2 e) 5-(4-Difluoromethoxy-phenyl)-2H-pyrazol-3-ylamine

The product was prepared according to the general procedure for aminopyrazole synthesis (route A2). The crude product was purified through SiO$_2$ column with gradient elution from 100% EtOAc to EtOAc-MeOH 80:20. The title product (826 mg, 59% yield) was obtained.

C10H9F2N3O

Mass (calculated) [225]; (found) [M+H$^+$]=226.

LC Rt=1.34 min, 100% (5 min method)

$^1$H-NMR (dmso-d6): 4.82 (2H, br s), 5.71 (1H, s), 7.15 (2H, d, J=8.4 Hz), 7.22 (1H, t, J=74.0 Hz), 7.67 (2H, d, J=8.8 Hz); 11.58 (1H, br s)

f) 4-Azepan-1-yl-N-[5-(4-difluoromethoxy-phenyl)-2H-pyrazol-3-yl]-butyramide The product was prepared according to the general synthetic method for the synthesis of ω-amino-alkanoic acid (1H-pyrazol-3-yl-5-aryl)-amides via the amino acid route, starting from 5-(4-difluoromethoxy-phenyl)-2H-pyrazol-3-ylamine (149.0 mg, 0.7 mmol, 1.0 eq). 90.0 mg of title compound were recovered as its formate salt after preparative HPLC purification (35% yield).

C20H26F2N4O2

Mass (calculated) [392]; (found) [M+H$^+$]=393, [M+2/2]=197.

LC Rt=2.26 min, 100% (10 min method)

$^1$H-NMR (dmso-d6 of HCOOH salt): 1.51-1.60 (8H, m); 1.72-1.76 (2H, m); 2.31 (2H, t, J=7.6 Hz); 2.56 (2H, t, J=7.2 Hz); 2.69 (4H, t, J=5.2 Hz); 6.80 (1H, s); 7.08-7.45 (3H, m); 7.73-7.76 (2H, m); 8.21 (1H, s); 10.50 (1H, br s).

Example 32

Trans (±)-2-piperidin-1-ylmethyl-cyclopropanecarboxylic acid (5-o-tolyl-2H-pyrazol-3-yl)-amide a) Trans (±)-2-piperidin-1-ylmethyl-cyclopropanecarboxylic acid ethyl ester Under N$_2$ atmosphere, ethyl 2-formyl-1-cyclopropanecarboxylate (3.0 g, 21.1 mmol, 1.2 eq) and piperidine (1.5 g, 17.6 mmol, 1.0 eq) were dissolved in DCM (45 mL); after 2 hours at room temperature, the mixture was cooled at 0° C. and sodium triacetoxyborohydride (5.6 g, 26.4 mmol, 1.5 eq) was added dropwise. The mixture was stirred at room temperature for 2.5 hours, then the organic phase was washed with NaOH aq and water to give 3.3 g of the title product (yield 89%).

C12H21NO2

$^1$H-NMR (CDCl$_3$): 0.70-0.75 (1H, m); 1.20-1.38 (4H, m); 1.39-1.43 (3H, m); 1.53-1.61 (5H, m); 2.22-2.27 (1H, m); 2.34-2.43 (5H, m); 4.08-4.17 (2H, m).

b) Trans (±)-2-piperidin-1-ylmethyl-cyclopropane carboxylic acid

The product was prepared according to the general procedure for ω-aminoacid synthesis (route C2). Evaporation of water under reduced pressure and trituration with diethyl ether afforded 1.3 g of the title compound (33% yield) as chloridrate salt.

C10H17NO2

Mass (calculated) [183]; (found) [M+H$^+$]=184.

LC Rt=0.19 min (5 min method)

¹H-NMR (dmso-d6 of HCl salt): 0.96-1.01 (1H, m), 1.06-1.11 (1H, m), 1.27-1.41 (1H, m), 1.62-1.85 (7H, m), 2.82-3.06 (4H, m), 3.36-3.37 (2H, m), 10.88 (1H, bs), 12.38 (1H, bs)

c) Trans (±)-2-piperidin-1-ylmethyl-cyclopropanecarboxylic acid (5-o-tolyl-2H-pyrazol-3-yl)-amide The product was prepared according to the general synthetic method for the synthesis of ω-amino-alkanoic acid (1H-pyrazol-3-yl-5-aryl)-amides via the amino acid route, starting from commercially available 5-o-tolyl-2H-pyrazol-3-ylamine (152.0 mg, 0.9 mmol, 1.0 eq). The crude product was purified with prep HPLC and SiO$_2$ column with gradient elution from 100% CH$_3$CN to CH$_3$CN/2N NH$_3$ in MeOH 80:20. The title product (18 mg, 6% yield) was obtained.

C20H26N4O

Mass (calculated) [338]; (found) [M+H$^+$]=339, [M+2/2]=170.

LC Rt=1.71 min, 100% (10 min method)

¹H-NMR (dmso-d6): 0.62 (1H, br s); 0.94-0.97 (1H, m); 1.27-1.37 (3H, m); 1.44-1.49 (4H, m); 1.65-1.68 (1H, m); 2.08-2.13 (1H, m); 2.30-2.35 (8H, m); 6.62 (1H, s); 7.24-7.27 (3H, m); 7.38 (1H, d, J=6.0 Hz); 10.64 (1H,s); 12.45 (1H, s).

Example 33

Trans (±)-2-piperidin-1-ylmethyl-cyclopropanecarboxylic acid [5-(2-difluoromethoxy-phenyl)-2H-pyrazol-3-yl]-amide a) 2-Difluoromethoxy-benzoic acid methyl ester 2.0 g of 2-difluoromethoxy-benzoic acid (10.6 mmol, 1.0 eq) were dissolved in MeOH (15 mL) and a catalytic quantity of sulfuric acid was added; the mixture was heated at reflux overnight. The solvent was then evaporated and the residue was dissolved in DCM and washed with saturated NaHCO$_3$. The organic phase was dried and evaporated to give 1.9 g of title product (yield 87%).

C9H8F2O3

¹H-NMR (dmso-d6): 3.82 (3H, s); 6.99-7.40 (2H, m); 7.31 (1H, d, J=8.4 Hz); 7.63-7.67 (1H, m); 7.82-7.84 (1H, m).

b) 3-(2-Difluoromethoxy-phenyl)-3-oxo-propionitrile

The product was prepared according to the general procedure for aminopyrazole synthesis from 1.5 g (7.4 mmol, 1.0 eq) of 2-Difluoromethoxy-benzoic acid methyl ester (route A1bis). The crude product was used directly for the next step.

C10H7F2NO2 c) 5-(2-Difluoromethoxy-phenyl)-2H-pyrazol-3-ylamine

The product was prepared according to general procedure for aminopyrazole synthesis (route A2). The crude product was purified through SiO2 column with gradient elution from 100% EtOAc to EtOAc-MeOH 90:10. The title product (1.3 g, 76% yield) was obtained.

C10H9F2N3O

¹H-NMR (dmso-d6): 4.82 (2H, bs), 5.79 (1H, s), 7.00-7.37 (4H, m), 7.79 (1H, d), 11.74 (1H, bs)

d) Trans (±)-2-piperidin-1-ylmethyl-cyclopropanecarboxylic acid [5-(2-difluoromethoxy-phenyl)-2H-pyrazol-3-yl]-amide The product was prepared according to the general synthetic method for the synthesis of ω-amino-alkanoic acid (1H-pyrazol-3-yl-5-aryl)-amides via the amino acid route, starting from trans (±)-2-piperidin-1-ylmethyl-cyclopropanecarboxylic acid (99.1 mg, 0.6 mmol, 1.3 eq) and 5-(2-difluoromethoxy-phenyl)-2H-pyrazol-3-ylamine (125.7 mg, 0.4 mmol, 1.0 eq). The crude product was purified through SiO2 column with gradient elution from 100% DCM to DCM-NH$_3$ in MeOH 2 N 80:20. The title product (39.9 mg, 23% yield) was obtained.

C20H24F2N4O2

Mass (calculated) [390]; (found) [M+H$^+$]=391.

LC Rt=1.68 min, 100% (10 min method)

¹H-NMR (dmso-d6): 0.62-0.65 (1H, m); 0.96-1.00 (1H, m); 1.21-1.69 (7H, br m); 2.13 (1H, br s); 2.30-2.49 (3H, m); 3.29-3.31 (3H, m); 6.91-7.42 (5H, m); 7.72 (1H, d, J=7.2 Hz); 10.67 (1H, s); 12.68 (1H, s)

Example 34

[5-(4-Chloro-phenyl)-2H-pyrazol-3-yl]-2-methyl-4-pyrrolidin-1-yl-butyramide

The product was prepared according to the general synthetic method for the synthesis of ω-amino-alkanoic acid (1H-pyrazol-3-yl-5-aryl)-amides via the amino acid route, starting from 5-(4-Chloro-phenyl)-2H-pyrazol-3-yl-amine (58.0 mg, 0.3 mmol, 1.0 eq) and 2-methyl-4-pyrrolidin-1-yl-butyric acid (77.0 mg, 0.45 mmol, 1.5 eq). After purification with HPLC prep, 21.1 mg of title compound were recovered as formate salt (18% yield).

C18H23ClN4O

Mass (calculated) [346]; (found) [M+H$^+$]=347, [M+2/2]=174.

LC Rt=1.84 min., 100% (10 min method)

¹H-NMR (dmso-d6 of HCOOH salt): 1.07 (3H, d, J=6.8 Hz); 1.47-1.52 (1H, m); 1.64-1.67 (4H, m); 1.74-1.79 (1H, m); 2.38-2.58 (4H, m); 3.79 (3H, s); 6.87-6.90 (1H, m); 7.25-7.27 (2H, m); 7.33 (1H, t, J=8.4 Hz); 10.42 (1H, br s)

Example 35

5-(4-Acetyl-[1,4]diazepan-1-yl)-2-methyl-pentanoic acid [5-(4-methoxy-phenyl)-2H-pyrazol-3-yl]-amide a) 5-Amino-3(4-methoxy-phenyl)-pyrazol-1-carboxylic acid tert-butyl ester Di-tert-butyl dicarbonate (605.0 mg, 2.8 mmol, 1.0 eq) in DCM (3 mL) was added to a vigorously stirred mixture of 5-amino-3-(4-methoxy-phenyl)-pyrazole (500.0 mg, 2.7 mmol, 1.0 eq), DCM (20 mL) and KOH 4.5M aqueous solution (4.7 mL, 21.1 mmol, 8 eq). The mixture was stirred at room temperature for 20 hours. The organic layer was collected and washed with a water/brine 1/1 solution. Evaporation of the solvent gave a crude product purified by SiO$_2$ column (elution DCM), to give the title product (720 mg, yield 94%).

C15H19N3O3

Mass (calculated) [289]; (found) [M+H$^+$]=290

LC Rt=1.43 min, 100% (3 min method)

$^1$H-NMR (dmso-d6): 1.58 (9H, s); 3.78 (3H, s); 5.69 (1H, s); 6.36 (2H, s); 6.96 (2H, br d, J=8.8 Hz); 7.68 (2H, br d, J=8.8 Hz).

b) 2-(3-Bromo-propyl)-2-methyl-malonic acid dimethyl ester

NaH at 60% in mineral oil (1.63 g, 40.8 mmol. 1.3 eq) was washed three times with hexane and subsequently dried. After addition of dried THF (30 mL) the suspension was cooled to 0° C. Dimethyl methylmalonate (4.7 g, 32.3 mmol, 1.0 eq) was slowly and carefully added and gas development was observed. The mixture was stirred for 15 minutes and subsequently 1,3-dibromopropane (24 g, 119.0 mmol, 3.7 eq) was added in one portion. The mixture was allowed to reach room temperature and was then stirred for further 16 hours. NaOH 1.0 M solution was added, the crude was extracted with ethyl acetate; the organic layers were collected and dried, the obtained oil was purified by SiO$_2$ column (elution: cyclohexane followed by EtOAc). The title product (6.6 g, 76% yield) was obtained.

C9H15BrO4

$^1$H-NMR (dmso-d6): 1.32 (3H, s); 1.67-1.72 (2H, m); 1.861-1.90 (2H, m); 3.51 (2H, t, J=6.4 Hz); 3.64 (6H, s).

c) 5-Bromo-2-methyl-pentanoic acid

HBr aq 48% (10 mL, 88.4 mmol) was added at room temperature to 2-(3-bromo-propyl)-2-methyl-malonic acid dimethyl ester (1.80 g, 6.74 mmol) and the mixture was stirred and heated at 120° C. for 24 hours. After cooling to room temperature, NaOH solution was added to reach pH 3 and the product was extracted using a mixture DCM:MeOH 95:5. The obtained crude (0.81 g, 62% yield) was clean enough to be used without further purification.

C6H11BrO2

$^1$H-NMR (dmso-d6): 1.05 (3H, d, J=7.2 Hz); 1.41-1.50 (1H, m); 1.61-1.70 (2H, m); 1.75-1.83 (2H, m); 2.31-2.40 (1H, m); 3.52 (2H, dd, J=6.8 Hz, 6.4 Hz).

d) 5-(5-Bromo-2-methyl-pentanoylamino)-3-(4-methoxy-phenyl)-pyrazole-1-carboxylic acid tert-butyl ester Oxalyl chloride (250.0 μL, 3.0 mmol, 1.5 eq) was slowly added to a solution of 5-bromo-2-methyl-pentanoic acid (390.0 mg, 2.0 mmol, 1.0 eq) in DCM (1 mL) at room temperature and the mixture was stirred for 2 hours under nitrogen. Evaporation of solvent and excess of oxalyl chloride gave a residue which was dissolved in DCM (1 mL) and added dropwise to a solution of 5-amino-3-(4-methoxy-phenyl)-pyrazole-1-carboxylic acid tert-butyl ester (656.0 mg, 2.3 mmol, 1.15 eq) and triethylamine (0.28 mL, 2.0 mmol, 1.0 eq) in DCM (1 mL). The mixture was stirred at room temperature for 48 hours, after which saturated NaHCO$_3$ solution was added and the organic layer was collected and dried. The crude was purified through SiO2 column (elution of cyclohexane-DCM from 10:0 to 1:1) obtaining the title compound (237.0 mg, yield 25%).

C21H28BrN3O4

Mass (calculated) [466]; (found) [M+H$^+$]=467

LC Rt=1.83 min, 92% (3 min method)

$^1$H-NMR (dmso-d6): 1.14 (3H, d, J=6.8 Hz); 1.62 (9H, s); 1.72-1.86 (4H, m); 2.63-2.70 (1H, m); 3.55 (2H, dd, J=6.8 Hz, 6.4 Hz); 3.78 (3H, s); 7.01 (2H, br d, J=8.8 Hz); 7.07 (1H, s); 7.79 (2H, br d, J=8.8 Hz); 10.09 (1H, s).

e) 5-[5-(4-Acetyl-[1,4]diazepan-1-yl)-2-methyl-pentanoylamino]-3-(4-methoxy-phenyl)-pyrazole-1-carboxylic acid tert-butyl ester 5-(5-Bromo-2-methyl-pentanoylamino)-3-(4-methoxy-phenyl)-pyrazole-1-carboxylic acid tert-butyl ester (280.0 mg, 0.6 mmol, 1.0 eq) was dissolved in DCM (3 mL). Triethylamine (80 μL, 0.6 mmol, 1.0 eq) and 1-[1,4]-diazepan-1-yl-ethanone (158 μL, 170.0 mg, 1.2 mmol, 2.0 eq) were added and the mixture was stirred at room temperature for 24 hours, then at 50° C. for 16 hours. NaHCO$_3$ saturated solution was added and the organic layer separated and collected. Evaporation of the solvent gave a crude product purified using SiO$_2$ column (elution DCM, DCM:MeOH 99:1 to 96:4) obtaining the title product (181.3 mg, yield 54%).

C28H41N5O5

Mass (calculated) [527]; (found) [M+H$^+$]=528

LC Rt=1.63 min, 100% (5 min method).

$^1$H-NMR (dmso-d6): 1.13 (3H, d, J=6.4 Hz); 1.33-1.50 (4H, m); 1.62 (9H, s); 1.65-1.81 (2H, m); 1.96 (3H, s); 2.34-2.44 (1H, m); 2.52-2.67 (3H, m); 2.98-3.13 (3H, m); 3.40-3.46 (4H, m); 3.80 (3H, s); 7.01 (2H, br d, J=8.8 Hz); 7.06 (1H, s); 7.79 (2H, br d, J=8.8 Hz); 10.07 (1H, s).

f) 5-(4-Acetyl-[1,4]diazepan-1-yl)-2-methyl-pentanoic acid [5-(4-methoxy-phenyl)-2H-pyrazol-3-yl]-amide 5-[5-(4-Acetyl-[1,4]diazepan-1-yl)-2-methyl-pentanoylamino]-3-(4-methoxy-phenyl)-pyrazole-1-carboxylic acid tert-butyl ester (181.0 mg, 0.34 mmol, 1.0 eq) was dissolved in DCM (3 mL) and HCl 4.0 M in dioxane (0.16 mL, 0.64 mmol, 1.9 eq) was added at room temperature. After 3 hours another 1.9 eq of HCl was added and the mixture stirred for 3 additional hours. NaHCO$_3$ saturated solution was added and the organic layer collected and dried. Evaporation of solvent gave the title product (120 mg; Yield 82%).

C23H33N5O3

Mass (calculated) [427]; (found) [M+H$^+$]=428.

LC Rt=1.58 min, 100% (10 min method)

$^1$H-NMR (dmso-d6): 1.05 (3H, d, J=6.4 Hz); 1.26-1.40 (3H, m); 1.50-1.57 (1H, m); 1.62-1.68 (1H, m); 1.70-1.76 (1H, m); 1.96 (3H, s); 2.36-2.42 (2H, m); 2.53-2.50 (2H, m); 2.59-2.62 (1H, m); 3.31-3.34 (2H, m); 3.37-3.47 (4H, m), 3.78 (3H, s); 6.80 (1H, s); 7.00 (2H, br d, J=8.8 Hz); 7.63 (2H, br d, J=8.8 Hz): 10.30 (1H, s); 12.6 (1H, s).

Example 36

5-(4-Acetyl-[1,4]diazepan-1-yl)-2-methyl-pentanoic acid [5-(4-chloro-phenyl)-2H-pyrazol-3-yl]-amide a) 5-Amino-3-(4-chloro-phenyl)-pyrazole-2-carboxylic acid tert-butyl ester

To a solution of 5-Amino-3-(4-chloro-phenyl)-pyrazole (2.8 g, 14.5 mmol, 1.0 eq) in DCM (30 mL) potassium hydroxide (27 mL of a 4.5 M solution) and di-tert-butyl dicarbonate (3.5 g, 16.0 mmol, 1.1 eq) were added in sequence. The mixture was stirred at room temperature until complete conversion was observed by LC-MS analysis. The organic layer was recovered by extraction from water and dried under reduced pressure. The solid was washed with MeOH and filtered, to give 3.6 g of a white solid (yield 85%).

C14H16ClN3O2

1H-NMR (dmso-d6): 1.68 (9H, br s); 5.34 (2H, br s); 7.25-7.27 (1H, m); 7.35 (2H, d, J=8.4 Hz); 7.74 (2H,d, J=8.4 Hz).

b) 5-(5-Bromo-2-methyl-pentanoylamino)-3-(4-chloro-phenyl)-pyrazole-1-carboxylic acid tert-butyl ester To a solution of 5-bromo-2-methyl-pentanoic acid (1.79 g, 9.2 mmol, 1 eq) in anhydrous DCM (8 mL) oxalyl chloride (1.0 mL, 12.0 mmol, 1.3 eq) was added dropwise and the mixture was stirred at room temperature for 16 hours. After evaporation of the solvent and the excess oxalyl chloride, the residue was dissolved in anhydrous DCM (8 mL) and a solution of 5-amino-3-(4-chloro-phenyl)-pyrazole-1-carboxylic acid tert-butyl ester (2.7 g, 9.2 mmol, 1.0 eq) and triethylamine (1.7 mL, 12 mmol, 1.3 eq) was added dropwise at 0° C. The mixture was allowed to reach room temperature and stirred at room temperature for 24 hours, after which another 0.5 eq of activated 5-bromo-2-methyl-pentanoic acid was added. HCl 1M was added; the crude was extracted with DCM and purified through SiO2 column (eluent DCM) to give 3.3 g (yield 97%) of the title product.

C20H25BrClN3O3

Mass (calculated) [370]; (found) [M+H+]=370/372.

LC Rt=2.33, 95% (5 min method)

c) 5-(4-Acetyl-[1,4]diazepan-1-yl)-2-methyl-pentanoic acid [5-(4-chloro-phenyl)-2H-pyrazol-3-yl]-amide 1-[1,4]Diazepan-1-yl-ethanone (1.4 mL, 10.8 mmol, 1.2 eq) was added to a solution of 5-(5-bromo-2-methyl-pentanoylamino)-3-(4-chloro-phenyl)-pyrazole-1-carboxylic acid tert-butyl ester (3.3 g, 9.0 mmol, 1.0 eq) and triethylamine (1.25 mL, 9.0 mmol, 1.0 eq) in 2-butanone (15 mL) and the mixture was stirred at reflux for 48 hours. After solvent removal, DCM (5 mL) and TFA (3 mL) were added and the mixture was stirred at room temperature for 3 hours. DCM and TFA were evaporated under reduced pressure and the crude was treated with a solution of saturated Na2CO3 and extracted with EtOAc. The crude was purified through SiO2 column (gradient elution from 100% DCM to DCM-NH3 in MeOH 2N 92:8).

1.7 g (yield 44%) of the title product was recovered.

C22H30ClN5O2

Mass (calculated) [431]; (found) [M+H+]=432.

LC Rt=1.80 min, 90% (10 min method)

1H-NMR (CDCl3): 1.14-1.21 (3H, d, J=6.58 Hz); 1.36-1.53 (1H, m); 1.53-2.0 (6H, m); 2.1 (3H, s); 2.48-3.07 (6H, m); 3.39-3.77 (4H, m); 6.93 (1H,s); 7.49 (2H, d, J=8.0 Hz); 7.71 (2H,d, J=8.0 Hz); 10.40 (1H, s); 12.87 (1H, s).

Example 37

4-Pyrrolidin-1-yl-pentanoic acid [5-(4-chloro-phenyl)-2H-pyrazol-3-yl]-amide a) 4-Pyrrolidin-1-yl-pentanoic acid methyl ester

Pyrrolidine (3 mL, 36 mmol, 1.2 eq) was dissolved in DCM (50 mL) and methyl levulinate (4 mL, 30 mmol, 1.0 eq) was added. The solution was stirred at room temperature for 1 hour, then Na(OAc)3BH (7.6 g, 36.0 mmol, 1.2 eq) was added. The mixture was stirred at room temperature for 16 hours, then brine was added, the crude was extracted with DCM and dried. 2.0 g of the title product were obtained (34% yield).

C10H19NO2

1H-NMR (CDCl3): 1.04 (3H, d, J=6.4 Hz); 1.67-1.90 (6H, m); 2.26-2.43 (3H, m); 2.51-2.54 (4H, m); 3.64 (3H, s).

b) 4-Pyrrolidin-1-yl-pentanoic acid

To a suspension of 4-pyrrolidin-l-yl-pentanoic acid methyl ester (2.0 g, 10.0 mmol) in water (20 mL), NaOH (0.8 g, 20.0 mmol, 2.0 eq) was added and the mixture was heated at reflux for 10 hours. The reaction was then allowed to cool to room temperature, the pH was adjusted to 3 with HCl 37% and the mixture was concentrated under reduced pressure. The residue was treated with EtOH, the sodium chloride precipitated was filtered off and the solvent was evaporated under reduced pressure, affording 1.7 g of the title compound as white solid (99% yield).

C9H17NO2

1H-NMR (dmso-d6): 1.22 (3H, d, J=6.4 Hz): 1.64-1.74 (1H, m); 1.81-1.96 (4H, m); 1.97-2.07 (1H, m); 2.23-2.30 (1H, m); 2.36-2.44 (1H, m); 2.97-3.02 (2H, m); 3.20-3.26 (1H, m); 3.35-3.46 (2H, m); 10.80 (1H, s)

c) 4-Pyrrolidin-1-yl-pentanoic acid [5-(4-chloro-phenyl)-2H-pyrazol-3-yl]-amide The product was prepared according to the general synthetic method for the synthesis of ω-amino-alkanoic acid (1H-pyrazol-3-yl-5-aryl)-amides via the amino acid route, starting from 5-(4-chloro-phenyl)-2H-pyrazol-3-ylamine (97.0 mg, 0.5 mmol, 1.0 eq) and 4-pyrrolidin-1-yl-pentanoic acid (128.0 mg, 0.7 mmol, 1.5 eq). The reaction was stirred at room temperature for 16 hours, then 8 hours at 50° C., to allow the complete formation of the exocyclic nitrogen acylated isomer. After purification via preparative HPLC, 150.3 mg of title compound were recovered as formate salt (87% yield).

C18H23ClN4O

Mass (calculated) [346]; (found) [M+H+]=347.

LC Rt=1.69 min, 100% (10 min method)

1H-NMR (dmso-d6 on the formate salt): 1.11 (3H, d, J=6.4 Hz); 1.63-1.80 (5H, m); 1.90-1.99 (1H, s); 2.29-2.42 (2H,m); 2.80-2.86 (5H, m); 6.82 (1H,s); 7.46-7.49 (2H, m); 7.70-7.73 (2H, m); 8.19 (1H, s); 10.55 (1H, br s)

TABLE 3

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 38 | 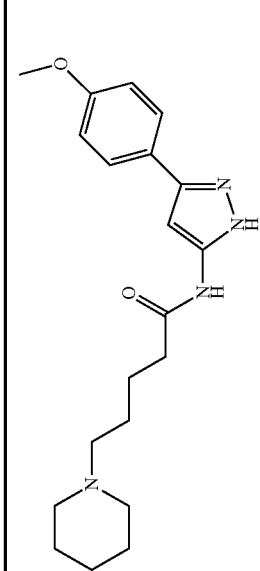 | | C20H28N4O2 | 356.46 | 357 | 100 | 1.64 | 10 | one-pot synthesis of ω-amino-alkanoic acid (1H-pyrazol-3-yl-5-aryl)-amides |
| 39 | 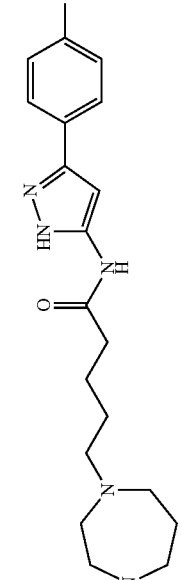 | HCOOH | C21H28N5O2Cl | 417.93 | 418 | 100 | 1.74 | 10 | one-pot synthesis of ω-amino-alkanoic acid (1H-pyrazol-3-yl-5-aryl)-amides |
| 40 | 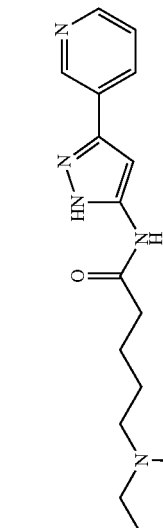 | | C18H25N5O | 327.43 | 328.15 | 99 | 0.23 | 10 | one-pot synthesis of ω-amino-alkanoic acid (1H-pyrazol-3-yl-5-aryl)-amides |
| 41 | 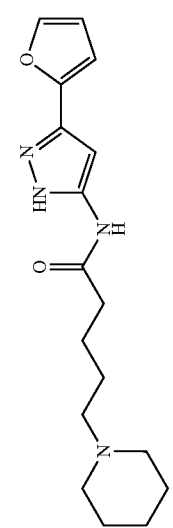 | HCOOH | C17H24N4O2 | 316.41 | 317.18 | 99 | Solvent Front 1.53 | 10 | one-pot synthesis of ω-amino-alkanoic acid (1H-pyrazol-3-yl-5-aryl)-amides |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 42 | 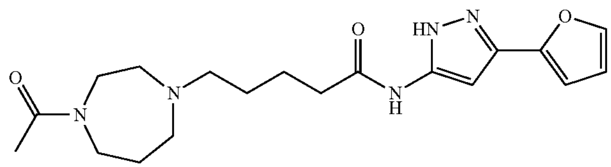 | HCOOH | C19H27N5O3 | 373.46 | 374.22 | 99 | Double peak 0.28 1.34 | 10 | one-pot synthesis of ω-amino-alkanoic acid (1H-pyrazol-3-yl-5-aryl)-amides |
| 43 | 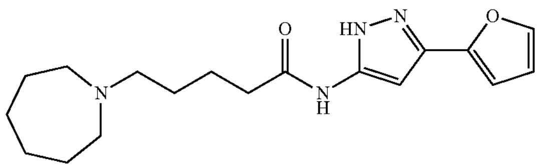 | HCOOH | C18H26N4O2 | 330.43 | 331.24 | 99 | 1.77 | 10 | one-pot synthesis of ω-amino-alkanoic acid (1H-pyrazol-3-yl-5-aryl)-amides |
| 44 | 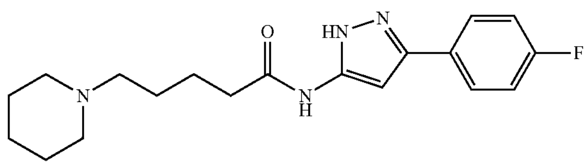 | HCOOH | C19H25FN4O | 344.44 | 345.22 | 99 | Fronted peak 1.96 | 10 | one-pot synthesis of ω-amino-alkanoic acid (1H-pyrazol-3-yl-5-aryl)-amides |
| 45 | 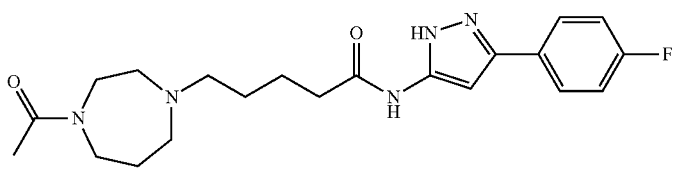 | HCOOH | C21H28FN5O2 | 401.49 | 402.23 | 99 | 1.74 | 10 | one-pot synthesis of ω-amino-alkanoic acid (1H-pyrazol-3-yl-5-aryl)-amides |
| 46 | 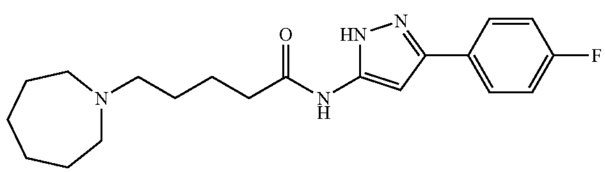 | HCOOH | C20H27FN4O | 358.46 | 359.2 | 99 | 2.06 | 10 | one-pot synthesis of ω-amino-alkanoic acid (1H-pyrazol-3-yl-5-aryl)-amides |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 47 | 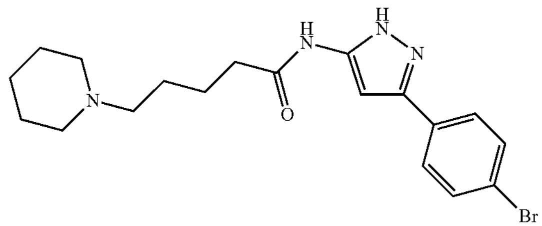 | | C29H25N4OBr | 405.33 | 405 | 100 | 1.98 | 10 | one-pot synthesis of ω-amino-alkanoic acid (1H-pyrazol-3-yl-5-aryl)-amides |
| 48 | 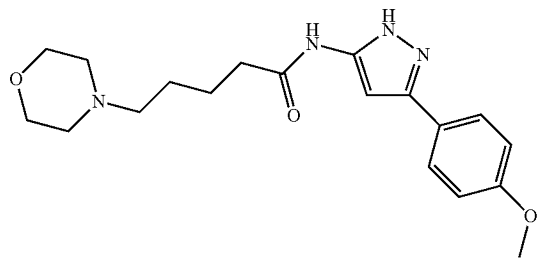 | HCOOH | C19H26N4O3 | 358.43 | 359 | 100 | 1.46 | 10 | one-pot synthesis of ω-amino-alkanoic acid (1H-pyrazol-3-yl-5-aryl)-amides |
| 49 | 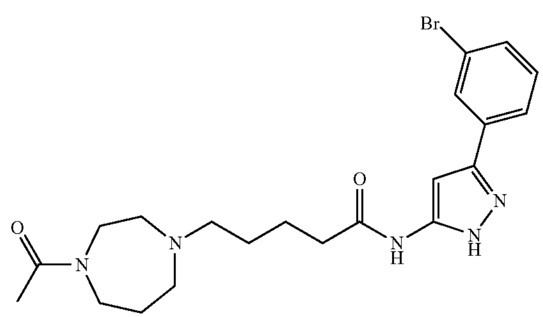 | HCOOH | C21H28N5O2Br | 462.38 | 462 | 100 | 1.9 | 10 | Route B1/B2 for aminopyrazole; one-pot synthesis of ω-amino-alkanoic acid (1H-pyrazol-3-yl-5-aryl)-amides |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 50 | 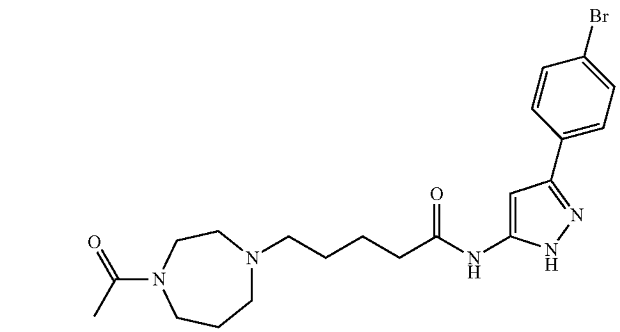 | HCOOH | C21H28N5O2Br | 462.38 | 462 | 100 | 1.94 | 10 | one-pot synthesis of ω-amino-alkanoic acid (1H-pyrazol-3-yl-5-aryl)-amides |
| 51 | 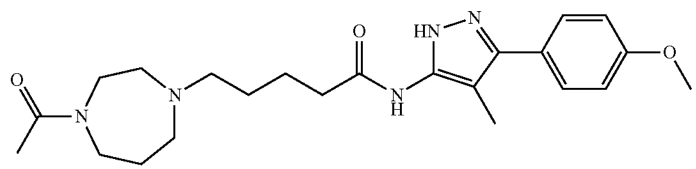 | | C23H33N5O3 | 427.55 | 428.31 | 99 | 1.48 | 10 | one-pot synthesis of ω-amino-alkanoic acid (1H-pyrazol-3-yl-5-aryl)-amides |
| 52 | 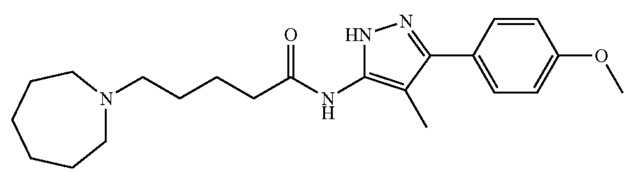 | | C22H32N4O2 | 384.53 | 385.28 | 99 | 1.74 | 10 | one-pot synthesis of ω-amino-alkanoic acid (1H-pyrazol-3-yl-5-aryl)-amides |
| 53 | 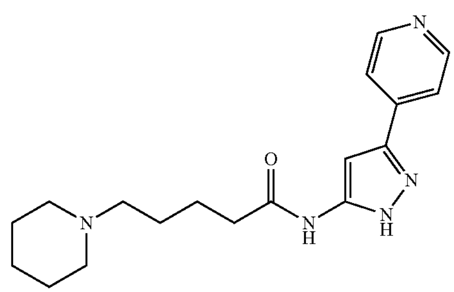 | | C18H25N5O | 327.42 | 328 | 95 | 0.21 | 10 | Route A1/A2 for aminopyrazole; one-pot synthesis of ω-amino-alkanoic acid (1H-pyrazol-3-yl-5-aryl)-amides |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 54 | 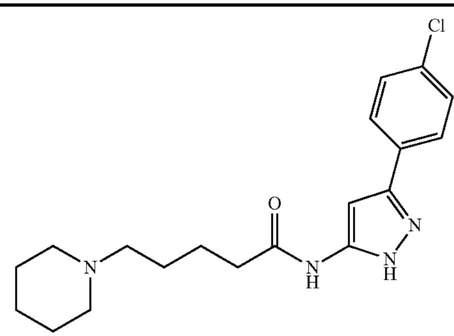 | | C19H25N4OCl | 360.88 | 361 | 100 | 1.88 | 10 | one-pot synthesis of ω-amino-alkanoic acid (1H-pyrazol-3-yl-5-aryl)-amides |
| 55 | 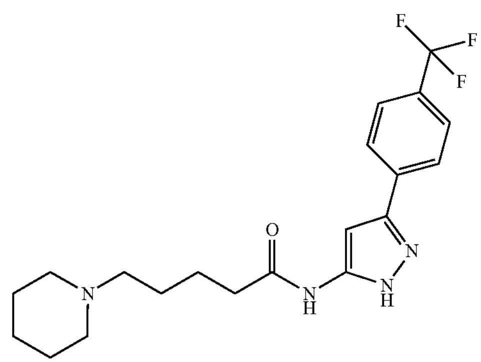 | | C20H25N4OF3 | 394.43 | 395 | 100 | 2.09 | 10 | Route A1/A2 for aminopyrazole; one-pot synthesis of ω-amino-alkanoic acid (1H-pyrazol-3-yl-5-aryl)-amides |
| 56 | 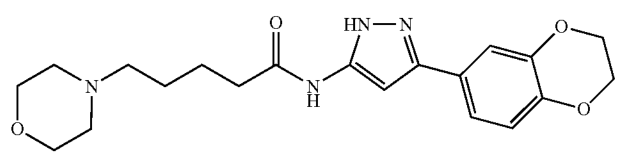 | | C20H26N4O4 | 386 | 387 | 100 | 0.24 and 1.40 | 10 | one-pot synthesis of ω-amino-alkanoic acid (1H-pyrazol-3-yl-5-aryl)-amides |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 57 | 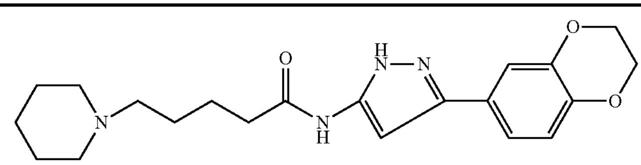 | HCOOH | C21H28N4O3 | 384 | 385 | 100 | 0.23 and 1.58 | 10 | one-pot synthesis of ω-amino-alkanoic acid (1H-pyrazol-3-yl-5-aryl)-amides |
| 58 | 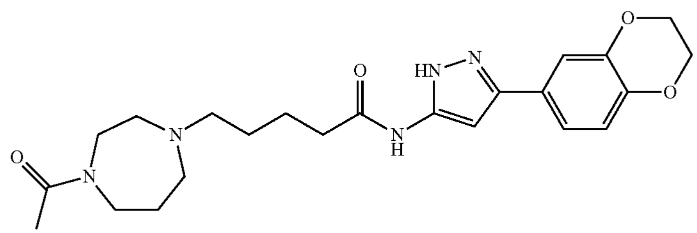 | HCOOH | C23H31N5O4 | 441 | 442 | 100 | 1.41 | 10 | one-pot synthesis of ω-amino-alkanoic acid (1H-pyrazol-3-yl-5-aryl)-amides |
| 59 | | | | C22H30N4O3 | 398 | 399 | 100 | 1.44 | 10 | one-pot synthesis of ω-amino-alkanoic acid (1H-pyrazol-3-yl-5-aryl)-amides |
| 60 | 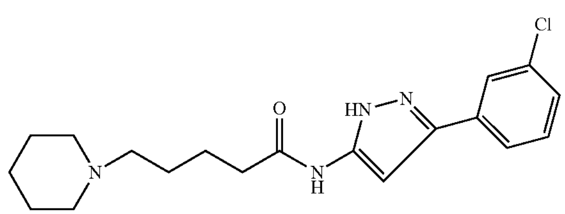 | | C19H25ClN4O | 360 | 361 | 98 | 1.81 | 10 | one-pot synthesis of ω-amino-alkanoic acid (1H-pyrazol-3-yl-5-aryl)-amides |
| 61 | 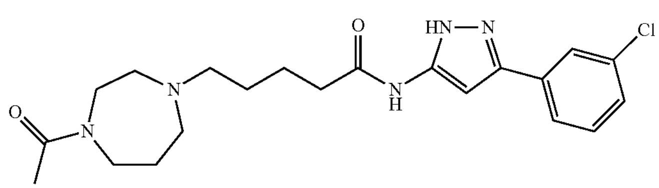 | HCOOH | C21H28ClN5O2 | 417 | 418 | 100 | 1.64 | 10 | one-pot synthesis of ω-amino-alkanoic acid (1H-pyrazol-3-yl-5-aryl)-amides |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 62 | 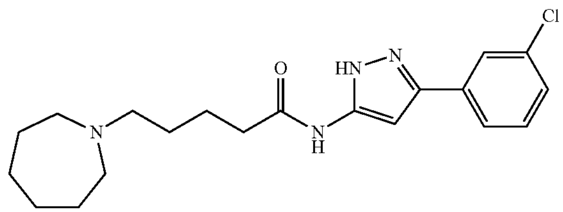 | HCOOH | C20H27ClN4O | 374 | 375 | 100 | 1.74 | 10 | one-pot synthesis of ω-amino-alkanoic acid (1H-pyrazol-3-yl-5-aryl)-amides |
| 63 | 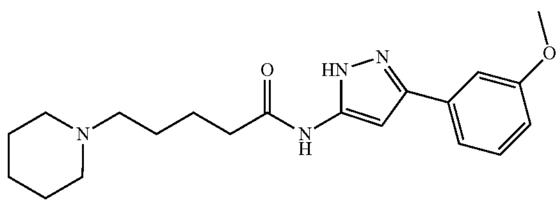 | | C20H28N4O2 | 356 | 357 | 95 | 1.63 | 10 | one-pot synthesis of ω-amino-alkanoic acid (1H-pyrazol-3-yl-5-aryl)-amides |
| 64 | 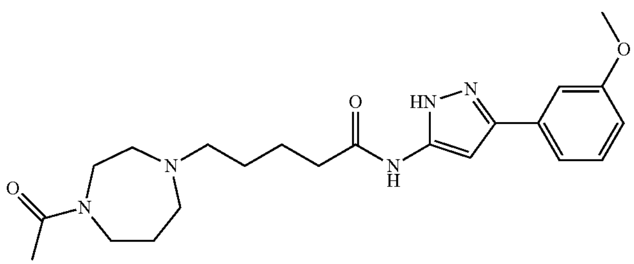 | HCOOH | C22H31N5O3 | 413 | 414 | 97 | 1.46 | 10 | one-pot synthesis of ω-amino-alkanoic acid (1H-pyrazol-3-yl-5-aryl)-amides |
| 65 | 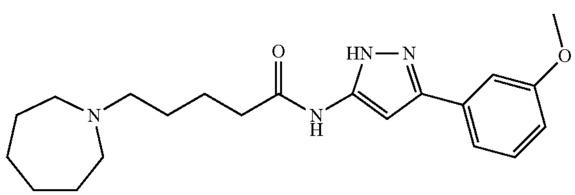 | | C21H30N4O2 | 370 | 371 | 99 | 1.78 | 10 | one-pot synthesis of ω-amino-alkanoic acid (1H-pyrazol-3-yl-5-aryl)-amides |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 66 | 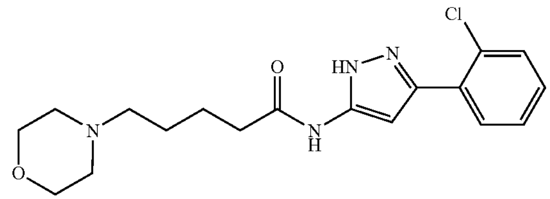 | HCOOH | C18H23ClN4O2 | 362 | 363 | 100 | 1.51 | 10 | one-pot synthesis of ω-amino-alkanoic acid (1H-pyrazol-3-yl-5-aryl)-amides |
| 67 | 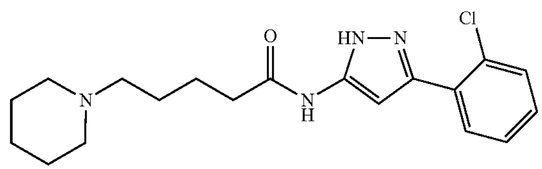 | | C19H25ClN4O | 360 | 361 | 99 | 1.64 | 10 | one-pot synthesis of ω-amino-alkanoic acid (1H-pyrazol-3-yl-5-aryl)-amides |
| 68 | 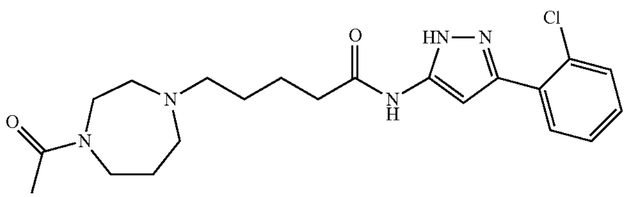 | HCOOH | C21H28ClN5O2 | 417 | 418 | 100 | 1.48 | 10 | one-pot synthesis of ω-amino-alkanoic acid (1H-pyrazol-3-yl-5-aryl)-amides |
| 69 | 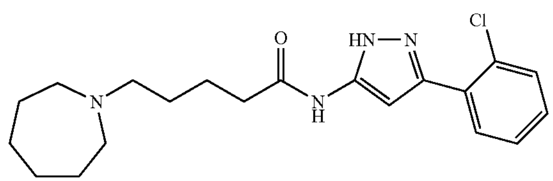 | | C20H27ClN4O | 374 | 375 | 97 | 1.78 | 10 | one-pot synthesis of ω-amino-alkanoic acid (1H-pyrazol-3-yl-5-aryl)-amides |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 70 | 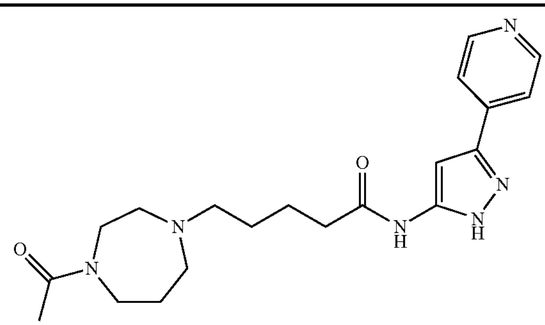 | | C20H28N6O2 | 384.47 | 385 | 100 | 0.19 | 10 | Route A1/A2 for aminopyrazole; one-pot synthesis of ω-amino-alkanoic acid (1H-pyrazol-3-yl-5-aryl)-amides |
| 71 | 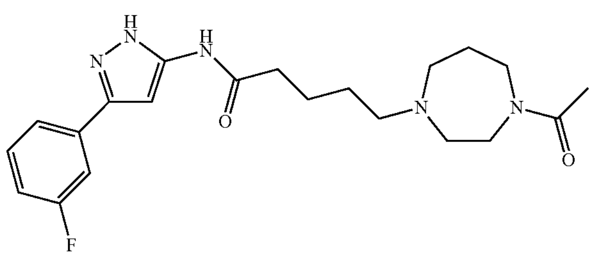 | HCOOH | C21H28N5O2F | 401.47 | 402 | 100 | 1.51 | 10 | one-pot synthesis of ω-amino-alkanoic acid (1H-pyrazol-3-yl-5-aryl)-amides |
| 72 | 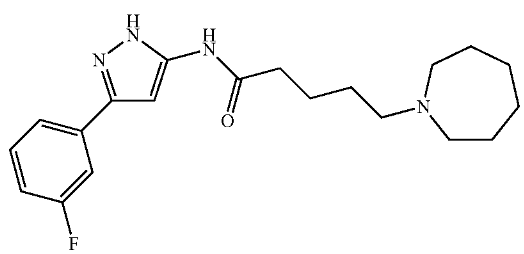 | HCOOH | C20H27N4OF | 358.45 | 359 | 100 | 1.81 | 10 | one-pot synthesis of ω-amino-alkanoic acid (1H-pyrazol-3-yl-5-aryl)-amides |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 73 | 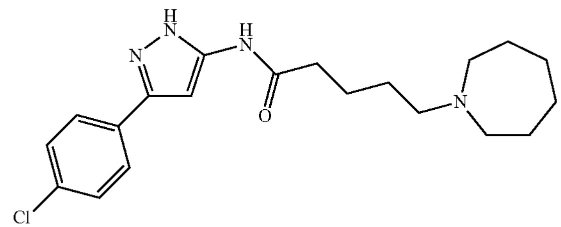 | HCOOH | C20H27N4OCl | 374.90 | 375 | 100 | 2.03 | 10 | one-pot synthesis of ω-amino-alkanoic acid (1H-pyrazol-3-yl-5-aryl)-amides |
| 74 | 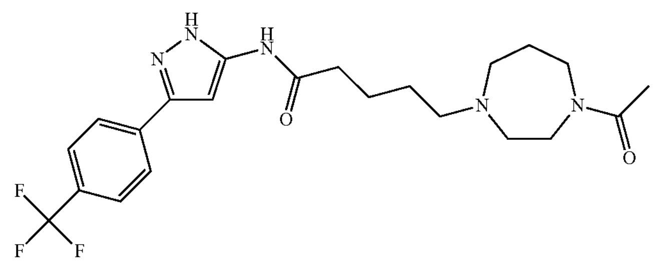 | HCOOH | C22H28N5O2F3 | 451.48 | 452 | 100 | 1.96 | 10 | Route A1/A2 for aminopyrazole; one-pot synthesis of ω-amino-alkanoic acid (1H-pyrazol-3-yl-5-aryl)-amides |
| 75 | 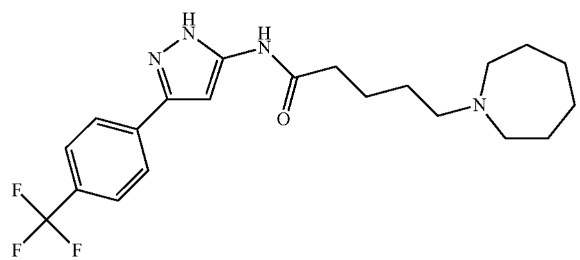 | HCOOH | C21H27N4OF3 | 408.46 | 409 | 100 | 2.21 | 10 | Route A1/A2 for aminopyrazole; one-pot synthesis of ω-amino-alkanoic acid (1H-pyrazol-3-yl-5-aryl)-amides |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 76 | 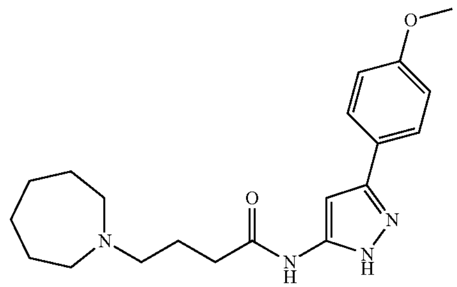 | HCOOH | C20H28N4O2 | 356.46 | 357 | 100 | 1.81 | 10 | one-pot synthesis of ω-amino-alkanoic acid (1H-pyrazol-3-yl-5-aryl)-amides |
| 77 | 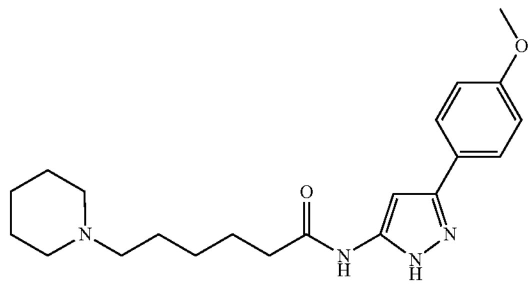 | HCOOH | C21H30N4O2 | 370.48 | 371 | 99 | 1.73 | 10 | one-pot synthesis of ω-amino-alkanoic acid (1H-pyrazol-3-yl-5-aryl)-amides |
| 78 | 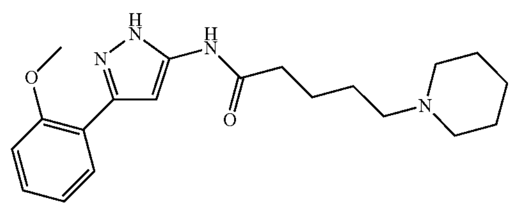 | HCOOH | C20H28N4O2 | 356.46 | 357 | 100 | 1.69 | 10 | Route A1/A2 for aminopyrazole; one-pot synthesis of ω-amino-alkanoic acid (1H-pyrazol-3-yl-5-aryl)-amides |
| 79 | 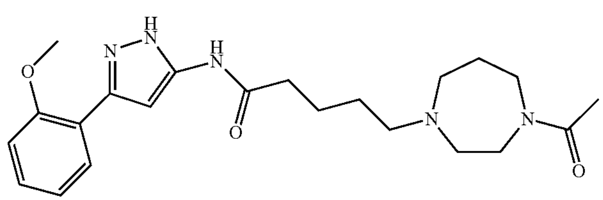 | | C22H31N5O3 | 413.51 | 414 | 100 | 1.58 | 10 | Route A1/A2 for aminopyrazole; one-pot synthesis of ω-amino-alkanoic acid (1H-pyrazol-3-yl-5-aryl)-amides |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 80 | 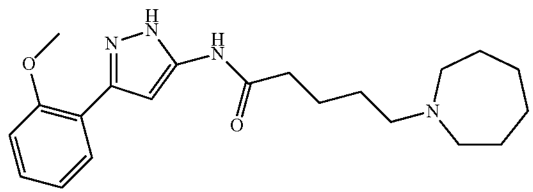 | HCOOH | C21H30N4O2 | 370.48 | 371 | 100 | 1.84 | 10 | Route A1/A2 for aminopyrazole; one-pot synthesis of ω-amino-alkanoic acid (1H-pyrazol-3-yl-5-aryl)-amides |
| 81 | 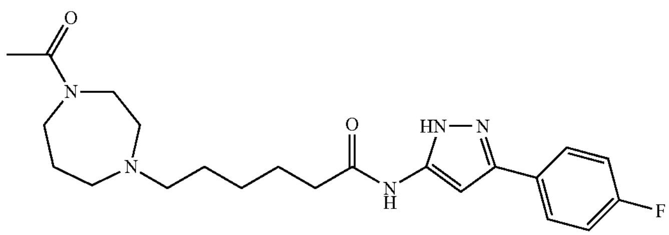 | | C22H30N5O2F | 415.50 | 416 | 100 | 1.58 | | one-pot synthesis of ω-amino-alkanoic acid (1H-pyrazol-3-yl-5-aryl)-amides |
| 82 | 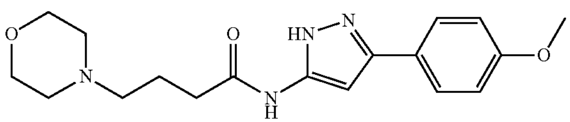 | | C18H24N4O3 | 344.40 | 345 | 97 | 1.38 | | one-pot synthesis of ω-amino-alkanoic acid (1H-pyrazol-3-yl-5-aryl)-amides |
| 83 | 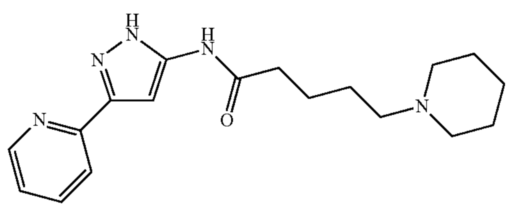 | | C18H25N5O | 327.42 | 318 | 90 | 0.23 | 10 | Route A1/A2 for aminopyrazole; one-pot synthesis of ω-amino-alkanoic acid (1H-pyrazol-3-yl-5-aryl)-amides |
| 84 | 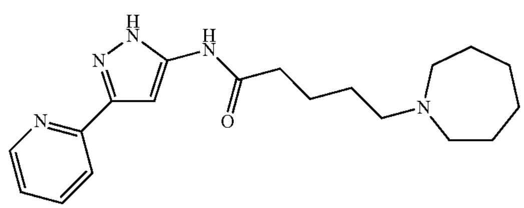 | | C19H27N5O | 341.45 | 342 | 100 | 0.23 | 10 | Route A1/A2 for aminopyrazole; one-pot synthesis of ω-amino-alkanoic acid (1H-pyrazol-3-yl-5-aryl)-amides |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 85 | 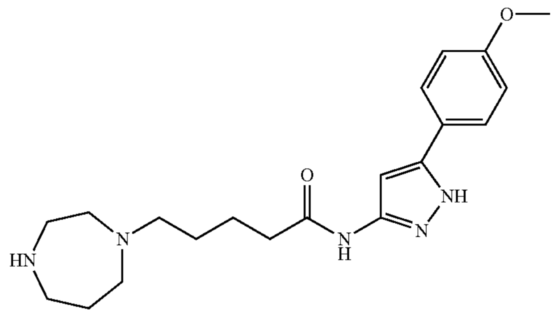 | | C20H29N5O2 | 371.49 | 372.3 | 97 | 0.68 | 10' | one-pot synthesis of ω-amino-alkanoic acid (1H-pyrazol-3-yl-5-aryl)-amides |
| 86 | 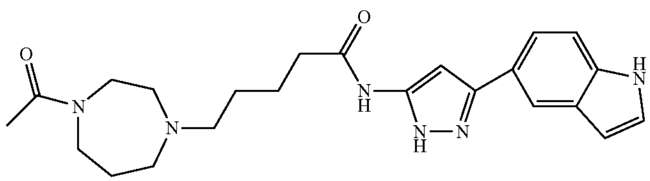 | HCOOH | C23H30N6O2 | 422 | 423 | 100 | 1.36 | 10 | one-pot synthesis of ω-amino-alkanoic acid (1H-pyrazol-3-yl-5-aryl)-amides |
| 87 | 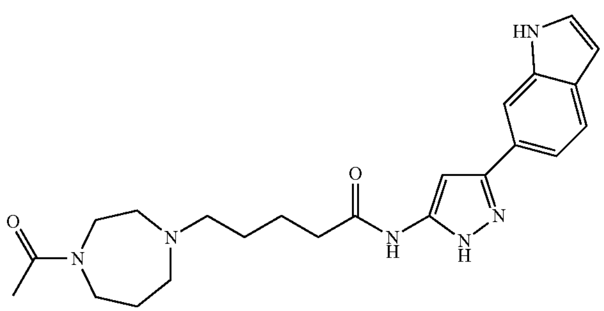 | HCOOH | C23H30N6O2 | 422 | 423 | 95 | 1.54 | 10 | one-pot synthesis of ω-amino-alkanoic acid (1H-pyrazol-3-yl-5-aryl)-amides |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 88 | 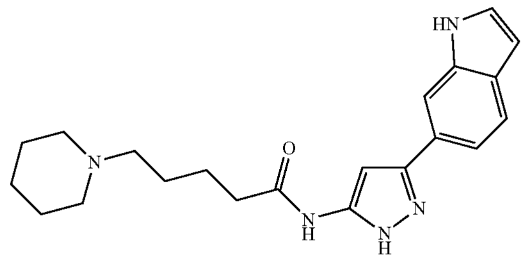 | HCOOH | C21H27N5O | 365 | 366 | 100 | 1.68 | 10 | one-pot synthesis of ω-amino-alkanoic acid (1H-pyrazol-3-yl-5-aryl)-amides |
| 89 | 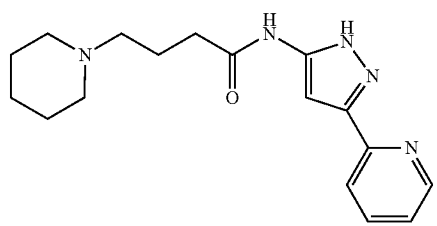 | | C17H23N5O | 313 | 314 | 100 | 0.53 | 10 | one-pot synthesis of ω-amino-alkanoic acid (1H-pyrazol-3-yl-5-aryl)-amides (room temperature) |
| 90 | 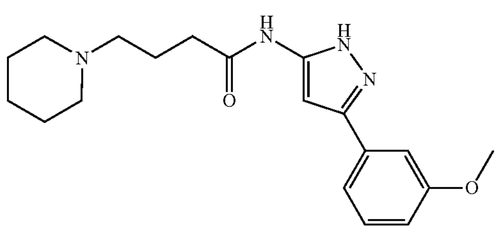 | | C19H26N4O2 | 342 | 343 | 100 | 1.59 | 10 | one-pot synthesis of ω-amino-alkanoic acid (1H-pyrazol-3-yl-5-aryl)-amides (room temperature) |
| 91 | 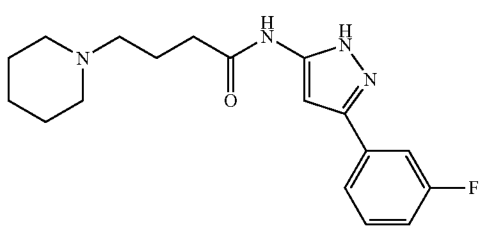 | HCOOH | C18H23FN4O | 330 | 331 | 100 | 1.56 | 10 | one-pot synthesis of ω-amino-alkanoic acid (1H-pyrazol-3-yl-5-aryl)-amides (room temperature) |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 92 | 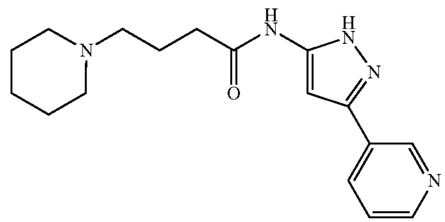 | | C17H23N5O | 313 | 314 | 100 | 0.22 and 0.32 | 10 | one-pot synthesis of ω-amino-alkanoic acid (1H-pyrazol-3-yl-5-aryl)-amides (room temperature) |
| 93 | 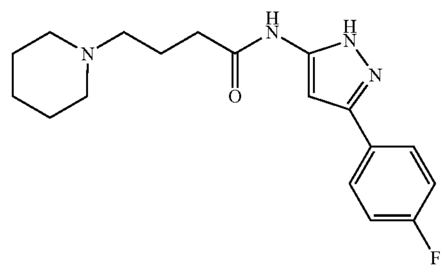 | | C18H23FN4O | 330 | 331 | 100 | 1.54 | 10 | one-pot synthesis of ω-amino-alkanoic acid (1H-pyrazol-3-yl-5-aryl)-amides (room temperature) |
| 94 | 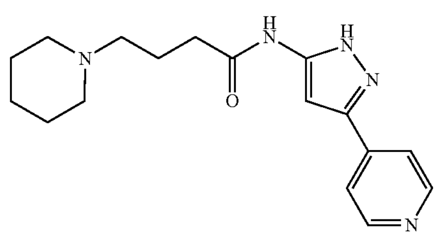 | | C17H23N5O | 313 | 314 | 100 | 0.22 | 10 | one-pot synthesis of ω-amino-alkanoic acid (1H-pyrazol-3-yl-5-aryl)-amides (room temperature) |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 95 | 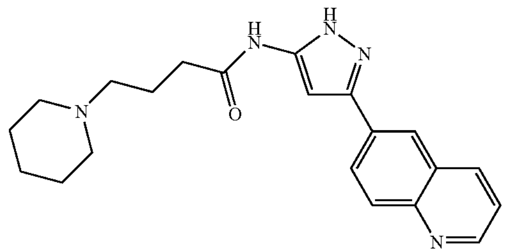 | | C21H25N5O | 363 | 364 | 100 | 1.33 | 10 | one-pot synthesis of ω-amino-alkanoic acid (1H-pyrazol-3-yl-5-aryl)-amides (room temperature) |
| 96 | 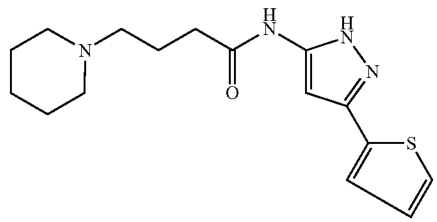 | | C16H22N4OS | 318 | 319 | 100 | 1.33 | 10 | one-pot synthesis of ω-amino-alkanoic acid (1H-pyrazol-3-yl-5-aryl)-amides (room temperature) |
| 97 | 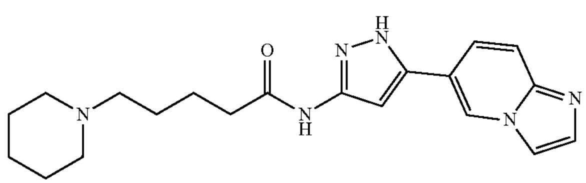 | | C20H26N6O | 366 | 367 | 95 | 0.27 | 10 | General two-step method (synthesis of ω-bromo-alkanoic acid (1H-pyrazol-3-yl-5-aryl)-amides followed by synthesis of ω-amino-alkanoic acid (1H-pyrazol-3-yl-5-aryl)-amides |
| 98 | 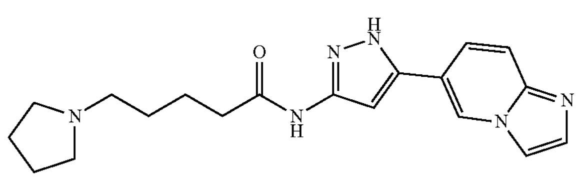 | | C19H24N6O | 352 | 353 | 95 | 0.25 | 10 | General two-step method (synthesis of ω-bromo-alkanoic acid (1H-pyrazol-3-yl-5-aryl)-amides followed by synthesis of ω-amino-alkanoic acid (1H-pyrazol-3-yl-5-aryl)-amides |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 99 | 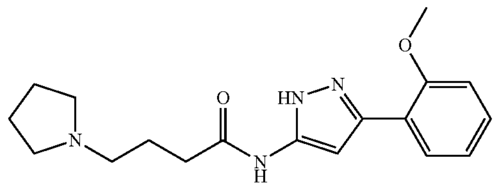 | HCOOH | C18H24N4O2 | 328.4 | 329 | 100 | 1.48 | 10 | General method for the synthesis of ω-amino-alkanoic acid (1H-pyrazol-3-yl-5-aryl)-amides via the amino acid route |
| 100 | 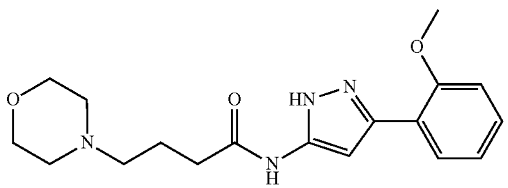 | HCOOH | C18H24N4O3 | 344.4 | 345 | 99 | 1.36 | 10 | General method for the synthesis of ω-amino-alkanoic acid (1H-pyrazol-3-yl-5-aryl)-amides via the amino acid route |
| 101 | 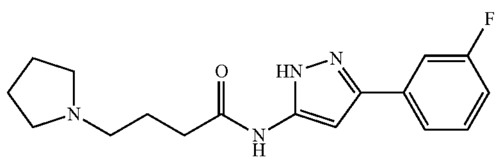 | HCOOH | C17H21N4OF | 316.4 | 317 | 100 | 1.43 | 10 | General method for the synthesis of ω-amino-alkanoic acid (1H-pyrazol-3-yl-5-aryl)-amides via the amino acid route |
| 102 | 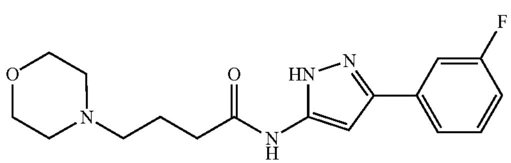 | HCOOH | C17H21N4O2F | 332.4 | 333 | 100 | 1.31 | 10 | General method for the synthesis of ω-amino-alkanoic acid (1H-pyrazol-3-yl-5-aryl)-amides via the amino acid route |
| 103 | 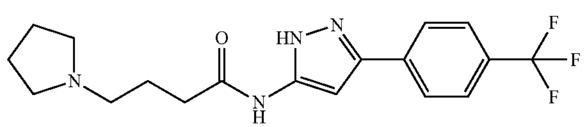 | HCOOH | C18H21N4OF3 | 366.4 | 367 | 100 | 1.89 | 10 | General method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 104 | 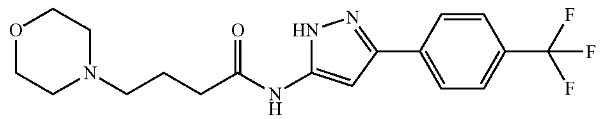 | HCOOH | C18H21N4O2F3 | 382.4 | 383 | 100 | 1.81 | 10 | General method for the synthesis of ω-amino-alkanoic acid (1H-pyrazol-3-yl-5-aryl)-amides via the amino acid route |
| 105 | 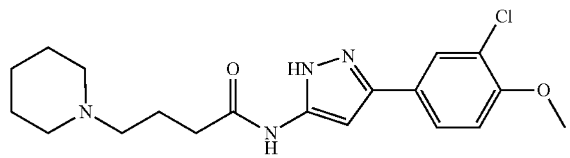 | HCOOH | C19H25N4O2Cl | 376.9 | 377 | 100 | 1.73 | 10 | General method for the synthesis of ω-amino-alkanoic acid (1H-pyrazol-3-yl-5-aryl)-amides via the amino acid route |
| 106 | 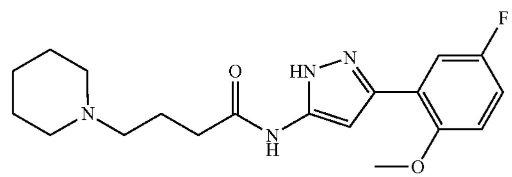 | HCOOH | C19H25N4O2F | 360.4 | 361 | 100 | 1.66 | 10 | General method for the synthesis of ω-amino-alkanoic acid (1H-pyrazol-3-yl-5-aryl)-amides via the amino acid route |
| 107 | 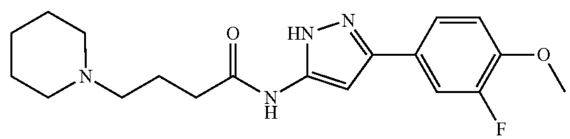 | HCOOH | C19H25N4O2F | 360.4 | 361 | 100 | 1.56 | 10 | General method for the synthesis of ω-amino-alkanoic acid (1H-pyrazol-3-yl-5-aryl)-amides via the amino acid route |
| 108 | 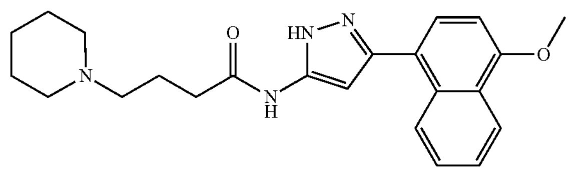 | HCOOH | C23H28N4O2 | 392.5 | 393 | 100 | 2.06 | 10 | General method for the synthesis of ω-amino-alkanoic acid (1H-pyrazol-3-yl-5-aryl)-amides via the amino acid route |
| 109 | 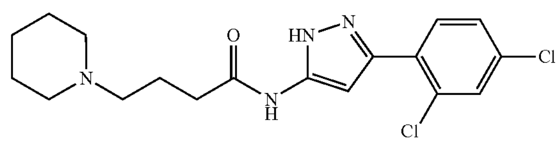 | HCOOH | C18H22N4OCl2 | 381.3 | 382 | 100 | 1.96 | 10 | General method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 110 | 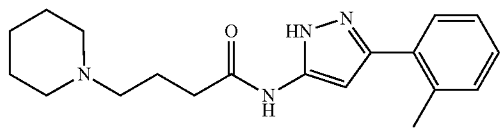 | HCOOH | C29H26N4O | 326.4 | 327 | 100 | 1.6 | 10 | General method for the synthesis of ω-amino-alkanoic acid (1H-pyrazol-3-yl-5-aryl)-amides via the amino acid route |
| 111 | 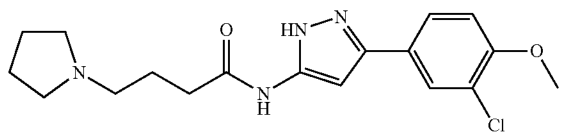 | HCOOH | C18H23N4O2Cl | 362.9 | 363 | 100 | 1.71 | 10 | General method for the synthesis of ω-amino-alkanoic acid (1H-pyrazol-3-yl-5-aryl)-amides via the amino acid route |
| 112 | 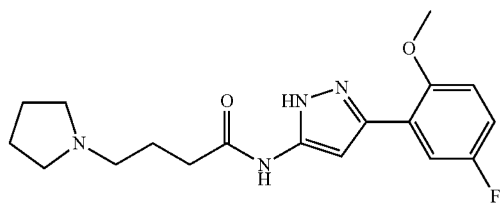 | HCOOH | C18H23N4O2F | 346.4 | 347 | 100 | 1.58 | 10 | General method for the synthesis of ω-amino-alkanoic acid (1H-pyrazol-3-yl-5-aryl)-amides via the amino acid route |
| 113 | 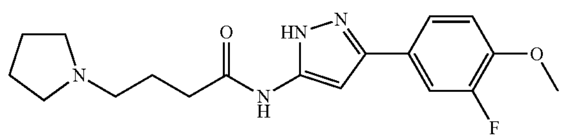 | HCOOH | C18H23N4O2F | 346.4 | 347 | 100 | 1.49 | 10 | General method for the synthesis of ω-amino-alkanoic acid (1H-pyrazol-3-yl-5-aryl)-amides via the amino acid route |
| 114 | 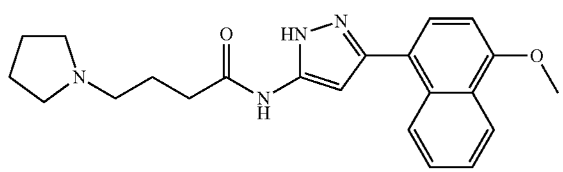 | HCOOH | C22H26N4O2 | 378.5 | 379 | 100 | 1.96 | 10 | General method for the synthesis of ω-amino-alkanoic acid (1H-pyrazol-3-yl-5-aryl)-amides via the amino acid route |
| 115 | 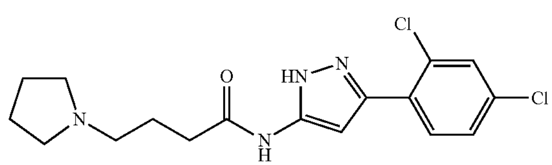 | HCOOH | C17H20N4OCl2 | 367.3 | 367 | 100 | 1.89 | 10 | General method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 116 | 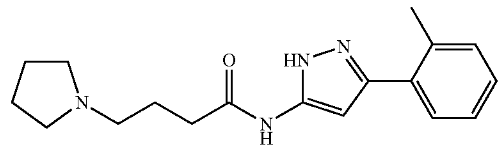 | HCOOH | C18H24N4O | 312.4 | 313 | 100 | 1.49 | 10 | General method for the synthesis of ω-amino-alkanoic acid (1H-pyrazol-3-yl-5-aryl)-amides via the amino acid route |
| 117 | 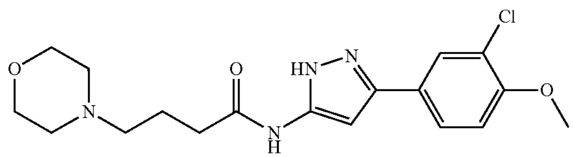 | HCOOH | C18H23N4O3Cl | 378.9 | 379 | 100 | 1.58 | 10 | General method for the synthesis of ω-amino-alkanoic acid (1H-pyrazol-3-yl-5-aryl)-amides via the amino acid route |
| 118 | 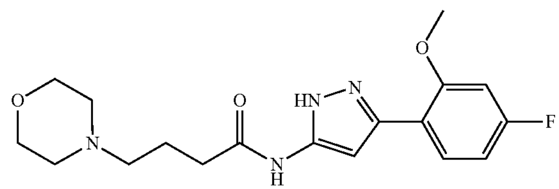 | HCOOH | C18H23N4O3F | 362.4 | 363 | 100 | 1.48 | 10 | General method for the synthesis of ω-amino-alkanoic acid (1H-pyrazol-3-yl-5-aryl)-amides via the amino acid route |
| 119 | 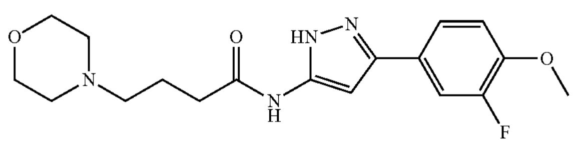 | HCOOH | C18H23N4O3F | 362.4 | 363 | 100 | 1.39 | 10 | General method for the synthesis of ω-amino-alkanoic acid (1H-pyrazol-3-yl-5-aryl)-amides via the amino acid route |
| 120 | 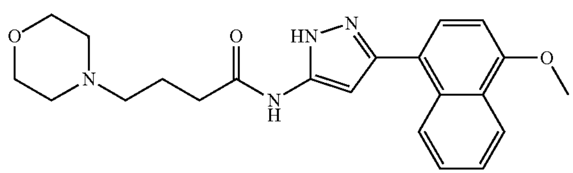 | HCOOH | C22H26N4O3 | 394.5 | 395 | 100 | 1.86 | 10 | General method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 121 | 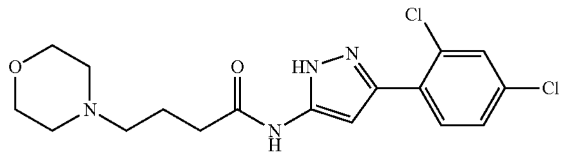 | HCOOH | C17H20N4O2Cl2 | 383.3 | 383 | 100 | 1.78 | 10 | General method for the synthesis of ω-amino-alkanoic acid (1H-pyrazol-3-yl-5-aryl)-amides via the amino acid route |
| 122 | 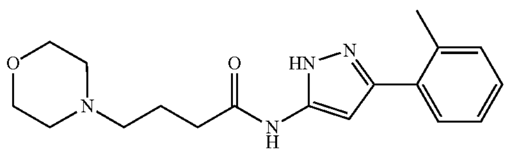 | HCOOH | C18H24N4O2 | 328.4 | 329 | 99 | 1.39 | 10 | General method for the synthesis of ω-amino-alkanoic acid (1H-pyrazol-3-yl-5-aryl)-amides via the amino acid route |
| 123 | 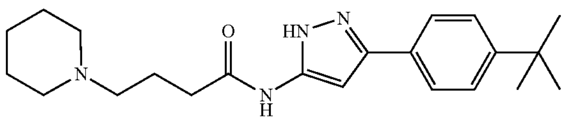 | HCOOH | | 368 | 369 | 100 | 2.33 | 10 | General method for the synthesis of ω-amino-alkanoic acid (1H-pyrazol-3-yl-5-aryl)-amides via the amino acid route |
| 124 | 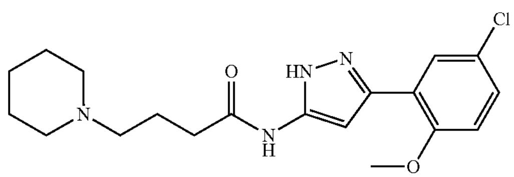 | HCOOH | | 376 | 377 | 100 | 1.89 | 10 | General method for the synthesis of ω-amino-alkanoic acid (1H-pyrazol-3-yl-5-aryl)-amides via the amino acid route |
| 125 | 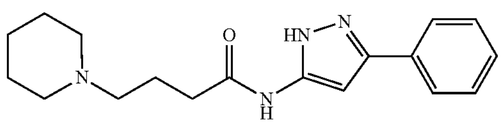 | HCOOH | | 312 | 313 | 95 | 1.48 | 10 | General method for the synthesis of ω-amino-alkanoic acid (1H-pyrazol-3-yl-5-aryl)-amides via the amino acid route |
| 126 | 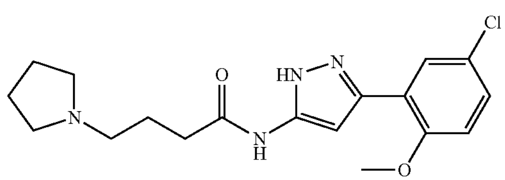 | HCOOH | | 362 | 363 | 100 | 1.83 | 10 | General method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 127 | 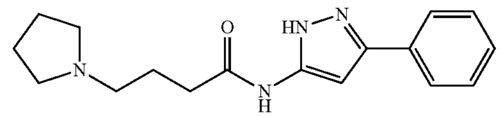 | HCOOH | | 298 | 299 | | 1.34 | 10 | General method for the synthesis of ω-amino-alkanoic acid (1H-pyrazol-3-yl-5-aryl)-amides via the amino acid route |
| 128 | 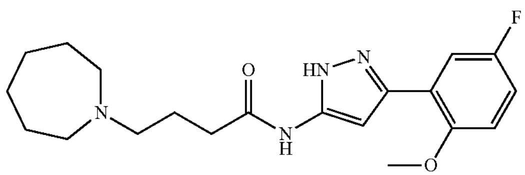 | HCOOH | C20H27N4O2F | 374.45 | 375.45 | 99 | 1.81 | 10 | General method for the synthesis of ω-amino-alkanoic acid (1H-pyrazol-3-yl-5-aryl)-amides via the amino acid route |
| 129 | 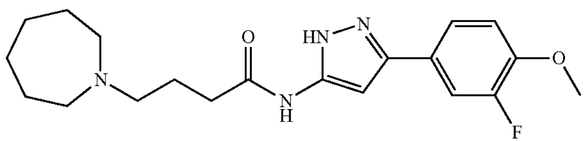 | HCOOH | C20H27N4O2F | 374.45 | 375.45 | 97 | 1.73 | 10 | General method for the synthesis of ω-amino-alkanoic acid (1H-pyrazol-3-yl-5-aryl)-amides via the amino acid route |
| 130 | 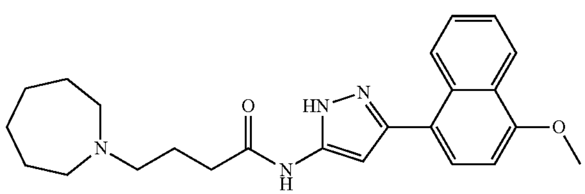 | HCOOH | C24H30N4O2 | 406.52 | 407.52 | 98 | 2.13 | 10 | General method for the synthesis of ω-amino-alkanoic acid (1H-pyrazol-3-yl-5-aryl)-amides via the amino acid route |
| 131 | 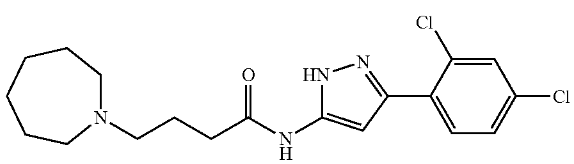 | HCOOH | C19H24N4OCl2 | 395.33 | 396.33 | 99 | 2.06 | 10 | General method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 132 | 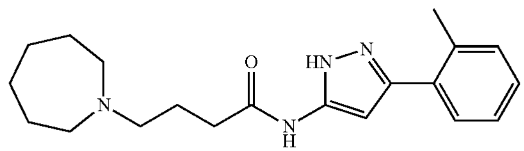 | HCOOH | C20H28N4O | 340.46 | 341.46 | 96 | 1.73 | 10 | General method for the synthesis of ω-amino-alkanoic acid (1H-pyrazol-3-yl-5-aryl)-amides via the amino acid route |
| 133 | 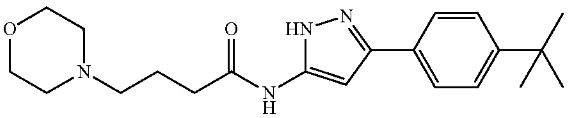 | N | C21H30N4O2 | 370.49 | 371.49 | 99 | 2.18 | 10 | General method for the synthesis of ω-amino-alkanoic acid (1H-pyrazol-3-yl-5-aryl)-amides via the amino acid route |
| 134 | 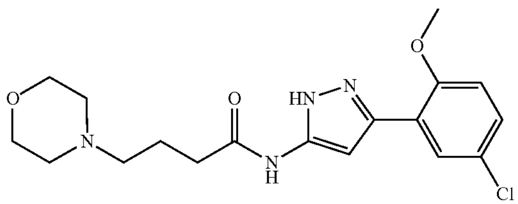 | HCOOH | C18H23N4O3Cl | 378.85 | 379.85 | 99 | 1.71 | 10 | General method for the synthesis of ω-amino-alkanoic acid (1H-pyrazol-3-yl-5-aryl)-amides via the amino acid route |
| 135 | 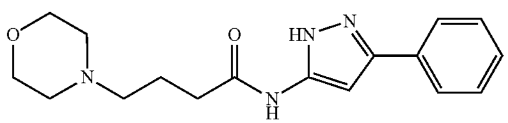 | HCOOH | C17H22N4O2 | 314.38 | 315.38 | 99 | Double peak 0.24 1.28 | 10 | General method for the synthesis of ω-amino-alkanoic acid (1H-pyrazol-3-yl-5-aryl)-amides via the amino acid route |
| 136 | 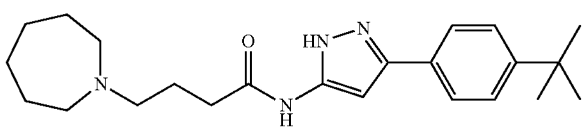 | HCOOH | C23H34N4O | 382.54 | 383.54 | 99 | 2.45 | 10 | General method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 137 | 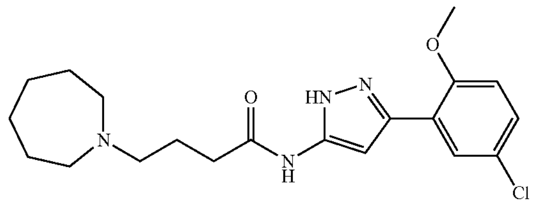 | HCOOH | C20H27N4O2Cl | 390.91 | 391.91 | 99 | 2.08 | 10 | General method for the synthesis of ω-amino-alkanoic acid (1H-pyrazol-3-yl-5-aryl)-amides via the amino acid route |
| 138 | 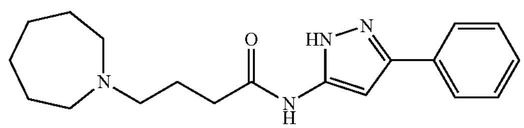 | HCOOH | C19H26N4O | 326.44 | 327.44 | 99 | 1.69 | 10 | General method for the synthesis of ω-amino-alkanoic acid (1H-pyrazol-3-yl-5-aryl)-amides via the amino acid route |
| 139 | 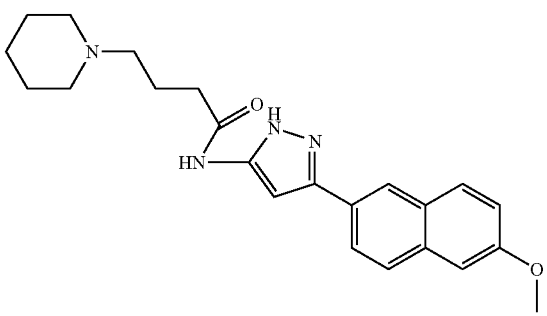 | HCOOH | C23H28N4O2 | 392.49 | 393, 197 | 100 | 2.04 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 140 | 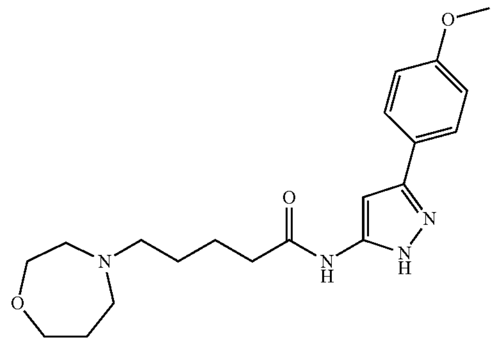 | HCOOH | C20H28N4O3 | 372.46 | 373, 187 | 100 | 1.48 | 10 | Route A1/A2 for aminopyrazole; general method for the synthesis of ω-amino-alkanoic acid (1H-pyrazol-3-yl-5-aryl)-amides via the amino acid route |
| 141 | 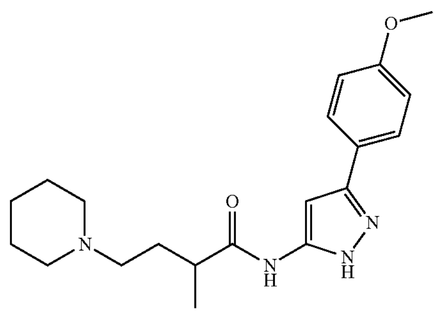 | | C20H28N4O2 | 356.46 | 357, 179 | 100 | 1.66 | 10 | Route A1/A2 for aminopyrazole; general method for the synthesis of ω-amino-alkanoic acid (1H-pyrazol-3-yl-5-aryl)-amides via the amino acid route |
| 142 | 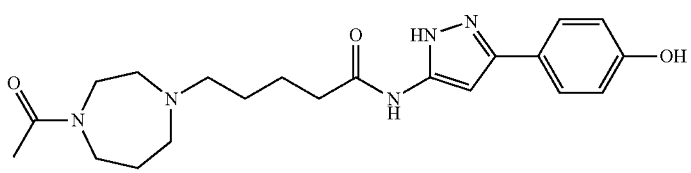 | | C21H29N5O3 | 399.49 | 400 | 98 | 1.01 | 10 | Route A1/A2 for 5-[6-(tetrahydro-pyran-2-yloxy)-pyridin-3-yl]-2H-pyrazol-3-ylamine; general method for the synthesis of ω-amino-alkanoic acid (1H-pyrazol-3-yl-5-aryl)-amides via the amino acid route; THP deprotection occurred during compound purification |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 143 | 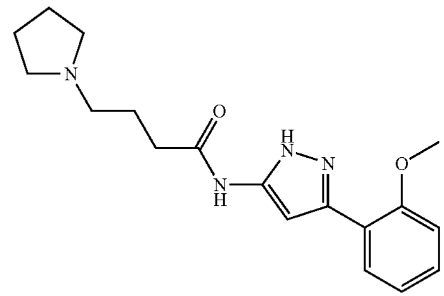 | HCOOH | C18H24N4O2 | 328.41 | 329, 258, 165 | 100 | 1.48 | 10 | Route A1/A2 for aminopyrazole; general method for the synthesis of ω-amino-alkanoic acid (1H-pyrazol-3-yl-5-aryl)-amides via the amino acid route |
| 144 | 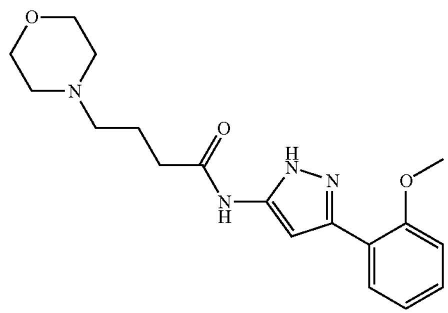 | HCOOH | C18H24N4O3 | 344.41 | 345, 173, 258 | 99 | 1.36 | 10 | Route A1/A2 for aminopyrazole; general method for the synthesis of ω-amino-alkanoic acid (1H-pyrazol-3-yl-5-aryl)-amides via the amino acid route |
| 145 | 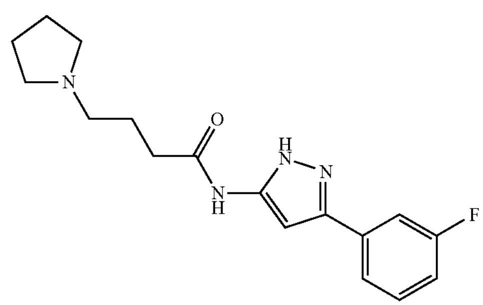 | HCOOH | C17H21N4OF | 316.37 | 317, 246, 159 | 100 | 1.43 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 146 | 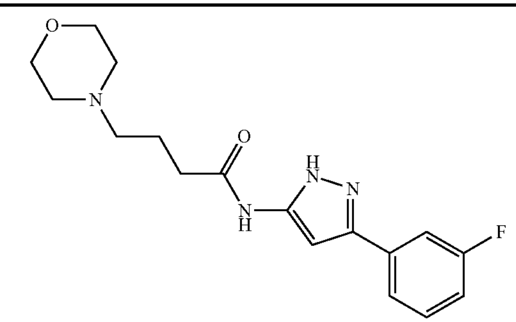 | HCOOH | C17H21N4O2F | 332.37 | 333, 246, 167 | 100 | 1.31 | 10 | Route A1/A2 for aminopyrazole; general method for the synthesis of ω-amino-alkanoic acid (1H-pyrazol-3-yl-5-aryl)-amides via the amino acid route |
| 147 | 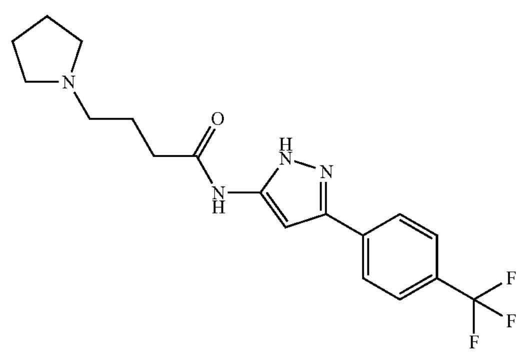 | HCl | C18H21N4OF3 | 366.38 | 367 | 100 | 1.89 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 148 | 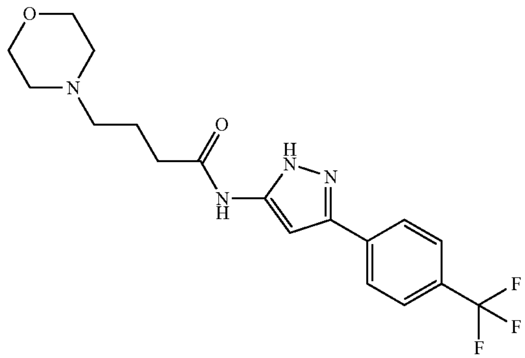 | HCOOH | C18H21N4O2F3 | 382.38 | 383, 296, 192 | 100 | 1.83 | 10 | Route A1/A2 for aminopyrazole; general method for the synthesis of o-amino-alkanoic acid (1H-pyrazol-3-yl-5-aryl)-amides via the amino acid route |
| 149 | 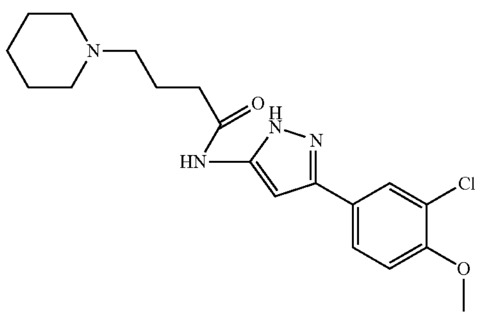 | HCOOH | C19H25N4O2Cl | 376.88 | 377, 292, 189 | 100 | 1.73 | 10 | Route A1/A2 for aminopyrazole; general method for the synthesis of o-amino-alkanoic acid (1H-pyrazol-3-yl-5-aryl)-amides via the amino acid route |
| 150 | 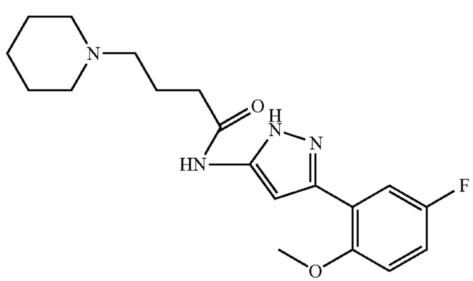 | HCOOH | C19H25N4O2F | 360.43 | 361, 181 | 100 | 1.66 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 151 | 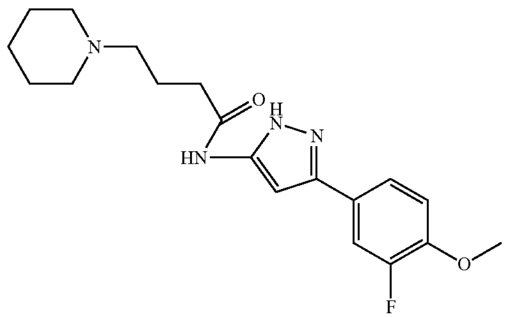 | HCOOH | C19H25N4O2F | 360.43 | 361, 276, 181 | 100 | 1.56 | 10 | Route A1/A2 for aminopyrazole; general method for the synthesis of ω-amino-alkanoic acid (1H-pyrazol-3-yl-5-aryl)-amides via the amino acid route |
| 152 | 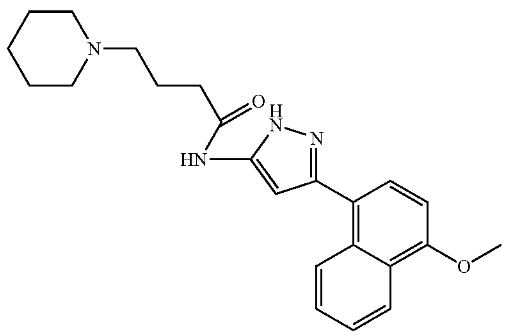 | HCOOH | C23H28N4O2 | 392.49 | 393, 308, 197 | 100 | 2.06 | 10 | Route A1/A2 for aminopyrazole; general method for the synthesis of ω-amino-alkanoic acid (1H-pyrazol-3-yl-5-aryl)-amides via the amino acid route |
| 153 | 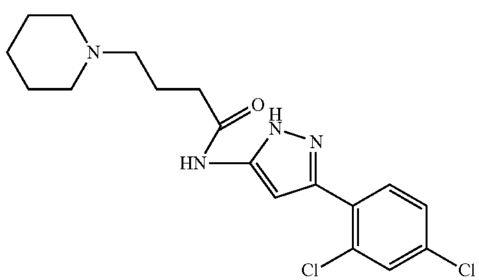 | HCOOH | C18H22N4OCl2 | 381.30 | 381, 191 | 100 | 1.96 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 154 | 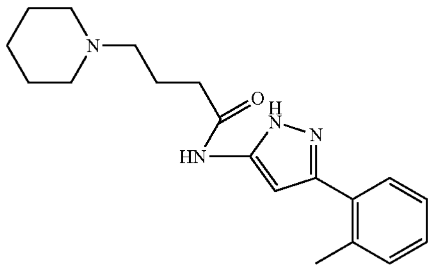 | HCOOH | C19H26N4O | 326.44 | 327, 242, 164 | 100 | 1.59 | 10 | Route A1/A2 for aminopyrazole; general method for the synthesis of ω-amino-alkanoic acid (1H-pyrazol-3-yl-5-aryl)-amides via the amino acid route |
| 155 | 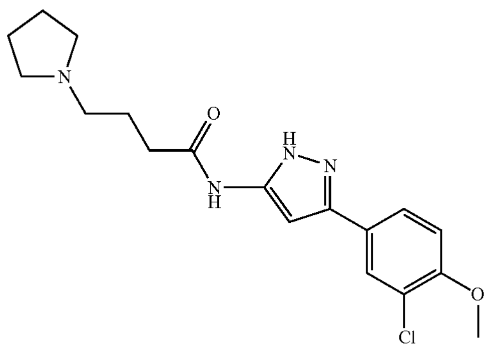 | HCOOH | C18H23N4O2Cl | 362.85 | 363, 292, 182 | 100 | 1.71 | 10 | Route A1/A2 for aminopyrazole; general method for the synthesis of ω-amino-alkanoic acid (1H-pyrazol-3-yl-5-aryl)-amides via the amino acid route |
| 156 | 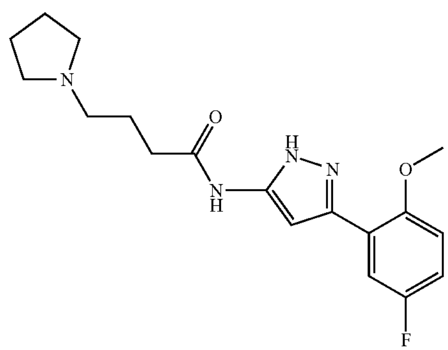 | HCOOH | C18H23N4O2F | 346.40 | 347, 276, 174 | 100 | 1.58 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 157 | 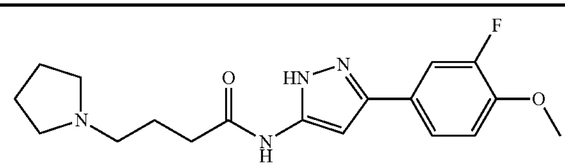 | | C18H23N4O2F | 346.40 | 347, 174 | 100 | 1.54 | 10 | Route A1/A2 for aminopyrazole; general method for the synthesis of ω-amino-alkanoic acid (1H-pyrazol-3-yl-5-aryl)-amides via the amino acid route |
| 158 | 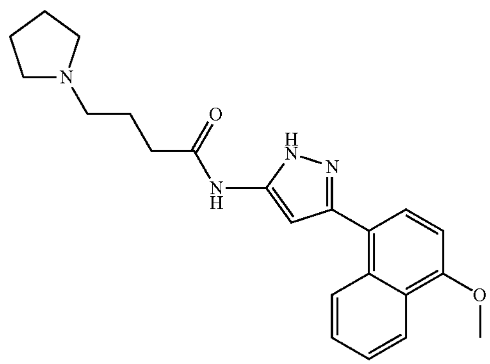 | HCOOH | C22H26N4O2 | 378.47 | 379, 308, 190 | 100 | 1.94 | 10 | Route A1/A2 for aminopyrazole; general method for the synthesis of ω-amino-alkanoic acid (1H-pyrazol-3-yl-5-aryl)-amides via the amino acid route |
| 159 | 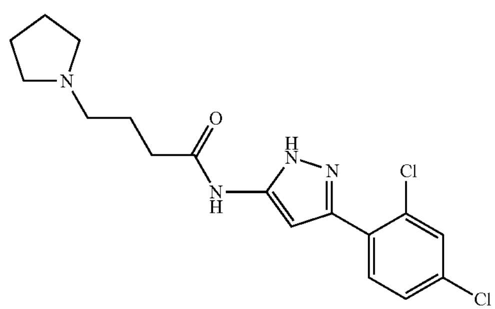 | HCOOH | C17H20N4OCl2 | 367.27 | 367, 296, 184 | 100 | 1.89 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 160 | 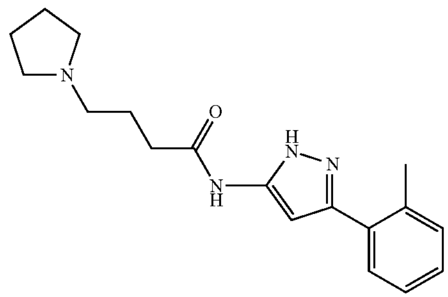 | HCOOH | C18H24N4O | 312.41 | 313, 157 | 99 | 2.38 | 10 | Route A1/A2 for aminopyrazole; general method for the synthesis of o-amino-alkanoic acid (1H-pyrazol-3-yl-5-aryl)-amides via the amino acid route |
| 161 | 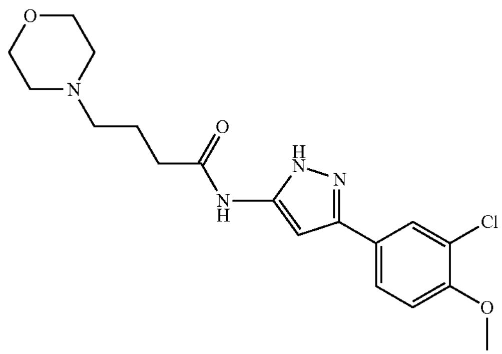 | HCOOH | C18H23N4O3Cl | 378.85 | 379, 291, 190 | 100 | 1.58 | 10 | Route A1/A2 for aminopyrazole; general method for the synthesis of o-amino-alkanoic acid (1H-pyrazol-3-yl-5-aryl)-amides via the amino acid route |
| 162 | 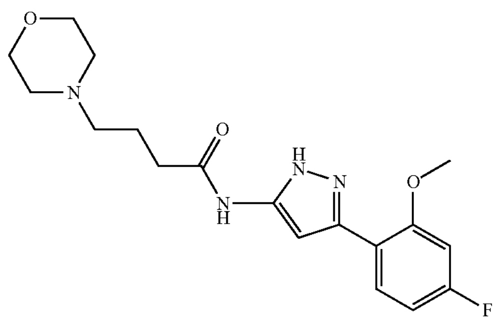 | HCOOH | C18H23N4O3F | 362.40 | 363, 276, 182 | 100 | 1.48 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 163 | 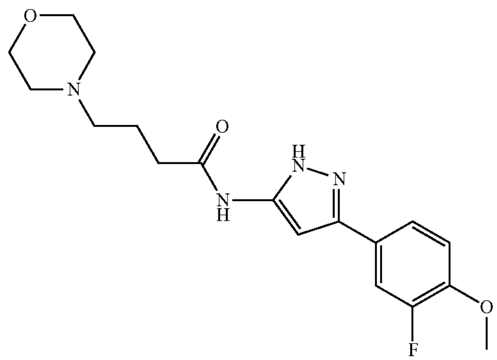 | | C18H23N4O3F | 362.40 | 363, 276, 182 | 100 | 1.39 | 10 | Route A1/A2 for aminopyrazole; general method for the synthesis of ω-amino-alkanoic acid (1H-pyrazol-3-yl-5-aryl)-amides via the amino acid route |
| 164 | 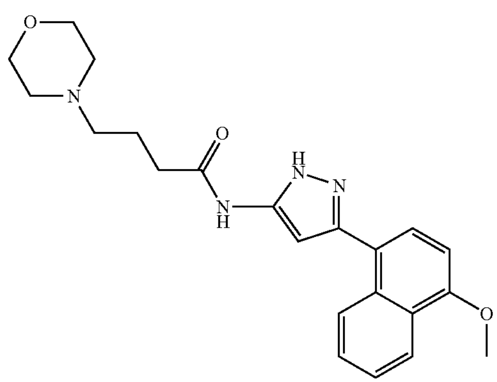 | HCOOH | C22H26N4O3 | 394.47 | 395, 308, 198 | 100 | 1.86 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 165 | 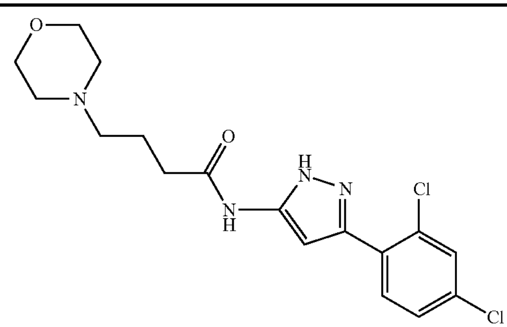 | HCOOH | C17H20N4O2Cl2 | 383.27 | 383, 192 | 100 | 1.78 | 10 | Route A1/A2 for aminopyrazole; general method for the synthesis of ω-amino-alkanoic acid (1H-pyrazol-3-yl-5-aryl)-amides via the amino acid route |
| 166 | 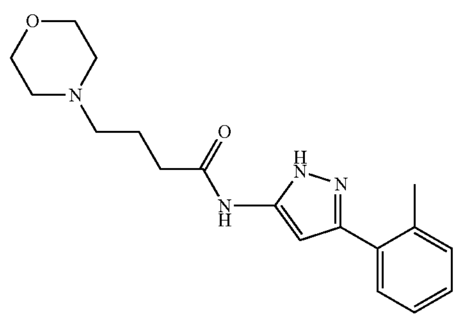 | HCOOH | C18H24N4O2 | 328.41 | 329 | 98 | 1.38 | 10 | Route A1/A2 for aminopyrazole; general method for the synthesis of ω-amino-alkanoic acid (1H-pyrazol-3-yl-5-aryl)-amides via the amino acid route |
| 167 | 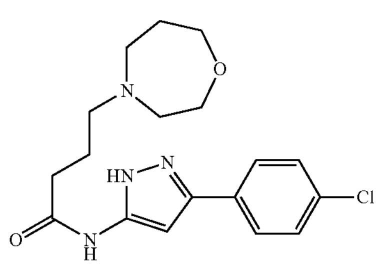 | HCOOH | C18H23N4O2Cl | 362.85 | 363, 182 | 100 | 1.66 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 168 | 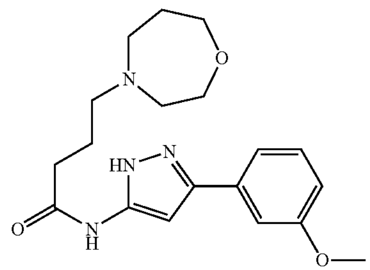 | HCOOH | C19H26N4O3 | 358.43 | 359, 258 | 100 | 1.43 | 10 | Route A1/A2 for aminopyrazole; general method for the synthesis of ω-amino-alkanoic acid (1H-pyrazol-3-yl-5-aryl)-amides via the amino acid route |
| 169 | 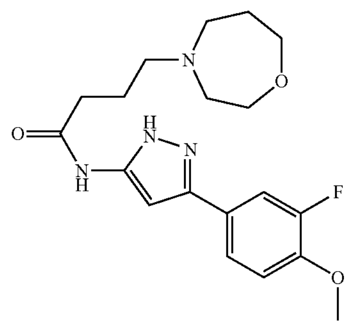 | HCOOH | C19H25N4O3F | 376.43 | 377, 276 | 100 | 1.41 | 10 | Route A1/A2 for aminopyrazole; general method for the synthesis of ω-amino-alkanoic acid (1H-pyrazol-3-yl-5-aryl)-amides via the amino acid route |
| 170 | 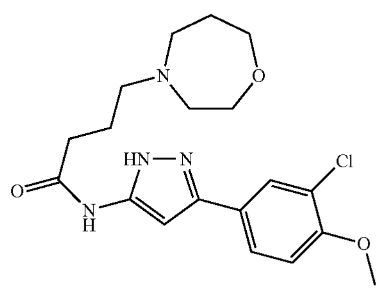 | HCOOH | C19H25N4O3Cl | 392.88 | 393, 292 | 100 | 1.64 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 171 | 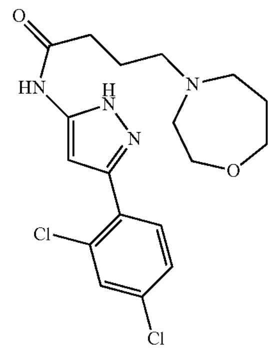 | HCOOH | C18H22N4O2Cl2 | 397.30 | 397 | 100 | 1.83 | 10 | Route A1/A2 for aminopyrazole; general method for the synthesis of ω-amino-alkanoic acid (1H-pyrazol-3-yl-5-aryl)-amides via the amino acid route |
| 172 | 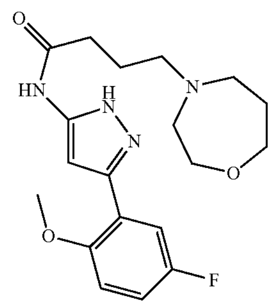 | HCOOH | C19H25N4O3F | 376.43 | 377, 276 | 100 | 1.58 | 10 | Route A1/A2 for aminopyrazole; general method for the synthesis of ω-amino-alkanoic acid (1H-pyrazol-3-yl-5-aryl)-amides via the amino acid route |
| 173 | 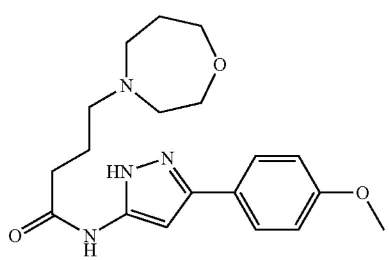 | | C19H26N4O3 | 358.43 | 359, 258 | 100 | 1.43 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 174 | 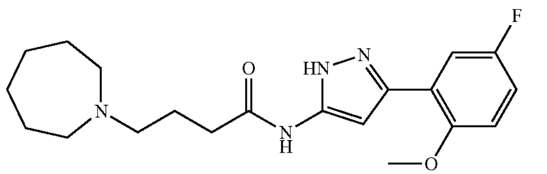 | HCOOH | C20H27N4O2F | 374.45 | 375, 188 | 98 | 1.81 | 10 | Route A1/A2 for aminopyrazole; general method for the synthesis of o-amino-alkanoic acid (1H-pyrazol-3-yl-5-aryl)-amides via the amino acid route |
| 175 | 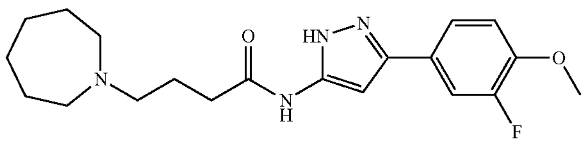 | HCOOH | C20H27N4O2F | 374.45 | 375, 188 | 97 | 1.73 | 10 | Route A1/A2 for aminopyrazole; general method for the synthesis of o-amino-alkanoic acid (1H-pyrazol-3-yl-5-aryl)-amides via the amino acid route |
| 176 | 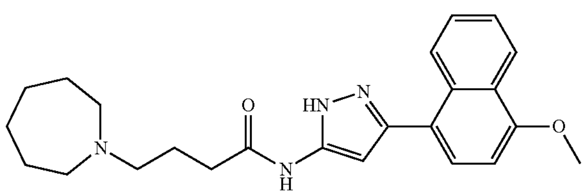 | HCOOH | C24H30N4O2 | 406.52 | 407, 204 | 98 | 2.13 | 10 | Route A1/A2 for aminopyrazole; general method for the synthesis of o-amino-alkanoic acid (1H-pyrazol-3-yl-5-aryl)-amides via the amino acid route |
| 177 | 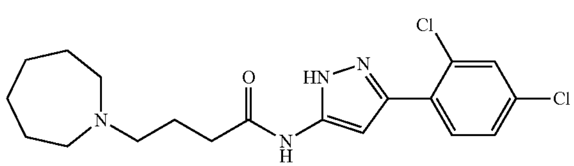 | HCOOH | C19H24N4OCl2 | 395.33 | 395 | 100 | 2.06 | 10 | Route A1/A2 for aminopyrazole; general method for the synthesis of o-amino-alkanoic acid (1H-pyrazol-3-yl-5-aryl)-amides via the amino acid route |
| 178 | 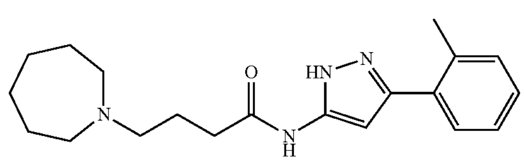 | HCOOH | C20H28N4O | 340.46 | 341 | 96 | 1.74 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 179 | 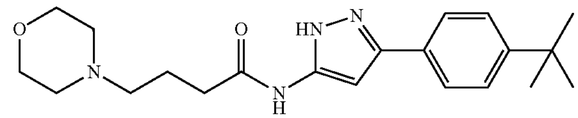 | | C21H30N4O2 | 370.49 | 371 | 98 | 2.18 | 10 | Route A1/A2 for aminopyrazole; general method for the synthesis of ω-amino-alkanoic acid (1H-pyrazol-3-yl-5-aryl)-amides via the amino acid route |
| 180 | 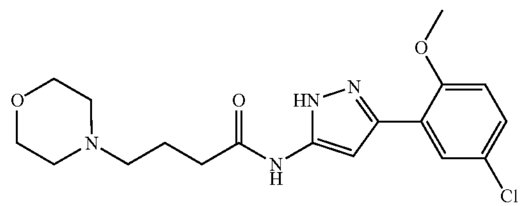 | HCOOH | C18H23N4O3Cl | 378.85 | 379 | 100 | 1.71 | 10 | Route A1/A2 for aminopyrazole; general method for the synthesis of ω-amino-alkanoic acid (1H-pyrazol-3-yl-5-aryl)-amides via the amino acid route |
| 181 | 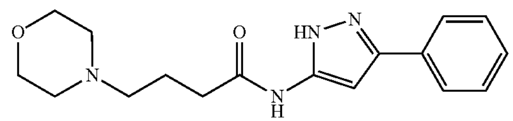 | HCOOH | C17H22N4O2 | 314.38 | 315, 158 | 100 | 1.26 | 10 | Route A1/A2 for aminopyrazole; general method for the synthesis of ω-amino-alkanoic acid (1H-pyrazol-3-yl-5-aryl)-amides via the amino acid route |
| 182 | 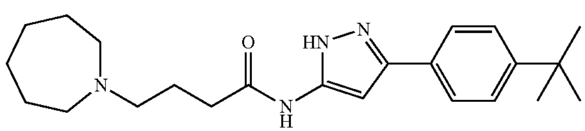 | HCOOH | C23H34N4O | 382.54 | 383 | 100 | 2.43 | 10 | Route A1/A2 for aminopyrazole; general method for the synthesis of ω-amino-alkanoic acid (1H-pyrazol-3-yl-5-aryl)-amides via the amino acid route |
| 183 | 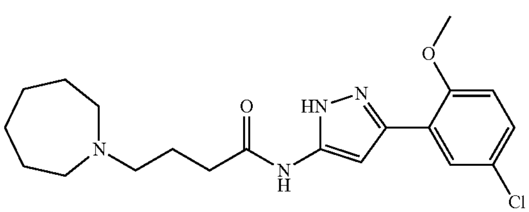 | HCOOH | C20H27N4O2Cl | 390.91 | 391 | 100 | 2.08 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 184 | 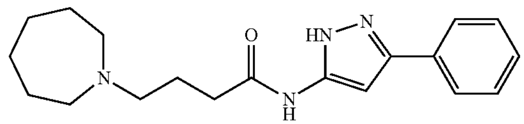 | HCOOH | C19H26N4O | 326.44 | 327 | 98 | 1.69 | 10 | Route A1/A2 for aminopyrazole; general method for the synthesis of ω-amino-alkanoic acid (1H-pyrazol-3-yl-5-aryl)-amides via the amino acid route |
| 185 | 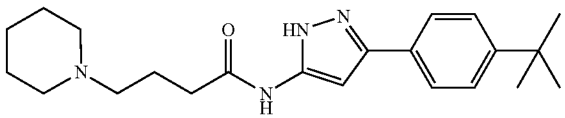 | HCOOH | C22H32N4O | 368.52 | 369, 185 | 100 | 2.33 | 10 | Route A1/A2 for aminopyrazole; general method for the synthesis of ω-amino-alkanoic acid (1H-pyrazol-3-yl-5-aryl)-amides via the amino acid route |
| 186 | 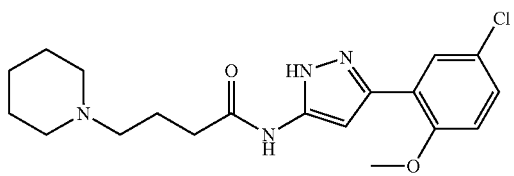 | HCOOH | C19H25N4O2Cl | 376.88 | 377, 189 | 100 | 1.89 | 10 | Route A1/A2 for aminopyrazole; general method for the synthesis of ω-amino-alkanoic acid (1H-pyrazol-3-yl-5-aryl)-amides via the amino acid route |
| 187 | 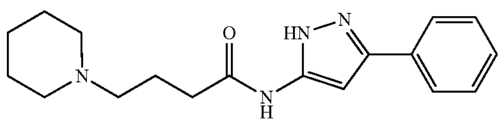 | HCOOH | C18H24N4O | 312.41 | 313, 157 | 95 | 1.48 | 10 | Route A1/A2 for aminopyrazole; general method for the synthesis of ω-amino-alkanoic acid (1H-pyrazol-3-yl-5-aryl)-amides via the amino acid route |
| 188 | 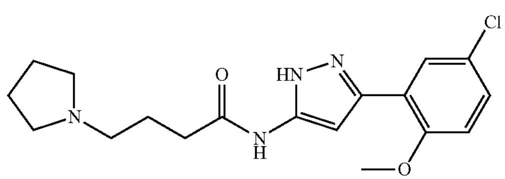 | HCOOH | C18H23N4O2Cl | 362.85 | 363, 182 | 100 | 1.83 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 189 | 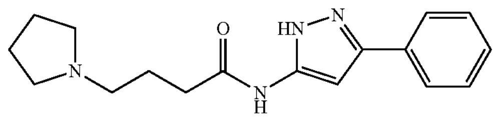 | HCOOH | C17H22N4O | 298.38 | 299, 150 | 97 | 1.44 | 10 | Route A1/A2 for aminopyrazole; general method for the synthesis of o-amino-alkanoic acid (1H-pyrazol-3-yl-5-aryl)-amides via the amino acid route |
| 190 | 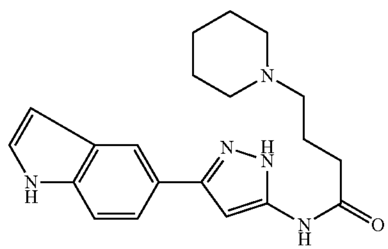 | HCOOH | C20H25N5O | 351.45 | 352, 177, 267 | 95 | 1.46 | 10 | Route A1/A2 for aminopyrazole; general method for the synthesis of o-amino-alkanoic acid (1H-pyrazol-3-yl-5-aryl)-amides via the amino acid route |
| 191 | 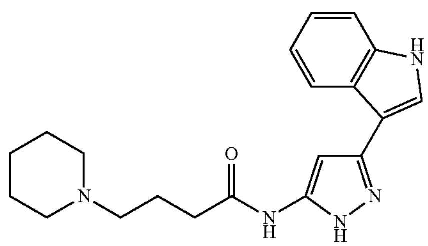 | HCOOH | C20H25N4O | 351.45 | 352, 177, 267 | 93 | 1.49 | 10 | Route A1/A2 for aminopyrazole; general method for the synthesis of o-amino-alkanoic acid (1H-pyrazol-3-yl-5-aryl)-amides via the amino acid route |
| 192 | 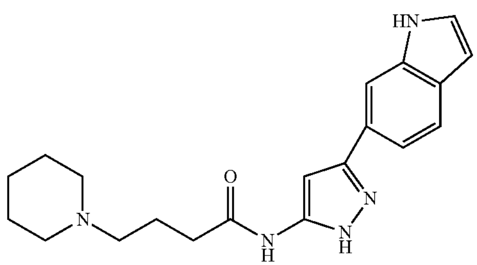 | HCOOH | C20H25N5O | 351.45 | 352, 177, 267 | 98 | 1.61 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 193 | 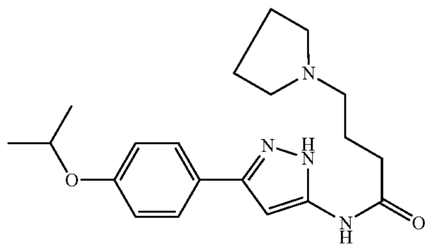 | | C20H28N4O2 | 356.46 | 357, 158 | 100 | 1.81 | 10 | Route A1/A2 for aminopyrazole; general method for the synthesis of o-amino-alkanoic acid (1H-pyrazol-3-yl-5-aryl)-amides via the amino acid route |
| 194 | 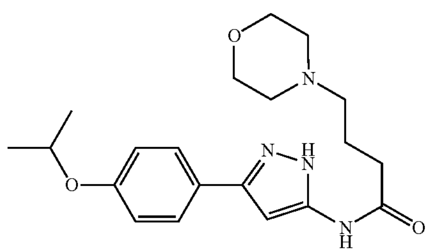 | | C20H28N4O3 | 372.46 | 373, 166 | 100 | 1.69 | 10 | Route A1/A2 for aminopyrazole; general method for the synthesis of o-amino-alkanoic acid (1H-pyrazol-3-yl-5-aryl)-amides via the amino acid route |
| 195 | 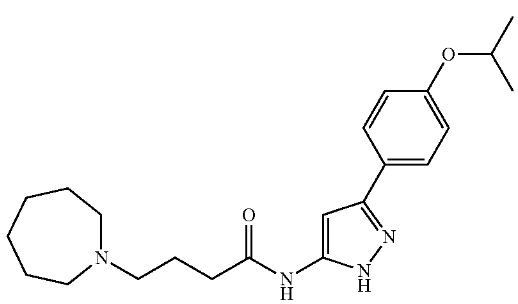 | HCOOH | C22H32N4O2 | 384.52 | 385, 172 | 100 | 2.08 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 196 | 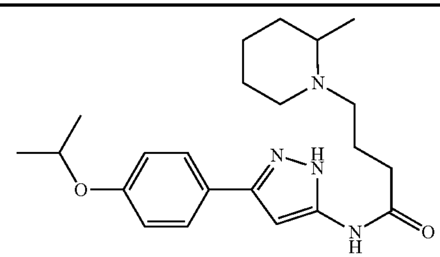 | | C22H32N4O2 | 384.52 | 385, 172 | 100 | 2.06 | 10 | Route A1/A2 for aminopyrazole; general method for the synthesis of o-amino-alkanoic acid (1H-pyrazol-3-yl-5-aryl)-amides via the amino acid route |
| 197 | 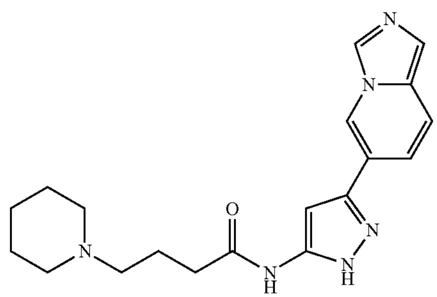 | HCOOH | C19H24N6O | 352.43 | 353 | 95 | 0.23 | 10 | Route A1/A2 for aminopyrazole; general method for the synthesis of o-amino-alkanoic acid (1H-pyrazol-3-yl-5-aryl)-amides via the amino acid route |
| 198 | 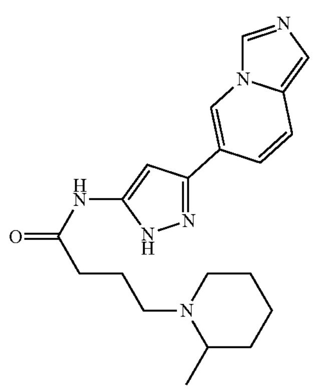 | HCOOH | C20H26N6O | 366.46 | 367, 184 | 95 | 0.23 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 199 | 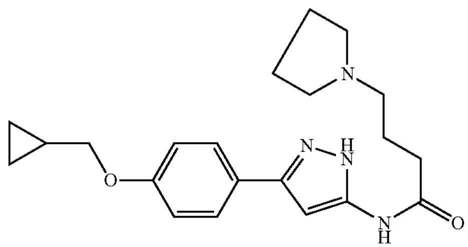 | | C21H28N4O2 | 368.47 | 369, 158 | 98 | 1.34 | 10 | Route A1/A2 for aminopyrazole; general method for the synthesis of ω-amino-alkanoic acid (1H-pyrazol-3-yl-5-aryl)-amides via the amino acid route |
| 200 | 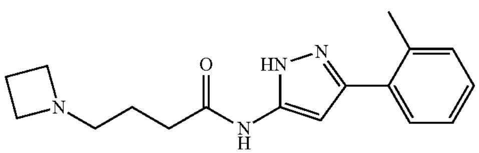 | | C17H22N4O | 298.38 | 299, 150 | 99 | 1.73 | 10 | Route A1/A2 for aminopyrazole; general method for the synthesis of ω-amino-alkanoic acid (1H-pyrazol-3-yl-5-aryl)-amides via the amino acid route |
| 201 | 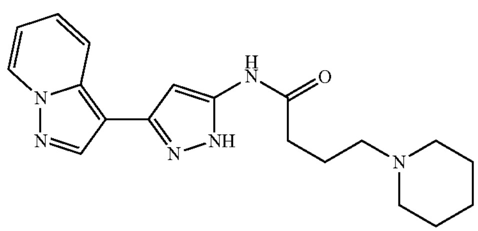 | HCOOH | C19H24N6O | 352.43 | 353, 177 | 98 | 1.36 | 10 | Route A1/A2 for aminopyrazole; general method for the synthesis of ω-amino-alkanoic acid (1H-pyrazol-3-yl-5-aryl)-amides via the amino acid route |
| 202 | 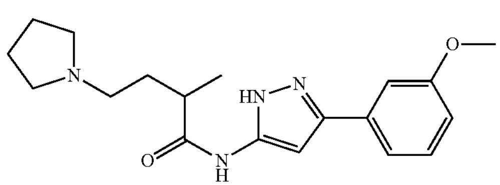 | HCOOH | C19H26N4O2 | 342.44 | 353, 172 | 97 | 1.59 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 203 | 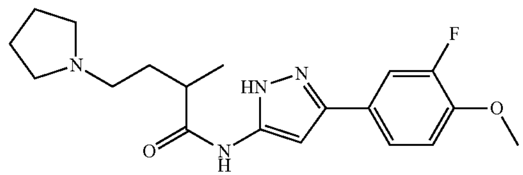 | HCOOH | C19H25N4O2F | 360.43 | 361, 181 | 95 | 1.66 | 10 | Route A1/A2 for aminopyrazole; general method for the synthesis of o-amino-alkanoic acid (1H-pyrazol-3-yl-5-aryl)-amides via the amino acid route |
| 204 | 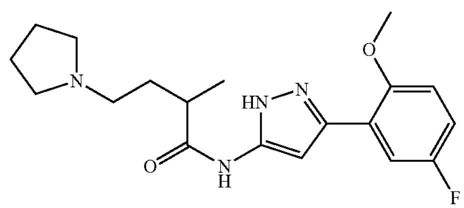 | HCOOH | C19H25N4O2F | 360.43 | 361, 181 | 100 | 1.76 | 10 | Route A1/A2 for aminopyrazole; general method for the synthesis of o-amino-alkanoic acid (1H-pyrazol-3-yl-5-aryl)-amides via the amino acid route |
| 205 | 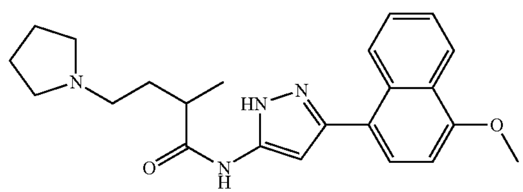 | HCOOH | C23H28N4O2 | 392.49 | 393, 197 | 100 | 2.09 | 10 | Route A1/A2 for aminopyrazole; general method for the synthesis of o-amino-alkanoic acid (1H-pyrazol-3-yl-5-aryl)-amides via the amino acid route |
| 206 | 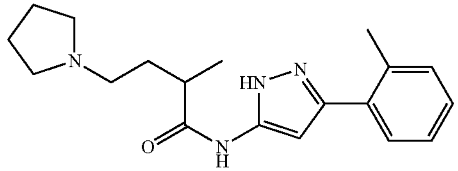 | HCOOH | C19H26N4O | 326.44 | 327, 165 | 95 | 1.59 | 10 | Route A1/A2 for aminopyrazole; general method for the synthesis of o-amino-alkanoic acid (1H-pyrazol-3-yl-5-aryl)-amides via the amino acid route |
| 207 | 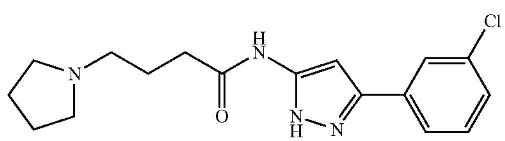 | HCOOH | C17H21N4OCl | 332.83 | 333, 167 | 100 | 1.71 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 208 | 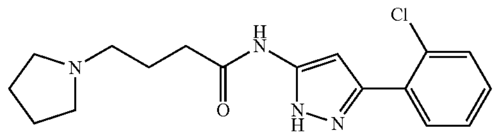 | HCOOH | C17H21N4OCl | 332.83 | 333, 167 | 100 | 1.54 | 10 | Route A1/A2 for aminopyrazole; general method for the synthesis of ω-amino-alkanoic acid (1H-pyrazol-3-yl-5-aryl)-amides via the amino acid route |
| 209 | 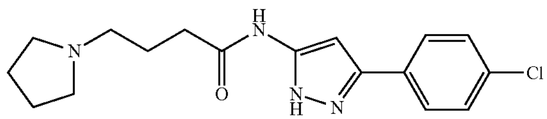 | HCOOH | C17H21N4OCl | 332.83 | 333, 167 | 100 | 1.71 | 10 | Route A1/A2 for aminopyrazole; general method for the synthesis of ω-amino-alkanoic acid (1H-pyrazol-3-yl-5-aryl)-amides via the amino acid route |
| 210 | 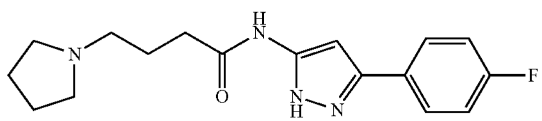 | | C17H21N4OF | 316.37 | 317, 159 | 100 | 1.49 | 10 | Route A1/A2 for aminopyrazole; general method for the synthesis of ω-amino-alkanoic acid (1H-pyrazol-3-yl-5-aryl)-amides via the amino acid route |
| 211 | 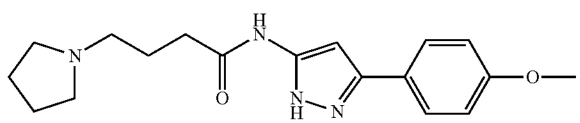 | | C18H24N4O2 | 328.41 | 329, 165 | 96 | 1.44 | 10 | Route A1/A2 for aminopyrazole; general method for the synthesis of ω-amino-alkanoic acid (1H-pyrazol-3-yl-5-aryl)-amides via the amino acid route |
| 212 | 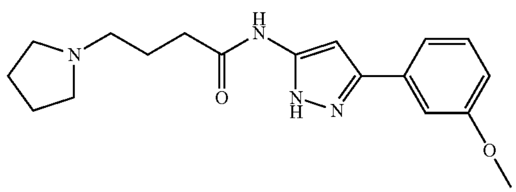 | | C18H24N4O2 | 328.41 | 329, 165 | 97 | 1.41 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 213 | 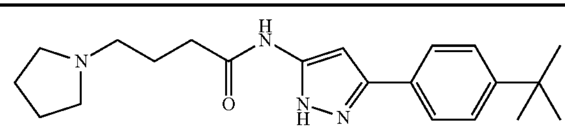 | HCOOH | C21H30N4O | 354.49 | 355, 178 | 100 | 2.23 | 10 | Route A1/A2 for aminopyrazole; general method for the synthesis of o-amino-alkanoic acid (1H-pyrazol-3-yl-5-aryl)-amides via the amino acid route |
| 214 | 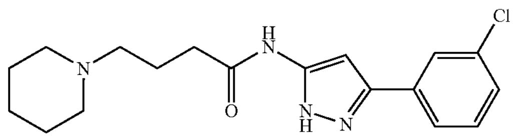 | HCOOH | C18H23N4OCl | 346.85 | 347, 174 | 100 | 1.79 | 10 | Route A1/A2 for aminopyrazole; general method for the synthesis of o-amino-alkanoic acid (1H-pyrazol-3-yl-5-aryl)-amides via the amino acid route |
| 215 | 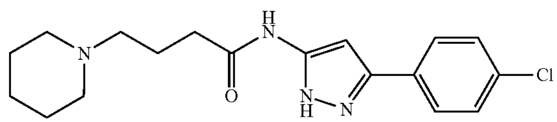 | HCOOH | C18H23N4OCl | 346.85 | 347, 174 | 100 | 1.81 | 10 | Route A1/A2 for aminopyrazole; general method for the synthesis of o-amino-alkanoic acid (1H-pyrazol-3-yl-5-aryl)-amides via the amino acid route |
| 216 | 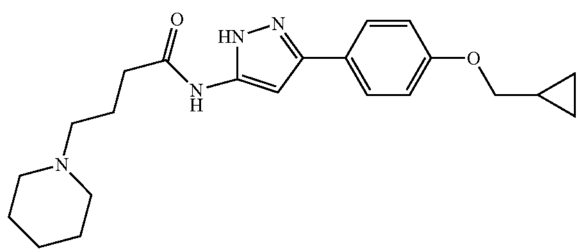 | HCOOH | C22H30N4O2 | 382.50 | 383 | 100 | 1.99 | 10 | Route A1/A2 for aminopyrazole; general method for the synthesis of o-amino-alkanoic acid (1H-pyrazol-3-yl-5-aryl)-amides via the amino acid route |
| 217 | 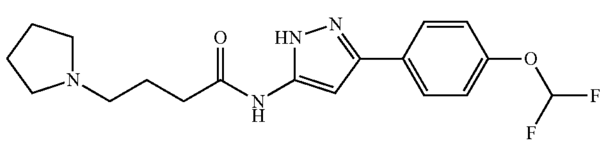 | HCOOH | C18H22N4O2F2 | 364.39 | 365, 183 | 100 | 2.04 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 218 | 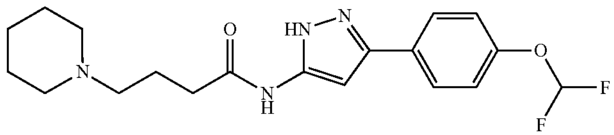 | HCOOH | C19H24N4O2F2 | 378.42 | 379, 190 | 100 | 2.74 | 10 | Route A1/A2 for aminopyrazole; general method for the synthesis of o-amino-alkanoic acid (1H-pyrazol-3-yl-5-aryl)-amides via the amino acid route |
| 219 | 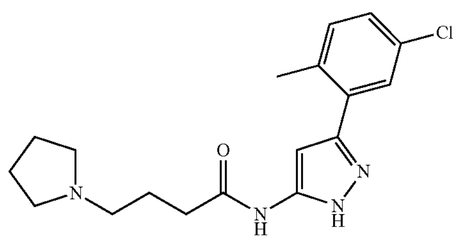 | HCOOH | C18H23N4OCl | 346.85 | 347, 174 | 100 | 1.84 | 10 | Route A1/A2 for aminopyrazole; general method for the synthesis of o-amino-alkanoic acid (1H-pyrazol-3-yl-5-aryl)-amides via the amino acid route |
| 220 | 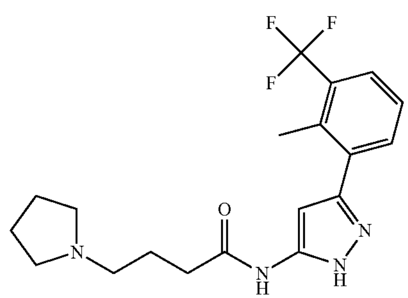 | | C19H23N4OF3 | 380.41 | 381, 198 | 100 | 2.01 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 221 | 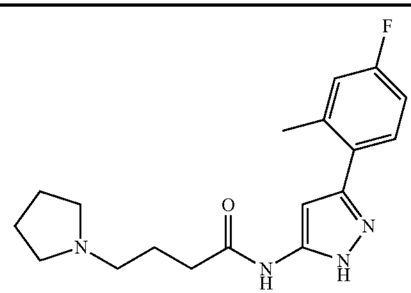 | HCOOH | C18H23N4OF | 330.40 | 331, 166 | 98 | 1.61 | 10 | Route A1/A2 for aminopyrazole; general method for the synthesis of o-amino-alkanoic acid (1H-pyrazol-3-yl-5-aryl)-amides via the amino acid route |
| 222 | 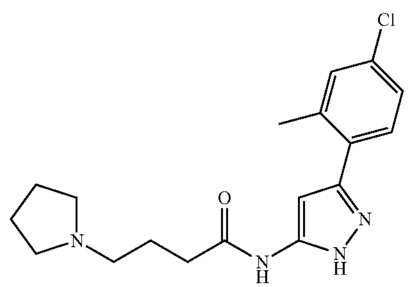 | | C18H23N4OCl | 346.85 | 347, 174 | 100 | 1.88 | 10 | Route A1/A2 for aminopyrazole; general method for the synthesis of o-amino-alkanoic acid (1H-pyrazol-3-yl-5-aryl)-amides via the amino acid route |
| 223 | 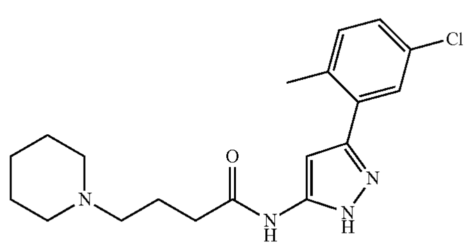 | HCOOH | C19H25N4OCl | 360.88 | 361, 181 | 100 | 1.93 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 224 | 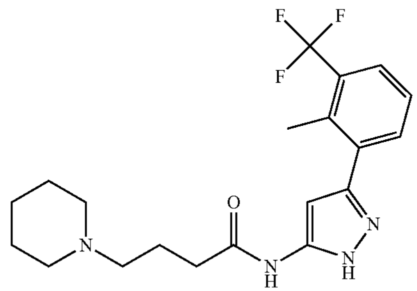 | HCOOH | C20H25N4OF3 | 394.43 | 395, 198 | 100 | 2.11 | 10 | Route A1/A2 for aminopyrazole; general method for the synthesis of o-amino-alkanoic acid (1H-pyrazol-3-yl-5-aryl)-amides via the amino acid route |
| 225 | 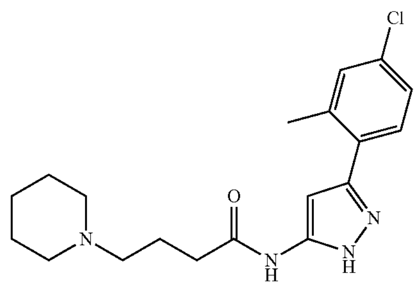 | HCOOH | C19H25N4OCl | 360.88 | 361 | 100 | 2.01 | 10 | Route A1/A2 for aminopyrazole; general method for the synthesis of o-amino-alkanoic acid (1H-pyrazol-3-yl-5-aryl)-amides via the amino acid route |
| 226 | 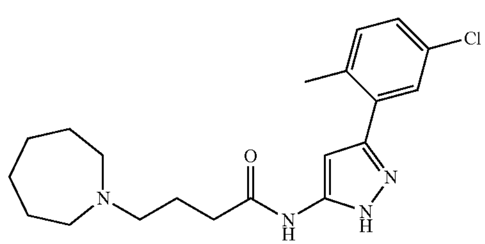 | HCOOH | C20H27N4OCl | 374.91 | 375, 188 | 100 | 2.13 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 227 | 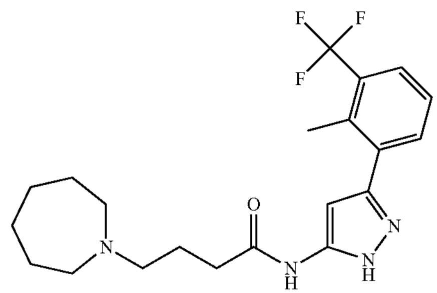 | | C21H27N4OF3 | 408.46 | 409, 205 | 100 | 2.26 | 10 | Route A1/A2 for aminopyrazole; general method for the synthesis of ω-amino-alkanoic acid (1H-pyrazol-3-yl-5-aryl)-amides via the amino acid route |
| 228 | 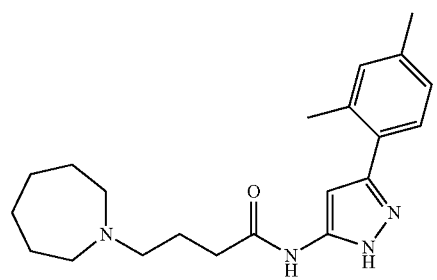 | HCl | C21H30N4O | 354.49 | 355, 176 | 100 | 2.03 | 10 | Route A1/A2 for aminopyrazole; general method for the synthesis of ω-amino-alkanoic acid (1H-pyrazol-3-yl-5-aryl)-amides via the amino acid route |
| 229 | 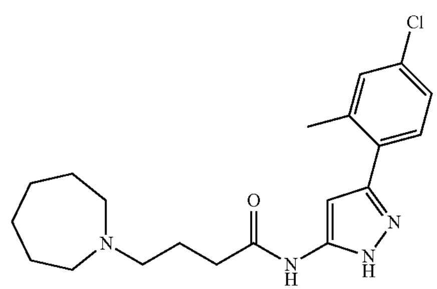 | HCl | C20H27N4OCl | 374.91 | 375, 188 | 100 | 2.13 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 230 | 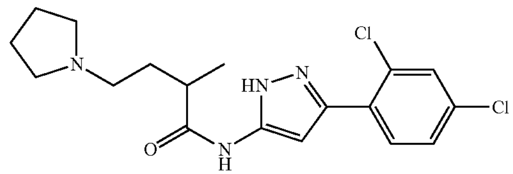 | HCOOH | C18H22N4OCl2 | 381.30 | 382, 191 | 100 | 2.03 | 10 | Route A1/A2 for aminopyrazole; general method for the synthesis of o-amino-alkanoic acid (1H-pyrazol-3-yl-5-aryl)-amides via the amino acid route |
| 231 | 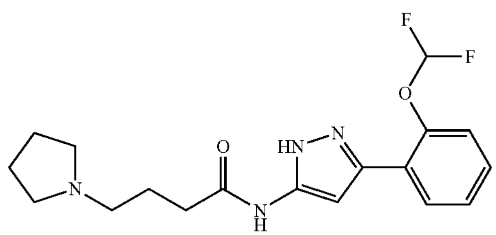 | HCOOH | C18H22N4O2F2 | 364.39 | 364 | 100 | 1.59 | 10 | Route A1/A2 for aminopyrazole; general method for the synthesis of o-amino-alkanoic acid (1H-pyrazol-3-yl-5-aryl)-amides via the amino acid route |
| 232 | 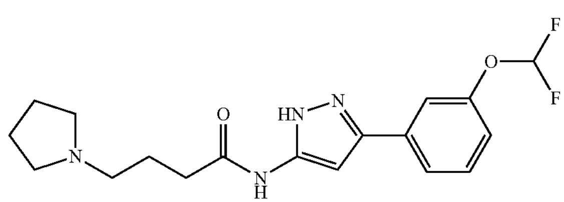 | HCOOH | C18H22N4O2F2 | 364.39 | 364, 182 | 100 | 1.71 | 10 | Route A1/A2 for aminopyrazole; general method for the synthesis of o-amino-alkanoic acid (1H-pyrazol-3-yl-5-aryl)-amides via the amino acid route |
| 233 | 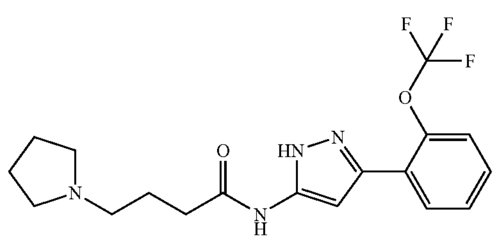 | HCOOH | C18H21N4O2F3 | 382.38 | 382 | 100 | 1.84 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 234 | 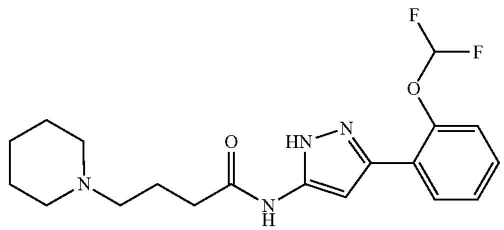 | HCOOH | C19H24N4O2F2 | 378.42 | 378, 169 | 100 | 1.74 | 10 | Route A1/A2 for aminopyrazole; general method for the synthesis of o-amino-alkanoic acid (1H-pyrazol-3-yl-5-aryl)-amides via the amino acid route |
| 235 | 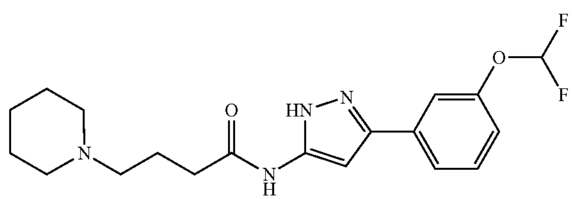 | HCOOH | C19H24N4O2F2 | 378.42 | 378 | 100 | 1.83 | 10 | Route A1/A2 for aminopyrazole; general method for the synthesis of o-amino-alkanoic acid (1H-pyrazol-3-yl-5-aryl)-amides via the amino acid route |
| 236 | 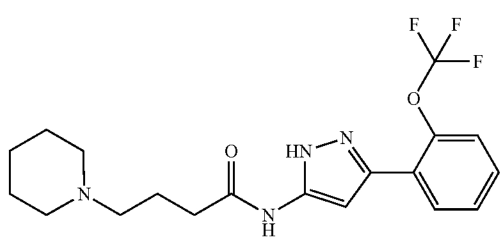 | HCOOH | C19H23N4O2F3 | 396.41 | 396 | 100 | 1.98 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 237 | 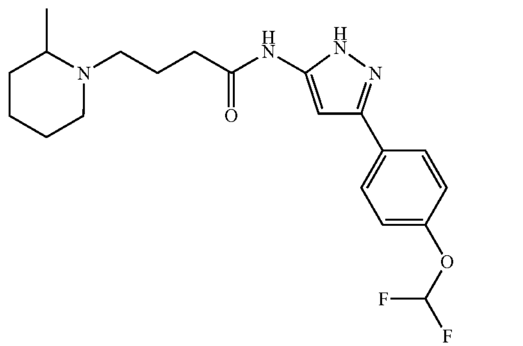 | HCOOH | C20H26N4O2F2 | 392.44 | 393, 197 | 100 | 1.94 | 10 | Route A1/A2 for aminopyrazole; general method for the synthesis of ω-amino-alkanoic acid (1H-pyrazol-3-yl-5-aryl)-amides via the amino acid route |
| 238 | 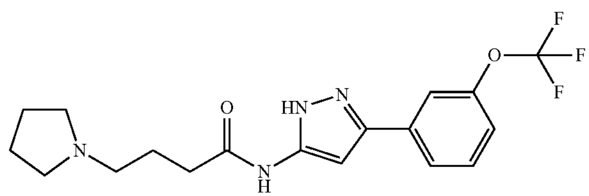 | HCOOH | C18H21N4O2F3 | 382.38 | 382, 191 | 100 | 2.01 | 10 | Route A1/A2 for aminopyrazole; general method for the synthesis of ω-amino-alkanoic acid (1H-pyrazol-3-yl-5-aryl)-amides via the amino acid route |
| 239 | 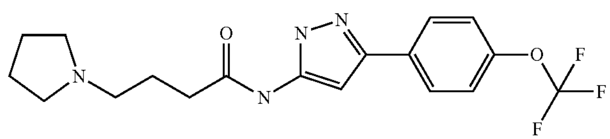 | HCOOH | C18H21N4O2F3 | 382.38 | 382, 191 | 100 | 2.03 | 10 | Route A1/A2 for aminopyrazole; general method for the synthesis of ω-amino-alkanoic acid (1H-pyrazol-3-yl-5-aryl)-amides via the amino acid route |
| 240 | 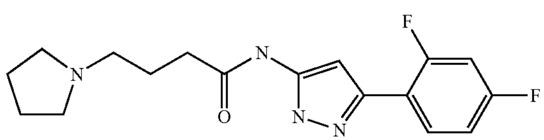 | HCl | C17H20N4OF2 | 334.36 | 335, 167 | 97 | 1.4 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 241 | 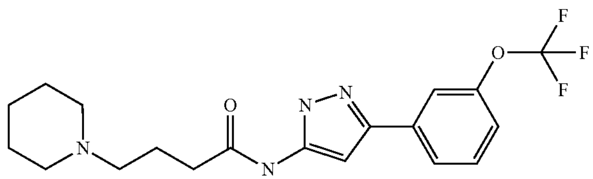 | HCOOH | C19H23N4O2F3 | 396.41 | 396, 198 | 100 | 2.09 | 10 | Route A1/A2 for aminopyrazole; general method for the synthesis of o-amino-alkanoic acid (1H-pyrazol-3-yl-5-aryl)-amides via the amino acid route |
| 242 | 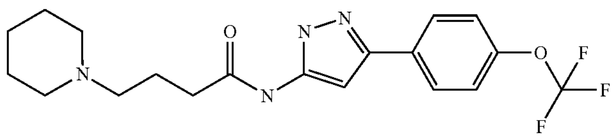 | HCOOH | C19H23N4O2F3 | 396.41 | 396, 198 | 100 | 2.14 | 10 | Route A1/A2 for aminopyrazole; general method for the synthesis of o-amino-alkanoic acid (1H-pyrazol-3-yl-5-aryl)-amides via the amino acid route |
| 243 | 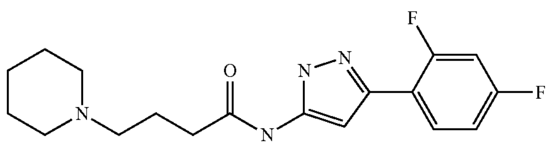 | HCOOH | C18H22N4OF2 | 348.39 | 348 | 100 | 1.64 | 10 | Route A1/A2 for aminopyrazole; general method for the synthesis of o-amino-alkanoic acid (1H-pyrazol-3-yl-5-aryl)-amides via the amino acid route |
| 244 | 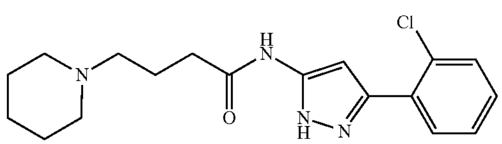 | HCOOH | C18H23N4OCl | 346.85 | 347 | 100 | 1.59 | 10 | Route A1/A2 for aminopyrazole; general method for the synthesis of o-amino-alkanoic acid (1H-pyrazol-3-yl-5-aryl)-amides via the amino acid route |
| 245 | 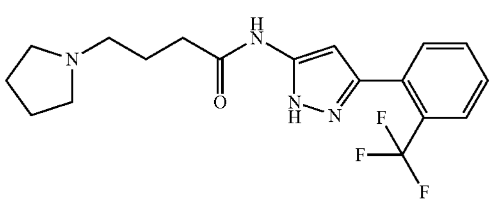 | HCOOH | C18H21N4OF3 | 366.38 | 367 | 100 | 1.63 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 246 | 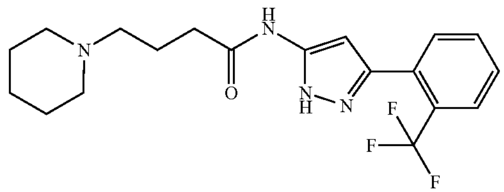 | HCOOH | C19H23N4OF3 | 380.41 | 381 | 100 | 1.74 | 10 | Route A1/A2 for aminopyrazole; general method for the synthesis of o-amino-alkanoic acid (1H-pyrazol-3-yl-5-aryl)-amides via the amino acid route |
| 247 | 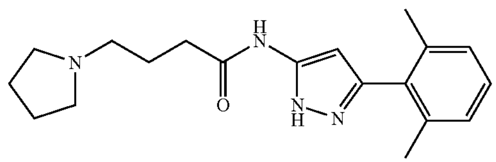 | HCOOH | C19H26N4O | 326.44 | 327, 164 | 96 | 1.61 | 10 | Route A1/A2 for aminopyrazole; general method for the synthesis of o-amino-alkanoic acid (1H-pyrazol-3-yl-5-aryl)-amides via the amino acid route |
| 248 | 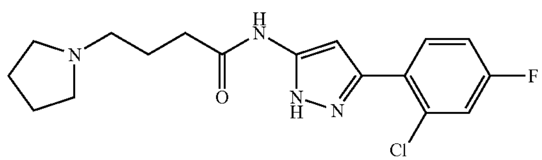 | HCOOH | C17H20N4OFCl | 350.82 | 351, 176 | 95 | 1.59 | 10 | Route A1/A2 for aminopyrazole; general method for the synthesis of o-amino-alkanoic acid (1H-pyrazol-3-yl-5-aryl)-amides via the amino acid route |
| 249 | 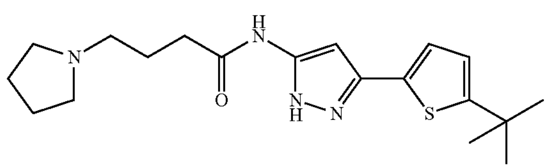 | HCOOH | C19H28N4OS | 360.52 | 361, 181 | 95 | 2.14 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 250 | 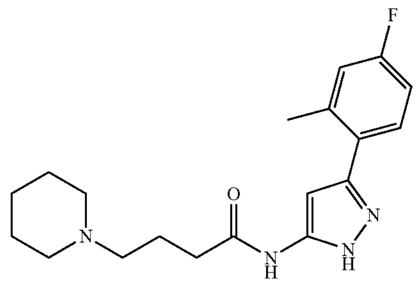 | HCOOH | C29H25N4OF | 344.43 | 345 | 96 | 1.74 | 10 | Route A1/A2 for aminopyrazole; general method for the synthesis of ω-amino-alkanoic acid (1H-pyrazol-3-yl-5-aryl)-amides via the amino acid route |
| 251 | 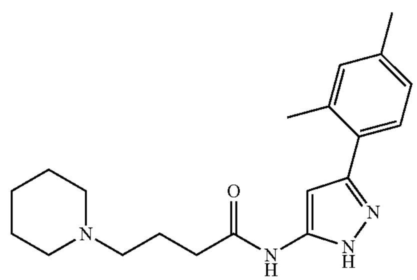 | HCOOH | C20H28N4O | 340.46 | 341 | 100 | 1.86 | 10 | Route A1/A2 for aminopyrazole; general method for the synthesis of ω-amino-alkanoic acid (1H-pyrazol-3-yl-5-aryl)-amides via the amino acid route |
| 252 | 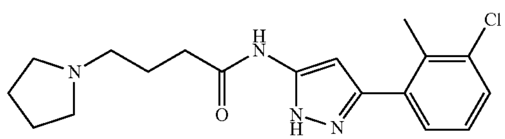 | | C18H23N4OCl | 346.85 | 347, 174 | 100 | 1.88 | 10 | Route A1/A2 for aminopyrazole; general method for the synthesis of ω-amino-alkanoic acid (1H-pyrazol-3-yl-5-aryl)-amides via the amino acid route |
| 253 | 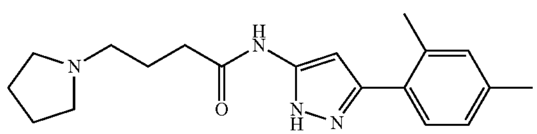 | | C19H26N4O | 326.44 | 327, 164 | 98 | 1.78 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 254 | 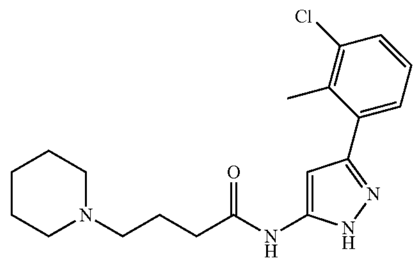 | HCl | C19H25N4OCl | 360.88 | 361, 181 | 100 | 1.98 | 10 | Route A1/A2 for aminopyrazole; general method for the synthesis of o-amino-alkanoic acid (1H-pyrazol-3-yl-5-aryl)-amides via the amino acid route |
| 255 | 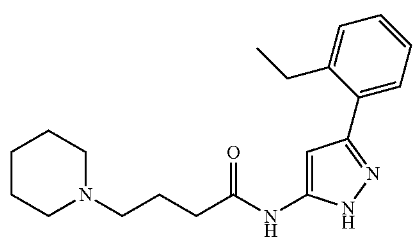 | | C20H28N4O | 340.46 | 341, 171 | 100 | 1.81 | 10 | Route A1/A2 for aminopyrazole; general method for the synthesis of o-amino-alkanoic acid (1H-pyrazol-3-yl-5-aryl)-amides via the amino acid route |
| 256 | 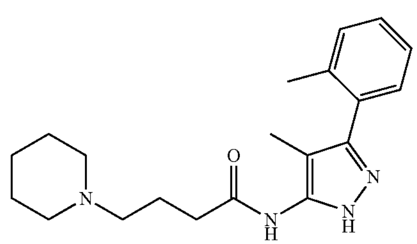 | | C20H28N4O | 340.46 | 341, 171 | 100 | 1.63 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 257 | 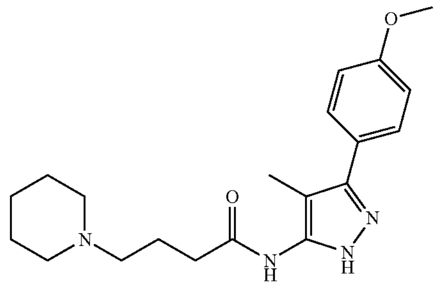 | | C20H28N4O2 | 356.46 | 357, 179 | 100 | 1.58 | 10 | Route A1/A2 for aminopyrazole; general method for the synthesis of ω-amino-alkanoic acid (1H-pyrazol-3-yl-5-aryl)-amides via the amino acid route |
| 258 | 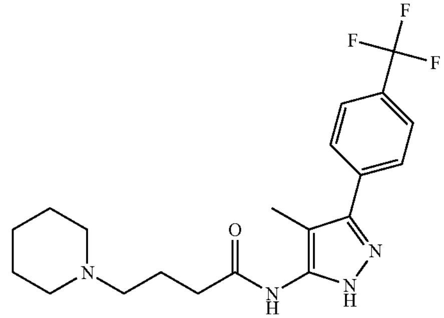 | | C20H25N4OF3 | 394.43 | 395, 198 | 100 | 2.08 | 10 | Route A1/A2 for aminopyrazole; general method for the synthesis of ω-amino-alkanoic acid (1H-pyrazol-3-yl-5-aryl)-amides via the amino acid route |
| 259 | 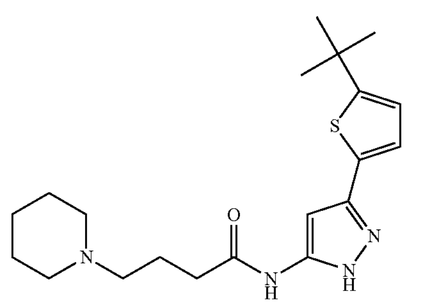 | | C20H30N4OS | 374.54 | 395, 198 | 100 | 2.28 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 260 | 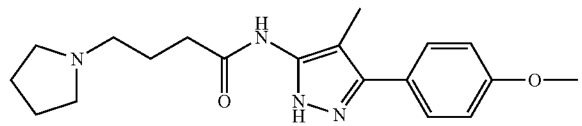 | | C19H26N4O2 | 342.44 | 343, 172 | 100 | 1.46 | 10 | Route A1/A2 for aminopyrazole; general method for the synthesis of o-amino-alkanoic acid (1H-pyrazol-3-yl-5-aryl)-amides via the amino acid route |
| 261 | 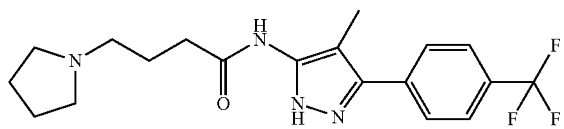 | | C19H23N4OF3 | 380.41 | 381, 191 | 100 | 1.98 | 10 | Route A1/A2 for aminopyrazole; general method for the synthesis of o-amino-alkanoic acid (1H-pyrazol-3-yl-5-aryl)-amides via the amino acid route |
| 262 | 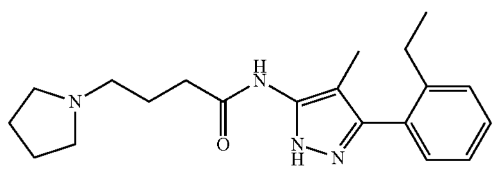 | | C19H26N4O | 326.44 | 327, 164 | 100 | 1.69 | 10 | Route A1/A2 for aminopyrazole; general method for the synthesis of o-amino-alkanoic acid (1H-pyrazol-3-yl-5-aryl)-amides via the amino acid route |
| 263 | 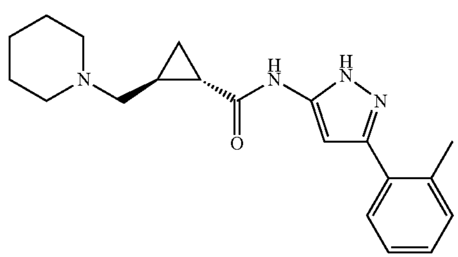 | | C20H26N4O | 338.45 | 339, 170 | 100 | 1.71 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 264 | 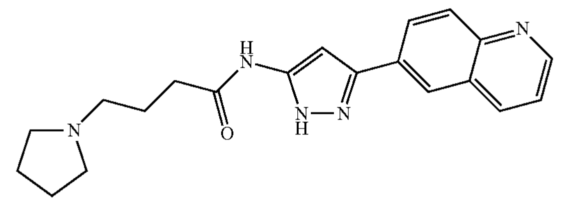 | HCOOH | C20H23N5O | 349.43 | 350, 175 | 100 | 0.81 | 10 | Route A1/A2 for aminopyrazole; general method for the synthesis of o-amino-alkanoic acid (1H-pyrazol-3-yl-5-aryl)-amides via the amino acid route |
| 265 | 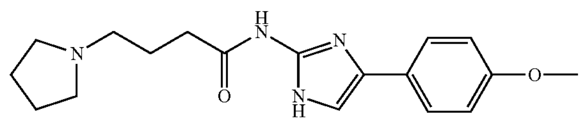 | HCOOH | C18H24N4O2 | 328.41 | 329, 165 | 95 | 0.71 | 10 | Route A1/A2 for aminopyrazole; general method for the synthesis of o-amino-alkanoic acid (1H-pyrazol-3-yl-5-aryl)-amides via the amino acid route |
| 266 | 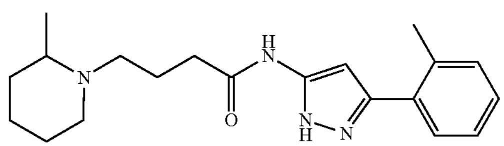 | HCOOH | C20H28N4O | 340.46 | 341 | 100 | 1.74 | 10 | Route A1/A2 for aminopyrazole; general method for the synthesis of o-amino-alkanoic acid (1H-pyrazol-3-yl-5-aryl)-amides via the amino acid route |
| 267 | 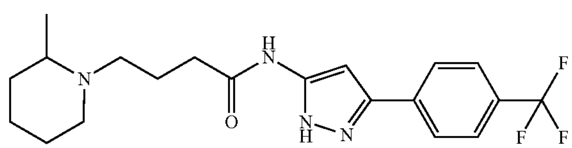 | HCOOH | C20H25N4OF3 | 394.43 | 395 | 100 | 2.11 | 10 | Route A1/A2 for aminopyrazole; general method for the synthesis of o-amino-alkanoic acid (1H-pyrazol-3-yl-5-aryl)-amides via the amino acid route |
| 268 | 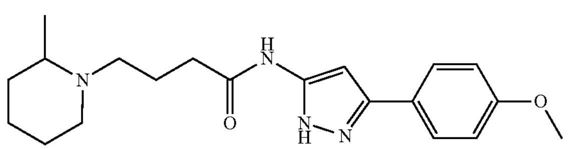 | HCOOH | C20H28N4O2 | 356.46 | 357 | 100 | 1.69 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 269 | 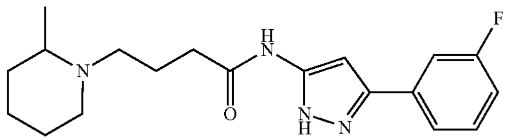 | HCOOH | C19H25N4OF | 344.43 | 345 | 100 | 1.71 | 10 | Route A1/A2 for aminopyrazole; general method for the synthesis of ω-amino-alkanoic acid (1H-pyrazol-3-yl-5-aryl)-amides via the amino acid route |
| 270 | 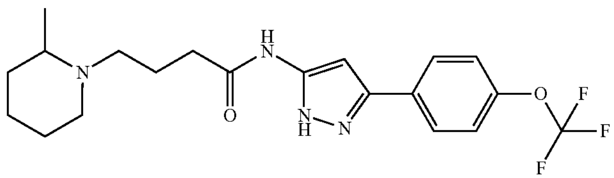 | HCOOH | C20H25N4O2F3 | 410.43 | 411 | 98 | 2.14 | 10 | Route A1/A2 for aminopyrazole; general method for the synthesis of ω-amino-alkanoic acid (1H-pyrazol-3-yl-5-aryl)-amides via the amino acid route |
| 271 | 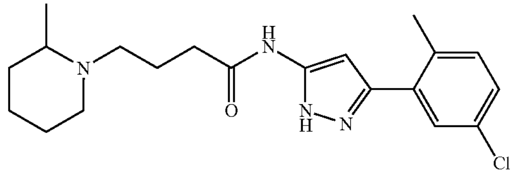 | HCOOH | C20H27N4OCl | 374.91 | 375 | 100 | 2.01 | 10 | Route A1/A2 for aminopyrazole; general method for the synthesis of ω-amino-alkanoic acid (1H-pyrazol-3-yl-5-aryl)-amides via the amino acid route |
| 272 | 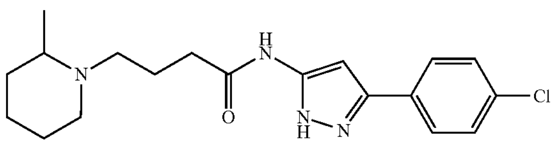 | HCOOH | C19H25N4OCl | 360.88 | 361 | 100 | 1.98 | 10 | Route A1/A2 for aminopyrazole; general method for the synthesis of ω-amino-alkanoic acid (1H-pyrazol-3-yl-5-aryl)-amides via the amino acid route |
| 273 | 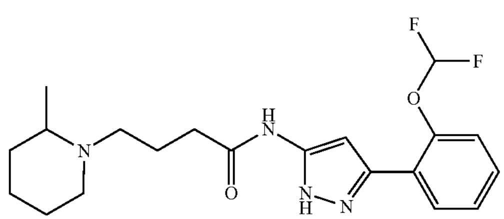 | HCOOH | C20H26N4O2F2 | 392.44 | 393 | 100 | 1.83 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 274 | 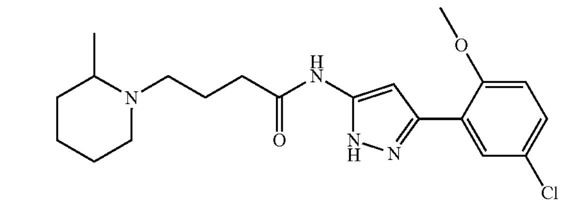 | HCOOH | C20H27N4O2Cl | 390.91 | 391 | 100 | 2.03 | 10 | Route A1/A2 for aminopyrazole; general method for the synthesis of o-amino-alkanoic acid (1H-pyrazol-3-yl-5-aryl)-amides via the amino acid route |
| 275 | 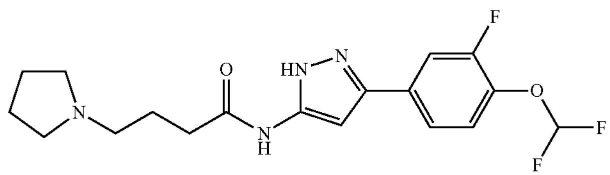 | HCOOH | C18H21N4O2F3 | 382.38 | 383 | 98 | 1.83 | 10 | Route A1/A2 for aminopyrazole; general method for the synthesis of o-amino-alkanoic acid (1H-pyrazol-3-yl-5-aryl)-amides via the amino acid route |
| 276 | 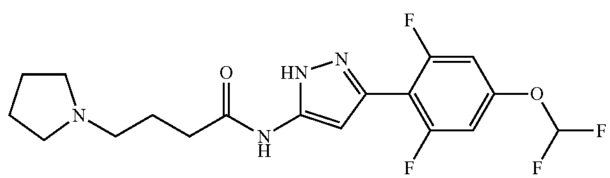 | HCOOH | C18H20N4O2F4 | 400.37 | 401 | 100 | 1.78 | 10 | Route A1/A2 for aminopyrazole; general method for the synthesis of o-amino-alkanoic acid (1H-pyrazol-3-yl-5-aryl)-amides via the amino acid route |
| 277 | 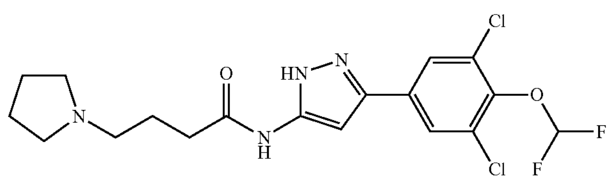 | HCOOH | C18H20N4O2F2Cl2 | 433.28 | 433 | 100 | 2.28 | 10 | Route A1/A2 for aminopyrazole; general method for the synthesis of o-amino-alkanoic acid (1H-pyrazol-3-yl-5-aryl)-amides via the amino acid route |
| 278 | 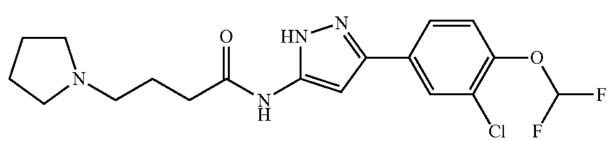 | HCOOH | C18H21N4O2F2Cl | 398.83 | 399 | 98 | 2.01 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 279 | 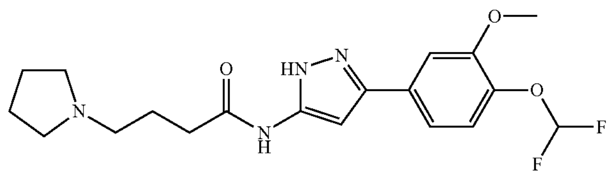 | HCOOH | C19H24N4O3F2 | 394.42 | 395 | 98 | 1.81 | 10 | Route A1/A2 for aminopyrazole; general method for the synthesis of o-amino-alkanoic acid (1H-pyrazol-3-yl-5-aryl)-amides via the amino acid route |
| 280 | 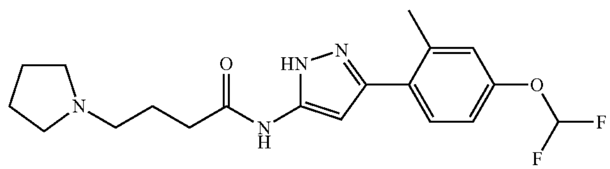 | HCOOH | C19H24N4O2F2 | 378.42 | 379 | 98 | 1.84 | 10 | Route A1/A2 for aminopyrazole; general method for the synthesis of o-amino-alkanoic acid (1H-pyrazol-3-yl-5-aryl)-amides via the amino acid route |
| 281 | 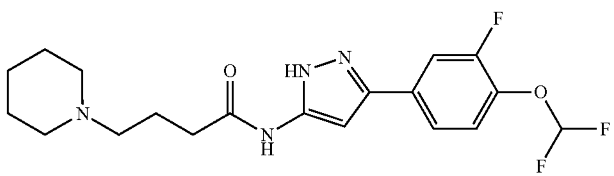 | HCOOH | C19H23N4O2F3 | 396.41 | 397 | 100 | 1.93 | 10 | Route A1/A2 for aminopyrazole; general method for the synthesis of o-amino-alkanoic acid (1H-pyrazol-3-yl-5-aryl)-amides via the amino acid route |
| 282 | 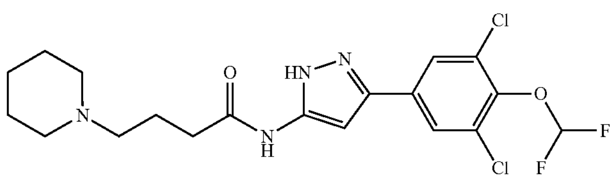 | HCOOH | C19H22N4O2F2Cl2 | 447.31 | 447 | 97 | 2.36 | 10 | Route A1/A2 for aminopyrazole; general method for the synthesis of o-amino-alkanoic acid (1H-pyrazol-3-yl-5-aryl)-amides via the amino acid route |
| 283 | 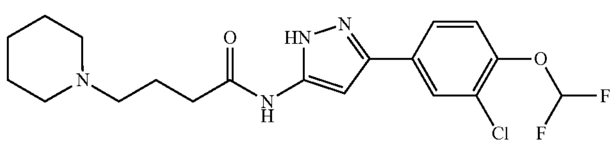 | HCOOH | C19H23N4O2F2Cl | 412.86 | 413 | 98 | 2.09 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 284 | | HCOOH | C20H26N4O3F2 | 408.44 | 409 | 100 | 1.89 | 10 | Route A1/A2 for aminopyrazole; general method for the synthesis of o-amino-alkanoic acid (1H-pyrazol-3-yl-5-aryl)-amides via the amino acid route |
| 285 | | HCOOH | C20H26N4O2F2 | 392.44 | 393 | 100 | 1.96 | 10 | Route A1/A2 for aminopyrazole; general method for the synthesis of o-amino-alkanoic acid (1H-pyrazol-3-yl-5-aryl)-amides via the amino acid route |
| 286 | | HCOOH | C20H27N4O2F | 374.45 | 375 | 100 | 1.74 | 10 | Route A1/A2 for aminopyrazole; general method for the synthesis of o-amino-alkanoic acid (1H-pyrazol-3-yl-5-aryl)-amides via the amino acid route |
| 287 | | HCOOH | C23H32N4O2 | 396.53 | 397, 199 | 100 | 2.14 | 10 | Route A1/A2 for aminopyrazole; general method for the synthesis of o-amino-alkanoic acid (1H-pyrazol-3-yl-5-aryl)-amides via the amino acid route |
| 288 | | HCOOH | C22H30N4O2 | 382.50 | 383 | 98 | 2.01 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 289 | 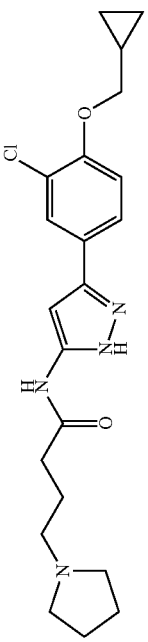 | HCOOH | C21H27N4O2Cl | 402.92 | 403 | 95 | 2.19 | 10 | Route A1/A2 for aminopyrazole; general method for the synthesis of o-amino-alkanoic acid (1H-pyrazol-3-yl-5-aryl)-amides via the amino acid route |
| 290 | 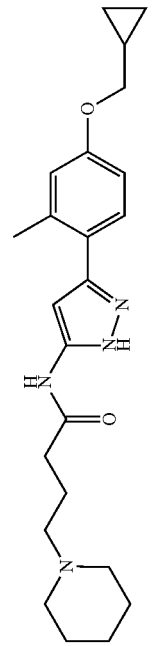 | HCOOH | C23H32N4O2 | 396.53 | 397 | 98 | 2.16 | 10 | Route A1/A2 for aminopyrazole; general method for the synthesis of o-amino-alkanoic acid (1H-pyrazol-3-yl-5-aryl)-amides via the amino acid route |
| 291 | 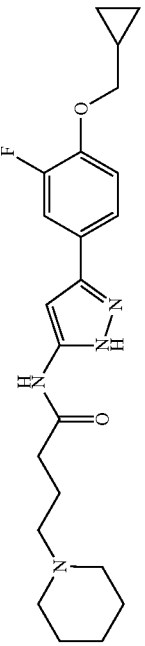 | HCOOH | C22H29N4O2F | 400.49 | 401 | 98 | 2.11 | 10 | Route A1/A2 for aminopyrazole; general method for the synthesis of o-amino-alkanoic acid (1H-pyrazol-3-yl-5-aryl)-amides via the amino acid route |
| 292 | 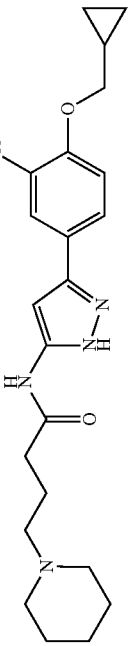 | HCOOH | C22H29N4O2Cl | 416.94 | 417 | 95 | 2.26 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 293 | 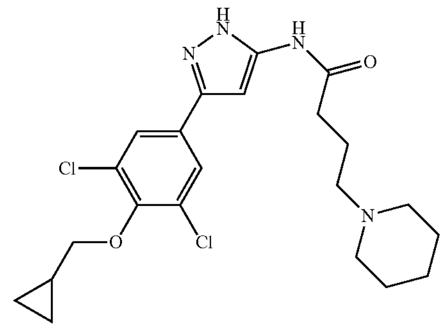 | | C22H28N4O2Cl2 | 451.39 | 451 | 96 | 2.53 | 10 | Route A1/A2 for aminopyrazole; general method for the synthesis of ω-amino-alkanoic acid (1H-pyrazol-3-yl-5-aryl)-amides via the amino acid route |
| 294 | 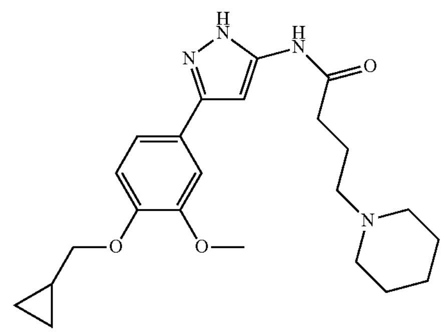 | | C23H32N4O3 | 412.53 | 413 | 98 | 1.96 | 10 | Route A1/A2 for aminopyrazole; general method for the synthesis of ω-amino-alkanoic acid (1H-pyrazol-3-yl-5-aryl)-amides via the amino acid route |
| 295 | 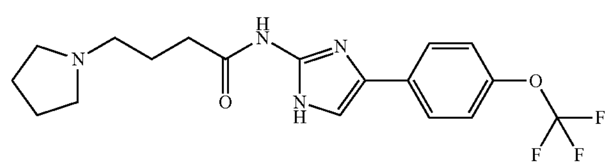 | HCOOH | C18H21N4O2F3 | 382.38 | 383, 192 | 98 | 1.66 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 296 | 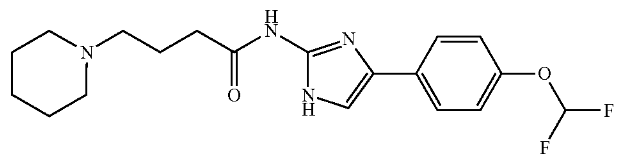 | HCOOH | C19H24N4O2F2 | 378.42 | 379, 190 | 97 | 1.24 | 10 | Route A1/A2 for aminopyrazole; general method for the synthesis of o-amino-alkanoic acid (1H-pyrazol-3-yl-5-aryl)-amides via the amino acid route |
| 297 | 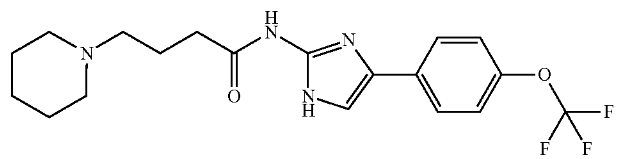 | HCOOH | C19H23N4O2F3 | 396.41 | 397, 199 | 100 | 1.78 | 10 | Route A1/A2 for aminopyrazole; general method for the synthesis of o-amino-alkanoic acid (1H-pyrazol-3-yl-5-aryl)-amides via the amino acid route |
| 298 | 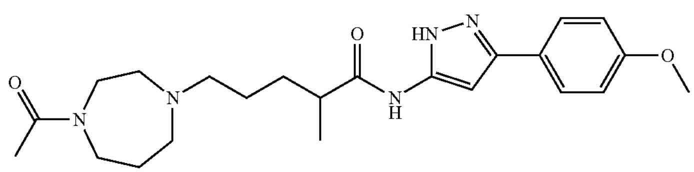 | | C23H33N5O3 | 427.54 | 428 | 98 | 1.58 | 10 | Route A1/A2 for aminopyrazole; general method for the synthesis of o-amino-alkanoic acid (1H-pyrazol-3-yl-5-aryl)-amides via the amino acid route |
| 299 | 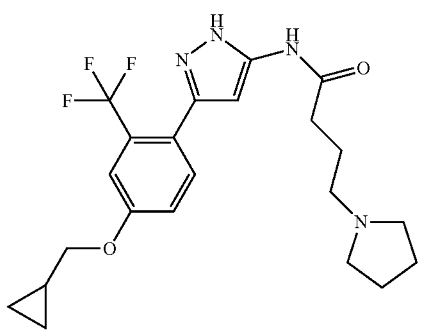 | HCOOH | C22H27N4O2F3 | 436.47 | 437 | 100 | 2.29 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 300 | 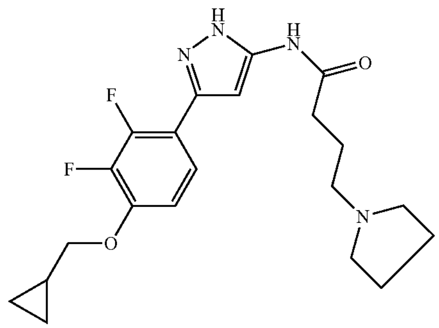 | | C21H26N4O2F2 | 404.45 | 405 | 100 | 2.13 | 10 | Route A1/A2 for aminopyrazole; general method for the synthesis of o-amino-alkanoic acid (1H-pyrazol-3-yl-5-aryl)-amides via the amino acid route |
| 301 | 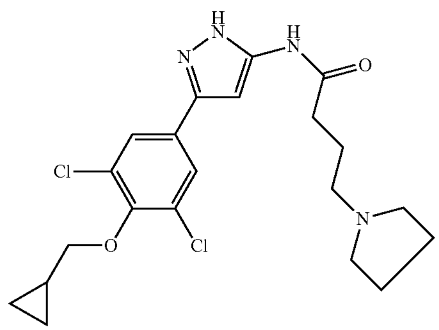 | | C21H26N4O2Cl2 | 437.36 | 437 | 98 | 2.43 | 10 | Route A1/A2 for aminopyrazole; general method for the synthesis of o-amino-alkanoic acid (1H-pyrazol-3-yl-5-aryl)-amides via the amino acid route |
| 302 | 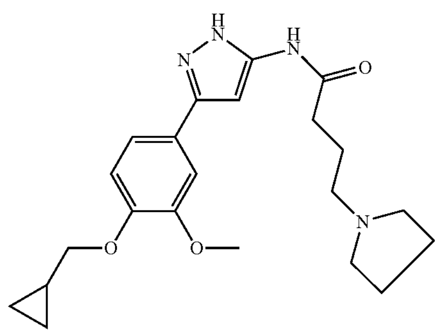 | | C22H30N4O3 | 398.50 | 399 | 98 | 1.84 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 303 | 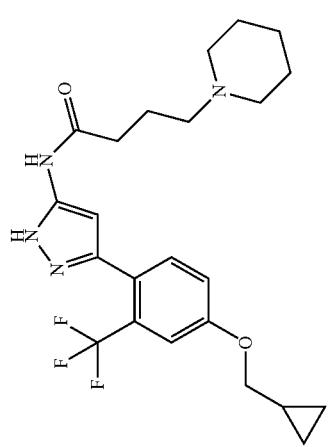 | | C23H29N4O2F3 | 450.50 | 451 | 100 | 2.34 | 10 | Route A1/A2 for aminopyrazole; general method for the synthesis of o-amino-alkanoic acid (1H-pyrazol-3-yl-5-aryl)-amides via the amino acid route |
| 304 | 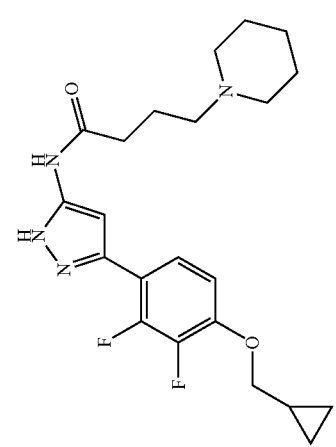 | | C22H28N4O2F2 | 418.48 | 419 | 100 | 2.23 | 10 | Route A1/A2 for aminopyrazole; general method for the synthesis of o-amino-alkanoic acid (1H-pyrazol-3-yl-5-aryl)-amides via the amino acid route |
| 305 | 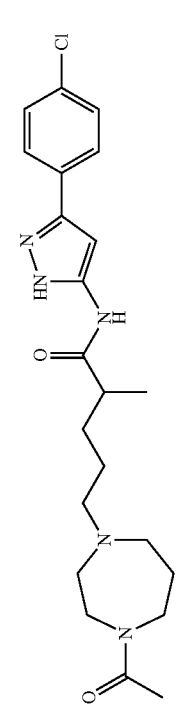 | | C22H30N5O2Cl | 431.96 | 432 | 98 | 1.83 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 306 | 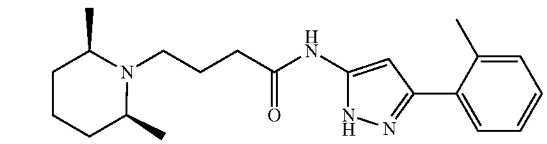 | HCOOH | C21H30N4O | 354.49 | 355 | 100 | 1.84 | 10 | Route A1/A2 for aminopyrazole; general method for the synthesis of o-amino-alkanoic acid (1H-pyrazol-3-yl-5-aryl)-amides via the amino acid route |
| 307 | 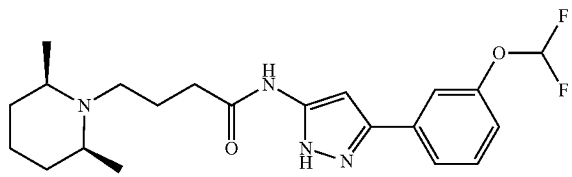 | HCOOH | C21H28N4O2F2 | 406.47 | 407 | 100 | 1.99 | 10 | Route A1/A2 for aminopyrazole; general method for the synthesis of o-amino-alkanoic acid (1H-pyrazol-3-yl-5-aryl)-amides via the amino acid route |
| 308 | 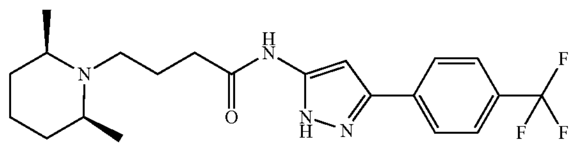 | HCOOH | C21H27N4OF3 | 408.46 | 409 | 100 | 2.19 | 10 | Route A1/A2 for aminopyrazole; general method for the synthesis of o-amino-alkanoic acid (1H-pyrazol-3-yl-5-aryl)-amides via the amino acid route |
| 309 | 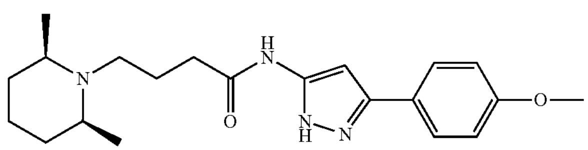 | HCOOH | C21H30N4O2 | 370.49 | 371 | 97 | 1.74 | 10 | Route A1/A2 for aminopyrazole; general method for the synthesis of o-amino-alkanoic acid (1H-pyrazol-3-yl-5-aryl)-amides via the amino acid route |
| 310 | 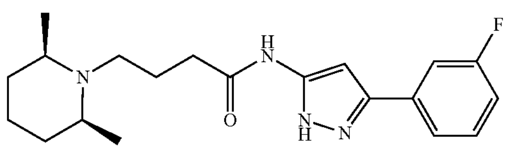 | | C20H27N4OF | 358.45 | 359 | 100 | 1.78 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 311 | 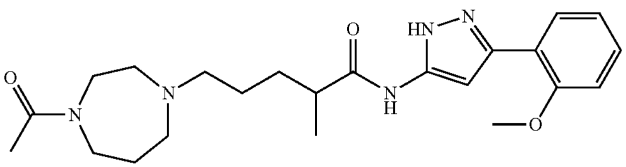 | | C23H33N5O3 | 427.54 | 428 | 98 | 1.64 | 10 | Route A1/A2 for aminopyrazole; general method for the synthesis of ω-amino-alkanoic acid (1H-pyrazol-3-yl-5-aryl)-amides via the amino acid route |
| 312 | 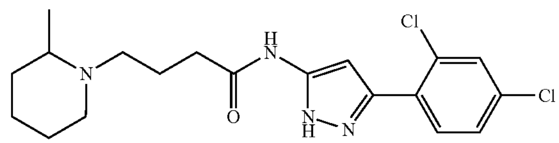 | HCOOH | C19H24N4OCl2 | 395.33 | 395 | 100 | 2.13 | 10 | Route A1/A2 for aminopyrazole; general method for the synthesis of ω-amino-alkanoic acid (1H-pyrazol-3-yl-5-aryl)-amides via the amino acid route |
| 313 | 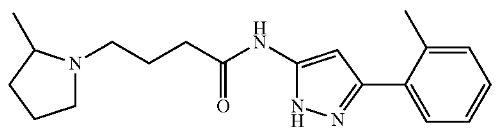 | HCOOH | C19H26N4O | 326.44 | 327, 164 | 97 | 1.59 | 10 | Route A1/A2 for aminopyrazole; general method for the synthesis of ω-amino-alkanoic acid (1H-pyrazol-3-yl-5-aryl)-amides via the amino acid route |
| 314 | 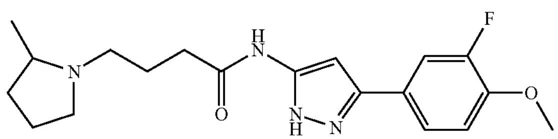 | HCOOH | C19H25N4O2F | 360.43 | 361, 181 | 100 | 1.63 | 10 | Route A1/A2 for aminopyrazole; general method for the synthesis of ω-amino-alkanoic acid (1H-pyrazol-3-yl-5-aryl)-amides via the amino acid route |
| 315 | 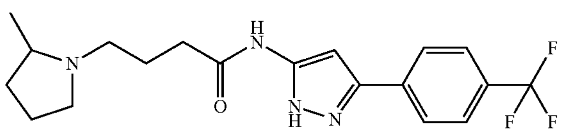 | HCOOH | C19H23N4OF3 | 380.41 | 381 | 100 | 1.98 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 316 | 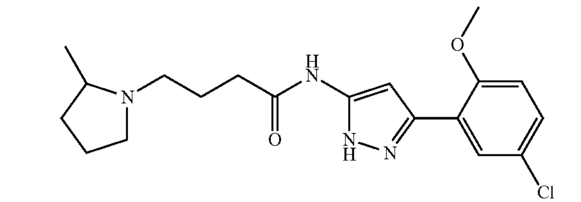 | HCOOH | C19H25N4O2Cl | 376.88 | 377 | 100 | 1.89 | 10 | Route A1/A2 for aminopyrazole; general method for the synthesis of o-amino-alkanoic acid (1H-pyrazol-3-yl-5-aryl)-amides via the amino acid route |
| 317 | 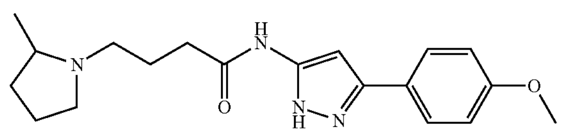 | HCOOH | C19H26N4O2 | 342.44 | 343, 172 | 100 | 1.56 | 10 | Route A1/A2 for aminopyrazole; general method for the synthesis of o-amino-alkanoic acid (1H-pyrazol-3-yl-5-aryl)-amides via the amino acid route |
| 318 | 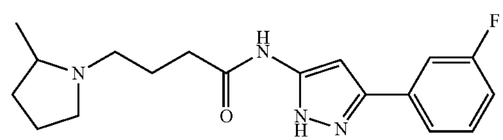 | HCOOH | C18H23N4OF | 330.40 | 331, 166 | 100 | 1.56 | 10 | Route A1/A2 for aminopyrazole; general method for the synthesis of o-amino-alkanoic acid (1H-pyrazol-3-yl-5-aryl)-amides via the amino acid route |
| 319 | 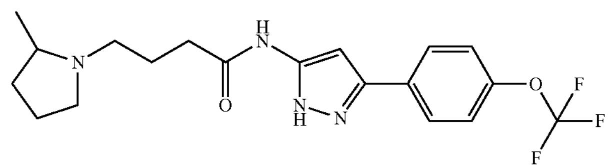 | HCOOH | C19H23N4O2F3 | 396.41 | 397 | 100 | 2.03 | 10 | Route A1/A2 for aminopyrazole; general method for the synthesis of o-amino-alkanoic acid (1H-pyrazol-3-yl-5-aryl)-amides via the amino acid route |
| 320 | 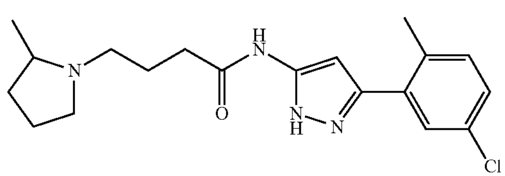 | HCOOH | C19H25N4OCl | 360.88 | 361 | 100 | 1.91 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 321 | 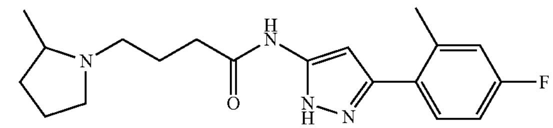 | HCOOH | C19H25N4OF | 344.43 | 345 | 100 | 1.69 | 10 | Route A1/A2 for aminopyrazole; general method for the synthesis of ω-amino-alkanoic acid (1H-pyrazol-3-yl-5-aryl)-amides via the amino acid route |
| 322 | 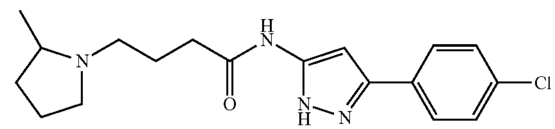 | HCOOH | C18H23N4OCl | 346.85 | 347, 174 | 100 | 1.78 | 10 | Route A1/A2 for aminopyrazole; general method for the synthesis of ω-amino-alkanoic acid (1H-pyrazol-3-yl-5-aryl)-amides via the amino acid route |
| 323 | 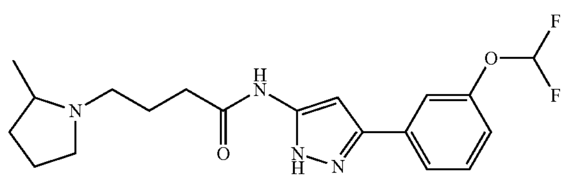 | HCOOH | C19H24N4O2F2 | 378.42 | 379 | 100 | 1.78 | 10 | Route A1/A2 for aminopyrazole; general method for the synthesis of ω-amino-alkanoic acid (1H-pyrazol-3-yl-5-aryl)-amides via the amino acid route |
| 324 | 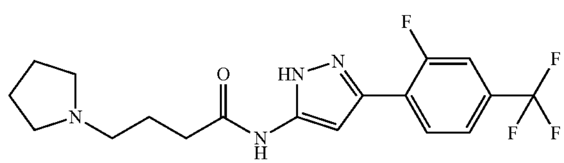 | HCOOH | C18H20N4OF4 | 384.37 | 385 | 99 | 2.01 | 10 | Route A1/A2 for aminopyrazole; general method for the synthesis of ω-amino-alkanoic acid (1H-pyrazol-3-yl-5-aryl)-amides via the amino acid route |
| 325 | 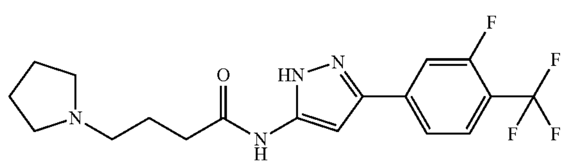 | HCOOH | C18H20N4OF4 | 384.37 | 385 | 99 | 2.09 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 326 | 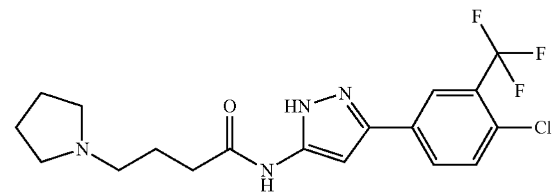 | HCOOH | C18H20N4OF3Cl | 400.83 | 401 | 99 | 2.21 | 10 | Route A1/A2 for aminopyrazole; general method for the synthesis of o-amino-alkanoic acid (1H-pyrazol-3-yl-5-aryl)-amides via the amino acid route |
| 327 | 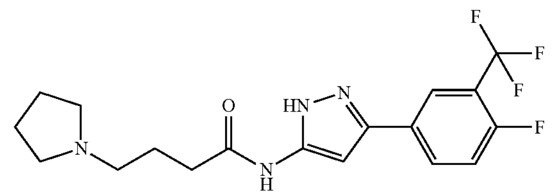 | HCOOH | C18H20N4OF4 | 384.37 | 385 | 99 | 2.01 | 10 | Route A1/A2 for aminopyrazole; general method for the synthesis of o-amino-alkanoic acid (1H-pyrazol-3-yl-5-aryl)-amides via the amino acid route |
| 328 | 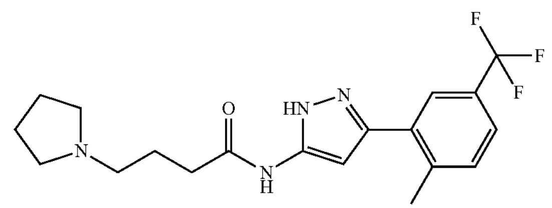 | HCOOH | C19H23N4OF3 | 380.41 | 381 | 99 | 1.99 | 10 | Route A1/A2 for aminopyrazole; general method for the synthesis of o-amino-alkanoic acid (1H-pyrazol-3-yl-5-aryl)-amides via the amino acid route |
| 329 | 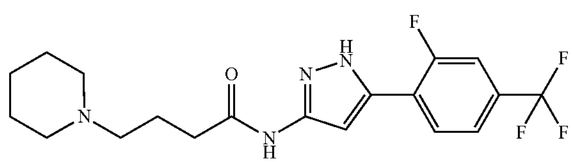 | HCOOH | C19H22N4OF4 | 398.40 | 399 | 99 | 2.11 | 10 | Route A1/A2 for aminopyrazole; general method for the synthesis of o-amino-alkanoic acid (1H-pyrazol-3-yl-5-aryl)-amides via the amino acid route |
| 330 | 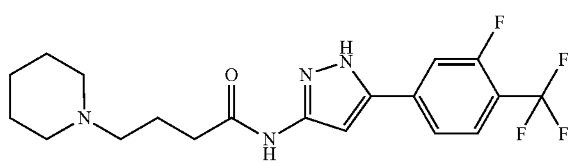 | HCOOH | C19H22N4OF4 | 398.40 | 399 | 99 | 2.19 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 331 | 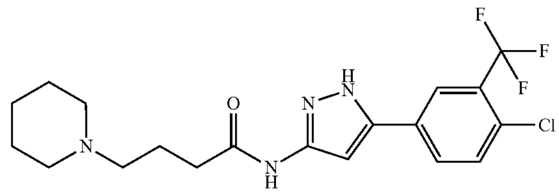 | HCOOH | C19H22N4OF3Cl | 414.85 | 415 | 95 | 2.31 | 10 | Route A1/A2 for aminopyrazole; general method for the synthesis of o-amino-alkanoic acid (1H-pyrazol-3-yl-5-aryl)-amides via the amino acid route |
| 332 | 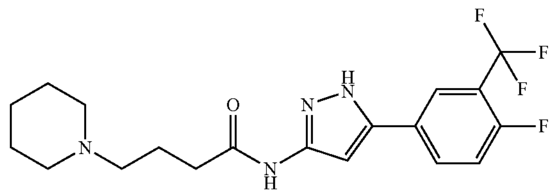 | HCOOH | C19H22N4OF4 | 398.40 | 399 | 99 | 2.04 | 10 | Route A1/A2 for aminopyrazole; general method for the synthesis of o-amino-alkanoic acid (1H-pyrazol-3-yl-5-aryl)-amides via the amino acid route |
| 333 | 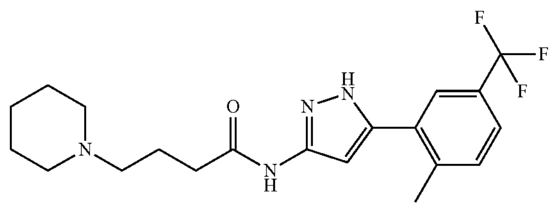 | HCOOH | C20H25N4OF3 | 394.43 | 395 | 99 | 2.08 | 10 | Route A1/A2 for aminopyrazole; general method for the synthesis of o-amino-alkanoic acid (1H-pyrazol-3-yl-5-aryl)-amides via the amino acid route |
| 334 | 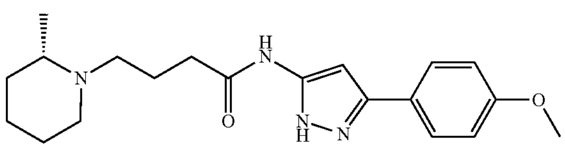 | HCl | C20H28N4O2 | 356.46 | 357, 179 | 98 | 1.62 | 10 | Route A1/A2 for aminopyrazole; general method for the synthesis of o-amino-alkanoic acid (1H-pyrazol-3-yl-5-aryl)-amides via the amino acid route |
| 335 | 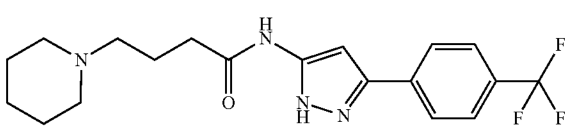 | HCl | C19H23N4OF3 | 380.41 | 381 | 100 | 2 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 336 | 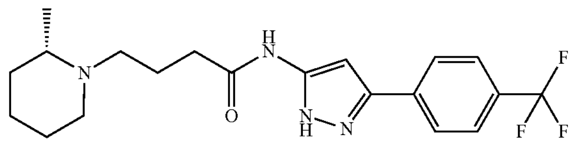 | HCOOH | C20H25N4OF3 | 394.43 | 395 | 100 | 1.94 | 10 | Route A1/A2 for aminopyrazole; general method for the synthesis of ω-amino-alkanoic acid (1H-pyrazol-3-yl-5-aryl)-amides via the amino acid route |
| 337 | 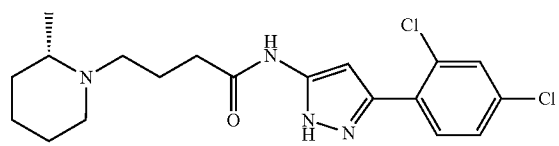 | HCOOH | C19H24N4OCl2 | 395.33 | 395 | 100 | 2 | 10 | Route A1/A2 for aminopyrazole; general method for the synthesis of ω-amino-alkanoic acid (1H-pyrazol-3-yl-5-aryl)-amides via the amino acid route |
| 338 | 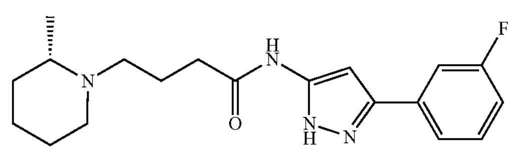 | HCOOH | C19H25N4OF | 344.43 | 345 | 95 | 1.62 | 10 | Route A1/A2 for aminopyrazole; general method for the synthesis of ω-amino-alkanoic acid (1H-pyrazol-3-yl-5-aryl)-amides via the amino acid route |
| 339 | 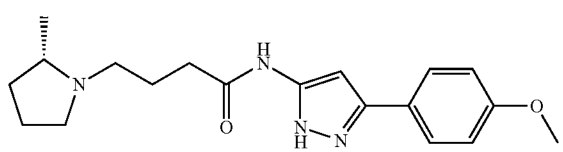 | HCOOH | C19H26N4O2 | 342.44 | 343 | 93 | 1.45 | 10 | Route A1/A2 for aminopyrazole; general method for the synthesis of ω-amino-alkanoic acid (1H-pyrazol-3-yl-5-aryl)-amides via the amino acid route |
| 340 | 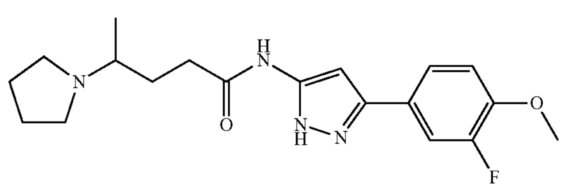 | HCOOH | C19H25N4O2F | 360.43 | 361 | 100 | 1.49 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 341 | 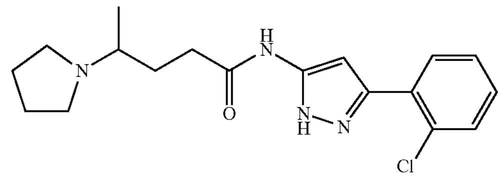 | HCOOH | C18H23N4OCl | 346.85 | 347 | 100 | 1.45 | 10 | Route A1/A2 for aminopyrazole; general method for the synthesis of o-amino-alkanoic acid (1H-pyrazol-3-yl-5-aryl)-amides via the amino acid route |
| 342 | 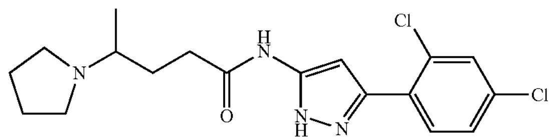 | HCOOH | C18H22N4OCl2 | 381.30 | 381 | 100 | 1.8 | 10 | Route A1/A2 for aminopyrazole; general method for the synthesis of o-amino-alkanoic acid (1H-pyrazol-3-yl-5-aryl)-amides via the amino acid route |
| 343 | 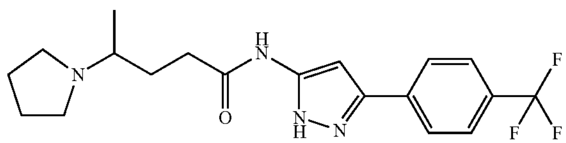 | HCOOH | C19H23N4OF3 | 380.41 | 381 | 100 | 1.9 | 10 | Route A1/A2 for aminopyrazole; general method for the synthesis of o-amino-alkanoic acid (1H-pyrazol-3-yl-5-aryl)-amides via the amino acid route |
| 344 | 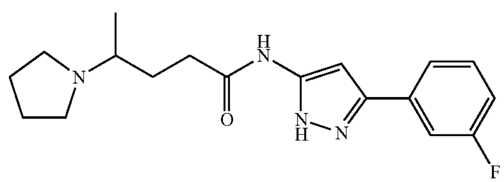 | HCOOH | C18H23N4OF | 330.40 | 331 | 100 | 1.4 | 10 | Route A1/A2 for aminopyrazole; general method for the synthesis of o-amino-alkanoic acid (1H-pyrazol-3-yl-5-aryl)-amides via the amino acid route |
| 345 | 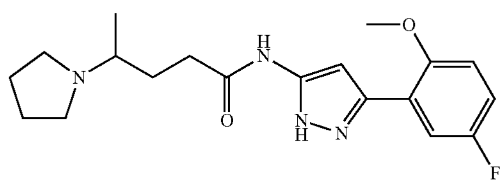 | HCOOH | C19H25N4O2F | 360.43 | 361 | 100 | 1.59 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 346 | 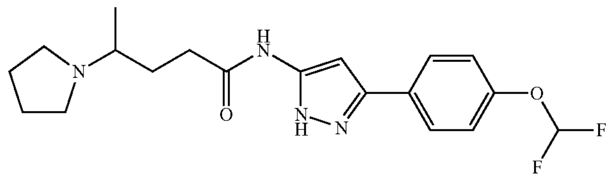 | HCOOH | C19H24N4O2F2 | 378.42 | 379 | 100 | 1.65 | 10 | Route A1/A2 for aminopyrazole; general method for the synthesis of ω-amino-alkanoic acid (1H-pyrazol-3-yl-5-aryl)-amides via the amino acid route |
| 347 | 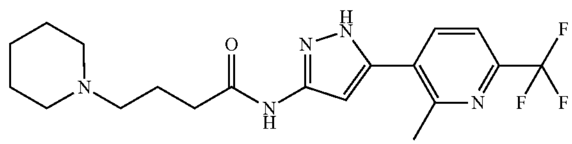 | HCOOH | C19H24N5OF3 | 395.42 | 396 | 98 | 1.62 | 10 | Route A1/A2 for aminopyrazole; general method for the synthesis of ω-amino-alkanoic acid (1H-pyrazol-3-yl-5-aryl)-amides via the amino acid route |
| 348 | 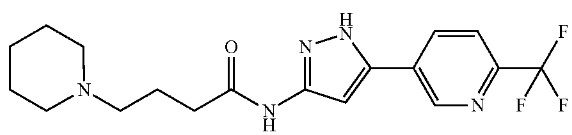 | HCOOH | C18H22N5OF3 | 381.40 | 382 | 100 | 1.57 | 10 | Route A1/A2 for aminopyrazole; general method for the synthesis of ω-amino-alkanoic acid (1H-pyrazol-3-yl-5-aryl)-amides via the amino acid route |
| 349 | 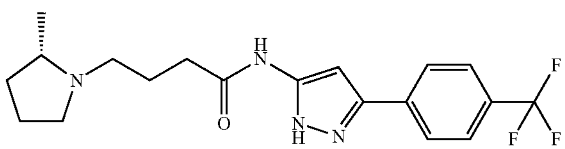 | HCOOH | C19H23N4OF3 | 380.41 | 381 | 100 | 1.84 | 10 | Route A1/A2 for aminopyrazole; general method for the synthesis of ω-amino-alkanoic acid (1H-pyrazol-3-yl-5-aryl)-amides via the amino acid route |
| 350 | 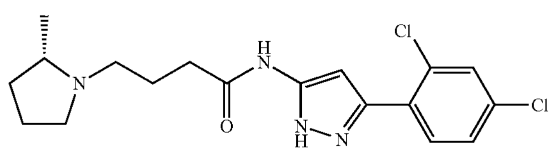 | HCOOH | C18H22N4OCl2 | 381.30 | 381 | 98 | 1.84 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 351 | 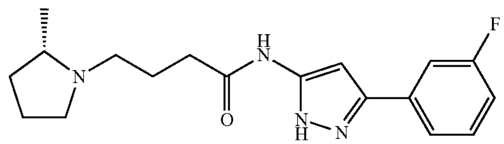 | HCOOH | C18H23N4OF | 330.40 | 331 | 98 | 1.45 | 10 | Route A1/A2 for aminopyrazole; general method for the synthesis of ω-amino-alkanoic acid (1H-pyrazol-3-yl-5-aryl)-amides via the amino acid route |
| 352 | 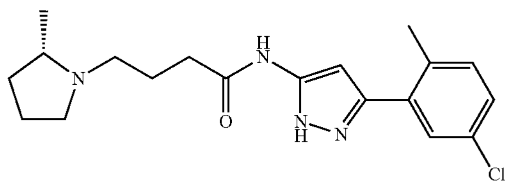 | HCOOH | C19H25N4OCl | 360.88 | 361 | 98 | 1.75 | 10 | Route A1/A2 for aminopyrazole; general method for the synthesis of ω-amino-alkanoic acid (1H-pyrazol-3-yl-5-aryl)-amides via the amino acid route |
| 353 | 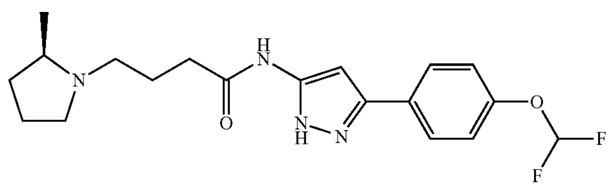 | HCOOH | C19H24N4O2F2 | 378.42 | 379 | 98 | 1.7 | 10 | Route A1/A2 for aminopyrazole; general method for the synthesis of ω-amino-alkanoic acid (1H-pyrazol-3-yl-5-aryl)-amides via the amino acid route |
| 354 | 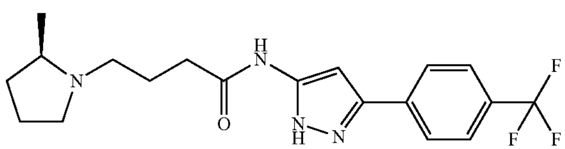 | HCOOH | C19H23N4OF3 | 380.41 | 381 | 100 | 1.93 | 10 | Route A1/A2 for aminopyrazole; general method for the synthesis of ω-amino-alkanoic acid (1H-pyrazol-3-yl-5-aryl)-amides via the amino acid route |
| 355 | 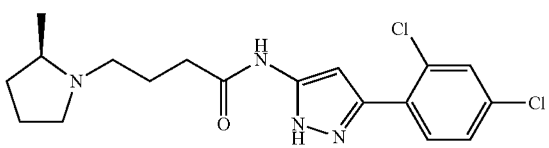 | HCOOH | C18H22N4OCl2 | 381.30 | 381 | 100 | 1.95 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 356 | 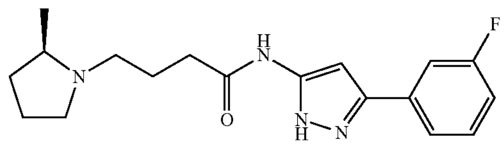 | HCOOH | C18H23N4OF | 330.40 | 331 | 100 | 1.47 | 10 | Route A1/A2 for aminopyrazole; general method for the synthesis of ω-amino-alkanoic acid (1H-pyrazol-3-yl-5-aryl)-amides via the amino acid route |
| 357 | 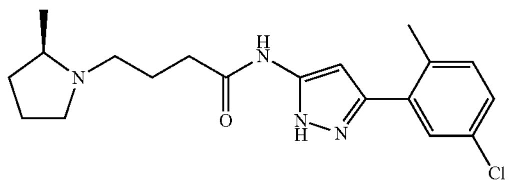 | HCOOH | C19H25N4OCl | 360.88 | 361 | 100 | 1.88 | 10 | Route A1/A2 for aminopyrazole; general method for the synthesis of ω-amino-alkanoic acid (1H-pyrazol-3-yl-5-aryl)-amides via the amino acid route |
| 358 | 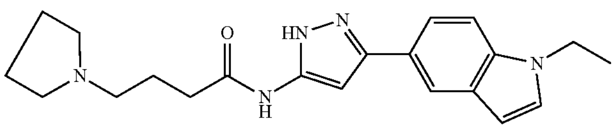 | HCOOH | C21H27N5O | 365.47 | 366 | 96 | 1.82 | 10 | Route A1/A2 for aminopyrazole; general method for the synthesis of ω-amino-alkanoic acid (1H-pyrazol-3-yl-5-aryl)-amides via the amino acid route |
| 359 | 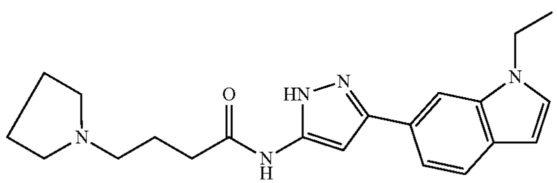 | HCOOH | C21H27N5O | 365.47 | 366 | 100 | 1.88 | 10 | Route A1/A2 for aminopyrazole; general method for the synthesis of ω-amino-alkanoic acid (1H-pyrazol-3-yl-5-aryl)-amides via the amino acid route |
| 360 | 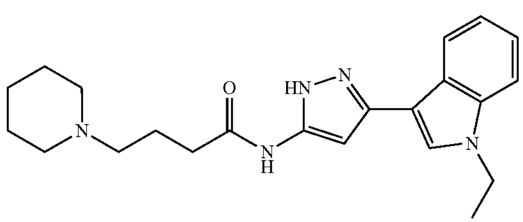 | HCOOH | C22H29N5O | 379.50 | 380, 190 | 100 | 1.95 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 361 | 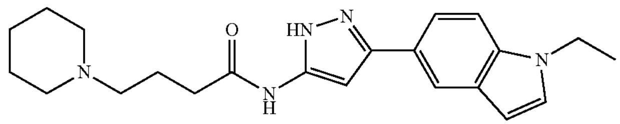 | HCOOH | C22H29N5O | 379.50 | 380 | 98 | 1.92 | 10 | Route A1/A2 for aminopyrazole; general method for the synthesis of ω-amino-alkanoic acid (1H-pyrazol-3-yl-5-aryl)-amides via the amino acid route |
| 362 | 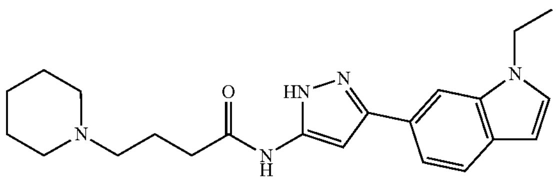 | HCOOH | C22H29N5O | 379.50 | 380 | 99 | 1.98 | 10 | Route A1/A2 for aminopyrazole; general method for the synthesis of ω-amino-alkanoic acid (1H-pyrazol-3-yl-5-aryl)-amides via the amino acid route |
| 363 | 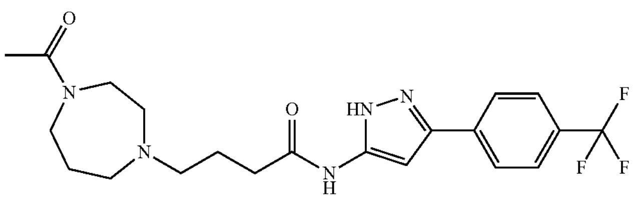 | HCOOH | C21H26N5O2F3 | 437.46 | 438 | 99 | 1.83 | 10 | Route A1/A2 for aminopyrazole; general method for the synthesis of ω-amino-alkanoic acid (1H-pyrazol-3-yl-5-aryl)-amides via the amino acid route |
| 364 | 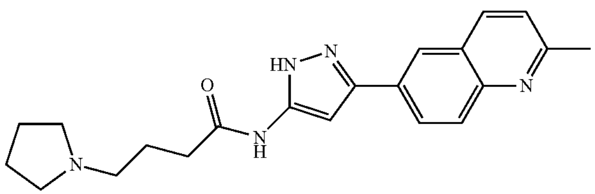 | | C21H25N5O | 363.46 | 364, 182 | 90 | 0.2 | 10 | Route A1/A2 for aminopyrazole; general method for the synthesis of ω-amino-alkanoic acid (1H-pyrazol-3-yl-5-aryl)-amides via the amino acid route |
| 365 | 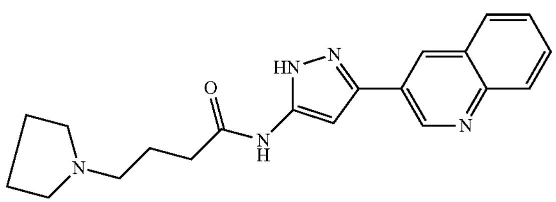 | | C20H23N5O | 349.43 | 350, 175 | 95 | 1.25 | 10 | Route A1/A2 for aminopyrazole; general method for the synthesis of ω-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 366 | 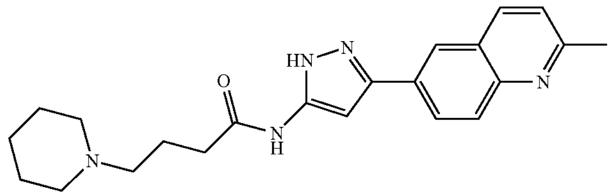 | | C22H27N5O | 377.48 | 378, 189 | 95 | 0.98 | 10 | Route A1/A2 for aminopyrazole; general method for the synthesis of o-amino-alkanoic acid (1H-pyrazol-3-yl-5-aryl)-amides via the amino acid route |
| 367 | 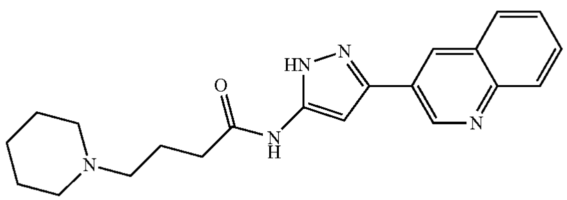 | | C21H25N5O | 363.46 | 364, 182 | 95 | 1.35 | 10 | Route A1/A2 for aminopyrazole; general method for the synthesis of o-amino-alkanoic acid (1H-pyrazol-3-yl-5-aryl)-amides via the amino acid route |
| 368 | 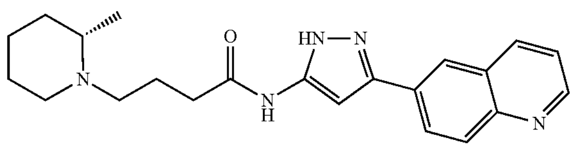 | | C22H27N5O | 377.48 | 378, 189 | 95 | 1.07 | 10 | Route A1/A2 for aminopyrazole; general method for the synthesis of o-amino-alkanoic acid (1H-pyrazol-3-yl-5-aryl)-amides via the amino acid route |
| 369 | 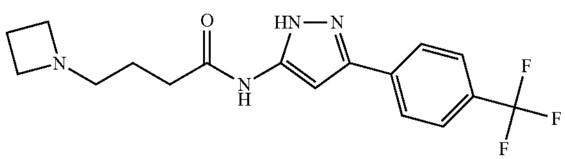 | HCOOH | C17H19N4OF3 | 352.35 | 353 | 99 | 1.8 | 10 | Route A1/A2 for aminopyrazole; general method for the synthesis of o-amino-alkanoic acid (1H-pyrazol-3-yl-5-aryl)-amides via the amino acid route |
| 370 | 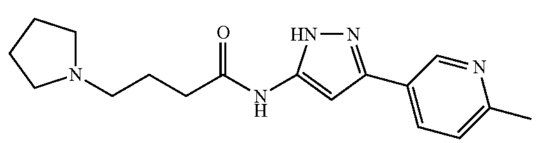 | HCOOH | C17H23N5O | 313.40 | 314, 157 | 99 | 0.15 | 10 | Route A1/A2 for aminopyrazole; general method for the synthesis of o-amino-alkanoic acid (1H-pyrazol-3-yl-5-aryl)-amides via the amino acid route |

TABLE 3-continued

Examples 38-372

| Example | Structure | Salt | Parent Formula | Parent MW | Mass found | LC purity % | LC Rt | LC method (min) | Synthetic Method |
|---|---|---|---|---|---|---|---|---|---|
| 371 | 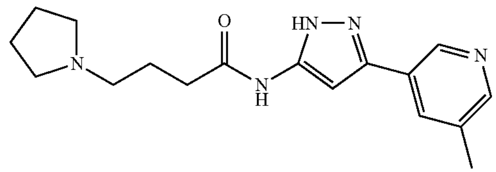 | | C17H23N5O | 313.40 | 314, 157 | 95 | 0.22 | 10 | Route A1/A2 for aminopyrazole; general method for the synthesis of ω-amino-alkanoic acid (1H-pyrazol-3-yl-5-aryl)-amides via the amino acid route |
| 372 | 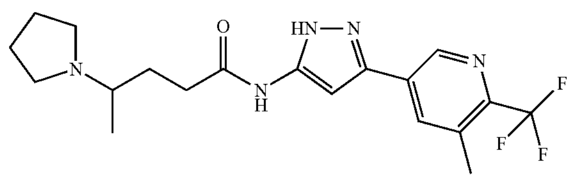 | HCOOH | C19H24N5OF3 | 395.42 | 396 | 96 | 5.27 | 10 | Route A1/A2 for aminopyrazole; general method for the synthesis of ω-amino-alkanoic acid (1H-pyrazol-3-yl-5-aryl)-amides via the amino acid route |

Table 3 shows a selection of the compounds synthesised, which were prepared according to the method indicated in the last column of the table and discussed in detail in the Experimental Procedures with the synthesis of Examples 1-37. When the compound is indicated as the HCl salt, the salt was formed by dissolution of the free base in methanol and addition of 1 eq 1M HCl in ether followed by evaporation of the solvents. When the compound is indicated as HCOOH (formic acid) salt, the compound was purified by preparative HPLC.

Biological Activity

Cloning of Alpha7 Nicotinic Acetylcholine Receptor and Generation of Stable Recombinant Alpha7 nAChR Expressing Cell Lines Full length cDNAs encoding the alpha7 nicotinic acetylcholine receptor were cloned from a rat brain cDNA library using standard molecular biology techniques. Rat GH4C1 cells were then transfected with the rat receptor, cloned and analyzed for functional alpha7 nicotinic receptor expression employing a FLIPR assay to measure changes in intracellular calcium concentrations. Cell clones showing the highest calcium-mediated fluorescence signals upon agonist (nicotine) application were further subcloned and subsequently stained with Texas red-labelled α-bungarotoxin (BgTX) to analyse the level and homogeneity of alpha7 nicotinic acetylcholine receptor expression using confocal microscopy. Three cell lines were then expanded and one characterised pharmacologically (see Table 4 below) prior to its subsequent use for compound screening.

TABLE 4

Pharmacological characterisation of alpha7 nAChR stably expressed in GH4C1 cells using the functional FLIPR assay

| Compound | $EC_{50}$ [microM] |
|---|---|
| Acetylcholine | 3.05 ± 0.08 (n = 4) |
| Choline | 24.22 ± 8.30 (n = 2) |
| Cytisine | 1.21 ± 0.13 (n = 5) |
| DMPP | 0.98 ± 0.47 (n = 6) |
| Epibatidine | 0.012 ± 0.002 (n = 7) |
| Nicotine | 1.03 ± 0.26 (n = 22) |

Development of a Functional FLIPR Assay for Primary Screening

A robust functional FLIPR assay (Z'=0.68) employing the stable recombinant GH4C1 cell line was developed to screen the alpha7 nicotinic acetylcholine receptor. The FLIPR system allows the measurements of real time $Ca^{2+}$-concentration changes in living cells using a $Ca^{2+}$ sensitive fluorescence dye (such as Fluo4). This instrument enables the screening for agonists and antagonists for alpha 7 nAChR channels stably expressed in GH4C1 cells.

Cell Culture

GH4C1 cells stably transfected with rat-alpha7-nAChR (see above) were used. These cells are poorly adherent and therefore pretreatment of flasks and plates with poly-D-lysine was carried out. Cells are grown in 150 $cm^2$ T-flasks, filled with 30 ml of medium at 37° C. and 5% $CO_2$.

Data Analysis $EC_{50}$ and $IC_{50}$ values were calculated using the IDBS XLfit4.1 software package employing a sigmoidal concentration-response (variable slope) equation:

$$Y=Bottom+((Top-Bottom)/(1+((EC_{50}/X)^{HillSlope}))$$

Assay Validation

The functional FLIPR assay was validated with the alpha7 nAChR agonists nicotine, cytisine, DMPP, epibatidine, choline and acetylcholine. Concentration-response curves were obtained in the concentration range from 0.001 to 30 microM. The resulting $EC_{50}$ values are listed in Table 2 and the obtained rank order of agonists is in agreement with published data (Quik et al., 1997, Mol. Pharmacol., 51, 499-506).

The assay was further validated with the specific alpha7 nAChR antagonist MLA (methyllycaconitine), which was used in the concentration range between 1 microM to 0.01 nM, together with a competing nicotine concentration of 10 microM. The $IC_{50}$ value was calculated as 1.31±0.43 nM in nine independent experiments.

Development of Functional FLIPR Assays for Selectivity Testing

Functional FLIPR assays were developed in order to test the selectivity of compounds against the alpha1 (muscular) and alpha3 (ganglionic) nACh receptors and the structurally related 5-HT3 receptor. For determination of activity at alpha1 receptors natively expressed in the rhabdomyosarcoma derived TE 671 cell line an assay employing membrane potential sensitive dyes was used, whereas alpha3 selectivity was determined by a calcium-monitoring assays using the native SH-SY5Y cell line. In order to test selectivity against the 5-HT3 receptor, a recombinant cell line was constructed expressing the human 5-HT3A receptor in HEK 293 cells and a calcium-monitoring FLIPR assay employed.

Screening of Compounds

The compounds were tested using the functional FLIPR primary screening assay employing the stable recombinant GH4C1 cell line expressing the alpha7 nAChR. Hits identified were validated further by generation of concentration-response curves. The potency of compounds from Examples 1-372 as measured in the functional FLIPR screening assay was found to range between 10 nM and 10 microM, with the majority showing a potency ranging between 100 nM and 5 microM.

The compounds were also demonstrated to be selective against the alpha1 nAChR, alpha3 nAChR and 5HT3 receptors.

The invention claimed is:
1. A compound of formula (I):

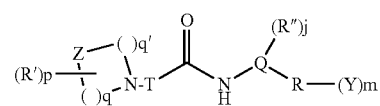

wherein
T is a (C3-C5) alkane-α,ω-diyl optionally substituted with one or more halogens; hydroxy groups; (C1-C5) alkyl, alkoxy, fluoroalkyl, hydroxyalkyl, alkylidene, fluoroalkylidene groups; (C3-C6) cycloalkane-1,1-diyl, oxacycloalkane-1,1-diyl groups; (C3-C6) cycloalkane-1,2-diyl, oxacycloalkane-1,2-diyl groups, where the bonds of the 1,2-diyl radical form a fused ring with the T chain;
Z is $CH_2$;
q and q' are 2;
p is 0, 1, or 2;
R', independently from one another for p=2, is selected from the group consisting of mono- or di-[linear, branched or cyclic (C1-C6) alkyl]aminocarbonyl; linear, branched or cyclic (C1-C6) alkyl, alkoxy, or acyl;
Q is a group of formula

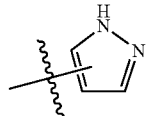

wherein "  " represents a bond to the nitrogen atom;
R" is C1-C3 alkyl;
j is 0 or 1;
R is a 5- to 10-member aromatic or heteroaromatic ring;
m is 0, 1, 2, or 3;

Y represents, independently from one another when m is greater than 1, halogen; hydroxy; mercapto; cyano; nitro; amino; linear, branched or cyclic (C1-C6) alkyl, trihaloalkyl, di- or trihaloalkoxy, alkoxy, or alkylcarbonyl; (C3-C6) cycloalkyl-(C1-C6) alkoxy; (C3-C6) cycloalkyl-(C1-C6) alkyl; linear, branched, or cyclic (C1-C6) alkylcarbonylamino; mono- or di-, linear, branched, or cyclic (C1-C6) alkylaminocarbonyl; carbamoyl; linear, branched, or cyclic (C1-C6) alkylsulphonylamino; linear, branched, or cyclic (C1-C6) alkylsulphonyl; mono- or di-, linear, branched, or cyclic (C1-C6) alkylsulphamoyl; linear, branched or cyclic (C1-C6) alkoxy-(C1-C6) alkyl; or, when m=2, two Y substituents, together with the atoms of the R group they are attached to, may form a ring;

or a salt, optical isomer, diastereomer, racemic mixture or isotopic composition thereof.

2. A compound according to claim 1 wherein:
T is propane-1,3-diyl optionally substituted with (C1-C3) alkyl or halogen.

3. A compound according to claim 2, wherein:
q and q' are, independently from one another, 1 or 2;
p is 0 or 1;
R' is selected from the group consisting of linear, branched or cyclic (C1-C6) alkyl, alkoxy, acyl; and
j is 0.

4. A compound according to claim 3, wherein:
T is propane-1,3-diyl;
R' is selected from the group consisting of linear, branched or cyclic (C1-C6) alkyl;
R is phenyl, pyridyl, or naphthyl;
m is 1 or 2; and
Y represents, independently from one another when m is greater than 1, halogen; hydroxy; linear, branched or cyclic (C1-C6) alkyl, trihaloalkyl, di- or trihaloalkoxy, alkoxy; (C3-C6) cycloalkyl-(C1-C6) alkoxyl.

5. A compound according to claim 4 wherein Q-R is

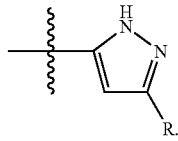

6. A pharmaceutical composition containing a compound according to claim 1, with a pharmaceutically acceptable carrier or excipient.

7. A compound according to claim 5, wherein R is pyridyl.
8. A compound according to claim 7, wherein m is 1.
9. A compound according to claim 7, wherein m is 2.
10. A compound according to claim 5, wherein R is phenyl.
11. A compound according to claim 10, wherein m is 1.
12. A compound according to claim 10, wherein m is 2.
13. A compound according to claim 5, wherein R is naphthyl.
14. A compound according to claim 13, wherein m is 1.
15. A compound according to claim 13, wherein m is 2.
16. A compound according to claim 5, wherein p is 0.
17. A compound according to claim 5, wherein p is 1.
18. A compound according to claim 5, wherein Y is linear, branched or cyclic (C1-C6) alkyl.
19. A compound according to claim 1, having the structure:

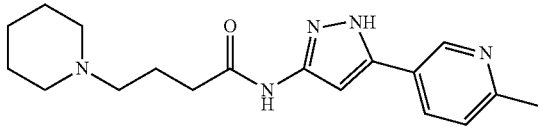

or a pharmaceutically acceptable salt thereof.

* * * * *